US012685753B2

(12) United States Patent
Culler et al.

(10) Patent No.: US 12,685,753 B2
(45) Date of Patent: Jul. 21, 2026

(54) COMPOSITIONS FOR MODULATING GUT MICROFLORA POPULATIONS, ENHANCING DRUG POTENCY AND TREATING CANCER, AND METHODS FOR MAKING AND USING SAME

(71) Applicant: PERSEPHONE BIOSCIENCES, INC., San Diego, CA (US)

(72) Inventors: Stephanie J. Culler, Del Mar, CA (US); Robert J. Haselbeck, San Diego, CA (US); Stephen Van Dien, San Diego, CA (US); Anandh Swaminathan, San Diego, CA (US); Hirokazu Sato, San Diego, CA (US)

(73) Assignee: PERSEPHONE BIOSCIENCES, INC., San Diego, CA (US)

( * ) Notice: Subject to any disclaimer, the term of this patent is extended or adjusted under 35 U.S.C. 154(b) by 692 days.

(21) Appl. No.: 17/787,518

(22) PCT Filed: Dec. 17, 2020

(86) PCT No.: PCT/US2020/065693
§ 371 (c)(1),
(2) Date: Jun. 20, 2022

(87) PCT Pub. No.: WO2021/127235
PCT Pub. Date: Jun. 24, 2021

(65) Prior Publication Data
US 2022/0378855 A1      Dec. 1, 2022

Related U.S. Application Data

(60) Provisional application No. 62/951,673, filed on Dec. 20, 2019.

(51) Int. Cl.
A61K 35/741      (2015.01)
A61K 45/06      (2006.01)
A61P 35/00      (2006.01)

(52) U.S. Cl.
CPC ............ *A61K 35/741* (2013.01); *A61K 45/06* (2013.01); *A61P 35/00* (2018.01)

(58) Field of Classification Search
CPC .................................................. A61K 35/741
(Continued)

(56) References Cited

U.S. PATENT DOCUMENTS

2016/0143962 A1* 5/2016 Berry ................... A61K 9/0053
424/93.3
2017/0143775 A1* 5/2017 Mulder ................... A61P 35/04

FOREIGN PATENT DOCUMENTS

WO      2016063263 A3      4/2016
WO      2016196605 A1      12/2016
(Continued)

OTHER PUBLICATIONS

Barroso-Sousa, R., et al., "Gut Microbiome and Breast Cancer in the Era of Cancer Immunotherapy", Current Breast Cancer Reports, Dec. 1, 2019, pp. 272-276, vol. 11, No. 4.
(Continued)

*Primary Examiner* — Robert B Mondesi
(74) *Attorney, Agent, or Firm* — Gregory P. Einhorn; Greer, Burns & Crain, Ltd.

(57)      ABSTRACT

Provided are compositions, including products of manufacture and kits, and methods, comprising combinations of microbes, such as non-pathogenic, live bacteria and/or bacterial spores, for the control, amelioration, prevention, and treatment of a disease or condition, for example, a cancer. In alternative embodiment, these non-pathogenic, live bacteria and/or bacterial spores are administered to an individual in
(Continued)

need thereof, thereby resulting in a modification or modulation of the individual's gut microfloral population(s). In alternative embodiments, by modulating or modifying the individual's gut microbial population(s) using compositions, products of manufacture and methods as provided herein, the pharmacodynamics of a drug administered to the individual is altered, thereby controlling, ameliorating, preventing and/or treating of that cancer. Combinations of microbes are administered with chemotherapy, radiation therapy, an immune checkpoint inhibitor, a Chimeric Antigen Receptor T-cell therapy or other immunotherapy or cancer treatment.

20 Claims, 65 Drawing Sheets

(58) Field of Classification Search
USPC ........................................................ 424/93.3
See application file for complete search history.

(56) References Cited

FOREIGN PATENT DOCUMENTS

| | | | |
|---|---|---|---|
| WO | 2018/064165 | A2 | 4/2018 |
| WO | 2018/222969 | A1 | 12/2018 |
| WO | 2018226690 | A1 | 12/2018 |
| WO | WO-2019178542 | A1 * | 9/2019 ........... A61K 31/352 |

OTHER PUBLICATIONS

Elkrief, A., et al., "The intimate relationship between gut microbiota and cancer immunotherapy", Gut Microbes, Oct. 19, 2018, pp. 1-3.
European Extended Search Report dated Jan. 11, 2024 for European Application No. 20900957.0-1112.
Yutin, N. et al., "A genomic update on clostridial phylogeny: Gram-negative spore formers and other misplaced clostridia", Environ Microbiol, (2013); pp. 2631-2641, vol. 15, No. 10.

* cited by examiner

| Primary carbon sources [a] | Compounds | Abbreviations | Akkermansia muciniphila | Faecalibacterium prausnitzii | Ruminococcus torques | Ruminococcus gnavus | Ruminococcus lactaris | Eubacterium hallii | Blautia obeum | Anaerostipes hadrus | Dorea formicigenerans | Coprococcus comes | Clostridium scindens | Coprococcus catus | Erysipelotrichaceae sp. |
|---|---|---|---|---|---|---|---|---|---|---|---|---|---|---|---|
| | D-glucose | glc_D | 0 | 1 | 1 | 1 | 1 | 1 | 1 | 1 | 1 | 1 | 1 | 1 | 1 |
| | fructose | fru | 0 | 1 | 1 | 0 | 1 | 1 | 1 | 1 | 1 | 1 | 1 | 1 | 0 |
| | cellobiose | cellb | 0 | 1 | 0 | 0 | 0 | 0 | 1 | 0 | 0 | 0 | 0 | 0 | 1 |
| | D-xylose | xyl_D | 0 | 0 | 1 | 1 | 0 | 1 | 0 | 0 | 1 | 1 | 1 | 0 | 0 |
| | fructooligosaccharides | kesto | 0 | 1 | 0 | 0 | 0 | 1 | 0 | 1 | 0 | 0 | 0 | 0 | 0 |
| | mannitol | mnl | 0 | 0 | 0 | 0 | 1 | 0 | 1 | 0 | 0 | 1 | 0 | 1 | 0 |
| | lactose | lcts | 0 | 0 | 1 | 1 | 1 | 0 | 1 | 1 | 1 | 1 | 1 | 0 | 0 |
| | maltose | malt | 0 | 1 | 1 | 1 | 1 | 0 | 0 | 0 | 1 | 0 | 0 | 0 | 1 |
| | maltotriose | malttr | 0 | 0 | 1 | 1 | 0 | 0 | 1 | 0 | 0 | 0 | 0 | 0 | 0 |
| | mucin | core6 | 1 | 0 | 1 | 0 | 1 | 1 | 0 | 1 | 1 | 1 | 0 | 0 | 0 |
| | N-acetylglucosamine | acgam | 1 | 1 | 0 | 0 | 0 | 1 | 0 | 0 | 0 | 0 | 0 | 1 | 1 |
| | inulin | inulin | 0 | 1 | 0 | 0 | 0 | | 0 | 0 | 0 | 0 | 0 | 0 | 0 |

FIG. 16A

| | | | | | | | | | | | | | | |
|---|---|---|---|---|---|---|---|---|---|---|---|---|---|---|
| Co-utilization [b] | acetate | ac | 1 | 1 | 1 | 1 | 1 | 1 | 1 | 1 | 1 | 1 | 1 | 1 |
| | lactate | lac_D, lac_L | 1 (D) | 1 (D) | 1 (D/L) | 1 (D) | 1 (D) | 1 (D/L) | 1 (D/L) | 1 (D/L) | 1 (L) | 1 (D/L) | 0 | 1 (L) | 1 (D) |
| Fermentation Products [c] | formate | for | 1 | 1 | 1 | 1 | 1 | 1 | 1 | 1 | 1 | 1 | 1 | 1 | 1 |
| | acetate | ac | 1 | 1 | 1 | 1 | 1 | 1 | 1 | 1 | 1 | 1 | 1 | 1 | 1- |
| | ethanol | etoh | 1 | 0 | 1 | 1 | 1 | 0 | 1 | 1 | 1 | 1 | 1 | 1- | 0 |
| | propionate | ppa | 1 | 1 | 1 | 0 | 1 | 1 | 1 | 1 | 1 | 1 | 0 | 1- | 0 |
| | lactate | lac_D, lac_L | 1 (D) | 1 (D) | 1 (D/L) | 1 (D) | 1 (D/L) | 1 (D/L) | 1 (D/L) | 1 (D/L) | 1 (L) | 1 (D/L) | 0 | 1 (L) | 1 (D) |
| | butyrate | but | 0 | 1 | 0 | 0 | 1 | 1 | 1 | 0 | 0 | 0 | 0 | - | 1 |
| | succinate | succ | 1 | 1 | 0 | 1 | 1 | 1 | 1 | 1 | 1 | 1 | 1 | 1 | 0 |
| | glycerol | glyc | 1 | 1 | 0 | 1 | 0 | 1 | 1 | 0 | 1 | 1 | 0 | 0 | 0 |
| | hydrogen | h2 | 0 | 0 | 0 | 0 | 0 | 0 | 0 | 0 | 0 | 0 | 0 | 0 | 0 |
| | hydrogen sulfide | h2s | 1 | 1 | 0 | 1 | 0 | 0 | 1 | 0 | 0 | 0 | | 0 | 0 |
| Auxotrophy [d] | glutamate | glu_L | 0 | x | x | x | x | x | x | x | x | x | 0 | 0 | 0 |
| | alanine | ala_L | 0 | x | x | x | x | x | x | x | x | x | x | x | 0 |
| | threonine | thr_L | x | 0 | 0 | 0 | 0 | 0 | 0 | 0 | 0 | 0 | 0 | 0 | 0 |
| | phenylalanine | phe_L | 0 | x | 0 | 0 | x | 0 | 0 | 0 | x | 0 | 0 | 0 | 0 |
| | tryptophan | trp_L | 0 | x | 0 | 0 | 0 | 0 | 0 | x | 0 | 0 | x | x | x |
| | tyrosine | tyr_L | 0 | x | 0 | 0 | x | x | 0 | 0 | 0 | 0 | 0 | 0 | 0 |
| | methionine | met_L | 0 | x | x | x | x | x | x | x | x | x | 0 | 0 | x |
| | cysteine | cys_L | 0 | 0 | x | x | 0 | 0 | 0 | 0 | 0 | 0 | 0 | x | x |

FIG. 16B

| | | | | | | | | | | | | | | | | |
|---|---|---|---|---|---|---|---|---|---|---|---|---|---|---|---|---|
| glycine | gly | o | o | o | o | o | o | x | o | o | o | o | o | o | o | o |
| asparagine | asn_L | x | o | o | o | o | o | x | o | o | o | x | o | o | o | o |
| Leucine | leu_L | o | o | o | o | o | o | o | x | x | o | o | o | o | o | o |
| uracil | ura | o | o | x | o | o | o | o | o | o | o | o | o | o | o | o |
| meso-2,6-Diaminoheptanedioate | 26dap_M | o | x | o | o | o | x | o | x | x | x | o | o | o | 1 | x |
| xanthine or hypoxanthine | xan, hxan | o | o | o | o | o | o | o | x | x | x | o | o | o | o | o |
| octadecanoate (n-C18:0) | ocdca | o | x | o | o | o | o | o | x | x | x | o | o | o | o | o |
| 1,2-diacylglycerol (n-C18:0) | 12dgr180 | o | o | o | o | o | o | o | o | o | o | o | o | o | x | o |
| thymidine | thymd | o | o | o | o | o | o | o | o | o | o | o | o | o | o | x |
| cytosine | csn | o | o | o | o | o | o | o | o | o | o | o | o | o | o | x |

FIG. 16C

| NCBI Taxonomy ID | p value (Mann Whitney U) | log 10 of Fold Change (Control vs Cancer) | Mean Abundance | Organism Name (Operational Species Unit) | Adjusted p value (q) Benjamini-Hochberg |
|---|---|---|---|---|---|
| 3002844 | 1.13356E-08 | -0.764382216 | 0.0011119483 | Erysipelotrichaceae bacterium GAM147 C2844 | 1.8477E-06 |
| 3002284 | 3.84213E-07 | -0.280259145 | 0.002625466 | Flavonifractor plautii C2284 | 2.08756E-05 |
| 3002906 | 3.1747E-07 | -0.415683892 | 0.001280695 | Blautia sp. AF19-10LB C2906 | 2.08756E-05 |
| 3002904 | 3.45381E-06 | -0.557690435 | 0.00258185 | Ruminococcus sp. OF03-6AA C2904 | 0.000140743 |
| 3002143 | 1.11816E-05 | -0.629434999 | 0.001723394 | [Clostridium] scindens C2143 | 0.000323857 |
| 3002644 | 1.19211E-05 | -0.565340143 | 0.002250277 | Firmicutes bacterium AF12-30 C2644 | 0.000323857 |
| 3002413 | 1.9624E-05 | -0.436129729 | 0.00522897 | Dorea longicatena C2413 | 0.000399838 |
| 3002152 | 1.77058E-05 | -0.449283525 | 0.007865 | Coprococcus comes C2152 | 0.000399838 |
| 3002131 | 3.44484E-05 | -0.516206872 | 0.013905768 | Dorea longicatena C2131 | 0.00056151 |
| 3002184 | 3.36506E-05 | -0.474788291 | 0.010719146 | Faecalibacterium prausnitzii C2184 | 0.00056151 |
| 3002137 | 4.24543E-05 | -0.249321416 | 0.001084693 | [Clostridium] bolteae C2137 | 0.000629095 |
| 3002129 | 4.96202E-05 | -0.504914016 | 0.017326911 | Blautia obeum C2129 | 0.000674008 |
| 3002890 | 7.0925E-05 | -0.442770588 | 0.000808117 | Dorea sp. OM07-5 C2890 | 0.00088929 |
| 3003392 | 8.27147E-05 | -0.599613718 | 0.001655855 | Lactobacillus salivarius C3392 | 0.000963036 |

FIG. 17A

| | | | | | |
|---|---|---|---|---|---|
| 3002865 | 0.000108676 | 0.559795019 | 0.00053901 | Blautia sp. N6H1-15 C2865 | 0.001135864 |
| 3002636 | 0.000111496 | 0.304525941 | 0.004616969 | [Ruminococcus] torques C2636 | 0.001135864 |
| 3003044 | 0.000240782 | 0.531527103 | 0.003808159 | Blautia hansenii C3044 | 0.002180418 |
| 3002913 | 0.000236114 | 0.432405099 | 0.000782336 | Dorea sp. AM58-8 C2913 | 0.002180418 |
| 3002884 | 0.000315287 | 0.436062031 | 0.000555406 | [Clostridium] aldenense C2884 | 0.002704826 |
| 3002643 | 0.000839149 | 0.201826507 | 0.009132287 | Fusicatenibacter saccharivorans C2643 | 0.006682958 |
| 3002650 | 0.000860995 | 0.417870861 | 0.001147196 | Faecalibacterium prausnitzii C2650 | 0.006682958 |
| 3002144 | 0.001048844 | 0.353929055 | 0.009418945 | Anaerostipes hadrus C2144 | 0.007433115 |
| 3002134 | 0.001041944 | 0.446480902 | 0.001302167 | Anaerostipes caccae C2134 | 0.007433115 |
| 3002841 | 0.001239483 | 0.344627962 | 0.002838094 | Blautia sp. TF11-31AT C2841 | 0.00808143 |
| 3003269 | 0.001201445 | 0.457446985 | 0.001092697 | Dorea sp. Marseille-P4003 C3269 | 0.00808143 |
| 3002443 | 0.001781271 | 0.198581902 | 0.004224894 | Oscillibacter sp. PEA192 C2443 | 0.011167197 |
| 3002810 | 0.001936194 | 0.255666512 | 0.000582608 | Faecalibacterium sp. AF28-13AC C2810 | 0.011688877 |
| 3002845 | 0.002091197 | 0.163492912 | 0.0010232 | Clostridium sp. AM18-55 C2845 | 0.012173751 |
| 3002436 | 0.002439804 | 0.251539605 | 0.008927625 | Blautia luti C2436 | 0.013713379 |
| 3002138 | 0.003783812 | 0.358288898 | 0.01593472 | Faecalibacterium prausnitzii C2138 | 0.018696023 |
| 3002581 | 0.003709187 | 0.419154573 | 0.001163731 | Blautia producta C2581 | 0.018696023 |
| 3002208 | 0.003785084 | 0.40212407 | 0.003188912 | Acidaminococcus intestini C2208 | 0.018696023 |
| 3002953 | 0.003544968 | 0.309520673 | 0.000746237 | Clostridiales bacterium CCNA10 C2953 | 0.018696023 |

FIG. 17B

| | | | | | |
|---|---|---|---|---|---|
| 3007338 | 0.004051648 | 0.386220508 | Streptococcus vestibularis C7338 | 0.001070314 | 0.019424077 |
| 3002921 | 0.004324117 | 0.206044424 | Clostridium sp. AF20-17LB C2921 | 0.000517826 | 0.019672311 |
| 3002440 | 0.004344805 | 0.352856347 | Ruminococcus callidus C2440 | 0.001443383 | 0.019672311 |
| 3002132 | 0.00457584 | 0.312675608 | Clostridium sp. OF10-22XD C2132 | 0.002348528 | 0.02015843 |
| 3002850 | 0.005147868 | 0.246601387 | Agathobaculum butyriciproducens C2850 | 0.002568207 | 0.022081645 |
| 3001933 | 0.005503739 | 0.476696467 | Collinsella aerofaciens C1933 | 0.012303392 | 0.023002807 |
| 3002557 | 0.006074794 | 0.502954606 | Ruminococcus sp. KGMB03662 C2557 | 0.011435865 | 0.024754784 |
| 3002206 | 0.00646676 | 0.421426117 | Anaerobutyricum hallii C2206 | 0.014420032 | 0.025709316 |
| 3003003 | 0.00812493 | 0.322415354 | Blautia sp. KGMB01111 C3003 | 0.000532795 | 0.031532465 |
| 3000005 | 0.008426878 | 0.517722756 | Bifidobacterium bifidum C0005 | 0.0041100758 | 0.031943748 |
| 3000099 | 0.008967584 | 0.003128369 | Bacteroides vulgatus C0099 | 0.015202259 | 0.033220821 |
| 3002863 | 0.009668016 | 0.242001524 | Faecalibacterium prausnitzii C2863 | 0.001258613 | 0.034047573 |
| 3002145 | 0.009756466 | 0.160264471 | Anaerotruncus colihominis C2145 | 0.000610841 | 0.034047573 |
| 3003123 | 0.009817398 | 0.391815999 | Romboutsia timonensis C3123 | 0.000935325 | 0.034047573 |
| 3002651 | 0.011792583 | -0.36246911 | Faecalibacterium prausnitzii C2651 | 0.002191973 | 0.040045645 |
| 3002275 | 0.012581011 | 0.193752289 | [Clostridium] clostridioforme C2275 | 0.000754264 | 0.041439426 |
| 3002881 | 0.01271148 | -0.27637531 | Coprococcus catus C2881 | 0.000961983 | 0.041439426 |
| 3002128 | 0.013186687 | 0.224153342 | Eubacterium ventriosum C2128 | 0.002019706 | 0.042145687 |

FIG. 17C

| ID | Value 1 | Value 2 | Value 3 | Species | Value 4 |
|---|---|---|---|---|---|
| 3000013 | 0.013509112 | 0.452532206 | 0.003724902 | Bifidobacterium pseudocatenulatum C0013 | 0.042345871 |
| 3002695 | 0.015331343 | -0.34579043 | 0.001285927 | Firmicutes bacterium AF25-13AC C2695 | 0.043842263 |
| 3002933 | 0.01512723 | 0.229970619 | 0.000726352 | Firmicutes bacterium AF22-6AC C2933 | 0.043842263 |
| 3002244 | 0.015329717 | 0.214252057 | 0.002866599 | Faecalimonas umbilicata C2244 | 0.043842263 |
| 3002580 | 0.014929144 | 0.247491324 | 0.002112826 | Oscillibacter sp. ER4 C2580 | 0.043842263 |
| 3003423 | 0.014886365 | 0.301353216 | 0.000518375 | Klebsiella pneumoniae C3423 | 0.043842263 |
| 3002893 | 0.016231058 | 0.392581823 | 0.001812244 | Clostridium sp. AF36-4 C2893 | 0.04506795 |
| 3002102 | 0.016312939 | -0.35259961 | 0.050500994 | [Eubacterium] rectale C2102 | 0.04506795 |
| 3004629 | 0.017483514 | 0.405385756 | 0.000960057 | Streptococcus sp. HSISS2 C4629 | 0.04749688 |
| 3002199 | 0.018474991 | 0.187542345 | 0.005475912 | [Ruminococcus] gnavus C2199 | 0.0493676 |
| 3002250 | 0.018826044 | 0.257161011 | 0.000541763 | Faecalitalea cylindroides C2250 | 0.049494277 |
| 3002149 | 0.019540986 | 0.319221468 | 0.007351815 | Ruminococcus lactaris C2149 | 0.049768449 |
| 3002870 | 0.019421399 | 0.326716726 | 0.006840623 | Subdoligranulum sp. APC924/74 C2870 | 0.049768449 |
| 3002934 | 0.023532312 | -0.26283664 | 0.001455496 | Clostridium sp. AM49-4BH C2934 | 0.059011797 |
| 3002894 | 0.025598358 | 0.081852178 | 0.000742415 | Ruminococcus sp. AF24-32LB C2894 | 0.063220187 |
| 3002887 | 0.026898361 | 0.165551333 | 0.00084904 | [Clostridium] amygdalinum C2887 | 0.064678076 |
| 3002161 | 0.026982265 | 0.243049812 | 0.001577497 | Blautia hansenii C2161 | 0.064678076 |
| 3002864 | 0.028683688 | 0.235792289 | 0.002124959 | Faecalibacterium prausnitzii C2864 | 0.067760016 |
| 3002435 | 0.029756309 | 0.185518308 | 0.000885444 | Eisenbergiella massiliensis C2435 | 0.069289691 |

FIG. 17D

| | | | | | |
|---|---|---|---|---|---|
| 3003345 | 0.032287699 | 0.40868596 | 0.000781557 | Streptococcus mutans C3345 | 0.073339454 |
| 3003282 | 0.032845277 | 0.27056853 | 0.00076404 | Dialister sp. Marseille-P5638 C3282 | 0.073339454 |
| 3002197 | 0.03257254 | 0.230812001 | 0.003346672 | Dorea formicigenerans C2197 | 0.073339454 |
| 3002945 | 0.035937114 | -0.32340108 | 0.003763895 | Ruminococcus sp. AM42-11 C2945 | 0.079158778 |
| 3002888 | 0.037011448 | 0.266781049 | 0.0015938 | Catenibacterium sp. AM22-15 C2888 | 0.080438213 |
| 3000239 | 0.03822743 | 0.274298289 | 0.000561488 | Odoribacter laneus YIT 12061 C0239 | 0.081630881 |
| 3002909 | 0.038561827 | 0.305064647 | 0.000989984 | Firmicutes bacterium TM09-10 C2909 | 0.081630881 |
| 3003263 | 0.039249769 | 0.240687636 | 0.001807216 | Anaerobutyricum hallii C3263 | 0.082021954 |
| 3004617 | 0.042390421 | 0.275685331 | 0.00054226 | Streptococcus lutetiensis C4617 | 0.087463779 |
| 3002903 | 0.044817697 | 0.161787704 | 0.000605901 | Ruminococcus sp. AF31-8BH C2903 | 0.091316058 |
| 3000098 | 0.048255061 | 0.200658318 | 0.003695957 | Bacteroides thetaiotaomicron C0098 | 0.097105863 |
| 3000131 | 0.049924088 | 0.041391195 | 0.009107869 | Bacteroides ovatus C0131 | 0.099239346 |
| 3002282 | 0.05055997 | 0.161011335 | 0.002231588 | Ruthenibacterium lactatiformans C2282 | 0.099292471 |
| 3000224 | 0.055377834 | 0.375605827 | 0.001031049 | Paraprevotella clara C0224 | 0.106195141 |
| 3004037 | 0.055346004 | 0.231236234 | 0.000688633 | Streptococcus parasanguinis C4037 | 0.106195141 |
| 3003118 | 0.060483219 | 0.213972847 | 0.000837773 | Alterileibacterium massiliense C3118 | 0.114636799 |
| 3002461 | 0.062932377 | 0.267120144 | 0.00069139 | Sellimonas intestinalis C2461 | 0.117907787 |
| 3002247 | 0.064505246 | 0.294636274 | 0.000874107 | Lachnospiraceae bacterium 2_1_46FAA C2247 | 0.119481309 |
| 3000132 | 0.072831555 | 0.103576385 | 0.015351044 | Bacteroides uniformis C0132 | 0.133388128 |
| 3003326 | 0.07671217 | 0.209757142 | 0.00066519 | Lactococcus lactis C3326 | 0.138934263 |
| 3002666 | 0.081102172 | 0.251398969 | 0.001277889 | Clostridium sp. AT4 C2666 | 0.142860614 |

FIG. 17E

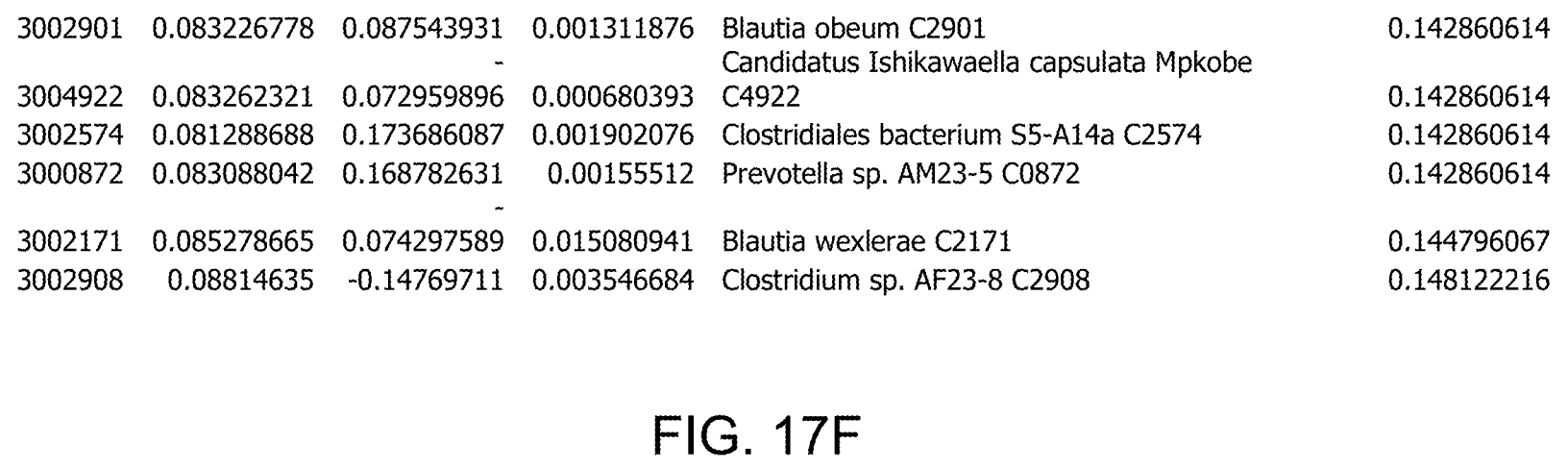

| | | | | | |
|---|---|---|---|---|---|
| 3002901 | 0.083226778 | 0.087543931 | 0.001311876 | Blautia obeum C2901 | 0.142860614 |
| 3004922 | 0.083262321 | 0.072959896 | 0.000680393 | Candidatus Ishikawaella capsulata Mpkobe C4922 | 0.142860614 |
| 3002574 | 0.081288688 | 0.173686087 | 0.001902076 | Clostridiales bacterium S5-A14a C2574 | 0.142860614 |
| 3000872 | 0.083088042 | 0.168782631 | 0.00155512 | Prevotella sp. AM23-5 C0872 | 0.142860614 |
| 3002171 | 0.085278665 | 0.074297589 | 0.015080941 | Blautia wexlerae C2171 | 0.144796067 |
| 3002908 | 0.08814635 | -0.14769711 | 0.003546684 | Clostridium sp. AF23-8 C2908 | 0.148122216 |

FIG. 17F

| taxID | Organism Name | p value (Mann Whitney) | log10 fold-change | log10 mean (Control Group) | log10 mean(Cancer Group) |
|---|---|---|---|---|---|
| 17565 | Blautia_A sp900066335 | 5.75168E-09 | 0.558484888 | -2.856086566 | -3.414571455 |
| 20338 | Collinsella sp900556415 | 1.417E-08 | 1.329997563 | -4.151272784 | -5.481270347 |
| 17558 | Blautia_A sp003474435 | 1.50789E-08 | -0.40883533 | -3.246957174 | -3.655792504 |
| 20262 | Collinsella sp900548935 | 5.39405E-08 | 0.853308793 | -4.33033294 | -5.183641734 |
| 21888 | Enterocloster clostridioformis | 8.7576E-08 | 0.656688671 | -4.45507737 | -3.798388699 |
| 17564 | Blautia_A sp900066205 | 8.98773E-08 | 0.458019688 | -3.011866347 | -3.469886035 |
| 21513 | Dorea sp900550865 | 1.78452E-07 | 0.553434182 | -3.757584337 | -4.311018519 |
| 21494 | Dorea longicatena_B | 2.29706E-07 | 0.385410696 | -2.429188719 | -2.814599416 |
| 22085 | Erysipelatoclostridium sp000752095 | 2.43061E-07 | -0.75614778 | -3.062660833 | -3.818808614 |
| 21493 | Dorea longicatena | 5.53264E-07 | 0.640406177 | -2.248306079 | -2.888712256 |
| 35585 | Raoultibacter massiliensis | 5.5731E-07 | 0.768077285 | -5.285512309 | -6.053589594 |
| 44424 | UMGS1611 sp900553435 | 6.8687E-07 | 0.649596356 | -4.440443148 | -5.090039505 |
| 17579 | Blautia_A sp900551715 | 9.02505E-07 | 0.479679944 | -3.914584527 | -4.39426447 |
| 20216 | Collinsella sp900543845 | 9.9813E-07 | -0.9544925 | -4.501436705 | -5.455929206 |
| 20332 | Collinsella sp900555765 | 2.02215E-06 | 0.669310875 | -3.80454744 | -4.473858316 |
| 20273 | Collinsella sp900549535 | 2.08147E-06 | 0.742268018 | -4.029065766 | -4.771333784 |
| 23067 | Flavonifractor plautii | 2.1578E-06 | 0.419718838 | -3.554361856 | -3.134643018 |
| 21886 | Enterocloster bolteae | 2.62535E-06 | 0.46017815 | -3.803018405 | -3.342840255 |
| 19958 | Clostridium sp900539375 | 2.82876E-06 | 0.595298103 | -5.918315316 | -6.513613419 |
| 20295 | Collinsella sp900551975 | 3.22556E-06 | 0.446259243 | -3.704001792 | -4.150261035 |
| 20229 | Collinsella sp900544865 | 3.32002E-06 | 0.896995559 | -4.160616948 | -5.057612507 |
| 20290 | Collinsella sp900551625 | 4.16E-06 | 0.689238396 | -4.074210617 | -4.763449013 |
| 20245 | Collinsella sp900546455 | 4.52324E-06 | 0.900012997 | -3.880615219 | -4.780628217 |
| 21889 | Enterocloster clostridioformis_A | 4.52982E-06 | 0.417272335 | -4.801257796 | -4.383985461 |
| 20203 | Collinsella sp900542305 | 4.6891E-06 | 0.755899649 | -3.896605996 | -4.652505645 |
| 20277 | Collinsella sp900550205 | 4.71776E-06 | -0.70894793 | -4.108594324 | -4.817542254 |
| 20217 | Collinsella sp900544065 | 5.26608E-06 | 0.811596322 | -4.222272583 | -5.033868904 |
| 20478 | Coprococcus_A sp900548825 | 5.47917E-06 | 0.478026952 | -3.393340859 | -3.871367811 |
| 17226 | Bariatricus comes | 5.47917E-06 | 0.450065888 | -2.602139025 | -3.052204913 |
| 20193 | Collinsella sp900541745 | 5.86175E-06 | 0.877138223 | -4.670264266 | -5.547402489 |
| 41906 | UBA1691 sp900544375 | 6.1569E-06 | 0.840717557 | -4.882319099 | -4.041601543 |
| 20233 | Collinsella sp900545075 | 6.42827E-06 | 0.736477047 | -4.433837385 | -5.170314432 |
| 20173 | Collinsella sp900541025 | 6.57097E-06 | 0.851535779 | -4.05015234 | -4.901688119 |

FIG. 18A

| | | | | | |
|---|---|---|---|---|---|
| 22087 | Erysipelatoclostridium sp003024675 | 7.14841E-06 | 0.586294711 | -3.799315214 | -4.385609925 |
| 20281 | Collinsella sp900550785 | 7.30455E-06 | 0.615149119 | -3.655197218 | -4.270346337 |
| 17229 | Bariatricus sp900554415 | 8.29148E-06 | 0.418033922 | -3.961961401 | -4.379995323 |
| 20288 | Collinsella sp900551555 | 8.31702E-06 | 0.683592188 | -3.797272167 | -4.480864355 |
| 17550 | Blautia_A obeum | 8.47496E-06 | 0.484455077 | -2.188821841 | -2.673276917 |
| 23068 | Flavonifractor sp000508885 | 8.70966E-06 | 0.338704021 | -3.384540136 | -3.045836116 |
| 17555 | Blautia_A sp000436615 | 8.70974E-06 | 0.305600239 | -3.225044229 | -3.530644468 |
| 20310 | Collinsella sp900553705 | 9.25119E-06 | 0.827572534 | -4.162638006 | -4.99021054 |
| 20194 | Collinsella sp900541785 | 9.70053E-06 | 0.839298696 | -4.567680898 | -5.406979594 |
| 20207 | Collinsella sp900542635 | 1.03313E-05 | 0.784688188 | -4.545596567 | -5.330284756 |
| 22277 | Evtepia sp004556345 | 1.06013E-05 | 0.772352737 | -5.270978884 | -6.043331621 |
| 21884 | Enterocloster aldenensis | 1.09428E-05 | 0.396987143 | -4.052714534 | -3.655727392 |
| 20192 | Collinsella sp900541725 | 1.09512E-05 | 0.809611939 | -3.922818952 | -4.732430891 |
| 15904 | Anaerostipes hadrus_A | 1.19296E-05 | 0.627971973 | -2.960534318 | -3.588506291 |
| 18473 | CAG-238 sp900551415 | 1.21234E-05 | 0.430295701 | -4.137572777 | -4.567868478 |
| 23770 | GCA-900066135 sp900543575 | 1.21236E-05 | 0.690679861 | -3.807406618 | -4.49808648 |
| 20265 | Collinsella sp900549185 | 1.42264E-05 | 0.739567714 | -4.307365508 | -5.046933222 |
| 22089 | Erysipelatoclostridium sp900544435 | 1.46242E-05 | -0.5813095 | -3.76473191 | -4.346041411 |
| 20324 | Collinsella sp900554905 | 1.53377E-05 | 0.670904858 | -3.869774709 | -4.540679567 |
| 43602 | UBA738 sp003522945 | 1.57234E-05 | 0.730159742 | -4.937709046 | -5.667868788 |
| 20345 | Collinsella sp900557455 | 1.57389E-05 | 1.045819615 | -4.346167919 | -5.391987535 |
| 20167 | Collinsella sp900540895 | 1.57579E-05 | 1.011271811 | -4.014543038 | -5.025814849 |
| 20328 | Collinsella sp900555515 | 1.60002E-05 | 0.767302734 | -4.618823133 | -5.386125867 |
| 21512 | Dorea sp900543415 | 1.62672E-05 | 0.611695164 | -4.521676345 | -3.909981182 |
| 31913 | Parabacteroides johnsonii | 1.66597E-05 | 0.467252993 | -4.726684034 | -4.259431041 |
| 27982 | Mediterraneibacter faecis | 1.73356E-05 | 0.462717508 | -2.698209246 | -3.160926754 |
| 20269 | Collinsella sp900549335 | 1.78269E-05 | 0.817339908 | -4.516525447 | -5.333865355 |
| 20177 | Collinsella sp900541135 | 2.16381E-05 | 0.792072749 | -4.302263394 | -5.094336143 |
| 20334 | Collinsella sp900555955 | 2.30024E-05 | 0.733186612 | -4.76320644 | -5.496393052 |
| 20225 | Collinsella sp900544645 | 2.38459E-05 | 0.896228426 | -4.443773183 | -5.340001609 |
| 36431 | Ruminococcus_A sp003011855 | 2.38832E-05 | 0.441901782 | -2.908721099 | -3.350622882 |
| 20199 | Collinsella sp900542125 | 2.6666E-05 | 0.756548551 | -4.34052156 | -5.097070111 |
| 20172 | Collinsella sp900541015 | 2.72234E-05 | 0.691725384 | -4.519008828 | -5.210734212 |
| 20280 | Collinsella sp900550595 | 2.77322E-05 | 0.714016453 | -4.885002642 | -5.599019095 |
| 20341 | Collinsella sp900556515 | 3.05121E-05 | -0.69599543 | -3.99653116 | -4.692526591 |
| 22484 | Faecalibacterium prausnitzii_C | 3.06261E-05 | 0.479016945 | -2.487109376 | -2.966126321 |

FIG. 18B

| | | | | | |
|---|---|---|---|---|---|
| 20187 | Collinsella sp900541665 | 3.12379E-05 | 0.704869149 | -4.366899887 | -5.071769036 |
| 20175 | Collinsella sp900541045 | 3.16246E-05 | 0.834596951 | -4.343367488 | -5.177964439 |
| 18795 | CAG-83 sp900556015 | 3.17044E-05 | 0.499589214 | -4.02497213 | -4.524561344 |
| 20318 | Collinsella sp900554495 | 3.18794E-05 | 0.868749614 | -4.432201957 | -5.300951572 |
| 20266 | Collinsella sp900549195 | 3.40453E-05 | 0.828814874 | -4.259563868 | -5.088378742 |
| 20252 | Collinsella sp900547765 | 3.43312E-05 | 0.818586559 | -4.455041912 | -5.273628471 |
| 36680 | SFFH01 sp900548125 | 3.4418E-05 | 0.677850851 | -4.82587679 | -5.503727641 |
| 27901 | Marvinbryantia sp900066075 | 3.49978E-05 | 0.348561238 | -3.913092134 | -4.261653372 |
| 20297 | Collinsella sp900552155 | 3.5417E-05 | 0.552410403 | -4.056346671 | -4.608757074 |
| 20191 | Collinsella sp900541715 | 3.62913E-05 | 0.855877425 | -4.176761404 | -5.03263883 |
| 36441 | Ruminococcus_C sp900545285 | 3.73359E-05 | 0.653771575 | -4.767188101 | -5.420959676 |
| 20221 | Collinsella sp900544205 | 3.8626E-05 | 0.793227512 | -4.43261656 | -5.225844072 |
| 20327 | Collinsella sp900555355 | 4.02422E-05 | 0.712059967 | -4.211707783 | -4.923767751 |
| 17536 | Blautia sp000432195 | 4.03632E-05 | 0.630986784 | -5.726720261 | -5.095733477 |
| 20232 | Collinsella sp900545055 | 4.04143E-05 | 0.795556791 | -4.48910068 | -5.284657471 |
| 20257 | Collinsella sp900548265 | 4.05549E-05 | 0.862510066 | -4.549044931 | -5.411554997 |
| 20055 | Clostridium_Q symbiosum | 4.06745E-05 | 0.540250259 | -4.416612443 | -3.876362184 |
| 20337 | Collinsella sp900556365 | 4.15777E-05 | -0.7717252 | -4.705458937 | -5.477184137 |
| 17575 | Blautia_A sp900548245 | 4.18253E-05 | 0.334220851 | -3.097429634 | -3.431650485 |
| 20272 | Collinsella sp900549455 | 4.31074E-05 | 0.458463813 | -3.907742745 | -4.366206558 |
| 20339 | Collinsella sp900556445 | 4.34572E-05 | 0.981393783 | -4.265001757 | -5.24639554 |
| 20336 | Collinsella sp900556285 | 4.52593E-05 | 0.736852752 | -3.903445249 | -4.640298002 |
| 20211 | Collinsella sp900542965 | 4.73674E-05 | 0.817345148 | -4.431722588 | -5.249067737 |
| 23776 | GCA-900066575 sp900553635 | 4.81777E-05 | 0.439054073 | -4.024560241 | -4.463614314 |
| 20162 | Collinsella sp900539735 | 4.87587E-05 | 0.837097883 | -4.359525864 | -5.196623748 |
| 20294 | Collinsella sp900551815 | 4.99457E-05 | 0.714213844 | -4.535228188 | -5.249442033 |
| 20160 | Collinsella sp900348712S | 5.03556E-05 | 0.879643545 | -4.009163649 | -4.888807195 |
| 21500 | Dorea sp000433215 | 5.04075E-05 | -0.37337106 | -3.353532888 | -3.726903948 |
| 41455 | UBA1191 sp900549125 | 5.04077E-05 | 0.493202341 | -3.483712256 | -3.976914597 |
| 20238 | Collinsella sp900545615 | 5.18944E-05 | 0.863877924 | -4.272758768 | -5.136636692 |
| 20282 | Collinsella sp900550825 | 5.326E-05 | 0.637682629 | -3.930945083 | -4.568627712 |
| 20302 | Collinsella sp900552735 | 5.44456E-05 | 0.635219905 | -4.460687621 | -5.095907527 |
| 20133 | Collinsella aerofaciens_I | 5.54961E-05 | 0.782783124 | -4.157719511 | -4.940502635 |
| 20251 | Collinsella sp900547505 | 5.96118E-05 | 0.484386331 | -4.358415452 | -4.842801782 |
| 20287 | Collinsella sp900551365 | 6.02681E-05 | 0.862956363 | -4.055253276 | -4.918209639 |
| 17549 | Blautia_A massiliensis | 6.18598E-05 | 0.430872416 | -2.095499345 | -2.526371761 |

<div align="center">FIG. 18C</div>

| | | | | | |
|---|---|---|---|---|---|
| 41907 | UBA1691 sp900544715 | 6.30511E-05 | 0.757585651 | -5.839822303 | -5.082236652 |
| 20298 | Collinsella sp900552295 | 6.30611E-05 | 0.808084477 | -4.093829756 | -4.901914233 |
| 20231 | Collinsella sp900544995 | 6.36138E-05 | 0.816199973 | -4.538810818 | -5.355010791 |
| 20127 | Collinsella aerofaciens | 6.37751E-05 | 0.831680729 | -4.136576284 | -4.968257013 |
| 20178 | Collinsella sp900541145 | 6.73795E-05 | 0.734423587 | -4.470803699 | -5.205227286 |
| 20306 | Collinsella sp900553165 | 6.88464E-05 | 0.642119985 | -3.912845406 | -4.554965392 |
| 20131 | Collinsella aerofaciens_G | 7.87422E-05 | 0.677380094 | -3.358385868 | -4.035765962 |
| 20319 | Collinsella sp900554585 | 8.10098E-05 | 0.531610588 | -4.24700709 | -4.778617678 |
| 20346 | Collinsella sp900557505 | 8.12613E-05 | 0.629103807 | -4.17970272 | -4.808806527 |
| 22205 | Eubacterium_I sp900557275 | 8.15151E-05 | 0.463960406 | -4.138208802 | -4.602169208 |
| 20242 | Collinsella sp900545995 | 8.22431E-05 | 0.801779294 | -4.340221419 | -5.142000713 |
| 36678 | SFFH01 sp900542395 | 8.80551E-05 | 0.609433796 | -4.921290756 | -5.530724552 |
| 21887 | Enterocloster citroniae | 8.85805E-05 | 0.265426791 | -4.192773493 | -3.927346702 |
| 20326 | Collinsella sp900555225 | 8.90068E-05 | 0.360106663 | -3.687316233 | -4.047422896 |
| 14115 | 43-108 sp001915545 | 9.07627E-05 | 0.269939357 | -3.283561037 | -3.013621679 |
| 20234 | Collinsella sp900545165 | 9.36511E-05 | 0.780670576 | -4.615810524 | -5.3964811 |
| 20171 | Collinsella sp900540995 | 9.48154E-05 | 0.709487266 | -4.51755469 | -5.227041956 |
| 20241 | Collinsella sp900545905 | 9.73479E-05 | 0.780597054 | -3.975507021 | -4.756104076 |
| 44304 | UCG-010 sp003150115 | 0.000100298 | 0.518085942 | -4.539659059 | -5.057745001 |
| 20213 | Collinsella sp900543515 | 0.000101101 | 0.887009354 | -4.265306738 | -5.152316092 |
| 20343 | Collinsella sp900556675 | 0.000104285 | 0.570273705 | -3.910134846 | -4.480408551 |
| 20255 | Collinsella sp900548075 | 0.000107021 | 0.718994832 | -4.340765755 | -5.059760588 |
| 20249 | Collinsella sp900547285 | 0.000107697 | 0.796672596 | -4.515850915 | -5.312523511 |
| 20303 | Collinsella sp900552755 | 0.000114967 | 0.664976065 | -3.7738149 | -4.438790965 |
| 20312 | Collinsella sp900554135 | 0.000117756 | -0.80073401 | -4.38250293 | -5.183236941 |
| 20174 | Collinsella sp900541035 | 0.000118589 | 0.869998926 | -4.213598994 | -5.08359792 |
| 20215 | Collinsella sp900543615 | 0.000120612 | 0.694219168 | -4.668601352 | -5.36282052 |
| 20130 | Collinsella aerofaciens_F | 0.000122093 | 0.811239559 | -4.161696907 | -4.972936466 |
| 20163 | Collinsella sp900540095 | 0.00012557 | 0.885642474 | -4.352658554 | -5.238301028 |
| 20180 | Collinsella sp900541195 | 0.000127108 | 0.701158733 | -4.575122504 | -5.276281237 |
| 20248 | Collinsella sp900547125 | 0.000127594 | 0.677724123 | -4.754454472 | -5.432178595 |
| 20183 | Collinsella sp900541245 | 0.000127644 | 0.732232383 | -4.337863075 | -5.070095458 |
| 20335 | Collinsella sp900556205 | 0.000128628 | 0.818883458 | -4.055677793 | -4.874561251 |
| 20342 | Collinsella sp900556605 | 0.000132358 | 1.262443576 | -3.095836503 | -4.35828008 |
| 17540 | Blautia sp003287895 | 0.000132742 | 0.35537663 | -4.347578552 | -3.992201922 |
| 20209 | Collinsella sp900542905 | 0.000136995 | 0.797157827 | -4.433764983 | -5.23092281 |

FIG. 18D

| | | | | | |
|---|---|---|---|---|---|
| 17566 | Blautia_A sp900066355 | 0.000138546 | 0.321853078 | -3.011019119 | -3.332872197 |
| 18485 | CAG-269 sp001916005 | 0.000143351 | 0.443592008 | -5.783310835 | -6.226902843 |
| 20224 | Collinsella sp900544425 | 0.000143616 | 0.602480107 | -3.64431815 | -4.246798257 |
| 15831 | Anaerobutyricum hallii | 0.000145274 | 0.546910167 | -2.302312294 | -2.849222461 |
| 22496 | Faecalibacterium sp003449675 | 0.000145635 | 0.606358825 | -3.635442768 | -4.241801593 |
| 20197 | Collinsella sp900541885 | 0.000146304 | 0.827137058 | -4.333469824 | -5.160606882 |
| 19694 | Christensenella minuta | 0.000148046 | 0.475328029 | -4.036969911 | -4.51229794 |
| 22483 | Faecalibacterium prausnitzii_A | 0.000158913 | 0.415001316 | -3.03371312 | -3.448714435 |
| 36440 | Ruminococcus_C sp000980705 | 0.000170522 | 0.538279508 | -3.630034288 | -4.168313796 |
| 20161 | Collinsella sp900539035 | 0.000172065 | 0.662430065 | -4.637330871 | -5.299760936 |
| 20185 | Collinsella sp900541475 | 0.000178581 | 0.702147011 | -4.28244438 | -4.984591391 |
| 25244 | Holdemanella sp003458715 | 0.000190305 | 0.558139951 | -4.712380076 | -5.270520028 |
| 20315 | Collinsella sp900554325 | 0.000195185 | 0.639754103 | -3.761265812 | -4.401019915 |
| 20247 | Collinsella sp900547025 | 0.000195274 | 0.833602224 | -4.314856406 | -5.148458629 |
| 25246 | Holdemanella sp900551285 | 0.000213266 | 0.247980361 | -3.162814891 | -3.410795252 |
| 20471 | Coprococcus sp000433075 | 0.000219266 | 0.322430684 | -4.276226699 | -4.598657383 |
| 20222 | Collinsella sp900544225 | 0.00022235 | -0.57227557 | -4.673408516 | -5.245684086 |
| 20271 | Collinsella sp900549355 | 0.000240369 | 0.509536498 | -3.855730489 | -4.365266987 |
| 21514 | Dorea sp900553355 | 0.000243764 | -0.32851141 | -3.99618989 | -4.3247013 |
| 21890 | Enterocloster lavalensis | 0.000256372 | 0.335620187 | -4.463281741 | -4.127661554 |
| 20196 | Collinsella sp900541875 | 0.000257581 | 0.716842088 | -4.540389057 | -5.257231145 |
| 27994 | Mediterraneibacter_A butyricigenes | 0.000265921 | 0.222246458 | -3.422894207 | -3.645140665 |
| 17554 | Blautia_A sp000433815 | 0.000272057 | 0.365072089 | -3.361730807 | -2.996658719 |
| 20214 | Collinsella sp900543605 | 0.000274419 | 0.756997417 | -4.467148176 | -5.224145593 |
| 20223 | Collinsella sp900544235 | 0.000278523 | 0.749101631 | -4.594249826 | -5.343351457 |
| 18445 | CAG-177 sp003538135 | 0.000283735 | 0.512882078 | -4.994871202 | -5.50775328 |
| 18839 | CAG-95 sp000438155 | 0.000284323 | 0.467254597 | -4.931655233 | -5.39890983 |
| 18578 | CAG-45 sp002299665 | 0.000284729 | 0.244845556 | -4.281322574 | -4.52616813 |
| 20184 | Collinsella sp900541285 | 0.000312394 | 0.374105648 | -4.002116547 | -4.376222195 |
| 20304 | Collinsella sp900552875 | 0.000320111 | 0.643021429 | -4.176209545 | -4.819230974 |
| 18450 | CAG-180 sp000432435 | 0.000320189 | 0.704922718 | -3.773859745 | -4.478782464 |
| 15836 | Anaerobutyricum sp900554965 | 0.000320314 | 0.227974612 | -2.430200135 | -2.658174747 |
| 20239 | Collinsella sp900545745 | 0.000322222 | 0.826097708 | -4.291982097 | -5.118079804 |
| 17191 | Bacteroides sp900066265 | 0.000336587 | 0.312061015 | -3.850010983 | -3.537949968 |
| 18438 | CAG-170 sp900556635 | 0.000342693 | 0.334128273 | -3.51214973 | -3.846278003 |
| 20299 | Collinsella sp900552345 | 0.000350104 | 0.532880732 | -4.128494062 | -4.661374794 |

FIG. 18E

| | | | | | |
|---|---|---|---|---|---|
| 20477 | Coprococcus_A catus | 0.000353632 | 0.305358264 | -3.098766141 | -3.404124404 |
| 20237 | Collinsella sp900545605 | 0.000367171 | 0.731655083 | -4.198586346 | -4.930241429 |
| 20235 | Collinsella sp900545445 | 0.000369866 | 0.706216233 | -4.444218124 | -5.150434357 |
| 18433 | CAG-170 sp900545925 | 0.000383266 | -0.51941725 | -4.086754497 | -4.606171747 |
| 20149 | Collinsella sp003458415 | 0.000392839 | 0.700899337 | -4.648858332 | -5.349757669 |
| 20139 | Collinsella sp000434535 | 0.000394046 | 0.793799295 | -4.458738641 | -5.252537936 |
| 22498 | Faecalibacterium sp900539945 | 0.000409712 | -0.57525261 | -3.208060214 | -3.783312823 |
| 20181 | Collinsella sp900541205 | 0.00041582 | 0.600091749 | -4.27457563 | -4.87466738 |
| 20169 | Collinsella sp900540935 | 0.000421858 | 0.862021148 | -4.296402166 | -5.158423314 |
| 20325 | Collinsella sp900554985 | 0.000433453 | -0.41029539 | -4.253701757 | -4.663997146 |
| 20261 | Collinsella sp900548815 | 0.000437656 | 0.747875452 | -4.437847972 | -5.185723424 |
| 18198 | Butyricimonas faecalis | 0.000461704 | 0.258569869 | -3.556648166 | -3.298078297 |
| 20195 | Collinsella sp900541855 | 0.00046361 | 0.753250297 | -4.186806028 | -4.940056325 |
| 22491 | Faecalibacterium prausnitzii_J | 0.000471984 | 0.396428164 | -2.828064839 | -3.224493003 |
| 20314 | Collinsella sp900554255 | 0.000475796 | 0.629485069 | -3.885016307 | -4.514501376 |
| 36429 | Ruminococcus_A sp000437095 | 0.00048673 | 0.358503524 | -3.229264245 | -3.58776777 |
| 36674 | SFEL01 sp004557245 | 0.000507205 | 0.550277418 | -4.454580075 | -5.004857493 |
| 20212 | Collinsella sp900543025 | 0.000519453 | 0.735895569 | -4.631665446 | -5.367561015 |
| 29763 | NK3B98 sp900545815 | 0.00054472 | -0.54827028 | -4.917938529 | -5.466208809 |
| 20226 | Collinsella sp900544725 | 0.000550252 | 0.674615752 | -4.81862198 | -5.493237732 |
| 20313 | Collinsella sp900554155 | 0.000559758 | 0.240973216 | -4.068190233 | -4.30916345 |
| 18785 | CAG-83 sp900548615 | 0.000568942 | 0.453349849 | -4.324505739 | -4.777855588 |
| 23215 | Fusicatenibacter saccharivorans | 0.000623803 | 0.385362276 | -2.047142784 | -2.43250506 |
| 17189 | Bacteroides sp003865075 | 0.000635847 | 0.298145955 | -3.474058697 | -3.175912743 |
| 18427 | CAG-170 sp000436735 | 0.000659947 | 0.555591008 | -4.919696741 | -5.475287749 |
| 20322 | Collinsella sp900554655 | 0.00066256 | 0.595563861 | -3.765302635 | -4.360866496 |
| 20331 | Collinsella sp900555745 | 0.000694789 | 0.723253441 | -4.677002864 | -5.400256304 |
| 21507 | Dorea sp900066555 | 0.000706594 | 0.336185683 | -3.292479127 | -3.62866481 |
| 41451 | UBA1191 sp900066305 | 0.000709623 | -0.38417959 | -4.158181709 | -4.5423613 |
| 20204 | Collinsella sp900542315 | 0.000716103 | 0.774075711 | -4.466616788 | -5.240692499 |
| 24119 | Gemmiger sp900540775 | 0.000724913 | 0.558247536 | -3.745201648 | -4.303449184 |
| 20260 | Collinsella sp900548565 | 0.000731591 | 0.575284519 | -4.339627567 | -4.914912086 |
| 20307 | Collinsella sp900553215 | 0.00075328 | 0.365274154 | -4.245334136 | -4.61060829 |
| 18331 | CAG-103 sp000432375 | 0.000754308 | 0.571934314 | -3.919546928 | -4.491481242 |
| 20291 | Collinsella sp900551635 | 0.000765935 | 0.512017868 | -3.94368581 | -4.455703678 |
| 20179 | Collinsella sp900541175 | 0.000777259 | -0.65378331 | -4.532999989 | -5.186783299 |

FIG. 18F

| 22200 | Eubacterium_I ramulus_A | 0.000779396 | 0.291547302 | -3.867762444 | -4.159309746 |
|---|---|---|---|---|---|
| 22493 | Faecalibacterium prausnitzii_M | 0.000797318 | 0.445567472 | -4.447611497 | -4.893178969 |
| 41996 | UBA1777 sp900547315 | 0.000809706 | -0.33607957 | -4.521908684 | -4.857988255 |
| 20278 | Collinsella sp900550355 | 0.00081327 | 0.589783907 | -4.401488895 | -4.991272802 |
| 43353 | UBA6398 sp003150315 | 0.000823565 | 0.313942082 | -3.944250868 | -4.25819295 |
| 21491 | Dorea formicigenerans | 0.000873722 | 0.347910807 | -2.758471686 | -3.106382492 |
| 17174 | Bacteroides oleiciplenus | 0.000896073 | 0.242878456 | -4.158321775 | -3.915443319 |
| 32148 | Paraprevotella clara | 0.000903635 | 0.32297246 | -3.744604963 | -3.421632503 |
| 20155 | Collinsella sp003469185 | 0.000910368 | 0.600022048 | -5.006157922 | -5.60617997 |
| 23769 | GCA-900066135 sp900066135 | 0.000915102 | 0.263180287 | -3.802966043 | -4.06614633 |
| 32654 | Phascolarctobacterium_A succinatutens | 0.000937977 | 0.520686008 | -5.058310103 | -5.578996111 |
| 17574 | Blautia_A sp900547615 | 0.000962278 | 0.285713279 | -4.73089654 | -4.445183261 |
| 17197 | Bacteroides sp900556625 | 0.00099088 | 0.319645074 | -3.659720527 | -3.340075453 |
| 20259 | Collinsella sp900548515 | 0.000991271 | 0.765660319 | -4.164118231 | -4.92977855 |
| 20228 | Collinsella sp900544845 | 0.000992797 | -0.76916591 | -4.34550038 | -5.114666289 |
| 36437 | Ruminococcus_C sp000433635 | 0.000994467 | 0.559529185 | -5.271428319 | -5.830957504 |
| 18362 | CAG-110 sp900549495 | 0.000998787 | -0.39838236 | -4.528596453 | -4.926978812 |
| 20289 | Collinsella sp900551605 | 0.000999127 | 0.580319566 | -4.053167739 | -4.633487304 |
| 26248 | Lachnospira sp900545725 | 0.001007341 | 0.383961289 | -4.773838066 | -5.157799355 |
| 36436 | Ruminococcus_C callidus | 0.001026621 | 0.330394007 | -4.282697623 | -4.613091629 |
| 18783 | CAG-83 sp900545585 | 0.001033024 | 0.417205808 | -4.157667274 | -4.574873082 |
| 32689 | Phocaeicola coprophilus | 0.001037365 | 0.356827431 | -4.054186287 | -3.697358857 |
| 39003 | Streptococcus vestibularis | 0.001046031 | 0.396583709 | -4.210511337 | -3.813927629 |
| 25300 | Hungatella sp005845265 | 0.001048208 | 0.357545644 | -4.607299672 | -4.249754028 |
| 18472 | CAG-238 sp900542245 | 0.001059104 | 0.362003851 | -4.46449823 | -4.826502081 |
| 19917 | Clostridioides difficile | 0.001088094 | 0.395985403 | -5.977332322 | -5.581346918 |
| 44377 | UMGS1322 sp900550765 | 0.001108557 | 0.329017475 | -4.215821927 | -4.544839402 |
| 22482 | Faecalibacterium prausnitzii | 0.001113189 | 0.449991333 | -2.561576306 | -3.011567639 |
| 22764 | Firm-11 sp900553905 | 0.001137185 | 0.467251787 | -4.651029427 | -5.118281214 |
| 18577 | CAG-45 sp000438375 | 0.001171488 | 0.428520818 | -5.494940796 | -5.923461614 |
| 20293 | Collinsella sp900551665 | 0.001187443 | 0.451554091 | -5.599794674 | -5.148240583 |
| 20292 | Collinsella sp900551655 | 0.001193919 | 0.575927163 | -3.937483037 | -4.5134102 |
| 24126 | Gemmiger variabilis_B | 0.001195006 | 0.441050588 | -4.40728901 | -4.848339598 |
| 20254 | Collinsella sp900547835 | 0.001207728 | 0.570609112 | -4.28833598 | -4.858945092 |
| 20333 | Collinsella sp900555815 | 0.001233248 | 0.465476712 | -3.801786409 | -4.267263121 |
| 20166 | Collinsella sp900540875 | 0.001234924 | 0.398408793 | -4.947546581 | -5.345955373 |
| 18776 | CAG-83 sp003487665 | 0.001323223 | 0.488532148 | -4.763091975 | -5.251624123 |
| 20323 | Collinsella sp900554665 | 0.001346701 | -0.66909364 | -4.418278913 | -5.087372552 |

<div align="center">FIG. 18G</div>

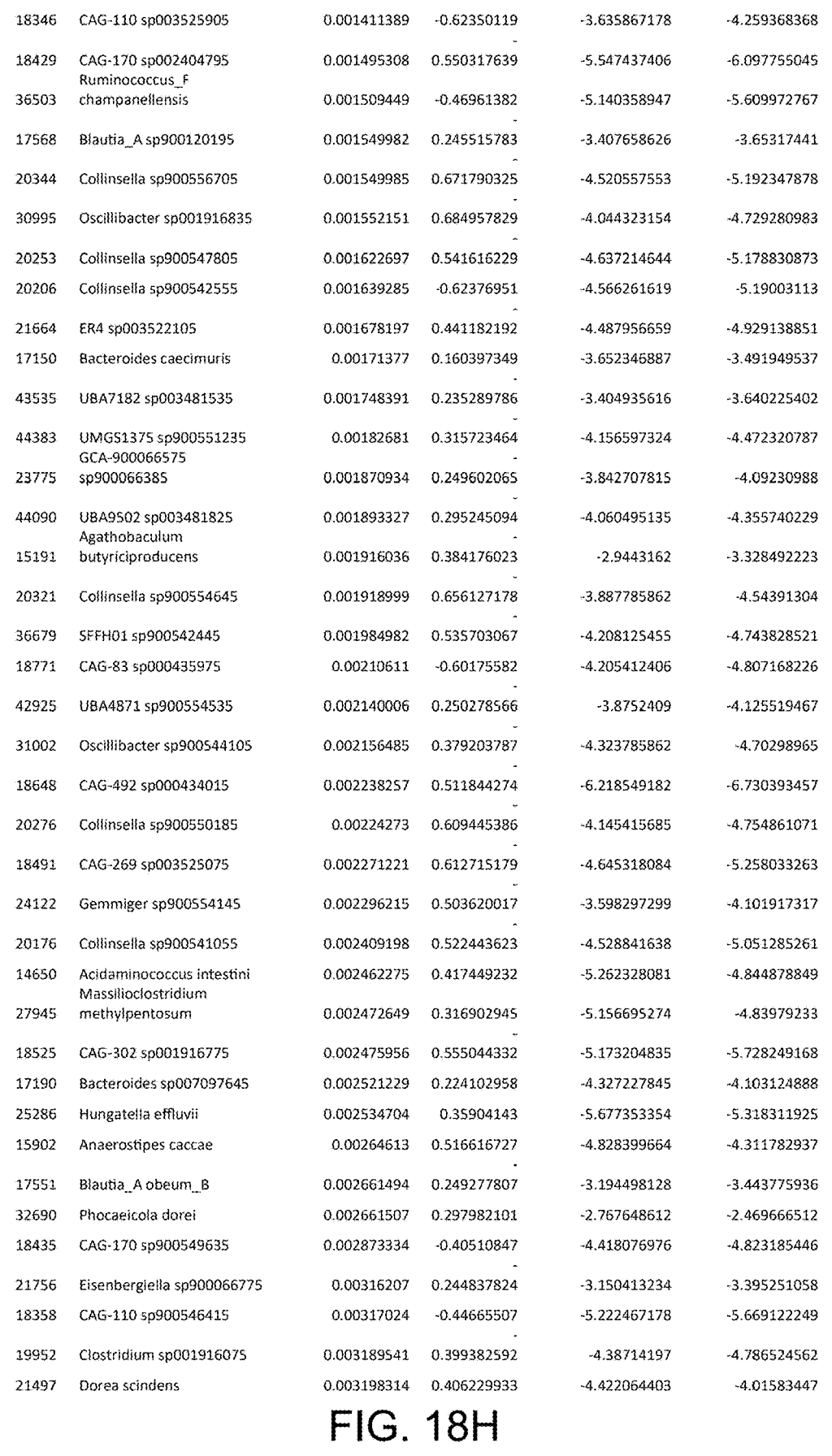

| | | | | | |
|---|---|---|---|---|---|
| 18346 | CAG-110 sp003525905 | 0.001411389 | -0.62350119 | -3.635867178 | -4.259368368 |
| 18429 | CAG-170 sp002404795 | 0.001495308 | 0.550317639 | -5.547437406 | -6.097755045 |
| 36503 | Ruminococcus_F champanellensis | 0.001509449 | -0.46961382 | -5.140358947 | -5.609972767 |
| 17568 | Blautia_A sp900120195 | 0.001549982 | 0.245515783 | -3.407658626 | -3.65317441 |
| 20344 | Collinsella sp900556705 | 0.001549985 | 0.671790325 | -4.520557553 | -5.192347878 |
| 30995 | Oscillibacter sp001916835 | 0.001552151 | 0.684957829 | -4.044323154 | -4.729280983 |
| 20253 | Collinsella sp900547805 | 0.001622697 | 0.541616229 | -4.637214644 | -5.178830873 |
| 20206 | Collinsella sp900542555 | 0.001639285 | -0.62376951 | -4.566261619 | -5.19003113 |
| 21664 | ER4 sp003522105 | 0.001678197 | 0.441182192 | -4.487956659 | -4.929138851 |
| 17150 | Bacteroides caecimuris | 0.00171377 | 0.160397349 | -3.652346887 | -3.491949537 |
| 43535 | UBA7182 sp003481535 | 0.001748391 | 0.235289786 | -3.404935616 | -3.640225402 |
| 44383 | UMGS1375 sp900551235 | 0.00182681 | 0.315723464 | -4.156597324 | -4.472320787 |
| 23775 | GCA-900066575 sp900066385 | 0.001870934 | 0.249602065 | -3.842707815 | -4.09230988 |
| 44090 | UBA9502 sp003481825 | 0.001893327 | 0.295245094 | -4.060495135 | -4.355740229 |
| 15191 | Agathobaculum butyriciproducens | 0.001916036 | 0.384176023 | -2.9443162 | -3.328492223 |
| 20321 | Collinsella sp900554645 | 0.001918999 | 0.656127178 | -3.887785862 | -4.54391304 |
| 36679 | SFFH01 sp900542445 | 0.001984982 | 0.535703067 | -4.208125455 | -4.743828521 |
| 18771 | CAG-83 sp000435975 | 0.00210611 | -0.60175582 | -4.205412406 | -4.807168226 |
| 42925 | UBA4871 sp900554535 | 0.002140006 | 0.250278566 | -3.8752409 | -4.125519467 |
| 31002 | Oscillibacter sp900544105 | 0.002156485 | 0.379203787 | -4.323785862 | -4.70298965 |
| 18648 | CAG-492 sp000434015 | 0.002238257 | 0.511844274 | -6.218549182 | -6.730393457 |
| 20276 | Collinsella sp900550185 | 0.00224273 | 0.609445386 | -4.145415685 | -4.754861071 |
| 18491 | CAG-269 sp003525075 | 0.002271221 | 0.612715179 | -4.645318084 | -5.258033263 |
| 24122 | Gemmiger sp900554145 | 0.002296215 | 0.503620017 | -3.598297299 | -4.101917317 |
| 20176 | Collinsella sp900541055 | 0.002409198 | 0.522443623 | -4.528841638 | -5.051285261 |
| 14650 | Acidaminococcus intestini | 0.002462275 | 0.417449232 | -5.262328081 | -4.844878849 |
| 27945 | Massilioclostridium methylpentosum | 0.002472649 | 0.316902945 | -5.156695274 | -4.83979233 |
| 18525 | CAG-302 sp001916775 | 0.002475956 | 0.555044332 | -5.173204835 | -5.728249168 |
| 17190 | Bacteroides sp007097645 | 0.002521229 | 0.224102958 | -4.327227845 | -4.103124888 |
| 25286 | Hungatella effluvii | 0.002534704 | 0.35904143 | -5.677353354 | -5.318311925 |
| 15902 | Anaerostipes caccae | 0.00264613 | 0.516616727 | -4.828399664 | -4.311782937 |
| 17551 | Blautia_A obeum_B | 0.002661494 | 0.249277807 | -3.194498128 | -3.443775936 |
| 32690 | Phocaeicola dorei | 0.002661507 | 0.297982101 | -2.767648612 | -2.469666512 |
| 18435 | CAG-170 sp900549635 | 0.002873334 | -0.40510847 | -4.418076976 | -4.823185446 |
| 21756 | Eisenbergiella sp900066775 | 0.00316207 | 0.244837824 | -3.150413234 | -3.395251058 |
| 18358 | CAG-110 sp900546415 | 0.00317024 | -0.44665507 | -5.222467178 | -5.669122249 |
| 19952 | Clostridium sp001916075 | 0.003189541 | 0.399382592 | -4.38714197 | -4.786524562 |
| 21497 | Dorea scindens | 0.003198314 | 0.406229933 | -4.422064403 | -4.01583447 |

FIG. 18H

| | | | | | |
|---|---|---|---|---|---|
| 20308 | Collinsella sp900553345 | 0.003210393 | 0.401607873 | -3.858258784 | -4.259866657 |
| 20305 | Collinsella sp900552995 | 0.0034429 | 0.592317638 | -4.251804818 | -4.844122456 |
| 42749 | UBA4285 sp900545225 | 0.003475175 | 0.513848935 | -4.688885384 | -5.202734319 |
| 20190 | Collinsella sp900541695 | 0.00352645 | 0.598837564 | -4.840530274 | -5.439367838 |
| 40012 | TF01-11 sp003529475 | 0.003568697 | 0.343984421 | -3.441368253 | -3.785352674 |
| 18431 | CAG-170 sp003516765 | 0.003571778 | 0.422764913 | -4.794751768 | -5.217516681 |
| 21501 | Dorea sp000433535 | 0.003582138 | 0.515869428 | -4.106550035 | -3.590680608 |
| 17180 | Bacteroides salyersiae | 0.003643052 | 0.291608351 | -3.763800221 | -3.47219187 |
| 38944 | Streptococcus sp000314795 | 0.003718137 | 0.292557338 | -5.020054743 | -4.727497405 |
| 17538 | Blautia sp001304935 | 0.00377521 | 0.335932531 | -4.21472572 | -3.878793189 |
| 20263 | Collinsella sp900549025 | 0.003841252 | 0.631236372 | -4.736412749 | -5.367649121 |
| 18763 | CAG-81 sp900556965 | 0.003889723 | 0.195732053 | -4.236580372 | -4.432312425 |
| 20316 | Collinsella sp900554455 | 0.003932838 | 0.444046505 | -3.66586009 | -4.109906595 |
| 18444 | CAG-177 sp003514385 | 0.003985921 | 0.422369131 | -5.556461724 | -5.978830855 |
| 22490 | Faecalibacterium prausnitzii_I | 0.003992532 | 0.375109033 | -3.176377121 | -3.551486153 |
| 44534 | UMGS911 sp900557415 | 0.004088529 | 0.330092504 | -4.849008687 | -5.179101192 |
| 44436 | UMGS1670 sp900553995 | 0.004143639 | 0.231940835 | -4.307591295 | -4.53953213 |
| 32139 | Paramuribaculum sp900551515 | 0.00418996 | 0.151685854 | -4.587867252 | -4.436181397 |
| 20275 | Collinsella sp900549655 | 0.004211281 | 0.597991968 | -4.412475931 | -5.010467899 |
| 17149 | Bacteroides caccae | 0.004284088 | 0.477526097 | -3.681104593 | -3.203578496 |
| 18469 | CAG-217 sp900547275 | 0.004460855 | 0.345203502 | -4.840618749 | -5.185822251 |
| 30848 | Odoribacter laneus | 0.004544479 | 0.456177765 | -5.387549103 | -4.931371339 |
| 15033 | Acutalibacter sp900543555 | 0.004588844 | 0.449952188 | -5.50611585 | -5.056163662 |
| 41420 | UBA11774 sp900556645 | 0.004731618 | 0.224256311 | -3.716403342 | -3.940659652 |
| 17386 | Bifidobacterium kashiwanohense_A | 0.004731702 | 0.511269291 | -5.133388993 | -5.644658285 |
| 24113 | Gemmiger qucibialis | 0.004749021 | 0.389883576 | -2.341112274 | -2.73099585 |
| 41454 | UBA1191 sp900545775 | 0.004802531 | 0.527485948 | -4.929102877 | -5.456588825 |
| 20182 | Collinsella sp900541235 | 0.004809992 | 0.760291345 | -4.201538248 | -4.961829592 |
| 44405 | UMGS1491 sp900554775 | 0.004841494 | 0.414071528 | -5.887656183 | -6.301727712 |
| 20128 | Collinsella aerofaciens_A | 0.004869228 | 0.551278876 | -4.867413277 | -5.418692153 |
| 20250 | Collinsella sp900547345 | 0.004886624 | 0.536964981 | -4.018015347 | -4.554980328 |
| 20168 | Collinsella sp900540905 | 0.004895326 | 0.689290652 | -4.39578362 | -5.085074272 |
| 18786 | CAG-83 sp900549395 | 0.004944751 | 0.428060059 | -4.925735187 | -5.353795246 |
| 22140 | Escherichia dysenteriae | 0.005114911 | 0.541161995 | -5.267453531 | -4.726291536 |
| 18782 | CAG-83 sp900545495 | 0.00512617 | 0.405358144 | -4.337757448 | -4.743115592 |
| 32728 | Phocea massiliensis | 0.005211599 | 0.150393456 | -4.290807248 | -4.140413792 |
| 37642 | Schaedlerella sp004556565 | 0.005240121 | 0.202417642 | -4.097382366 | -3.894964724 |

FIG. 18I

| | | | | | |
|---|---|---|---|---|---|
| 15188 | Agathobacter sp900550845 | 0.005278263 | 0.190303843 | -2.915215564 | -3.105519408 |
| 24117 | Gemmiger sp900539695 | 0.005374636 | 0.432457995 | -3.56591382 | -3.998371815 |
| 15193 | Agathobaculum sp003481705 | 0.005374694 | 0.330855555 | -3.669087035 | -3.99994259 |
| 14553 | Acetatifactor sp900554205 | 0.005413463 | 0.298584459 | -4.354949932 | -4.653534391 |
| 31012 | Oscillibacter welbionis | 0.005572414 | 0.131858746 | -2.823821534 | -2.691962788 |
| 21907 | Enterococcus faecalis | 0.005609289 | 0.514481828 | -6.304326678 | -5.789844851 |
| 20473 | Coprococcus sp900066115 | 0.00565329 | 0.376516948 | -4.743099707 | -5.119616654 |
| 18784 | CAG-83 sp900547745 | 0.005712329 | 0.449829125 | -4.646785717 | -5.096614842 |
| 20147 | Collinsella sp003438495 | 0.005738458 | 0.719587069 | -4.098704113 | -4.818291182 |
| 20052 | Clostridium_Q sp003024715 | 0.005818298 | 0.284697269 | -3.08507516 | -3.369772429 |
| 22489 | Faecalibacterium prausnitzii_H | 0.005860207 | -0.43118609 | -3.101943279 | -3.533129369 |
| 20240 | Collinsella sp900545875 | 0.005987057 | 0.359764187 | -4.121833963 | -4.48159815 |
| 17560 | Blautia_A sp003478765 | 0.006009085 | 0.200589285 | -3.067280567 | -3.267869853 |
| 37643 | Schaedlerella sp900066545 | 0.006073922 | 0.170445064 | -3.780123121 | -3.950568184 |
| 32699 | Phocaeicola sartorii | 0.006183382 | 0.22226566 | -3.742107243 | -3.519841583 |
| 18336 | CAG-103 sp900543625 | 0.006248964 | 0.377770694 | -4.20796435 | -4.585735044 |
| 18338 | CAG-110 sp000434635 | 0.006562471 | 0.483443329 | -4.789305435 | -5.272748764 |
| 36078 | Romboutsia timonensis | 0.006780947 | 0.453408697 | -3.593856497 | -4.047265194 |
| 25848 | KLE1615 sp900066985 | 0.006829856 | 0.331909554 | -3.187609609 | -3.519519163 |
| 20150 | Collinsella sp003459245 | 0.0068356 | 0.407790688 | -5.307371107 | -5.715161795 |
| 15803 | An200 sp900550095 | 0.006865908 | 0.296950621 | -4.450768086 | -4.747718707 |
| 18401 | CAG-1427 sp000435675 | 0.006901813 | 0.525000434 | -4.768180556 | -5.29318099 |
| 24124 | Gemmiger variabilis | 0.007025342 | -0.29304732 | -3.774775096 | -4.067822416 |
| 18699 | CAG-603 sp900066105 | 0.007225951 | 0.275464634 | -3.885259983 | -4.160724617 |
| 25245 | Holdemanella sp900547815 | 0.007328117 | 0.427792066 | -4.840189567 | -5.267981633 |
| 34941 | QALS01 sp003150575 | 0.007349274 | 0.396533632 | -5.248660617 | -5.645194249 |
| 17542 | Blautia sp900539145 | 0.007379724 | 0.208701235 | -4.612819864 | -4.404118629 |
| 17195 | Bacteroides sp900555635 | 0.007405636 | 0.238036723 | -4.461124965 | -4.223088241 |
| 18337 | CAG-1031 sp000431215 | 0.007427076 | 0.357077607 | -6.174821037 | -5.817743431 |
| 19390 | Catenibacterium sp900540685 | 0.007454303 | 0.404774225 | -5.354847963 | -5.759622188 |
| 17196 | Bacteroides sp900556215 | 0.007615893 | 0.217716401 | -3.732604122 | -3.514887721 |
| 18197 | Butyricicoccus_A sp004555915 | 0.007641676 | -0.36398714 | -4.364089574 | -4.728076715 |
| 22486 | Faecalibacterium prausnitzii_E | 0.007696104 | 0.339778458 | -3.187423714 | -3.527202172 |
| 18397 | CAG-127 sp900553925 | 0.007705473 | 0.288713497 | -5.033132336 | -5.321845833 |
| 44095 | UBA9502 sp900538475 | 0.008136842 | 0.276517058 | -4.077047098 | -3.800530039 |
| 17205 | Bacteroides xylanisolvens | 0.008165123 | 0.256645617 | -3.083266187 | -2.82662057 |
| 22144 | Escherichia sp000208585 | 0.008170754 | 0.434311978 | -6.16359105 | -5.729279071 |

FIG. 18J

| | | | | | |
|---|---|---|---|---|---|
| 20140 | Collinsella sp000763055 | 0.008238547 | 0.621912258 | -4.314447436 | -4.936359694 |
| 44081 | UBA9475 sp002161675 | 0.008278743 | 0.277166634 | -5.326453536 | -5.603620169 |
| 36508 | Ruminococcus_H sp003531055 | 0.008719454 | 0.461545663 | -2.971474675 | -3.433020338 |
| 17179 | Bacteroides rodentium | 0.008779718 | 0.200295188 | -3.461950954 | -3.261655766 |
| 36386 | Ruminiclostridium_E sp003512525 | 0.008880001 | -0.44918715 | -5.269916349 | -5.719103499 |
| 20170 | Collinsella sp900540945 | 0.009068018 | -0.5037754 | -4.894739292 | -5.398514691 |
| 18791 | CAG-83 sp900552475 | 0.009191081 | 0.400934652 | -4.619469282 | -5.020403934 |
| 18436 | CAG-170 sp900553545 | 0.009304029 | 0.534052393 | -4.949074473 | -5.483126866 |
| 23074 | Flavonifractor sp900199495 | 0.009339052 | 0.161678468 | -4.340468904 | -4.178790435 |
| 31909 | Parabacteroides distasonis | 0.009339066 | 0.157692876 | -2.855206333 | -2.697513457 |
| 15903 | Anaerostipes hadrus | 0.010031655 | 0.409345581 | -2.087708181 | -2.497053762 |
| 44089 | UBA9502 sp003480315 | 0.010272405 | 0.260851334 | -3.954820019 | -4.215671353 |
| 29331 | Murimonas intestini | 0.010272405 | 0.286861085 | -5.477946554 | -5.191085469 |
| 15908 | Anaerostipes sp900066705 | 0.010307302 | 0.221487685 | -3.518443282 | -3.739930968 |
| 36428 | Ruminococcus_A sp000432335 | 0.010412317 | 0.277894619 | -4.849299891 | -4.571405272 |
| 27983 | Mediterraneibacter lactaris | 0.010412394 | -0.31098751 | -3.083579871 | -3.394567381 |
| 21661 | ER4 sp000765235 | 0.010447633 | 0.306845262 | -3.308778788 | -3.61562405 |
| 24123 | Gemmiger sp900556255 | 0.010673791 | 0.469173073 | -4.015141777 | -4.484314849 |
| 22185 | Eubacterium_G sp900556905 | 0.010842362 | 0.109709857 | -3.645526528 | -3.535816671 |
| 20218 | Collinsella sp900544095 | 0.010942427 | 0.453408174 | -5.117600204 | -5.571008378 |
| 17545 | Blautia sp900547685 | 0.010989136 | 0.256237168 | -4.846447539 | -4.590210371 |
| 17563 | Blautia_A sp900066165 | 0.011137706 | -0.28156557 | -2.461081014 | -2.742646584 |
| 18434 | CAG-170 sp900548625 | 0.011167924 | 0.323616735 | -4.527863626 | -4.851480361 |
| 20129 | Collinsella aerofaciens_E | 0.011604264 | 0.399831112 | -5.069893314 | -5.469724426 |
| 22082 | Erysipelatoclostridium ramosum | 0.011867965 | 0.388967614 | -4.013008777 | -3.624041164 |
| 15912 | Anaerotignum sp000436415 | 0.011907533 | 0.207920781 | -3.705323928 | -3.913244709 |
| 20311 | Collinsella sp900553935 | 0.012186697 | 0.269458899 | -4.537547317 | -4.807006216 |
| 20301 | Collinsella sp900552705 | 0.012467761 | 0.372961551 | -4.810089127 | -5.183050678 |
| 21667 | ER4 sp900550165 | 0.012602802 | -0.42740408 | -4.486723281 | -4.914127361 |
| 41975 | UBA1777 sp002320035 | 0.012735663 | 0.198320243 | -5.641401586 | -5.83972183 |
| 20274 | Collinsella sp900549555 | 0.012858044 | -0.43566555 | -4.862595537 | -5.298261087 |
| 18761 | CAG-81 sp900066785 | 0.01289337 | -0.21311311 | -3.515922677 | -3.729035788 |
| 44446 | UMGS1766 sp900554855 | 0.012922711 | 0.450642997 | -4.157937541 | -4.608580538 |
| 18777 | CAG-83 sp003539495 | 0.013049589 | 0.368372114 | -4.652445086 | -5.0208172 |
| 44418 | UMGS1600 sp900553295 | 0.01363334 | 0.274003191 | -4.972936272 | -5.246939463 |
| 17578 | Blautia_A sp900551465 | 0.013791121 | 0.328737309 | -5.061442103 | -4.732704794 |
| 18547 | CAG-314 sp000437915 | 0.013822942 | 0.457657745 | -5.740867763 | -6.198525509 |
| 22510 | Faecalimonas sp900551895 | 0.013852426 | 0.386832408 | -5.431480535 | -5.044648127 |

FIG. 18K

| 14548 | Acetatifactor sp003447295 | 0.013858408 | 0.406480169 | -4.19448549 | -4.600965659 |
|---|---|---|---|---|---|
| 22142 | Escherichia flexneri | 0.013941019 | 0.475044118 | -4.95057471 | -4.475530592 |
| 26867 | Limosilactobacillus fermentum_A | 0.014110742 | 0.282519327 | -4.835839474 | -4.553320147 |
| 17186 | Bacteroides sp002491635 | 0.014319798 | 0.165319562 | -3.526548157 | -3.361228595 |
| 18649 | CAG-492 sp000434335 | 0.014453794 | 0.100504172 | -6.633422999 | -6.73392717 |
| 17534 | Blautia hansenii | 0.014460394 | 0.214562762 | -4.116664295 | -3.902101534 |
| 32719 | Phocaeicola sp900551645 | 0.014460409 | 0.110585066 | -3.898410023 | -3.787824957 |
| 22173 | Eubacterium_F sp003491505 | 0.01479283 | 0.401797355 | -3.768660276 | -4.170457631 |
| 17198 | Bacteroides sp900557355 | 0.015083894 | 0.162010164 | -3.287336085 | -3.12532592 |
| 18759 | CAG-81 sp900066055 | 0.015132821 | 0.226528189 | -3.835705391 | -4.06223358 |
| 17171 | Bacteroides ndongoniae | 0.015280337 | 0.148029008 | -4.247154547 | -4.099125539 |
| 18576 | CAG-449 sp900551385 | 0.015429036 | 0.217052409 | -4.057581082 | -4.274633491 |
| 21668 | ER4 sp900552015 | 0.015577998 | 0.276820655 | -4.53706897 | -4.813889624 |
| 23075 | Flavonifractor sp900549565 | 0.015604199 | 0.157768401 | -5.424363688 | -5.266595287 |
| 24118 | Gemmiger sp900540595 | 0.015629719 | 0.315161406 | -3.622622892 | -3.937784298 |
| 18843 | CAG-95 sp900066375 | 0.015680305 | 0.206949448 | -3.643375961 | -3.850325409 |
| 32688 | Phocaeicola coprocola | 0.015883647 | 0.339593849 | -3.187384801 | -2.847790952 |
| 20267 | Collinsella sp900549245 | 0.015903262 | 0.309097983 | -4.516522648 | -4.82562063 |
| 36447 | Ruminococcus_D bicirculans | 0.016193062 | 0.457673602 | -3.121705045 | -3.579378647 |
| 18772 | CAG-83 sp001916855 | 0.016205078 | 0.441962262 | -4.576285542 | -5.018247804 |
| 18396 | CAG-127 sp900539705 | 0.016507089 | 0.303671129 | -4.809372457 | -5.113043586 |
| 26240 | Lachnospira sp000436475 | 0.016610769 | 0.319659543 | -4.470296794 | -4.789956337 |
| 44371 | UMGS1251 sp900549995 | 0.016720497 | 0.170172736 | -4.723683826 | -4.55351109 |
| 25573 | Intestinimonas butyriciproducens | 0.016773869 | 0.211020442 | -4.469685123 | -4.258664681 |
| 17188 | Bacteroides sp003545565 | 0.016827721 | 0.259110394 | -4.082185605 | -3.823075211 |
| 32682 | Phil12 sp002633275 | 0.016881642 | 0.149361347 | -3.585280403 | -3.435919056 |
| 18488 | CAG-269 sp001916065 | 0.017021468 | 0.286676079 | -6.362166679 | -6.648842759 |
| 22186 | Eubacterium_G ventriosum | 0.017484112 | 0.281514719 | -3.466793825 | -3.748308544 |
| 21894 | Enterocloster sp001517625 | 0.017539929 | 0.245987474 | -3.845289754 | -3.59930228 |
| 17543 | Blautia sp900541955 | 0.017764282 | 0.28626055 | -4.793347743 | -4.507087194 |
| 18555 | CAG-353 sp900066885 | 0.017991191 | 0.248021354 | -4.055664658 | -4.303686012 |
| 18426 | CAG-170 sp000432135 | 0.018104888 | 0.459594369 | -4.038163204 | -4.497757573 |
| 18510 | CAG-273 sp003507395 | 0.01823363 | 0.385470975 | -6.285766678 | -6.671237653 |
| 19959 | Clostridium sp900540255 | 0.018269746 | 0.467505001 | -4.912765218 | -5.380270219 |
| 31910 | Parabacteroides distasonis_A | 0.018336281 | 0.223077422 | -4.001345731 | -3.77826831 |
| 36460 | Ruminococcus_D sp900539095 | 0.018387415 | 0.471821607 | -4.890003004 | -5.36182461 |
| 18679 | CAG-536 sp000434355 | 0.018864443 | 0.276540759 | -4.381061044 | -4.657601803 |
| 31001 | Oscillibacter sp900542115 | 0.019587904 | 0.325957967 | -4.349995566 | -4.675953533 |

FIG. 18L

| | | | | | |
|---|---|---|---|---|---|
| 20690 | Cronobacter sakazakii | 0.019649584 | 0.135554729 | -6.857406171 | -6.721851441 |
| 31921 | Parabacteroides sp900155425 | 0.019837253 | 0.1898253 | -4.038701682 | -3.848876382 |
| 17233 | Barnesiella sp003150885 | 0.01991579 | 0.279384153 | -5.642666603 | -5.36328245 |
| 17154 | Bacteroides cutis | 0.020055693 | 0.271945573 | -4.358707647 | -4.086762073 |
| 18790 | CAG-83 sp900551995 | 0.020358269 | 0.332155601 | -4.984237562 | -5.316393162 |
| 40006 | TF01-11 sp001916135 | 0.020467012 | 0.165415777 | -4.79760649 | -4.963022267 |
| 17227 | Bariatricus massiliensis | 0.020626173 | 0.350851155 | -5.50864074 | -5.157789585 |
| 36439 | Ruminococcus_C sp000437255 | 0.020633833 | 0.349758334 | -5.833910605 | -6.18366894 |
| 18357 | CAG-110 sp900546075 | 0.021007471 | 0.332884952 | -4.715502375 | -5.048387328 |
| 23217 | Fusobacterium animalis | 0.021035235 | 0.29714328 | -6.724513999 | -6.427370719 |
| 20220 | Collinsella sp900544135 | 0.021421587 | 0.534962132 | -4.8888841 | -5.423846233 |
| 22761 | Firm-11 sp900540045 | 0.021511012 | 0.337680999 | -4.167974724 | -4.505655723 |
| 36075 | Romboutsia ilealis | 0.021557635 | 0.369046039 | -4.994357558 | -5.363403597 |
| 17567 | Blautia_A sp900066505 | 0.02161124 | 0.125446668 | -3.088815072 | -3.21426174 |
| 21401 | Dialister sp900343095 | 0.021651409 | 0.356737956 | -6.304025952 | -5.947287996 |
| 33455 | Prevotella sp900556825 | 0.021914286 | 0.221528528 | -4.043161181 | -4.264689709 |
| 15918 | Anaerotruncus colihominis | 0.021914306 | 0.076139676 | -3.512318415 | -3.436178739 |
| 38946 | Streptococcus sp000448565 | 0.022049817 | 0.24166609 | -4.391580275 | -4.149914184 |
| 20134 | Collinsella bouchesdurhonensis | 0.022079658 | 0.283245433 | -6.1922096 | -6.475455033 |
| 34959 | QAND01 sp003150225 | 0.022139014 | 0.490194625 | -4.817869328 | -5.308063953 |
| 14375 | AM51-8 sp900546435 | 0.022324121 | 0.340091767 | -3.889679718 | -4.229771485 |
| 18792 | CAG-83 sp900552725 | 0.022406941 | 0.400023369 | -4.637847915 | -5.037871284 |
| 18439 | CAG-177 sp000431775 | 0.022659571 | 0.328574499 | -6.048631359 | -6.377205859 |
| 23777 | GCA-900066755 sp900066755 | 0.022670726 | 0.135156317 | -4.4523312 | -4.317174884 |
| 17347 | Bifidobacterium angulatum | 0.022716002 | 0.337069927 | -5.436154554 | -5.773224481 |
| 38979 | Streptococcus sp900550895 | 0.022740394 | 0.186861448 | -4.855158292 | -4.668296844 |
| 44359 | UMGS1071 sp900542375 | 0.023022018 | 0.273039925 | -3.484072425 | -3.75711235 |
| 36433 | Ruminococcus_A sp004562915 | 0.023092837 | 0.092123137 | -4.62473744 | -4.532614303 |
| 25241 | Holdemanella biformis | 0.02388383 | 0.334839714 | -4.046416916 | -4.381256629 |
| 31003 | Oscillibacter sp900544615 | 0.024027624 | 0.355277799 | -4.565662955 | -4.920940754 |
| 36509 | Ruminococcus_H sp900549945 | 0.024030819 | 0.248272422 | -4.629803528 | -4.381531106 |
| 22090 | Erysipelatoclostridium spiroforme | 0.024320204 | 0.401088365 | -4.477341084 | -4.878429449 |
| 20317 | Collinsella sp900554465 | 0.025006969 | 0.282944675 | -4.408598105 | -4.691542781 |
| 36435 | Ruminococcus_B sp900544395 | 0.025230514 | 0.190125684 | -4.183337489 | -3.993211804 |
| 17366 | Bifidobacterium catenulatum | 0.02527974 | 0.426773127 | -4.447163787 | -4.873936915 |
| 36521 | Ruthenibacterium lactatiformans | 0.02546114 | 0.115571684 | -3.073864251 | -2.958292567 |
| 15044 | Adlercreutzia equolifaciens | 0.02615541 | 0.392667932 | -3.659502307 | -4.052170239 |

FIG. 18M

| | | | | | |
|---|---|---|---|---|---|
| 21898 | Enterocloster sp900541315 | 0.026243092 | 0.316225821 | -3.615680535 | -3.931906357 |
| 18353 | CAG-110 sp900544405 | 0.026441157 | 0.223119741 | -4.682624284 | -4.905744025 |
| 18243 | Butyrivibrio_A sp900543865 | 0.026561636 | 0.166120606 | -3.074206173 | -3.240326779 |
| 18403 | CAG-1427 sp900538545 | 0.026960302 | 0.429161017 | -5.090558412 | -5.519719429 |
| 24112 | Gemmiger formicilis | 0.027208755 | 0.342917632 | -2.811945066 | -3.154862698 |
| 17173 | Bacteroides nordii | 0.027619422 | 0.235908713 | -4.446218341 | -4.210309628 |
| 15906 | Anaerostipes sp000508985 | 0.027702544 | 0.20336801 | -4.564553466 | -4.361185455 |
| 32290 | Pauljensenia sp000278725 | 0.027966551 | 0.344288882 | -5.099242017 | -5.443530899 |
| 34934 | QAKS01 sp003343685 | 0.027988827 | 0.368992656 | -5.749022707 | -6.118015363 |
| 17161 | Bacteroides fragilis_A | 0.028036309 | 0.315502647 | -5.392756492 | -5.077253844 |
| 33438 | Prevotella sp900551275 | 0.028458671 | 0.321550843 | -4.181320546 | -4.502871389 |
| 20468 | Coprococcus eutactus | 0.028629108 | 0.269517651 | -4.18131391 | -4.450831561 |
| 18424 | CAG-145 sp900542565 | 0.029489648 | 0.252623336 | -4.875819585 | -5.128442921 |
| 38891 | Streptococcus parasanguinis_D | 0.029494051 | 0.258363352 | -4.304795661 | -4.046432309 |
| 32727 | Phocaeicola vulgatus | 0.029581941 | 0.153878728 | -1.943022308 | -1.789143581 |
| 17537 | Blautia sp000436935 | 0.029669728 | 0.166532827 | -3.647283783 | -3.813816609 |
| 21924 | Enterococcus_A avium | 0.029679378 | 0.271436543 | -6.728409747 | -6.456973204 |
| 31925 | Parabacteroides sp900548175 | 0.029758067 | 0.086200787 | -4.28343886 | -4.197238072 |
| 17199 | Bacteroides stercorirosoris | 0.030201869 | 0.260399146 | -4.913402231 | -4.653003085 |
| 26805 | Ligilactobacillus salivarius | 0.030486055 | 0.281523705 | -6.31428563 | -6.032761925 |
| 17162 | Bacteroides gallinarum | 0.030651817 | 0.244044621 | -4.540226012 | -4.29618139 |
| 23216 | Fusicatenibacter sp900543115 | 0.030871262 | 0.30010482 | -5.664723997 | -5.364619177 |
| 26428 | Lawsonibacter sp900066825 | 0.030925011 | 0.133909222 | -3.459632475 | -3.325723253 |
| 44097 | UBA9502 sp900555625 | 0.031016381 | 0.222965146 | -4.004509508 | -4.227474654 |
| 20300 | Collinsella sp900552425 | 0.031103249 | 0.307217808 | -4.514084279 | -4.821302086 |
| 17204 | Bacteroides uniformis | 0.031476715 | 0.193350839 | -2.11444762 | -1.921096781 |
| 38888 | Streptococcus parasanguinis_A | 0.031942726 | 0.233085394 | -4.402891272 | -4.169805877 |
| 18793 | CAG-83 sp900554275 | 0.031987376 | 0.253040871 | -4.538824031 | -4.791864902 |
| 36434 | Ruminococcus_B gnavus | 0.032131021 | 0.20597649 | -2.979198077 | -2.773221587 |
| 23244 | Fusobacterium_B sp900541465 | 0.032250056 | 0.207233222 | -6.779203369 | -6.571970147 |
| 40827 | Tidjanibacter inops | 0.032431693 | 0.244968468 | -5.675336123 | -5.920304591 |
| 43588 | UBA737 sp900547445 | 0.032835616 | 0.373097354 | -5.090183572 | -5.463280925 |
| 25980 | Klebsiella variicola | 0.032844846 | 0.350716643 | -6.373117097 | -6.022400455 |
| 17535 | Blautia hominis | 0.033864018 | 0.329315144 | -6.554898268 | -6.225583124 |
| 34958 | QANA01 sp900554725 | 0.034038782 | 0.37662215 | -5.592274199 | -5.215652049 |
| 33129 | Porphyromonas sp001552775 | 0.035289856 | 0.124486241 | -6.792014993 | -6.667528752 |
| 24375 | Gordonibacter urolithinfaciens | 0.035371487 | 0.382471449 | -4.042860796 | -4.425332245 |
| 18241 | Butyrivibrio_A crossotus | 0.035374324 | 0.337626428 | -4.114127348 | -4.451753776 |

FIG. 18N

| | | | | | |
|---|---|---|---|---|---|
| 15965 | Angelakisella sp900552845 | 0.035456126 | 0.337596488 | -4.563054823 | -4.900651311 |
| 15181 | Agathobacter sp900317585 | 0.035786398 | 0.396534054 | -2.918708955 | -3.315243009 |
| 20309 | Collinsella sp900553415 | 0.035987369 | 0.311492629 | -4.306327408 | -4.617820038 |
| 15194 | Agathobaculum sp900291975 | 0.036097731 | 0.088519447 | -3.658149879 | -3.569630432 |
| 17413 | Bifidobacterium sp002742445 | 0.036506374 | 0.461837094 | -4.720138963 | -5.181976057 |
| 18656 | CAG-495 sp001917125 | 0.036721196 | 0.365409465 | -6.443544452 | -6.078134987 |
| 33819 | Providencia rettgeri_D | 0.036954428 | 0.099465065 | -6.988091954 | -6.888626888 |
| 22497 | Faecalibacterium sp900539885 | 0.037045659 | 0.299042782 | -3.160751067 | -3.459793849 |
| 37776 | Senegalimassilia sp900550055 | 0.03715375 | 0.331592295 | -5.051836092 | -5.383428387 |
| 32715 | Phocaeicola sp900546355 | 0.037905158 | 0.195402607 | -4.369944317 | -4.17454171 |
| 20464 | Coprobacter fastidiosus | 0.037971293 | 0.352249325 | -5.301018074 | -4.948768749 |
| 15468 | Alistipes sp000434235 | 0.037997591 | 0.209810274 | -6.549939285 | -6.340129012 |
| 15183 | Agathobacter sp900546625 | 0.039452398 | 0.342893018 | -3.148988341 | -3.491881359 |
| 22488 | Faecalibacterium prausnitzii_G | 0.040131373 | -0.30497324 | -2.871263774 | -3.176237014 |
| 18356 | CAG-110 sp900544975 | 0.040407464 | 0.237999198 | -4.781044055 | -5.019043253 |
| 17532 | Blautia coccoides | 0.040474561 | 0.213362689 | -4.43110478 | -4.217742091 |
| 18416 | CAG-1427 sp900556585 | 0.040695156 | 0.262967734 | -6.410416947 | -6.673384681 |
| 21885 | Enterocloster asparagiformis | 0.041168405 | 0.189701306 | -4.578649469 | -4.388948163 |
| 17193 | Bacteroides sp900552405 | 0.04128503 | 0.133444827 | -4.113497539 | -3.980052712 |
| 43057 | UBA5394 sp003150565 | 0.041866553 | 0.300232719 | -4.713925828 | -5.014158547 |
| 14374 | AM51-8 sp003478275 | 0.0419906 | 0.237416575 | -3.875901576 | -4.113318151 |
| 21940 | Enterococcus_B faecium | 0.043253446 | 0.404961596 | -6.569018599 | -6.164057003 |
| 15909 | Anaerotignum lactatifermentans | 0.043676737 | 0.192297662 | -4.428824524 | -4.236526862 |
| 31924 | Parabacteroides sp900547435 | 0.044788234 | 0.092239282 | -4.805119186 | -4.712879904 |
| 18402 | CAG-1427 sp000436075 | 0.04492207 | -0.55888389 | -5.78627325 | -6.345157141 |
| 15176 | Agathobacter rectalis | 0.046184422 | 0.333342497 | -2.102113046 | -2.435455543 |
| 44754 | Veillonella sp900556785 | 0.047346669 | 0.335239533 | -5.780297407 | -5.445057874 |
| 40010 | TF01-11 sp003149875 | 0.047396568 | 0.290847293 | -5.290391673 | -4.999544381 |
| 17153 | Bacteroides congonensis | 0.048076994 | 0.117940087 | -4.684999582 | -4.567059494 |
| 17148 | Bacteroides bouchesdurhonensis | 0.048410036 | 0.115559355 | -4.003380609 | -3.887821254 |
| 27989 | Mediterraneibacter sp900120155 | 0.048809771 | 0.297193801 | -4.528449241 | -4.825643042 |
| 18495 | CAG-269 sp900553985 | 0.048830745 | 0.319776835 | -6.002763537 | -5.682986701 |
| 44369 | UMGS1241 sp900549955 | 0.049192208 | 0.290586837 | -5.67855638 | -5.969143217 |
| 17547 | Blautia sp900556555 | 0.049488264 | 0.119471503 | -4.304829192 | -4.185357689 |
| 18503 | CAG-269 sp900556945 | 0.049759801 | 0.165549876 | -4.929554095 | -4.764004219 |

FIG. 18O

| Immune Marker (Gate) | OSU ID Number | Spearman p value (All Samples) | Spearman Correlation (All Samples) | Spearman Correlation (Cancer Samples) | Spearman p value (Cancer Samples) | Spearman Correlation (Control Samples) | Spearman p value (Control Samples) | Mean Abundance (Control) | Mean Abundance (Cancer) | Adjusted p value (All Samples) | Organism Name (Operational Species Unit) |
|---|---|---|---|---|---|---|---|---|---|---|---|
| CD3+ | 3002013 | 3.459E-06 | 0.5040 | 0.3929 | 0.0147 | 0.3728 | 0.0211 | 5.554E-05 | 1.127E-05 | 0.0381 | Raoultibacter massiliensis C2013 |
| CD4+ | 3002013 | 8.921E-06 | 0.4852 | 0.4509 | 0.0045 | 0.3566 | 0.0280 | 5.554E-05 | 1.127E-05 | 0.0381 | Raoultibacter massiliensis C2013 |
| CD3+CD56+ | 3002844 | 1.059E-05 | 0.4816 | 0.4903 | 0.0018 | 0.3940 | 0.0144 | 2.423E-03 | 5.348E-04 | 0.0381 | Erysipelotrichaceae bacterium GAM147 C2844 |
| CD3+ | 3002930 | 1.505E-05 | 0.4743 | 0.3164 | 0.0529 | 0.4755 | 0.0025 | 9.417E-05 | 3.817E-05 | 0.0381 | Lachnotalea sp. AF33-28 C2930 |
| CD8+HLA-DR+ | 3001923 | 1.570E-05 | -0.4734 | -0.3161 | 0.0532 | -0.5642 | 0.0002 | 1.451E-04 | 2.764E-05 | 0.0381 | Akkermansia muciniphila C1923 |
| CD4+ | 3002893 | 3.843E-05 | 0.4538 | 0.3575 | 0.0276 | 0.3492 | 0.0317 | 1.962E-03 | 1.235E-03 | 0.0699 | Clostridium sp. AF36-4 C2893 |
| CD14-CD15+ | 3003280 | 4.505E-05 | -0.4501 | -0.5188 | 0.0008 | -0.4136 | 0.0098 | 2.356E-04 | 1.392E-04 | 0.0699 | Mordavella sp. Marseille-P3756 C3280 |
| CD3+ | 3002129 | 6.415E-05 | 0.4420 | 0.2109 | 0.2038 | 0.2323 | 0.1605 | 4.191E-02 | 1.119E-02 | 0.0699 | Blautia obeum C2129 |
| CD8+ | 3002636 | 6.620E-05 | 0.4412 | 0.3019 | 0.0655 | 0.2625 | 0.1113 | 6.922E-03 | 2.259E-03 | 0.0699 | [Ruminococcus] torques C2636 |
| CD4+ | 3001596 | 6.907E-05 | -0.4402 | -0.5150 | 0.0009 | -0.1817 | 0.2750 | 2.758E-05 | 2.415E-05 | 0.0699 | Bacteroides sp. HF-5092 C1596 |
| CD8+HLA-DR+ | 3002161 | 7.694E-05 | 0.4377 | 0.3507 | 0.0309 | 0.4021 | 0.0123 | 1.749E-04 | 2.001E-04 | 0.0699 | Blautia hansenii C2161 |
| CD4+ | 3002925 | 7.744E-05 | 0.4375 | 0.3826 | 0.0178 | 0.3472 | 0.0327 | 1.508E-03 | 5.440E-04 | 0.0699 | Anaeromassilibacillus sp. Marseille-P3876 C2925 |
| CD14+CD15- | 3003008 | 8.452E-05 | 0.4354 | 0.4383 | 0.0059 | 0.3797 | 0.0187 | 3.095E-05 | 8.576E-05 | 0.0699 | Cuneatibacter caecimuris C3008 |
| CD14-CD15+ | 3002774 | 8.702E-05 | -0.4347 | -0.3951 | 0.0141 | -0.4976 | 0.0015 | 2.426E-05 | 1.560E-05 | 0.0699 | Lachnoclostridium sp. An169 C2774 |
| CD8+HLA-DR+ | 3002945 | 8.969E-05 | -0.4340 | -0.3953 | 0.0140 | -0.3741 | 0.0207 | 5.692E-03 | 3.367E-03 | 0.0699 | Ruminococcus sp. AMA2-11 C2945 |
| CD4+ | 3002897 | 9.218E-05 | 0.4334 | 0.2807 | 0.0879 | 0.3308 | 0.0425 | 5.111E-04 | 1.602E-04 | 0.0699 | Ruminococcus sp. AF14-10 C2897 |
| CD3+CD56+ | 3002931 | 1.021E-04 | 0.4309 | 0.5330 | 0.0006 | 0.2653 | 0.1074 | 6.210E-05 | 3.473E-05 | 0.0720 | Clostridium sp. OM02-18AC C2931 |
| CD3+ | 3003005 | 1.068E-04 | 0.4298 | 0.3112 | 0.0572 | 0.3834 | 0.0175 | 3.088E-05 | 7.560E-06 | 0.0720 | Candidatus Borkfalkia ceftriaxoniphila C3005 |
| CD3+ | 3002284 | 1.254E-04 | -0.4259 | -0.4844 | 0.0021 | -0.1682 | 0.3128 | 1.397E-03 | 3.047E-03 | 0.0801 | Flavonifractor plautii C2284 |

FIG. 19A

| | | | | | | | | | | | |
|---|---|---|---|---|---|---|---|---|---|---|---|
| CD11b+ | 3002703 | 1.632E-04 | -0.4193 | -0.2379 | 0.1504 | -0.4941 | 0.0016 | 8.225E-06 | 2.456E-06 | 0.0911 | Criibacterium bergeronii C2703 |
| CD3+CD56+ | 3002151 | 1.641E-04 | 0.4192 | 0.4028 | 0.0122 | 0.4312 | 0.0069 | 5.365E-05 | 9.239E-05 | 0.0911 | [Bacteroides] pectinophilus ATCC 43243 C2151 |
| CD3+ | 3002897 | 1.684E-04 | 0.4185 | 0.1765 | 0.2891 | 0.3330 | 0.0411 | 5.111E-04 | 1.602E-04 | 0.0911 | Ruminococcus sp. AF14-10 C2897 |
| CD3+ | 3002844 | 1.726E-04 | 0.4179 | 0.0782 | 0.6406 | 0.4238 | 0.0080 | 2.423E-03 | 5.348E-04 | 0.0911 | Erysipelotrichaceae bacterium GAM147 C2844 |
| CD8+HLA-DR+ | 3001917 | 1.851E-04 | -0.4161 | -0.3486 | 0.0319 | -0.4065 | 0.0113 | 9.828E-03 | 3.525E-03 | 0.0930 | Akkermansia muciniphila C1917 |
| CD3+CD56+ | 3002913 | 1.914E-04 | 0.4153 | 0.3036 | 0.0638 | 0.5028 | 0.0013 | 1.127E-03 | 4.498E-04 | 0.0930 | Dorea sp. AM58-8 C2913 |
| CD4+ | 3002930 | 2.027E-04 | 0.4138 | 0.3821 | 0.0179 | 0.2785 | 0.0904 | 9.417E-05 | 3.817E-05 | 0.0942 | Lachnotalea sp. AF33-28 C2930 |
| CD4+ | 3002162 | 2.094E-04 | 0.4130 | 0.1590 | 0.3404 | 0.5188 | 0.0008 | 1.392E-04 | 5.708E-05 | 0.0942 | Subdoligranulum variabile DSM 15176 C2162 |
| CD4+ | 3002249 | 2.356E-04 | 0.4099 | 0.2949 | 0.0723 | 0.2978 | 0.0694 | 5.379E-05 | 4.487E-04 | 0.0978 | Ruminococcus champanellensis C2249 |
| CD8+HLA-DR+ | 3005864 | 2.461E-04 | 0.4088 | 0.4199 | 0.0087 | 0.4175 | 0.0091 | 1.621E-03 | 4.210E-06 | 0.0978 | Klebsiella sp. PO552 C5864 |
| CD4+ | 3003005 | 2.469E-04 | 0.4087 | 0.3652 | 0.0242 | 0.3295 | 0.0434 | 3.088E-05 | 7.560E-06 | 0.0978 | Candidatus Borkfalkia ceftriaxoniphila C3005 |
| CD15+CD14- | 3003280 | 2.549E-04 | -0.4079 | -0.3805 | 0.0185 | -0.4078 | 0.0110 | 2.356E-04 | 1.392E-04 | 0.0978 | Mordavella sp. Marseille-P3756 C3280 |
| CD8+ | 3002300 | 2.582E-04 | 0.4075 | 0.3103 | 0.0579 | 0.3857 | 0.0168 | 1.545E-06 | 1.056E-06 | 0.0978 | Clostridium sp. SY8519 C2300 |
| CD11b+ | 3002775 | 2.674E-04 | 0.4066 | 0.5621 | 0.0002 | 0.2318 | 0.1615 | 3.436E-05 | 4.789E-05 | 0.0978 | Lachnoclostridium sp. An14 C2775 |
| CD3+ | 3002971 | 2.765E-04 | 0.4057 | 0.5269 | 0.0007 | 0.2487 | 0.1322 | 1.515E-05 | 1.417E-05 | 0.0978 | Clostridium sp. YH-panp20 C2971 |
| CD4+ | 3002865 | 2.820E-04 | -0.4052 | -0.4439 | 0.0052 | -0.1757 | 0.2912 | 4.445E-05 | 1.319E-03 | 0.0978 | Blautia sp. N6H1-15 C2865 |
| CD4+ | 3002666 | 2.909E-04 | -0.4044 | -0.4240 | 0.0080 | -0.3678 | 0.0231 | 1.030E-03 | 2.043E-03 | 0.0981 | Clostridium sp. AT4 C2666 |
| Foxp3+ | 3005820 | 3.042E-04 | 0.4032 | 0.6040 | 0.0001 | 0.1670 | 0.3162 | 5.853E-05 | 2.268E-05 | 0.0990 | Oxalobacter formigenes C5820 |
| CD14+CD15- | 3002775 | 3.113E-04 | 0.4026 | 0.5008 | 0.0014 | 0.3144 | 0.0546 | 3.436E-05 | 4.789E-05 | 0.0990 | Lachnoclostridium sp. An14 C2775 |
| CD11b+ | 3003008 | 3.263E-04 | 0.4014 | 0.4266 | 0.0076 | 0.2952 | 0.0720 | 3.095E-05 | 8.576E-05 | 0.0990 | Cuneatibacter caecimuris C3008 |
| CD4+ | 3002129 | 3.397E-04 | 0.4003 | 0.2907 | 0.0766 | 0.0938 | 0.5755 | 4.191E-02 | 1.119E-02 | 0.0990 | Blautia obeum C2129 |
| CD4+ | 3002580 | 3.418E-04 | 0.4001 | 0.4448 | 0.0051 | 0.0736 | 0.6604 | 2.040E-03 | 1.156E-03 | 0.0990 | Oscillibacter sp. ER4 C2580 |
| CD4+ | 3002951 | 3.425E-04 | 0.4001 | 0.3698 | 0.0223 | 0.4528 | 0.0043 | 2.665E-05 | 1.501E-05 | 0.0990 | Coprococcus sp. OM04-5BH C2951 |
| CD14+CD15- | 3002438 | 3.510E-04 | 0.3994 | 0.5042 | 0.0012 | 0.2643 | 0.1089 | 1.282E-04 | 2.006E-04 | 0.0991 | Clostridium sp. ATCC 29733 C2438 |
| CD4+ | 3002906 | 3.756E-04 | 0.3976 | 0.4842 | 0.0021 | -0.0183 | 0.9133 | 6.237E-04 | 3.254E-04 | 0.1036 | Blautia sp. AF19-10LB C2906 |
| Foxp3+ | 3001653 | 3.894E-04 | 0.3966 | 0.4917 | 0.0017 | 0.3111 | 0.0573 | 4.252E-05 | 6.781E-06 | 0.1045 | Alistipes sp. CHKCI003 C1653 |
| CD3+ | 3001596 | 4.079E-04 | -0.3954 | -0.3497 | 0.0314 | -0.2574 | 0.1187 | 2.758E-05 | 2.415E-05 | 0.1045 | Bacteroides sp. HF-5092 C1596 |

FIG. 19B

| | | | | | | | | | | |
|---|---|---|---|---|---|---|---|---|---|---|
| CD3+ | 3002913 | 4.100E-04 | 0.3952 | 0.0715 | 0.6699 | 0.4247 | 0.0079 | 1.127E-03 | 4.498E-04 | 0.1045 | Dorea sp. AM58-8 C2913 |
| CD3+HLADR+ | 3001923 | 4.166E-04 | -0.3948 | -0.2034 | 0.2207 | -0.4999 | 0.0014 | 1.451E-04 | 2.764E-05 | 0.1045 | Akkermansia muciniphila C1923 |
| CD3+ | 3002893 | 4.217E-04 | 0.3945 | 0.3461 | 0.0333 | 0.2879 | 0.0797 | 1.962E-03 | 1.235E-03 | 0.1045 | Clostridium sp. AF36-4 C2893 |
| CD15+CD14- | 3002774 | 4.785E-04 | -0.3910 | -0.2777 | 0.0914 | -0.4892 | 0.0018 | 2.426E-05 | 1.560E-05 | 0.1162 | Lachnoclostridium sp. An169 C2774 |
| Foxp3+ | 3002932 | 5.090E-04 | 0.3893 | 0.4072 | 0.0112 | 0.3137 | 0.0551 | 6.445E-04 | 1.310E-05 | 0.1211 | Eisenbergiella sp. OF01-20 C2932 |
| CD4+ | 3003059 | 5.344E-04 | 0.3880 | 0.4249 | 0.0078 | 0.3181 | 0.0516 | 7.539E-04 | 3.149E-03 | 0.1239 | Neglecta timonensis C3059 |
| CD4+ | 3003061 | 5.408E-04 | 0.3876 | 0.2884 | 0.0791 | 0.3590 | 0.0269 | 1.452E-04 | 1.272E-04 | 0.1239 | Anaeromassilibacillus sp. Marseille-P4683 C3061 |
| CD3+HLADR+ | 3002161 | 5.861E-04 | 0.3854 | 0.2920 | 0.0752 | 0.3708 | 0.0219 | 1.749E-04 | 2.001E-03 | 0.1317 | Blautia hansenii C2161 |
| CD8+HLA-DR+ | 3001992 | 6.220E-04 | -0.3837 | -0.2581 | 0.1177 | -0.4369 | 0.0061 | 3.664E-06 | 3.709E-06 | 0.1362 | Parolsenella catena C1992 |
| CD3+CD56+ | 3002197 | 6.323E-04 | 0.3833 | 0.4645 | 0.0033 | 0.1154 | 0.4901 | 4.004E-03 | 3.683E-03 | 0.1362 | Dorea formicigenerans C2197 |
| CD4+ | 3002932 | 6.395E-04 | 0.3829 | 0.2481 | 0.1331 | 0.4597 | 0.0037 | 6.445E-04 | 1.310E-05 | 0.1362 | Eisenbergiella sp. OF01-20 C2932 |
| CD3+CD56+ | 3002339 | 6.619E-04 | 0.3820 | 0.4161 | 0.0094 | 0.3140 | 0.0549 | 1.308E-05 | 1.401E-06 | 0.1374 | Holdemania massiliensis AP2 C2339 |
| CD3+ | 3002249 | 6.771E-04 | 0.3813 | 0.1456 | 0.3830 | 0.3317 | 0.0419 | 5.379E-05 | 4.487E-04 | 0.1374 | Ruminococcus champanellensis C2249 |
| CD4+ | 3002284 | 6.792E-04 | -0.3812 | -0.4645 | 0.0033 | -0.0531 | 0.7517 | 1.397E-03 | 3.047E-03 | 0.1374 | Flavonifractor plautii C2284 |
| CD3+CD56+ | 3002133 | 7.367E-04 | 0.3789 | 0.5421 | 0.0004 | 0.2356 | 0.1545 | 4.319E-05 | 1.446E-04 | 0.1465 | Absiella dolichum C2133 |
| CD3+HLADR+ | 3005864 | 7.484E-04 | 0.3785 | 0.3481 | 0.0322 | 0.3919 | 0.0150 | 1.621E-03 | 4.210E-06 | 0.1465 | Klebsiella sp. PO552 C5864 |
| CD3+CD56+ | 3002887 | 7.687E-04 | 0.3777 | 0.4056 | 0.0115 | 0.2187 | 0.1870 | 6.433E-04 | 6.225E-04 | 0.1481 | [Clostridium] amygdalinum C2887 |
| CD15+CD14- | 3004617 | 7.948E-04 | -0.3768 | -0.3679 | 0.0231 | -0.4015 | 0.0125 | 1.390E-06 | 3.688E-05 | 0.1489 | Streptococcus lutetiensis C4617 |
| CD3+CD56+ | 3002606 | 7.972E-04 | 0.3767 | 0.3447 | 0.0340 | 0.3608 | 0.0261 | 1.805E-04 | 1.909E-04 | 0.1489 | Coprobacillus sp. 8_1_38FAA C2606 |
| CD3+CD56+ | 3002149 | 8.100E-04 | 0.3762 | 0.3866 | 0.0165 | 0.2575 | 0.1186 | 4.944E-03 | 6.780E-03 | 0.1490 | Ruminococcus lactaris C2149 |

FIG. 19C

| Immune Marker (Gate) | OSU ID Number | Spearman p value (All Samples) | Spearman Correlation (All Samples) | Spearman Correlation (Cancer Samples) | Spearman p value (Cancer Samples) | Spearman Correlation (Control Samples) | Spearman p value (Control Samples) | Mean Abundance (Control) | Mean Abundance (Cancer) | Adjusted p value (All Samples) | Organism Name (Operational Species Unit) |
|---|---|---|---|---|---|---|---|---|---|---|---|
| CD3+ | 3002013 | 3.459E-06 | 0.5040 | 0.3929 | 0.0147 | 0.3728 | 0.0211 | 5.554E-05 | 1.127E-05 | 0.0381 | Raoultibacter massiliensis C2013 |
| CD4+ | 3002013 | 8.921E-06 | 0.4852 | 0.4509 | 0.0045 | 0.3566 | 0.0280 | 5.554E-05 | 1.127E-05 | 0.0381 | Raoultibacter massiliensis C2013 |
| CD3+CD56+ | 3002844 | 1.059E-05 | 0.4816 | 0.4903 | 0.0018 | 0.3940 | 0.0144 | 2.423E-03 | 5.348E-04 | 0.0381 | Erysipelotrichaceae bacterium GAM147 C2844 |
| CD3+ | 3002930 | 1.505E-05 | 0.4743 | 0.3164 | 0.0529 | 0.4755 | 0.0025 | 9.417E-05 | 3.817E-05 | 0.0381 | Lachnotalea sp. AF33-28 C2930 |
| CD8+HLA-DR+ | 3001923 | 1.570E-05 | -0.4734 | -0.3161 | 0.0532 | -0.5642 | 0.0002 | 1.451E-04 | 2.764E-05 | 0.0381 | Akkermansia muciniphila C1923 |
| CD4+ | 3002893 | 3.843E-05 | 0.4538 | 0.3575 | 0.0276 | 0.3492 | 0.0317 | 1.962E-03 | 1.235E-03 | 0.0699 | Clostridium sp. AF36-4 C2893 |
| CD14-CD15+ | 3003280 | 4.505E-05 | -0.4501 | -0.5188 | 0.0008 | -0.4136 | 0.0098 | 2.356E-04 | 1.392E-04 | 0.0699 | Mordavella sp. Marseille-P3756 C3280 |
| CD3+ | 3002129 | 6.415E-05 | 0.4420 | 0.2109 | 0.2038 | 0.2323 | 0.1605 | 4.191E-02 | 1.119E-02 | 0.0699 | Blautia obeum C2129 |
| CD8+ | 3002636 | 6.620E-05 | 0.4412 | 0.3019 | 0.0655 | 0.2625 | 0.1113 | 6.922E-03 | 2.259E-03 | 0.0699 | [Ruminococcus] torques C2636 |
| CD4+ | 3001596 | 6.907E-05 | -0.4402 | -0.5150 | 0.0009 | -0.1817 | 0.2750 | 2.758E-05 | 2.415E-05 | 0.0699 | Bacteroides sp. HF-5092 C1596 |
| CD8+HLA-DR+ | 3002161 | 7.694E-05 | 0.4377 | 0.3507 | 0.0309 | 0.4021 | 0.0123 | 1.749E-04 | 2.001E-03 | 0.0699 | Blautia hansenii C2161 |
| CD4+ | 3002925 | 7.744E-05 | 0.4375 | 0.3826 | 0.0178 | 0.3472 | 0.0327 | 1.508E-03 | 5.440E-04 | 0.0699 | Anaeromassilibacillus sp. Marseille-P3876 C2925 |
| CD14+CD15- | 3003008 | 8.452E-05 | 0.4354 | 0.4383 | 0.0059 | 0.3797 | 0.0187 | 3.095E-05 | 8.576E-05 | 0.0699 | Cuneatibacter caecimuris C3008 |
| CD14-CD15+ | 3002774 | 8.702E-05 | -0.4347 | -0.3951 | 0.0141 | -0.4976 | 0.0015 | 2.426E-05 | 1.560E-05 | 0.0699 | Lachnoclostridium sp. An169 C2774 |
| CD8+HLA-DR+ | 3002945 | 8.969E-05 | -0.4340 | -0.3953 | 0.0140 | -0.3741 | 0.0207 | 5.692E-03 | 3.367E-03 | 0.0699 | Ruminococcus sp. AM42-11 C2945 |
| CD4+ | 3002897 | 9.218E-05 | 0.4334 | 0.2807 | 0.0879 | 0.3308 | 0.0425 | 5.111E-04 | 1.602E-04 | 0.0699 | Ruminococcus sp. AF14-10 C2897 |
| CD3+CD56+ | 3002931 | 1.021E-04 | 0.4309 | 0.5330 | 0.0006 | 0.2653 | 0.1074 | 6.210E-05 | 3.473E-05 | 0.0720 | Clostridium sp. OM02-18AC C2931 |
| CD3+ | 3003005 | 1.068E-04 | 0.4298 | 0.3112 | 0.0572 | 0.3834 | 0.0175 | 3.088E-05 | 7.560E-06 | 0.0720 | Candidatus Borkfalkia ceftriaxoniphila C3005 |
| CD3+ | 3002284 | 1.254E-04 | -0.4259 | -0.4844 | 0.0021 | -0.1682 | 0.3128 | 1.397E-03 | 3.047E-03 | 0.0801 | Flavonifractor plautii C2284 |
| CD11b+ | 3002703 | 1.632E-04 | -0.4193 | -0.2379 | 0.1504 | -0.4941 | 0.0016 | 8.225E-06 | 2.456E-06 | 0.0911 | Cribbacterium bergeronii C2703 |

FIG. 20A

| Marker | | | | | | | | | | | Species |
|---|---|---|---|---|---|---|---|---|---|---|---|
| CD3+CD56+ | 3002151 | 1.641E-04 | 0.4192 | 0.4028 | 0.0122 | 0.4312 | 0.0069 | 5.365E-05 | 9.239E-05 | 0.0911 | [Bacteroides] pectinophilus ATCC 43243 C2151 |
| CD3+ | 3002897 | 1.684E-04 | 0.4185 | 0.1765 | 0.2891 | 0.3330 | 0.0411 | 5.111E-04 | 1.602E-04 | 0.0911 | Ruminococcus sp. AF14-10 C2897 |
| CD3+ | 3002844 | 1.726E-04 | 0.4179 | 0.0782 | 0.6406 | 0.4238 | 0.0080 | 2.423E-03 | 5.348E-04 | 0.0911 | Erysipelotrichaceae bacterium GAM147 C2844 |
| CD8+HLA-DR+ | 3001917 | 1.851E-04 | -0.4161 | -0.3486 | 0.0319 | -0.4065 | 0.0113 | 9.828E-03 | 3.525E-03 | 0.0930 | Akkermansia muciniphila C1917 |
| CD3+CD56+ | 3002913 | 1.914E-04 | 0.4153 | 0.3036 | 0.0638 | 0.5028 | 0.0013 | 1.127E-03 | 4.498E-04 | 0.0930 | Dorea sp. AM58-8 C2913 |
| CD4+ | 3002930 | 2.027E-04 | 0.4138 | 0.3821 | 0.0179 | 0.2785 | 0.0904 | 9.417E-05 | 3.817E-05 | 0.0942 | Lachnotalea sp. AF33-28 C2930 |
| CD4+ | 3002162 | 2.094E-04 | 0.4130 | 0.1590 | 0.3404 | 0.5188 | 0.0008 | 1.392E-04 | 5.708E-05 | 0.0942 | Subdoligranulum variabile DSM 15176 C2162 |
| CD4+ | 3002249 | 2.356E-04 | 0.4099 | 0.2949 | 0.0723 | 0.2978 | 0.0694 | 5.379E-05 | 4.487E-04 | 0.0978 | Ruminococcus champanellensis C2249 |
| CD8+HLA-DR+ | 3005864 | 2.461E-04 | 0.4088 | 0.4199 | 0.0087 | 0.4175 | 0.0091 | 1.621E-03 | 4.210E-06 | 0.0978 | Klebsiella sp. PO552 C5864 |
| CD4+ | 3003005 | 2.469E-04 | 0.4087 | 0.3652 | 0.0242 | 0.3295 | 0.0434 | 3.088E-05 | 7.560E-06 | 0.0978 | Candidatus Borkfalkia ceftriaxoniphila C3005 |
| CD15+CD14- | 3003280 | 2.549E-04 | -0.4079 | -0.3805 | 0.0185 | -0.4078 | 0.0110 | 2.356E-04 | 1.392E-04 | 0.0978 | Mordavella sp. Marseille-P3756 C3280 |
| CD8+ | 3002300 | 2.582E-04 | 0.4075 | 0.3103 | 0.0579 | 0.3857 | 0.0168 | 1.545E-06 | 1.056E-06 | 0.0978 | Clostridium sp. SY8519 C2300 |
| CD11b+ | 3002775 | 2.674E-04 | 0.4066 | 0.5621 | 0.0002 | 0.2318 | 0.1615 | 3.436E-05 | 4.789E-05 | 0.0978 | Lachnoclostridium sp. An14 C2775 |
| CD3+ | 3002971 | 2.765E-04 | 0.4057 | 0.5269 | 0.0007 | 0.2487 | 0.1322 | 1.515E-05 | 1.417E-05 | 0.0978 | Clostridium sp. YH-panp20 C2971 |
| CD4+ | 3002865 | 2.820E-04 | -0.4052 | -0.4439 | 0.0052 | -0.1757 | 0.2912 | 4.445E-05 | 1.319E-03 | 0.0978 | Blautia sp. N6H1-15 C2865 |
| CD4+ | 3002666 | 2.909E-04 | -0.4044 | -0.4240 | 0.0080 | -0.3678 | 0.0231 | 1.030E-03 | 2.043E-03 | 0.0981 | Clostridium sp. AT4 C2666 |
| Foxp3+ | 3005820 | 3.042E-04 | 0.4032 | 0.6040 | 0.0001 | 0.1670 | 0.3162 | 5.853E-05 | 2.268E-05 | 0.0990 | Oxalobacter formigenes C5820 |
| CD14+CD15- | 3002775 | 3.113E-04 | 0.4026 | 0.5008 | 0.0014 | 0.3144 | 0.0546 | 3.436E-05 | 4.789E-05 | 0.0990 | Lachnoclostridium sp. An14 C2775 |
| CD11b+ | 3003008 | 3.263E-04 | 0.4014 | 0.4266 | 0.0076 | 0.2952 | 0.0720 | 3.095E-05 | 8.576E-05 | 0.0990 | Cuneatibacter caecimuris C3008 |
| CD4+ | 3002129 | 3.397E-04 | 0.4003 | 0.2907 | 0.0766 | 0.0938 | 0.5755 | 4.191E-02 | 1.119E-02 | 0.0990 | Blautia obeum C2129 |
| CD4+ | 3002580 | 3.418E-04 | 0.4001 | 0.4448 | 0.0051 | 0.0736 | 0.6604 | 2.040E-03 | 1.156E-03 | 0.0990 | Oscillibacter sp. ER4 C2580 |
| CD4+ | 3002951 | 3.425E-04 | 0.4001 | 0.3698 | 0.0223 | 0.4528 | 0.0043 | 2.665E-05 | 1.501E-05 | 0.0990 | Coprococcus sp. OM04-5BH C2951 |
| CD14+CD15- | 3002438 | 3.510E-04 | 0.3994 | 0.5042 | 0.0012 | 0.2643 | 0.1089 | 1.282E-04 | 2.006E-04 | 0.0991 | Clostridium sp. ATCC 29733 C2438 |
| CD4+ | 3002906 | 3.756E-04 | 0.3976 | 0.4842 | 0.0021 | -0.0183 | 0.9133 | 6.237E-04 | 3.254E-04 | 0.1036 | Blautia sp. AF19-10LB C2906 |
| Foxp3+ | 3001653 | 3.894E-04 | 0.3966 | 0.4917 | 0.0017 | 0.3111 | 0.0573 | 4.252E-05 | 6.781E-06 | 0.1045 | Alistipes sp. CHKCI003 C1653 |
| CD3+ | 3001596 | 4.079E-04 | -0.3954 | -0.3497 | 0.0314 | -0.2574 | 0.1187 | 2.758E-05 | 2.415E-05 | 0.1045 | Bacteroides sp. HF-5092 C1596 |
| CD3+ | 3002913 | 4.100E-04 | 0.3952 | 0.0715 | 0.6699 | 0.4247 | 0.0079 | 1.127E-03 | 4.498E-04 | 0.1045 | Dorea sp. AM58-8 C2913 |

FIG. 20B

| | | | | | | | | | | |
|---|---|---|---|---|---|---|---|---|---|---|
| CD3+HLADR+ | 3001923 | 4.166E-04 | -0.3948 | -0.2034 | 0.2207 | -0.4999 | 0.0014 | 1.451E-04 | 2.764E-05 | 0.1045 | Akkermansia muciniphila C1923 |
| CD3+ | 3002893 | 4.217E-04 | 0.3945 | 0.3461 | 0.0333 | 0.2879 | 0.0797 | 1.962E-03 | 1.235E-03 | 0.1045 | Clostridium sp. AF36-4 C2893 |
| CD15+CD14- | 3002774 | 4.785E-04 | -0.3910 | -0.2777 | 0.0914 | -0.4892 | 0.0018 | 2.426E-05 | 1.560E-05 | 0.1162 | Lachnoclostridium sp. An169 C2774 |
| Foxp3+ | 3002932 | 5.090E-04 | 0.3893 | 0.4072 | 0.0112 | 0.3137 | 0.0551 | 6.445E-04 | 1.310E-05 | 0.1211 | Eisenbergiella sp. OF01-20 C2932 |
| CD4+ | 3003059 | 5.344E-04 | 0.3880 | 0.4249 | 0.0078 | 0.3181 | 0.0516 | 7.539E-04 | 3.149E-03 | 0.1239 | Neglecta timonensis C3059 |
| CD4+ | 3003061 | 5.408E-04 | 0.3876 | 0.2884 | 0.0791 | 0.3590 | 0.0269 | 1.452E-04 | 1.272E-04 | 0.1239 | Anaeromassilibacillus sp. Marseille-P4683 C3061 |
| CD3+HLADR+ | 3002161 | 5.861E-04 | 0.3854 | 0.2920 | 0.0752 | 0.3708 | 0.0219 | 1.749E-04 | 2.001E-03 | 0.1317 | Blautia hansenii C2161 |
| CD8+HLA-DR+ | 3001992 | 6.220E-04 | -0.3837 | -0.2581 | 0.1177 | -0.4369 | 0.0061 | 3.664E-06 | 3.709E-06 | 0.1362 | Parolsenella catena C1992 |
| CD3+CD56+ | 3002197 | 6.323E-04 | 0.3833 | 0.4645 | 0.0033 | 0.1154 | 0.4901 | 4.004E-03 | 3.683E-03 | 0.1362 | Dorea formicigenerans C2197 |
| CD4+ | 3002932 | 6.395E-04 | 0.3829 | 0.2481 | 0.1331 | 0.4597 | 0.0037 | 6.445E-04 | 1.310E-05 | 0.1362 | Eisenbergiella sp. OF01-20 C2932 |
| CD3+CD56+ | 3002339 | 6.619E-04 | 0.3820 | 0.4161 | 0.0094 | 0.3140 | 0.0549 | 1.308E-05 | 1.401E-06 | 0.1374 | Holdemania massiliensis AP2 C2339 |
| CD3+ | 3002249 | 6.771E-04 | 0.3813 | 0.1456 | 0.3830 | 0.3317 | 0.0419 | 5.379E-05 | 4.487E-04 | 0.1374 | Ruminococcus champanellensis C2249 |
| CD4+ | 3002284 | 6.792E-04 | -0.3812 | -0.4645 | 0.0033 | -0.0531 | 0.7517 | 1.397E-03 | 3.047E-03 | 0.1374 | Flavonifractor plautii C2284 |
| CD3+CD56+ | 3002133 | 7.367E-04 | 0.3789 | 0.5421 | 0.0004 | 0.2356 | 0.1545 | 4.319E-05 | 1.446E-04 | 0.1465 | Absiella dolichum C2133 |
| CD3+HLADR+ | 3005864 | 7.484E-04 | 0.3785 | 0.3481 | 0.0322 | 0.3919 | 0.0150 | 1.621E-03 | 4.210E-06 | 0.1465 | Klebsiella sp. PO552 C5864 |
| CD3+CD56+ | 3002887 | 7.687E-04 | 0.3777 | 0.4056 | 0.0115 | 0.2187 | 0.1870 | 6.433E-04 | 6.225E-04 | 0.1481 | [Clostridium] amygdalinum C2887 |
| CD15+CD14- | 3004617 | 7.948E-04 | -0.3768 | -0.3679 | 0.0231 | -0.4015 | 0.0125 | 1.390E-06 | 3.688E-05 | 0.1489 | Streptococcus lutetiensis C4617 |
| CD3+CD56+ | 3002606 | 7.972E-04 | 0.3767 | 0.3447 | 0.0340 | 0.3608 | 0.0261 | 1.805E-04 | 1.909E-04 | 0.1489 | Coprobacillus sp. 8_1_38FAA C2606 |
| CD3+CD56+ | 3002149 | 8.100E-04 | 0.3762 | 0.3866 | 0.0165 | 0.2575 | 0.1186 | 4.944E-03 | 6.780E-03 | 0.1490 | Ruminococcus lactaris C2149 |

FIG. 20C

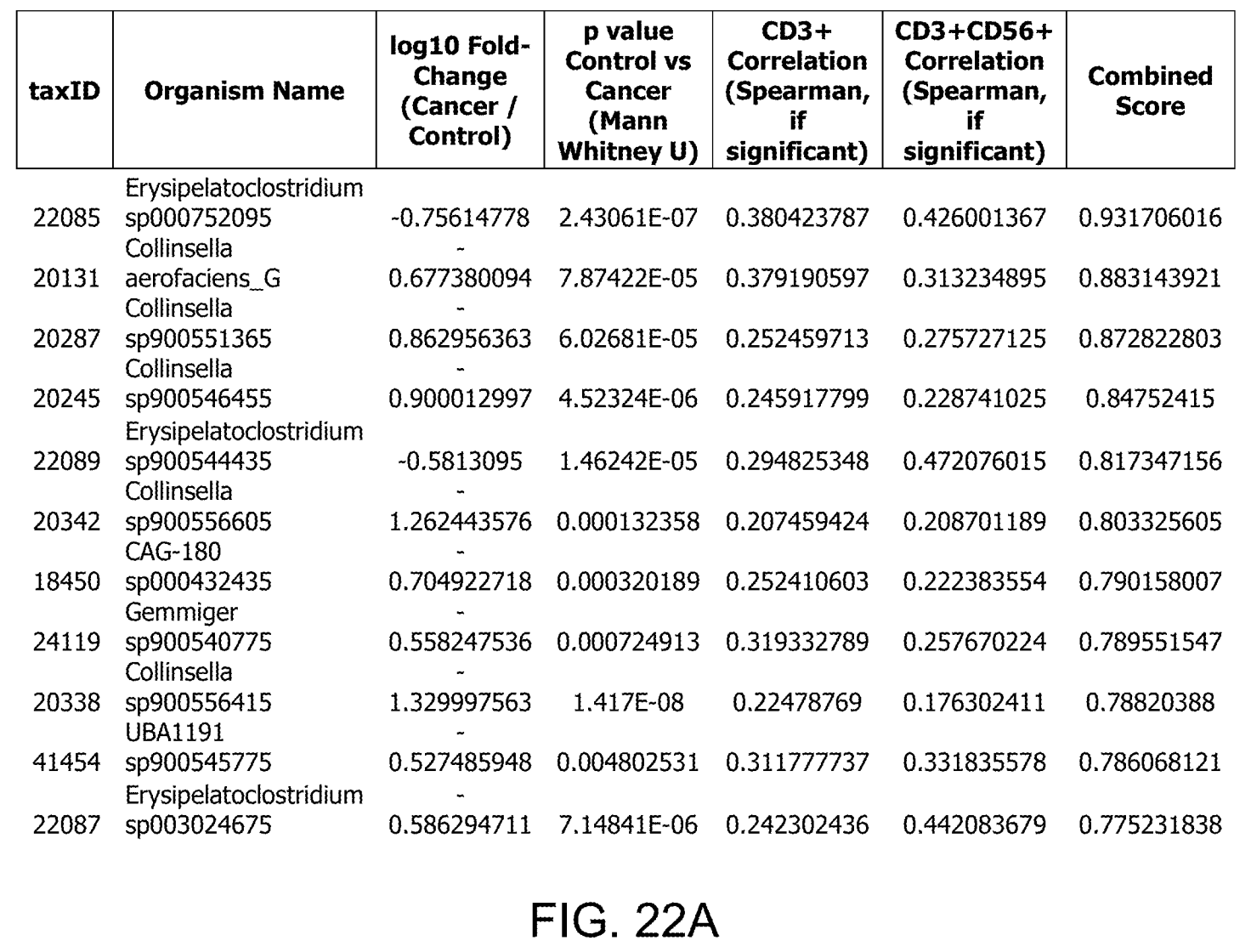

| taxID | Organism Name | log10 Fold-Change (Cancer / Control) | p value Control vs Cancer (Mann Whitney U) | CD3+ Correlation (Spearman, if significant) | CD3+CD56+ Correlation (Spearman, if significant) | Combined Score |
|---|---|---|---|---|---|---|
| 22085 | Erysipelatoclostridium sp000752095 Collinsella | -0.75614778 | 2.43061E-07 | 0.380423787 | 0.426001367 | 0.931706016 |
| 20131 | aerofaciens_G Collinsella | 0.677380094 | 7.87422E-05 | 0.379190597 | 0.313234895 | 0.883143921 |
| 20287 | sp900551365 Collinsella | 0.862956363 | 6.02681E-05 | 0.252459713 | 0.275727125 | 0.872822803 |
| 20245 | sp900546455 Erysipelatoclostridium | 0.900012997 | 4.52324E-06 | 0.245917799 | 0.228741025 | 0.84752415 |
| 22089 | sp900544435 Collinsella | -0.5813095 | 1.46242E-05 | 0.294825348 | 0.472076015 | 0.817347156 |
| 20342 | sp900556605 CAG-180 | 1.262443576 | 0.000132358 | 0.207459424 | 0.208701189 | 0.803325605 |
| 18450 | sp000432435 Gemmiger | 0.704922718 | 0.000320189 | 0.252410603 | 0.223383554 | 0.790158007 |
| 24119 | sp900540775 Collinsella | 0.558247536 | 0.000724913 | 0.319332789 | 0.257670224 | 0.789551547 |
| 20338 | sp900556415 UBA1191 | 1.329997563 | 1.417E-08 | 0.22478769 | 0.176302411 | 0.78820388 |
| 41454 | sp900545775 Erysipelatoclostridium | 0.527485948 | 0.004802531 | 0.311777737 | 0.331835578 | 0.786068121 |
| 22087 | sp003024675 | 0.586294711 | 7.14841E-06 | 0.242302436 | 0.442083679 | 0.775231838 |

FIG. 22A

| ID | Name | | | | | |
|---|---|---|---|---|---|---|
| 17550 | Blautia_A obeum Blautia_A | -0.484455077 | 8.47496E-06 | 0.42354067 | 0.228790157 | 0.762048074 |
| 17565 | sp900066335 UBA1191 | -0.558484888 | 5.75168E-09 | 0.314121668 | 0.188899522 | 0.745016911 |
| 41455 | sp900549125 Mediterraneibacter | -0.493202341 | 5.04077E-05 | 0.525586166 | 0.189076492 | 0.740788257 |
| 27982 | faecis SFFH01 | -0.462717508 | 1.73356E-05 | 0.313602187 | 0.231879699 | 0.719803166 |
| 36679 | sp900542445 CAG-103 | -0.535703067 | 0.001984982 | 0.417388206 | 0.140279458 | 0.707879466 |
| 18331 | sp000432375 Faecalibacterium | -0.571934314 | 0.000754308 | 0.336393046 | 0.136603601 | 0.701825313 |
| 22484 | prausnitzii_C Collinsella | -0.479016945 | 3.06261E-05 | 0.31595352 | 0.188434723 | 0.70134561 |
| 20182 | sp900541235 CAG-110 | -0.760291345 | 0.004809992 | 0.230115896 | 0.130482257 | 0.697327246 |
| 18346 | sp003525905 Gemmiger | -0.62350119 | 0.001411389 | 0.437870157 | 0.105312277 | 0.691004901 |
| 24117 | sp900539695 Anaerostipes | -0.432457995 | 0.005374636 | 0.345108547 | 0.216219172 | 0.687363322 |
| 15904 | hadrus_A | -0.627971973 | 1.19296E-05 | 0.245604921 | 0.132084757 | 0.665972642 |
| 21494 | Dorea longicatena_B Coprococcus_A | -0.385410696 | 2.29706E-07 | 0.38406015 | 0.266466165 | 0.66452268 |
| 20478 | sp900548825 Adlercreutzia | -0.478026952 | 5.47917E-06 | 0.368122817 | 0.127533339 | 0.654882227 |
| 15044 | equolifaciens Blautia_A | -0.392667932 | 0.02615541 | 0.296862679 | 0.279098272 | 0.642655213 |
| 17564 | sp900066205 | -0.458019688 | 8.98773E-08 | 0.256131237 | 0.170444293 | 0.639893534 |

FIG. 22B

| ID | Name | | | | | |
|---|---|---|---|---|---|---|
| 22496 | Faecalibacterium sp003449675 | -0.606358825 | 0.000145635 | 0.199652471 | 0.137781573 | 0.634023835 |
| 21507 | Dorea sp900066555 | -0.336185683 | 0.000706594 | 0.444101162 | 0.45140123 | 0.622192898 |
| 15903 | Anaerostipes hadrus | -0.409345581 | 0.010031655 | 0.229583049 | 0.232563226 | 0.613943954 |
| 36431 | Ruminococcus_A sp003011855 | -0.441901782 | 2.38832E-05 | 0.170006835 | 0.331784005 | 0.610168264 |
| 22491 | Faecalibacterium prausnitzii_J | -0.396428164 | 0.000471984 | 0.286782548 | 0.196624721 | 0.607631164 |
| 25241 | Holdemanella biformis | -0.334839714 | 0.02388383 | 0.353629528 | 0.353875598 | 0.601532002 |
| 20167 | Collinsella sp900540895 | -1.011271811 | 1.57579E-05 | 0.126073318 | 0.136788713 | 0.596441694 |
| 17226 | Bariatricus comes CAG-269 | -0.450065888 | 5.47917E-06 | 0.2567054 | 0.123718387 | 0.585076339 |
| 18491 | Collinsella sp003525075 | -0.612715179 | 0.002271221 | 0.225375407 | 0.090045682 | 0.583117596 |
| 20133 | Collinsella aerofaciens_I | -0.782783124 | 5.54961E-05 | 0.200083815 | 0.074763829 | 0.582996557 |
| 20339 | Collinsella sp900556445 | -0.981393783 | 4.35572E-05 | 0.129838002 | 0.113158704 | 0.577910572 |
| 21493 | Dorea longicatena | -0.640406177 | 5.53264E-07 | 0.173561176 | 0.106766917 | 0.576546693 |
| 24112 | Gemmiger formicilis | -0.342917632 | 0.027208755 | 0.26203691 | 0.283718387 | 0.575459842 |
| 22483 | Faecalibacterium prausnitzii_A | -0.415001316 | 0.000158913 | 0.221353383 | 0.170909091 | 0.575246048 |
| 21491 | Dorea formicigenerans | -0.347910807 | 0.000873722 | 0.226438824 | 0.416787423 | 0.568996182 |

FIG. 22C

| | | | | | | |
|---|---|---|---|---|---|---|
| 23215 | Fusicatenibacter saccharivorans | -0.385362276 | 0.000623803 | 0.193492823 | 0.264224197 | 0.564046545 |
| 22482 | Faecalibacterium prausnitzii | -0.449991333 | 0.001113189 | 0.274723172 | 0.101572112 | 0.559769899 |
| 17549 | Blautia_A massiliensis | -0.430872416 | 6.18598E-05 | 0.234805195 | 0.127464115 | 0.5535351 |
| 36429 | Ruminococcus_A sp000437095 | -0.358503524 | 0.00048673 | 0.22102529 | 0.238168148 | 0.548348206 |
| 22498 | Faecalibacterium sp900539945 | -0.57525261 | 0.000409712 | 0.180667215 | 0.095351382 | 0.545211287 |
| 17566 | Blautia_A sp900066355 | -0.321853078 | 0.000138546 | 0.270266576 | 0.406315789 | 0.535780025 |
| 24118 | Gemmiger sp900540595 | -0.315161406 | 0.015629719 | 0.301182583 | 0.353434959 | 0.535298991 |
| 22761 | Firm-11 sp900540045 | -0.337680999 | 0.021511012 | 0.242311978 | 0.223774599 | 0.535287994 |
| 24375 | Gordonibacter urolithinfaciens | -0.382471449 | 0.035371487 | 0.238047387 | 0.157330877 | 0.535155248 |
| 22489 | Faecalibacterium prausnitzii_H GCA-900066135 | -0.43118609 | 0.005860207 | 0.149204353 | 0.208399409 | 0.53433597 |
| 23770 | sp900543575 | 0.690679861 | 1.21236E-05 | 0.158719309 | 0.085935364 | 0.53051054 |
| 17558 | Blautia_A sp003474435 | -0.40883533 | 1.50789E-08 | 0.309993165 | 0.090690362 | 0.522675634 |
| 36078 | Romboutsia timonensis | 0.453408697 | 0.006780947 | 0.194524234 | 0.097152711 | 0.506832742 |
| 20147 | Collinsella sp003438495 KLE1615 | 0.719587069 | 0.005738458 | 0.129985796 | 0.088225653 | 0.501831518 |
| 25848 | sp900066985 | 0.331909554 | 0.006829856 | 0.296924129 | 0.153246753 | 0.50036059 |

FIG. 22D

| ID | Name | | | | | |
|---|---|---|---|---|---|---|
| 36508 | Ruminococcus_H sp003531055 | -0.461545663 | 0.008719454 | 0.370280246 | 0.044894053 | 0.491230333 |
| 30995 | Oscillibacter sp001916835 CAG-110 | -0.684957829 | 0.001552151 | 0.166013751 | 0.054761288 | 0.483764849 |
| 18338 | sp000434635 Eubacterium_F | -0.483443329 | 0.006562471 | 0.155466106 | 0.099729324 | 0.481958337 |
| 22173 | sp003491505 Blautia_A | -0.401797355 | 0.01479283 | 0.365251984 | 0.064142612 | 0.48058002 |
| 17555 | sp000436615 CAG-170 | -0.305600239 | 8.70974E-06 | 0.352371839 | 0.157593985 | 0.471210441 |
| 18438 | sp900556635 Agathobaculum butyriciproducens CAG-273 | -0.334128273 | 0.000342693 | 0.300617229 | 0.110019214 | 0.468311625 |
| 15191 | sp003507395 | -0.384176023 | 0.001916036 | 0.137252221 | 0.190211893 | 0.464964482 |
| 18510 | Eubacterium_G ventriosum | -0.385470975 | 0.01823363 | 0.247380303 | 0.084042591 | 0.46014609 |
| 22186 | Collinsella sp900554905 | -0.281514719 | 0.017484112 | 0.338673958 | 0.253233083 | 0.459303079 |
| 20324 | Blautia_A sp900548245 CAG-103 | -0.670904858 | 1.53377E-05 | 0.179752547 | 0.034520473 | 0.457634779 |
| 17575 | sp900543625 | -0.334220851 | 4.18253E-05 | 0.169952153 | 0.151524265 | 0.433053989 |
| 18336 | CAG-83 sp001916855 CAG-170 | -0.377770694 | 0.006248964 | 0.279997832 | 0.059981952 | 0.424991606 |
| 18772 | sp000432135 | -0.441962262 | 0.016205078 | 0.246033669 | 0.034725887 | 0.421533773 |
| 18426 | Faecalibacterium prausnitzii_E | -0.459594369 | 0.018104888 | 0.306765384 | 0.009670626 | 0.413706316 |
| 22486 | | -0.339778458 | 0.007696104 | 0.150157211 | 0.136349966 | 0.408913318 |

FIG. 22E

| | | | | | | |
|---|---|---|---|---|---|---|
| 27983 | Mediterraneibacter lactaris | -0.31098751 | 0.010412394 | 0.137990431 | 0.303021189 | 0.406848039 |
| 25246 | Holdemanella sp900551285 | 0.247980361 | 0.000213266 | 0.345399863 | 0.318831852 | 0.406694539 |
| 18771 | CAG-83 sp000435975 | -0.60175582 | 0.00210611 | 0.354938031 | -0.035352393 | 0.392187179 |
| 19959 | Clostridium sp900540255 | 0.467505001 | 0.018269746 | 0.128662 | 0.064234552 | 0.389619287 |
| 20477 | Coprococcus_A catus | 0.305358264 | 0.000353632 | 0.376814764 | 0.078386876 | 0.387298031 |
| 15831 | Anaerobutyricum hallii | 0.546910167 | 0.000145274 | 0.043581681 | 0.230485304 | 0.386204402 |
| 36437 | Ruminococcus_C sp000433635 | 0.559529185 | 0.000994467 | 0.162530775 | 0.011664154 | 0.378114267 |
| 22490 | Faecalibacterium prausnitzii_I | 0.375109033 | 0.003992532 | 0.165144638 | 0.06537431 | 0.372004682 |
| 36440 | Ruminococcus_C sp000980705 | 0.538279508 | 0.000170522 | 0.424974025 | -0.047711489 | 0.368527483 |
| 24113 | Gemmiger qucibialis | 0.389883576 | 0.004749021 | 0.194477102 | 0.037265892 | 0.364368231 |
| 17568 | Blautia_A sp900120195 | 0.245515783 | 0.001549982 | 0.218427888 | 0.353438141 | 0.362375762 |
| 36447 | Ruminococcus_D bicirculans | 0.457673602 | 0.016193062 | 0.278961039 | -0.03898838 | 0.327942707 |
| 17551 | Blautia_A obeum_B TF01-11 | 0.249277807 | 0.002661494 | 0.146657553 | 0.356773753 | 0.326111371 |
| 40012 | Collinsella sp003529475 | 0.343984421 | 0.003568697 | 0.127163363 | 0.067012987 | 0.318279389 |
| 20345 | Collinsella sp900557455 | 1.045819615 | 1.57389E-05 | 0.05954084 | 0.017707526 | 0.312200337 |

FIG. 22F

| ID | Name | | | | | |
|---|---|---|---|---|---|---|
| 21661 | ER4 sp000765235 CAG-536 | 0.306845262 | 0.010447633 | 0.25897471 | 0.027313739 | 0.306036075 |
| 18679 | sp000434355 AM51-8 | -0.276540759 | 0.018864443 | 0.196993828 | 0.085072352 | 0.303008745 |
| 14374 | sp003478275 Collinsella | -0.237416575 | 0.0419906 | 0.207305736 | 0.179471756 | 0.302120932 |
| 20321 | sp900554645 Faecalibacterium | 0.656127178 | 0.001918999 | 0.230333209 | -0.075770589 | 0.296538101 |
| 22488 | prausnitzii_G | -0.30497324 | 0.040131373 | 0.10406015 | 0.098783322 | 0.278380498 |
| 18241 | Butyrivibrio_A crossotus | -0.337626428 | 0.035374324 | 0.046879486 | 0.139927542 | 0.266126304 |
| 18783 | CAG-83 sp900545585 Bifidobacterium | -0.417205808 | 0.001033024 | 0.002378739 | 0.193170012 | 0.255139073 |
| 17413 | sp002742445 Eisenbergiella | -0.461837094 | 0.036506374 | 0.143694233 | -0.053885337 | 0.255017931 |
| 21756 | sp900066775 UBA7182 | -0.244837824 | 0.00316207 | 0.122132604 | 0.147942584 | 0.243569697 |
| 43535 | sp003481535 Faecalibacterium | 0.235289786 | 0.001748391 | 0.127108681 | 0.153656869 | 0.238347826 |
| 22497 | sp900539885 | -0.299042782 | 0.037045659 | 0.135229906 | 0.022966664 | 0.233700423 |
| 40827 | Tidjanibacter inops Gemmiger | 0.244968468 | 0.032431693 | 0.325550337 | 0.013070648 | 0.225116408 |
| 24122 | sp900554145 | -0.503620017 | 0.002296215 | 0.264743677 | -0.118441558 | 0.218821111 |
| 18843 | CAG-95 sp900066375 Blautia_A | 0.206949448 | 0.015680305 | 0.18151743 | 0.184771018 | 0.218794458 |
| 17563 | sp900066165 | -0.28156557 | 0.011137706 | 0.16177717 | -0.013643199 | 0.199589531 |

FIG. 22G

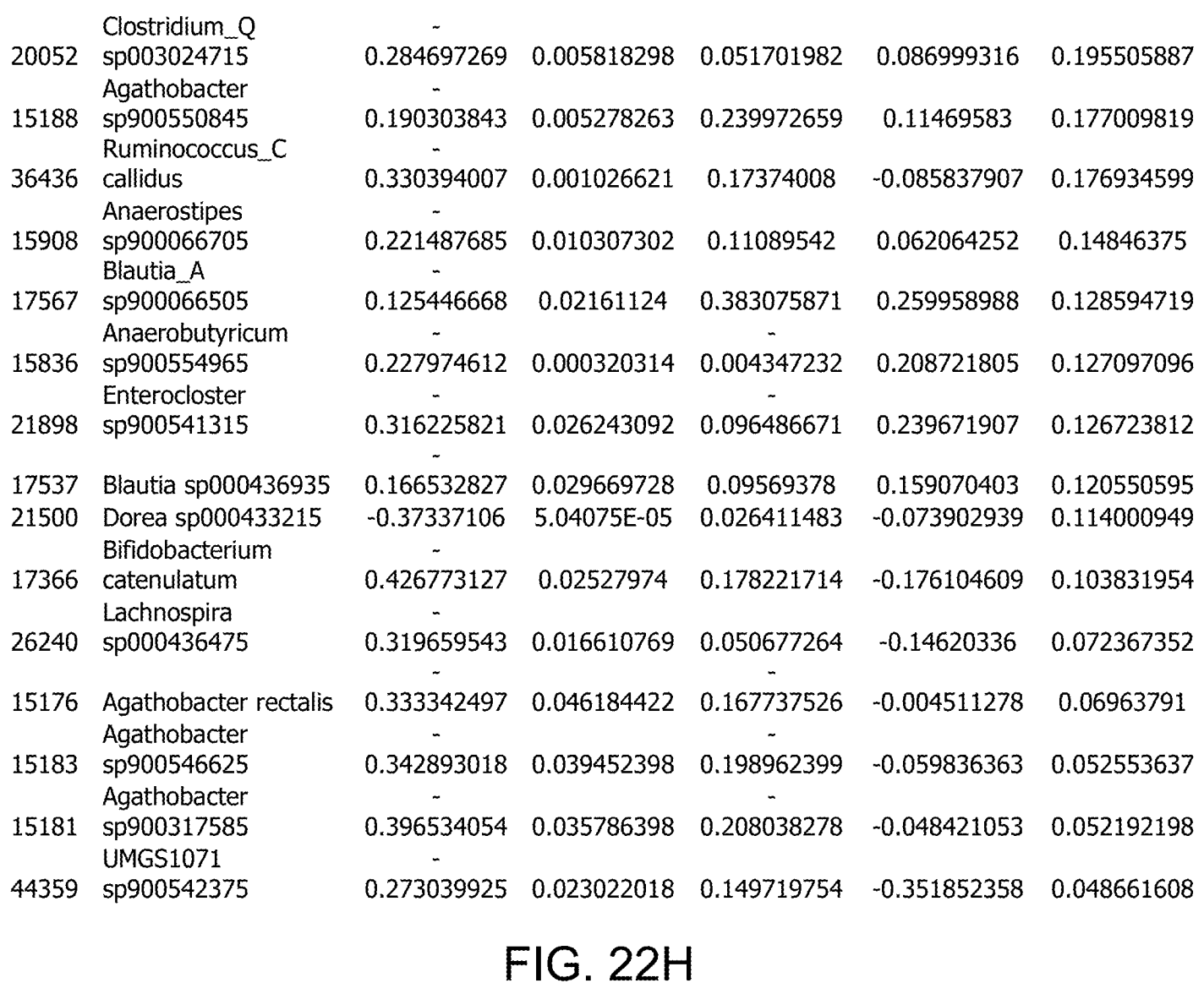

| 20052 | Clostridium_Q sp003024715 | -0.284697269 | 0.005818298 | 0.051701982 | 0.086999316 | 0.195505887 |
|---|---|---|---|---|---|---|
| 15188 | Agathobacter sp900550845 | -0.190303843 | 0.005278263 | 0.239972659 | 0.11469583 | 0.177009819 |
| 36436 | Ruminococcus_C callidus | -0.330394007 | 0.001026621 | 0.17374008 | -0.085837907 | 0.176934599 |
| 15908 | Anaerostipes sp900066705 | -0.221487685 | 0.010307302 | 0.11089542 | 0.062064252 | 0.14846375 |
| 17567 | Blautia_A sp900066505 | -0.125446668 | 0.02161124 | 0.383075871 | 0.259958988 | 0.128594719 |
| 15836 | Anaerobutyricum sp900554965 | -0.227974612 | 0.000320314 | -0.004347232 | 0.208721805 | 0.127097096 |
| 21898 | Enterocloster sp900541315 | -0.316225821 | 0.026243092 | 0.096486671 | 0.239671907 | 0.126723812 |
| 17537 | Blautia sp000436935 | -0.166532827 | 0.029669728 | 0.09569378 | 0.159070403 | 0.120550595 |
| 21500 | Dorea sp000433215 | -0.37337106 | 5.04075E-05 | 0.026411483 | -0.073902939 | 0.114000949 |
| 17366 | Bifidobacterium catenulatum | -0.426773127 | 0.02527974 | 0.178221714 | -0.176104609 | 0.103831954 |
| 26240 | Lachnospira sp000436475 | -0.319659543 | 0.016610769 | 0.050677264 | -0.14620336 | 0.072367352 |
| 15176 | Agathobacter rectalis | -0.333342497 | 0.046184422 | 0.167737526 | -0.004511278 | 0.06963791 |
| 15183 | Agathobacter sp900546625 | -0.342893018 | 0.039452398 | 0.198962399 | -0.059836363 | 0.052553637 |
| 15181 | Agathobacter sp900317585 | -0.396534054 | 0.035786398 | 0.208038278 | -0.048421053 | 0.052192198 |
| 44359 | UMGS1071 sp900542375 | -0.273039925 | 0.023022018 | 0.149719754 | -0.351852358 | 0.048661608 |

FIG. 22H

|       |                     |              |             |              |              |
|-------|---------------------|--------------|-------------|--------------|--------------|
| 18243 | Butyrivibrio_A sp900543865 | -0.166120606 | 0.026561636 | 0.08962406   | -0.071032126 | 0.047485148 |
| 17560 | Blautia_A sp003478765 | -0.200589285 | 0.006009085 | -0.052303486 | 0.019767601  | 0.046072254 |
| 33438 | Prevotella sp900551275 | -0.321550843 | 0.028458671 | -0.246399497 | -0.135872426 | 0.020117849 |

FIG. 22I

| taxID | Organism Name | LDA Score (log10) | p-value (Kruskal-Wallis test) | CD3+ Correlation (Spearman, if significant) | CD3+CD56+ Correlation (Spearman, if significant) | Combined Score |
|---|---|---|---|---|---|---|
| 22085 | Erysipelatoclostridium sp000752095 | -2.967691967 | 4.21529E-11 | 0.384087491 | 0.427751196 | 0.933003475 |
| 17550 | Blautia_A obeum | -3.289660505 | 5.87805E-05 | 0.426028708 | 0.231606288 | 0.917997598 |
| 21494 | Dorea longicatena_B | -3.015262589 | 4.84949E-07 | 0.383239918 | 0.264716336 | 0.90412145 |
| 27982 | Mediterraneibacter faecis | -3.120510014 | 3.79965E-09 | 0.31696514 | 0.235980861 | 0.859974822 |
| 22484 | Faecalibacterium prausnitzii_C | -3.144268803 | 3.49956E-08 | 0.319371155 | 0.190293917 | 0.84052139 |
| 18480 | CAG-269 sp000431335 | -3.049943732 | 6.96986E-06 | 0.430202715 | 0.147448511 | 0.833094421 |
| 18450 | CAG-180 sp000432435 | -3.285075841 | 0.001074071 | 0.252410603 | 0.222383554 | 0.813805755 |
| 15903 | Anaerostipes hadrus | -3.4516105 | 4.07263E-05 | 0.230102529 | 0.233656869 | 0.805092345 |
| 25241 | Holdemanella biformis | -2.52659905 | 0.001287488 | 0.3534108 | 0.353957621 | 0.802928626 |
| 20131 | Collinsella aerofaciens_G | -2.506995421 | 9.18498E-06 | 0.380257045 | 0.314656825 | 0.797299601 |
| 17555 | Blautia_A sp000436615 | -2.774549776 | 1.50755E-07 | 0.354668489 | 0.154012303 | 0.784852861 |
| 21491 | Dorea formicigenerans | -2.808696877 | 5.93297E-06 | 0.224114833 | 0.413205742 | 0.784369725 |
| 17565 | Blautia_A sp900066335 | -2.755947293 | 9.24086E-11 | 0.312891319 | 0.187942584 | 0.780615286 |
| 15193 | Agathobaculum sp003481705 | -2.724595276 | 2.55177E-06 | 0.317949419 | 0.184196856 | 0.774596646 |
| 24119 | Gemmiger sp900540775 | -2.569664955 | 1.80894E-07 | 0.315942032 | 0.256713155 | 0.771725816 |
| 17566 | Blautia_A sp900066355 | -2.558054848 | 5.85243E-06 | 0.268051948 | 0.405878332 | 0.76999358 |
| 23215 | Fusicatenibacter saccharivorans | -3.441594559 | 2.62501E-06 | 0.191606288 | 0.263212577 | 0.765280355 |

FIG. 23A

| ID | Name | | | | | |
|---|---|---|---|---|---|---|
| 18331 | CAG-103 sp000432375 | -2.877834007 | 5.58314E-07 | 0.336393046 | 0.136603601 | 0.761503609 |
| 41455 | UBA1191 sp900549125 UBA11774 | -2.508742699 | 8.12599E-05 | 0.52460182 | 0.189185864 | 0.759018696 |
| 41419 | Collinsella sp003507655 | -2.483369175 | 0.045016928 | 0.340323727 | 0.258599005 | 0.744606006 |
| 20342 | Ruminococcus_E sp900556605 | -3.125825313 | 9.53489E-05 | 0.206640988 | 0.205624998 | 0.742646355 |
| 36477 | sp003526955 | -3.3777780855 | 0.014413721 | 0.293615858 | 0.116773753 | 0.737523389 |
| 22491 | Faecalibacterium prausnitzii_J | -2.613162989 | 1.05262E-06 | 0.290309572 | 0.195339681 | 0.737408275 |
| 36087 | Roseburia intestinalis | -3.094074046 | 0.027985782 | 0.264333561 | 0.13367054 | 0.731210193 |
| 17226 | Bariatricus comes | -3.176907533 | 4.00993E-10 | 0.254354067 | 0.121230349 | 0.718545419 |
| 22089 | Erysipelatoclostridium sp900544435 | -2.42398533 | 1.11329E-06 | 0.295973751 | 0.472376787 | 0.71760167 |
| 15904 | Anaerostipes hadrus_A | -3.041521259 | 7.21487E-09 | 0.245085441 | 0.134572796 | 0.710790169 |
| 17549 | Blautia_A massiliensis | -3.354829469 | 9.06785E-06 | 0.233875598 | 0.123499658 | 0.710130688 |
| 25246 | Holdemanella sp900551285 | -2.393726421 | 5.39072E-06 | 0.342911825 | 0.316855776 | 0.707743515 |
| 25848 | KLE1615 sp900066985 | -2.608063424 | 1.08359E-05 | 0.295857826 | 0.152289815 | 0.704986253 |
| 22482 | Faecalibacterium prausnitzii | -3.190928563 | 2.18288E-06 | 0.278605605 | 0.101435407 | 0.692592322 |
| 26235 | Lachnospira eligens_B | -2.565016151 | 0.015486583 | 0.231115729 | 0.213849719 | 0.690785117 |
| 24112 | Gemmiger formicilis | -2.445041901 | 0.003337702 | 0.261845523 | 0.284784689 | 0.68822202 |
| 17564 | Blautia_A sp900066205 | -2.578521912 | 3.49087E-11 | 0.254381408 | 0.167190704 | 0.683856949 |
| 36431 | Ruminococcus_A sp003011855 | -2.66427386 | 5.49451E-08 | 0.168284347 | 0.327983595 | 0.675879131 |
| 36679 | SFFH01 sp900542445 | -2.410588283 | 3.30022E-06 | 0.415471446 | 0.139978253 | 0.656251621 |
| 36473 | Ruminococcus_E sp003438075 | -2.364645097 | 0.011641627 | 0.328557758 | 0.212604238 | 0.65208275 |

FIG. 23B

| | | | | | | |
|---|---|---|---|---|---|---|
| 22483 | Faecalibacterium prausnitzii_A | -2.53716654 | 1.4841E-07 | 0.226001367 | 0.172057416 | 0.642573467 |
| 27983 | Mediterraneibacter lactaris | -2.829007595 | 3.28993E-05 | 0.137252221 | 0.303021189 | 0.632406282 |
| 36508 | Ruminococcus_H sp003531055 | -2.957796111 | 0.000800746 | 0.367136022 | 0.040410116 | 0.630182245 |
| 18510 | CAG-273 sp003507395 | -3.106479384 | 7.55801E-06 | 0.249745215 | 0.084219077 | 0.630167325 |
| 36429 | Ruminococcus_A sp000437095 | -2.425184014 | 7.2307E-05 | 0.222064252 | 0.240109364 | 0.62234784 |
| 22489 | Faecalibacterium prausnitzii_H | -2.773892132 | 3.98763E-06 | 0.148220047 | 0.207141685 | 0.615765224 |
| 19952 | Clostridium sp001916075 | -2.472492067 | 9.76605E-06 | 0.282054445 | 0.119328095 | 0.612637076 |
| 18491 | CAG-269 sp003525075 | -2.948156936 | 1.10382E-06 | 0.226035284 | 0.090733054 | 0.612525502 |
| 21493 | Dorea longicatena | -3.316037731 | 5.28875E-09 | 0.174299385 | 0.108243336 | 0.603240279 |
| 17575 | Blautia_A sp900548245 | -2.618917472 | 1.33648E-07 | 0.173533835 | 0.153602187 | 0.593155857 |
| 22087 | Erysipelatoclostridium sp003024675 | -2.257831924 | 2.64721E-10 | 0.241946953 | 0.445419747 | 0.583246895 |
| 18843 | CAG-95 sp900066375 | -2.501084076 | 0.001406879 | 0.179767601 | 0.183130554 | 0.582741949 |
| 20478 | Coprococcus_A sp900548825 | -2.31291869 | 1.03016E-08 | 0.367712698 | 0.129419887 | 0.578695276 |
| 41454 | UBA1191 sp900545775 | -2.214471713 | 9.43643E-06 | 0.311386092 | 0.332031401 | 0.574988123 |
| 22498 | Faecalibacterium sp900539945 | -2.931890775 | 8.29722E-07 | 0.180257043 | 0.095925623 | 0.574071508 |
| 18346 | CAG-110 sp003525905 | -2.331705455 | 0.001757398 | 0.437322511 | 0.104901543 | 0.56187187 |
| 18679 | CAG-536 sp000434355 | -2.822119323 | 0.004566211 | 0.198688986 | 0.081709376 | 0.559415938 |
| 36440 | Ruminococcus_C sp000980705 | -3.204071211 | 1.21039E-08 | 0.422923388 | -0.049051239 | 0.554742519 |
| 18651 | CAG-492 sp900553225 | -2.533889973 | 0.000269275 | 0.141621015 | 0.199061498 | 0.544398237 |

FIG. 23C

| | | | | | | |
|---|---|---|---|---|---|---|
| 22237 | Eubacterium_R sp000433975 | -2.420858256 | 0.002099148 | 0.358906911 | 0.074469029 | 0.54346404 |
| 24118 | Gemmiger sp900540595 | -2.161365685 | 1.26206E-05 | 0.298967804 | 0.352970129 | 0.5414718 |
| 18338 | CAG-110 sp000434635 | -2.744368254 | 6.4493E-05 | 0.159251897 | 0.103128245 | 0.529954529 |
| 24113 | Gemmiger qucibialis | -3.160984156 | 2.99843E-05 | 0.192754614 | 0.033848257 | 0.52689114 |
| 36447 | Ruminococcus_D bicirculans | -3.3907133 | 6.09725E-06 | 0.277265892 | -0.039398496 | 0.524392805 |
| 15188 | Agathobacter sp900550845 | -2.363419901 | 0.0004116 | 0.244319891 | 0.115762133 | 0.518014123 |
| 22173 | Eubacterium_F sp003491505 | -2.368584804 | 3.51184E-05 | 0.364240357 | 0.06474412 | 0.511011168 |
| 20469 | Coprococcus eutactus_A | -2.963346355 | 0.004900284 | 0.174053315 | 0.062365003 | 0.50479743 |
| 36078 | Romboutsia timonensis UMGS1375 | -2.473608638 | 0.000416035 | 0.19427807 | 0.095894539 | 0.504519428 |
| 44382 | sp900066615 | -2.314797115 | 0.002049082 | 0.150539986 | 0.265126452 | 0.499146036 |
| 18771 | CAG-83 sp000435975 | -2.582268214 | 0.00441888 | 0.355742124 | -0.034076935 | 0.49662929 |
| 20477 | Coprococcus_A catus | -2.293793385 | 1.01476E-06 | 0.37520164 | 0.076746411 | 0.494955324 |
| 26245 | Lachnospira sp003451515 | -2.561362198 | 0.002326761 | 0.054409121 | 0.334041928 | 0.491917241 |
| 22490 | Faecalibacterium prausnitzii_I | -2.655729915 | 1.1944E-05 | 0.166183628 | 0.064991524 | 0.483989413 |
| 15831 | Anaerobutyricum hallii | -3.095278178 | 0.000147461 | 0.044702666 | 0.230047847 | 0.483724111 |
| 15191 | Agathobaculum butyriciproducens | -2.400499748 | 9.30926E-05 | 0.139302802 | 0.190239234 | 0.482765504 |
| 26247 | Lachnospira sp900316325 | -2.631006094 | 0.014181707 | 0.220193797 | 0.002668767 | 0.466855904 |
| 20287 | Collinsella sp900551365 | -2.10822971 | 5.77069E-06 | 0.252376813 | 0.276058728 | 0.464349727 |

FIG. 23D

| ID | Name | | | | | |
|---|---|---|---|---|---|---|
| 20133 | Collinsella aerofaciens_I | -2.42591014 | 4.45271E-07 | 0.199205533 | 0.072952371 | 0.461724509 |
| 22488 | Faecalibacterium prausnitzii_G | -2.982346002 | 1.81753E-05 | 0.102228298 | 0.098646617 | 0.458873621 |
| 22496 | Faecalibacterium sp0034449675 | -2.236127116 | 1.90745E-07 | 0.198447105 | 0.136466628 | 0.451302759 |
| 18426 | CAG-170 sp000432135 | -2.412070388 | 0.000193773 | 0.306847454 | 0.009068776 | 0.45078291 |
| 17230 | Barnesiella intestinihominis | -2.456874494 | 0.001109479 | 0.236426811 | 0.016301525 | 0.448136981 |
| 22486 | Faecalibacterium prausnitzii_E | -2.314520852 | 6.15296E-06 | 0.154488722 | 0.135994532 | 0.444168325 |
| 18509 | CAG-273 sp000438355 UMGS1241 | -2.764619868 | 0.030543876 | 0.177058971 | -0.005465462 | 0.439402398 |
| 44369 | sp900549955 | -2.486506014 | 0.000229158 | 0.065314427 | 0.186089693 | 0.438140625 |
| 40005 | TF01-11 sp001414325 | -2.666552655 | 0.000363497 | 0.05265892 | 0.129186603 | 0.433883416 |
| 18438 | CAG-170 sp900556635 | -2.156686973 | 2.45053E-05 | 0.299468896 | 0.110554413 | 0.433166763 |
| 21661 | ER4 sp000765235 | -2.346730543 | 0.000662819 | 0.261353383 | 0.029145591 | 0.430716271 |
| 19959 | Clostridium sp900540255 | -2.642884273 | 0.000134947 | 0.130012276 | 0.067734246 | 0.430222814 |
| 20167 | Collinsella sp900540895 | -2.394472961 | 9.35633E-09 | 0.125961699 | 0.136677094 | 0.429977797 |
| 21892 | Enterocloster sp000431375 | -2.389931687 | 0.008571079 | 0.106001367 | 0.181490089 | 0.423103983 |
| 19946 | Clostridium saudiense | -2.17730076 | 0.023070525 | 0.180295893 | 0.145409236 | 0.42063356 |
| 17563 | Blautia_A sp900066165 | -2.880481701 | 0.002983386 | 0.160273411 | -0.014654819 | 0.419635816 |
| 15836 | Anaerobutyricum sp900554965 | -2.703705239 | 0.00091644 | -0.008311688 | 0.208667122 | 0.409027199 |
| 40012 | TF01-11 sp003529475 | -2.5555399 | 2.41121E-06 | 0.12910458 | 0.068680793 | 0.408483763 |
| 25571 | Intestinibacter sp900540355 | -2.278611974 | 0.049771066 | 0.144977318 | 0.119261934 | 0.401737418 |
| 18475 | CAG-245 sp000435175 | -2.221651141 | 0.043537205 | 0.207435933 | 0.086332757 | 0.399727886 |

FIG. 23E

| | | | | | | |
|---|---|---|---|---|---|---|
| 17558 | Blautia_A sp003474435 Acetatifactor | -2.112658319 | 1.13586E-09 | 0.310348599 | 0.093342447 | 0.392754461 |
| 14550 | sp900066365 | -2.289788277 | 0.003507139 | 0.141982228 | 0.110457963 | 0.384791989 |
| 36088 | Roseburia inulinivorans | -2.430352103 | 0.026509658 | 0.00481203 | 0.263595352 | 0.384609167 |
| 18783 | CAG-83 sp900545585 Collinsella | -2.515571065 | 4.66505E-06 | 0.000738229 | 0.195193307 | 0.381044897 |
| 20339 | sp900556445 CAG-1427 | -2.313958981 | 1.12521E-05 | 0.129838002 | 0.113158704 | 0.380887049 |
| 18401 | sp000435675 | -2.058609363 | 0.000239442 | 0.363662956 | 0.257553779 | 0.379400819 |
| 17551 | Blautia_A obeum_B Coprococcus | -2.101051135 | 0.001175607 | 0.14479836 | 0.357429938 | 0.363891203 |
| 20473 | sp900066115 Faecalibacterium | -2.257398249 | 1.14391E-08 | 0.247655502 | -0.00530417 | 0.360154147 |
| 22497 | sp900539885 Butyrivibrio_A | -2.450209093 | 0.001140348 | 0.136542287 | 0.020150514 | 0.35665179 |
| 18241 | crossotus | -2.372773021 | 0.001261777 | 0.048465377 | 0.137083875 | 0.35177222 |
| 15043 | Adlercreutzia celatus_A Collinsella | -2.074392098 | 0.016455086 | 0.215161666 | 0.269697177 | 0.349470942 |
| 20324 | sp900554905 Gemmiger | -2.215978345 | 1.04126E-08 | 0.184947707 | 0.035586848 | 0.338431327 |
| 24117 | sp900539695 Collinsella | -2.053406267 | 4.66989E-05 | 0.350795647 | 0.218652595 | 0.336412223 |
| 20272 | sp900549455 Bifidobacterium | -2.49443119 | 1.41646E-08 | 0.123269412 | -0.001763922 | 0.335585654 |
| 17413 | sp002742445 Collinsella | -2.508492149 | 0.001264334 | 0.143804767 | -0.054603808 | 0.325903198 |
| 20185 | sp900541475 | -2.458930407 | 1.78087E-07 | 0.04814088 | 0.08533067 | 0.324953994 |
| 17559 | Blautia_A sp003477525 GCA-900066135 | -2.260514561 | 0.003400348 | 0.065782638 | 0.116336295 | 0.324025549 |
| 23770 | sp900543575 | -2.136017831 | 2.91177E-08 | 0.161453492 | 0.085908022 | 0.318648788 |
| 40011 | TF01-11 sp003524945 | -2.992990905 | 0.01064601 | -0.09129249 | 0.118838816 | 0.310808081 |

FIG. 23F

| 18482 | CAG-269 sp000437215 | -2.725716074 | 0.028711054 | 0.213232776 | -0.139048151 | 0.306049811 |
|---|---|---|---|---|---|---|
| 24122 | Gemmiger sp900554145 | -2.361546343 | 4.05221E-06 | 0.26608339 | -0.119179768 | 0.30291519 |
| 22199 | Eubacterium_I ramulus | -2.449933112 | 0.000781474 | 0.051866029 | 0.033738893 | 0.301069091 |
| 43535 | UBA7182 sp003481535 | -2.095759324 | 1.84717E-07 | 0.128475735 | 0.154231032 | 0.290875217 |
| 17358 | Bifidobacterium bifidum | -2.906928906 | 0.003955133 | 0.098498027 | -0.077572157 | 0.288725315 |
| 36437 | Ruminococcus_C sp000433635 | -2.144306056 | 8.48213E-05 | 0.162530775 | 0.011664154 | 0.276089048 |
| 30995 | Oscillibacter sp001916835 | -2.103141573 | 0.000287892 | 0.163522714 | 0.053958621 | 0.273650234 |
| 29933 | Negativibacillus sp000435195 | -2.171994964 | 0.042201514 | 0.09082289 | 0.078892358 | 0.272593874 |
| 21907 | Enterococcus faecalis | -2.552683836 | 0.000973238 | 0.202005059 | -0.14148588 | 0.270739436 |
| 14374 | AM51-8 sp003478275 | -2.047472027 | 0.001001971 | 0.204489528 | 0.178596817 | 0.26719741 |
| 22499 | Faecalibacterium sp900540455 | -2.404699514 | 0.000272278 | -0.095969815 | 0.185377591 | 0.266952373 |
| 15198 | Agathobaculum sp900625105 | -2.459290942 | 0.006875346 | 0.123158737 | -0.080561043 | 0.258486409 |
| 40350 | Terrisporobacter sp900557165 | -2.27319203 | 0.020195614 | 0.133027765 | -0.062257541 | 0.250513551 |
| 20052 | Clostridium_Q sp003024715 | -2.134197883 | 5.46071E-05 | 0.051619959 | 0.087546138 | 0.240262401 |
| 37771 | Sellimonas sp002161525 | -2.515380678 | 0.030776019 | -0.052905351 | 0.026534699 | 0.23556001 |
| 17344 | Bifidobacterium adolescentis | -3.892164183 | 0.047224091 | 0.113834482 | -0.143821151 | 0.23380926 |
| 44737 | Veillonella dispar_A | -2.585904272 | 0.011756073 | 0.109279139 | -0.135133467 | 0.233318713 |
| 36096 | Roseburia sp900552665 | -2.243229204 | 0.023110617 | -0.076062884 | 0.117429938 | 0.223072802 |

FIG. 23G

| 18243 | Butyrivibrio_A sp900543865 | -2.299929059 | 0.000757328 | 0.089760766 | -0.073656869 | 0.222437972 |
| 36438 | Ruminococcus_C sp000437175 | -2.50386582 | 0.002158294 | 0.186846514 | -0.148521542 | 0.220778128 |
| 28004 | Megasphaera sp000417505 | -2.705068629 | 0.048859902 | -0.151339443 | 0.064262161 | 0.220310174 |
| 17562 | Blautia_A sp900066145 | -2.063120078 | 0.000228185 | 0.111524265 | 0.1184689 | 0.219501554 |
| 23216 | Fusicatenibacter sp900543115 | -2.624764443 | 0.006842543 | -0.027378903 | -0.072290151 | 0.217181681 |
| 17560 | Blautia_A sp003478765 | -2.332602676 | 2.52783E-06 | -0.051674641 | 0.01848257 | 0.204732928 |
| 17200 | Bacteroides stercoris | -3.051360196 | 0.042749137 | -0.203909774 | 0.132194122 | 0.203567225 |
| 30848 | Odoribacter laneus | -2.428035315 | 0.028301766 | -0.147324349 | 0.064688808 | 0.199038588 |
| 21500 | Dorea sp000433215 | -2.337152844 | 1.97115E-08 | 0.025481887 | -0.075816815 | 0.198012598 |
| 17538 | Blautia sp001304935 | -2.762516361 | 0.000214771 | -0.025126452 | -0.122241969 | 0.194896308 |
| 15176 | Agathobacter rectalis | -3.419214211 | 0.000310178 | -0.166425154 | -0.009159262 | 0.190427187 |
| 17404 | Bifidobacterium ruminantium | -2.668408291 | 0.008554023 | 0.163875283 | -0.200022214 | 0.189017092 |
| 32723 | Phocaeicola sp900553715 | -2.614124018 | 0.032610596 | -0.197101846 | 0.029583049 | 0.173401327 |
| 26240 | Lachnospira sp000436475 | -2.556181043 | 0.000628363 | 0.050595174 | -0.14565609 | 0.16648183 |
| 15186 | Agathobacter sp900549895 | -2.340438615 | 0.034866603 | -0.113878712 | -0.047738831 | 0.157306493 |
| 17366 | Bifidobacterium catenulatum | -2.207648583 | 0.01140381 | 0.180256334 | -0.174509907 | 0.144712731 |
| 18511 | CAG-273 sp003534295 | -2.707584768 | 0.015931923 | 0.076683178 | -0.220151383 | 0.137278549 |
| 44517 | UMGS743 sp900545085 | -2.140804161 | 0.004585474 | 0.008461849 | -0.138095081 | 0.121696456 |
| 15183 | Agathobacter sp900546625 | -2.451778 | 0.000176787 | -0.198743669 | -0.060273823 | 0.120809894 |
| 21409 | Dialister sp900555245 | -2.634357436 | 0.003337702 | 0.089405332 | -0.236336295 | 0.11798386 |

FIG. 23H

| | | | | | |
|---|---|---|---|---|---|
| 15181 | Agathobacter sp900317585 | -2.821229905 | 0.000142396 | -0.205960355 | -0.052467532 | 0.115253917 |
| 33197 | Prevotella copri_A Collinsella | -2.654311623 | 0.028379146 | -0.162012479 | -0.142358371 | 0.111861885 |
| 20321 | sp900554645 Prevotella | -2.004247169 | 0.000781585 | 0.233644378 | -0.076294857 | 0.076731109 |
| 33438 | sp900551275 UMGS1071 | -2.635025289 | 0.010587212 | -0.245989378 | -0.131771236 | 0.068055318 |
| 44359 | sp900542375 Collinsella | -2.098824301 | 0.0009749 | 0.150868079 | -0.350731374 | 0.064952435 |
| 20345 | sp900557455 | -2.001513113 | 2.54488E-07 | 0.059770064 | 0.015386637 | 0 |

COMPOSITIONS FOR MODULATING GUT MICROFLORA POPULATIONS, ENHANCING DRUG POTENCY AND TREATING CANCER, AND METHODS FOR MAKING AND USING SAME

RELATED APPLICATIONS

This national phase application claims benefit of priority under 35 U.S.C. § 371 to Patent Convention Treaty (PCT) International Application PCT/US2020/065693, filed Dec. 17, 2020, now pending, which claims the benefit of priority under 35 U.S.C. § 119 (e) of U.S. Provisional Patent Application Ser. No. (USSN) 62/951,673, Dec. 20, 2019. The aforementioned application is applications are expressly incorporated herein by reference in their entirety and for all purposes. All publications, patents, patent applications cited herein are hereby expressly incorporated by reference for all purposes.

TECHNICAL FIELD

This invention generally relates to microbiology, pharmacology and cancer therapies. In alternative embodiments, provided are compositions, including products of manufacture and kits, and methods, comprising combinations of microbes, such as non-pathogenic, live bacteria and/or bacterial spores, for the control, amelioration, prevention, and treatment of a disease or condition, for example, a cancer. In alternative embodiment, these non-pathogenic, live bacteria and/or bacterial spores are administered to an individual in need thereof, thereby resulting in a modification or modulation of the individual's gut microfloral population(s). In alternative embodiments, by modulating or modifying the individual's gut microbial population(s) using compositions, products of manufacture and methods as provided herein, the pharmacodynamics of a drug administered to the individual is altered, for example, the pharmacodynamics of the drug is enhanced, e.g., the individual's ability to absorb a drug is modified (e.g., accelerated or slowed, or enhanced), or the dose efficacy of a drug is increased (e.g., resulting in the requirement for a lower dose of drug to provide an intended effect), which can result in lowering the effective toxicity of the drug. For example, in alternative embodiments, the modulating or modifying of the individual's gut microbial population(s) increases the dose efficacy of a cancer drug, thereby controlling, ameliorating, preventing and/or treating of that cancer. In alternative embodiments, the amount, identity, presence, and/or ratio of gut microbiota in a subject is manipulated to facilitate one or more co-treatments, for example, in alternative embodiments, combinations of microbes as provided herein are administered with a chemotherapy, a radiation therapy, an immune checkpoint inhibitor, a Chimeric Antigen Receptor (CAR) T-cell therapy (CAR-T) or other immunotherapy or cancer treatment.

BACKGROUND

Checkpoint inhibitors are a class of cancer drugs that function by enabling the patient's own immune system to fight the tumor, a treatment approach known as immunotherapy. These agents bind to and block inhibitory signals from either antigen presenting cells or cancer cells, thereby allowing excitatory signals to prevail that result in T cell cancer recognition, activation and proliferation, ultimately leading to cancer rejection and elimination. Examples of T-cell inhibitory signal targets and their corresponding immunotherapy (as immunostimulating) agents include: cytotoxic T-lymphocyte-associated protein 4 (CTLA-4), targeted by, e.g., YERVOY®/Ipilimumab; the programmed cell death protein 1 (PD-1), targeted by, e.g., KEYTRUDA®/Pembrolizumab, OPDIVO®/Nivolumab; and its ligand PD-L1, targeted by, e.g. TECENTRIQ®/Atezolizumab, BAVENCIO®/Avelumab and IMFINZI®/Durvalumab; cemiplimab (or LIBTAYO®) (Regeneron). Blockade of these inhibitory signals by checkpoint inhibitor immunotherapies has been shown to be particularly effective against advanced melanoma, non-small cell lung cancer, and renal cell carcinoma, yet more than 50% of cancer patients subjected to checkpoint inhibitor therapies fail to respond to the treatment (Ribas A, Wolchok J D (2018) Science (80-) 359: 1350-1355).

New findings indicate that the likelihood of response or non-response to checkpoint inhibitors are directly correlated to the state of the gut microbiome and its contribution to immunological function of the gastrointestinal tract (Peled et al. (2017) J Clin Oncol 15:1650-1659; Iida et al. (2013) Science 342, 967-970; Daillere et al. (2016) Immunity 45:931-943; Vetizou et al. (2015) Science 350:1079-1084; Sivan et al. (2015) Science 350:1084-1089; Routy, B. et al. (2018) Science 359, 91-97; Gopalakrishnan, V. et al. (2018) Science (80-). 359, 97-103; Matson, V. et al. (2018) Science (80-). 359, 104-108).

For example, among melanoma patients undergoing anti-PD-1 immunotherapy, those more likely to respond to the therapy tended to have gut microbiomes enriched in anti-inflammatory gut microbes like *Faecalibacterium prausnitzii* or *Akkermansia muciniphila*, while non-responding patients were enriched in microbes more associated with chronic inflammation such as *Bacteroides* species and those of the Proteobacteria phylum (Routy, B. et al. (2018) Science 359, 91-97; Gopalakrishnan, V. et al. (2018) Science (80-). 359, 97-103). It was posited that possession of a more anti-inflammatory gut microbiome better primed T-cells of the responder patients to respond to activation by checkpoint inhibition, while the chronic inflammatory state brought on by the dysbiotic microbiota of non-responders led to T-cell exhaustion and a relative inability to be activated by checkpoint inhibition. Thus, an opportunity arises to improve the likelihood of response to checkpoint inhibitor therapies by modification of the composition of the gut microbiome to include immunomodulatory microbes that might be lacking in some patients.

SUMMARY

In alternative embodiments, provided are methods for controlling, ameliorating, preventing or treating a cancer in an individual in need thereof, comprising:

(a) administering or having administered to an individual in need thereof a formulation comprising at least two different species or genera (or types) of non-pathogenic bacteria, wherein each of the non-pathogenic bacteria comprise (or are in the form of) a plurality of non-pathogenic colony forming live bacteria, a plurality of non-pathogenic germinable bacterial spores, or a combination thereof; or, (b) (i) providing a formulation comprising at least two different species or genera (or types) of non-pathogenic bacteria, wherein each of the non-pathogenic bacteria comprise (or are in the form of) a plurality of non-pathogenic colony forming live bacteria, a plurality of non-pathogenic germinable bacterial spores, or a combination thereof, and (ii) administering or having administered to an individual in need thereof the formulation;

wherein the formulation comprises a or any combination of at least two different species or genera of non-pathogenic, live bacteria, or spore thereof, if the bacteria is spore forming, as described Table 1, 5, 10, 11, or 12, or live biotherapeutic compositions or combinations of bacteria as set forth in Table 15 or 16, and optionally the different species or genera (or types) of non-pathogenic, live bacteria are present in approximately equal amounts, or each of the different species or genera (or types) of non-pathogenic, live bacteria or non-pathogenic germinable bacterial spores represent at least about 1%, 5%, 10%, 20%, 30%, 40%, or 50% or more, or between about 1% and 75%, of the total amount of non-pathogenic, live bacteria and non-pathogenic germinable bacterial spores in the formulation, and optionally only or substantially only non-pathogenic, live bacteria are present in the formulation, or only or substantially only non-pathogenic germinable bacterial spores are present in the formulation, or approximately equal amounts of non-pathogenic, live bacteria and non-pathogenic germinable bacterial spores are present in the formulation.

In alternative embodiments of methods as provided herein:

the method further comprises administering or having administered one or any one of: a chemotherapy, a radiation therapy, an immune checkpoint inhibitor, a Chimeric Antigen Receptor (CAR) T-cell therapy (CAR-T) or an immunotherapy or a cancer treatment, or a combination thereof, and optionally the chemotherapy, the radiation therapy, the immune checkpoint inhibitor, the Chimeric Antigen Receptor (CAR) T-cell therapy (CAR-T) or the immunotherapy or the cancer treatment, or the combination thereof, is administered before, during (concurrently with) and/or after administration the formulation;

the formulation comprises an inner core surrounded by an outer layer of polymeric material enveloping the inner core, wherein the non-pathogenic bacteria or the non-pathogenic germinable bacterial spores are substantially in the inner core, and optionally the polymeric material comprises a natural polymeric material;

the formulation is formulated or manufactured as or in: a nano-suspension delivery system; an encochleated formulation; or, as a multilayer crystalline, spiral structure with no internal aqueous space;

the formulation is formulated or manufactured as a delayed or gradual enteric release composition or formulation, and optionally the formulation comprises a gastro-resistant coating designed to dissolve at a pH of 7 in the terminal ileum, optionally an active ingredient is coated with an acrylic based resin or equivalent, optionally a poly(meth)acrylate, optionally a methacrylic acid copolymer B, NF, optionally EUDRAGIT S™ (Evonik Industries AG, Essen, Germany), which dissolves at pH 7 or greater, optionally comprises a multimatrix (MMX) formulation, and optionally manufactured as enteric coated to bypass the acid of the stomach and bile of the duodenum;

the plurality of non-pathogenic colony forming live bacteria are substantially dormant colony forming live bacteria, or the plurality of non-pathogenic colony forming live bacteria or the plurality of non-pathogenic germinable bacterial spores are lyophilized, wherein optionally the dormant colony forming live bacteria comprise live vegetative bacterial cells that have been rendered dormant by lyophilization or freeze drying;

the formulation comprises at least about $1 \times 10^4$ colony forming units (CFUs), or between about $1 \times 10^1$ and $1 \times 10^{13}$ CFUs, $1 \times 10^2$ and $1 \times 10^{10}$ CFUs, $1 \times 10^2$ and $1 \times 10^8$ CFUs, $1 \times 10^3$ and $1 \times 10^7$ CFUs, or $1 \times 10^4$ and $1 \times 10^6$ CFUs, of non-pathogenic live bacteria and/or non-pathogenic germinable bacterial spores;

the formulation comprises at least one (or any one, several, or all of) non-pathogenic bacteria or spore of the family or genus (or class): Agathobaculum (TaxID: 2048137), *Alistipes* (TaxID: 239759), Anaeromassilibacillus (TaxID: 1924093), *Anaerostipes* (TaxID: 207244), *Asaccharobacter* (TaxID: 553372), *Bacteroides* (TaxID: 816), *Barnesiella* (TaxID: 397864), *Bifidobacterium* (TaxID: 1678), *Blautia* (TaxID: 572511), *Butyricicoccus* (TaxID: 580596), *Clostridium* (TaxID: 1485), *Collinsella* (TaxID: 102106), *Coprococcus* (TaxID: 33042), *Dorea* (TaxID: 189330), *Eubacterium* (TaxID: 1730), *Faecalibacterium* (TaxID: 216851), *Fusicatenibacter* (TaxID: 1407607), *Gemmiger* (TaxID: 204475), *Gordonibacter* (TaxID: 644652), Lachnoclostridium (TaxID: 1506553), *Methanobrevibacter* (TaxID: 2172), *Parabacteroides* (TaxID: 375288), Romboutsia (TaxID: 1501226), *Roseburia* (TaxID: 841), *Ruminococcus* (TaxID: 1263), Erysipelotrichaceae (TaxID: 128827), *Coprobacillus* (TaxID: 100883), Erysipelatoclostridium sp. SNUG30099 (TaxID: 1982626), Erysipelatoclostridium (TaxID: 1505663), Acetatifactor (TaxID: 1427378), *Adlercreutzia* (TaxID: 447020), Agathobacter (TaxID: 1766253), *Anaerotruncus* (TaxID: 244127), Bariatricus (TaxID: 1924081), *Butyrivibrio* (TaxID: 830), Christensenellaceae (TaxID: 990719), Clostridiales (TaxID: 186802), *Dialister* (TaxID: 39948), Drancourtella (TaxID: 1903506), *Eggerthella* (TaxID: 84111), Eisenbergiella (TaxID: 1432051), Enterocloster (TaxID: 2719313), *Enterococcus* (TaxID: 1350), Intestinibacter (TaxID: 1505657), *Lachnospira* (TaxID: 28050), Lachnospiraceae (TaxID: 186803), Mediterraneibacter (TaxID: 2316020), Negativibacillus (TaxID: 1980693), *Oscillibacter* (TaxID: 459786), *Phocaeicola* (TaxID: 909656), *Pseudobutyrivibrio* (TaxID: 46205), *Pseudoflavonifractor* (TaxID: 1017280), Ruminococcaceae (TaxID: 541000), Sellimonas (TaxID: 1769710), *Solobacterium* (TaxID: 123375), Terrisporobacter (TaxID: 1505652), Tidjanibacter (TaxID: 1929083), *Veillonella* (TaxID: 29465), or a combination thereof;

wherein the formulation comprises at least one (or any one, several, or all of) non-pathogenic bacteria or spore form thereof as set forth in Tables 1, 5, 10, 11, or 12, or included in the combination of non-pathogenic bacteria and/or spores thereof (or spore derived from) as set forth in Table 15 or 16;

the formulation comprises combination of non-pathogenic bacteria and/or spores thereof (or spore derived from) as set forth in Tables 15 and 16;

the formulation comprises water, sterile water, saline, sterile saline, a pharmaceutically acceptable preservative, a carrier, a buffer, a diluent, an adjuvant or a combination thereof;

the formulation is administered orally or rectally, or is formulated and/or administered as a liquid, a food, a gel, a candy, an ice, a lozenge, a tablet, pill or capsule, or a suppository or as an enema formulation, or the formulation is administered as an or is in a form for intra-rectal or intra-colonic administration;

the formulation is administered to the individual in need thereof in one, two, three, or four or more doses, and wherein the one, two, three, four or five or more doses are administered on a daily basis (optionally once a day, bid or tid or more), every other day, every third day, or about once a week, and optionally the two, three, or four or more doses are administered at least a week apart (or dosages are separated by about a week);

the formulation further comprises an antibiotic, or the method further comprises administration of an antibiotic, and optionally at least one dose of the antibiotic is administered before a first administration of the formulation, optionally at least one dose of the antibiotic is administered one day or two days, or more, before a first administration of the formulation;

the inhibitor of the inhibitory immune checkpoint molecule comprises a protein or polypeptide that binds to an inhibitory immune checkpoint protein, and optionally inhibitor of the inhibitory immune checkpoint protein is an antibody or an antigen binding fragment thereof that specifically binds to the inhibitory immune checkpoint protein;

the inhibitor of the inhibitory immune checkpoint molecule targets a compound or protein comprising: a CTLA4 or CTLA-4 (cytotoxic T-lymphocyte-associated protein 4, also known as CD152, or cluster of differentiation 152); Programmed cell Death protein 1, also known as PD-1 or CD279; Programmed Death-Ligand 1 (PD-L1), also known as cluster of differentiation 274 (CD274) or B7 homolog 1 (B7-H1)); PD-L2; A2AR (adenosine $A_{2A}$ receptor, also known as ADORA2A); B7-H3; B7-H4; BTLA (B- and T-lymphocyte attenuator protein); KIR (Killer-cell Immunoglobulin-like Receptor); IDO (Indoleamine-pyrrole 2,3-dioxygenase); LAG3 (Lymphocyte-Activation Gene 3 protein); TIM-3; VISTA (V-domain Ig suppressor of T cell activation protein); or any combination thereof;

the inhibitor of an inhibitory immune checkpoint molecule comprises: ipilimumab or YERVOY®; pembrolizumab or KEYTRUDA®; nivolumab or OPDIVO®; atezolizumab or TECENTRIQ®; avelumab or BAVENCIO®; durvalumab or IMFINZI®; AMP-224 (MedImmune), AMP-514 (an anti-programmed cell death 1 (PD-1) monoclonal antibody (mAb) (MedImmune)), PDR001 (a humanized mAb that targets PD-1), STI-A1110 or STI-A1010 (Sorrento Therapeutics), BMS-936559 (Bristol-Myers Squibb), BMS-986016 (Bristol-Myers Squibb), TSR-042 (Tesaro), JNJ-61610588 (Janssen Research & Development), MSB-0020718C, AUR-012, enoblituzumab (also known as MGA271) (MacroGenics, Inc.), MBG453, LAG525 (Novartis), BMS-986015 (Bristol-Myers Squibb), cemiplimab (or LIBTAYO®) (Regeneron), or any combination thereof;

the inhibitor of the inhibitory immune checkpoint molecule, or the stimulatory immune checkpoint molecule, is administered by: intravenous (IV) injection, intramuscular (IM) injection, intratumoral injection or subcutaneous injection; or, is administered orally or by suppository; or the formulation further comprises at least one immune checkpoint inhibitor;

the cancer is melanoma, advanced melanoma, cutaneous or intraocular melanoma, primary neuroendocrine carcinoma of the skin, breast cancer, a cancer of the head and neck, uterine cancer, rectal and colorectal cancer, a cancer of the head and neck, cancer of the small intestine, a colon cancer, a cancer of the anal region, a stomach cancer, lung cancer, brain cancer, non-small-cell lung cancer, ovarian cancer, angiosarcoma, bone cancer, osteosarcoma, prostate cancer; cancer of the bladder; cancer of the kidney or ureter or renal cell carcinoma, or carcinoma of the renal pelvis; a neoplasm of the central nervous system (CNS) or renal cell carcinoma; and/or the method comprises, or further comprises, administering, or having administered, or delivering, a genetically (or recombinantly) engineered cell, wherein optionally the genetically engineered cell is: a microbe or spore derived from a microbe as used in a method of any of the preceding claims, or a method as provided herein; or, a non-pathogenic bacteria or spore form thereof as set forth in Tables 1, 5, 10, 11, or 12, or included in the combination of non-pathogenic bacteria and/or spores thereof (or spore derived from) as set forth in Table 15 or 16, and optionally the microbe is genetically engineered to express or secrete a heterologous or overexpress an endogenous immunomodulatory molecule, and optionally the immunomodulatory molecule is an immunomodulatory protein or peptide, and optionally the immunomodulatory molecule is an immunostimulatory molecule, and optionally the microbe is genetically engineered to overexpress a pathway for production of at least one short chain fatty acid (SCFA), and optionally the SCFA comprises butyrate or butyric acid, propionate or acetate, and optionally the microbe is genetically engineered by inserting a heterologous nucleic acid into the microbe, and optionally the heterologous nucleic acid encodes an exogenous membrane protein, and optionally the immunostimulatory molecule, protein or peptide comprises a non-specific immunostimulatory protein, and optionally the non-specific immunostimulatory protein comprises a cytokine, and optionally the cytokine comprises an interferon (optionally an IFN-α2a, IFN-α2b), and interleukin (optionally IL-2, IL-4, IL-7, IL-12), an interferon (IFN), a TNF-α, a granulocyte colony-stimulating factor (G-CSF, also known as filgrastim, lenograstim or Neupogen®), a granulocyte monocyte colony-stimulating factor (GM-CSF, also known as molgramostim, sargramostim, Leukomax®, Mielogen® or Leukine®), or any combination thereof, and optionally the immunostimulatory molecule, protein or peptide comprises a specific immunostimulatory protein or peptide, and optionally the specific immunostimulatory protein or peptide comprises an immunogen that can generate a specific humeral or cellular immune response or an immune response to a cancer antigen, and optionally the genetically engineered cell is a lymphocyte, and optionally the genetically engineered cell expresses a chimeric antigen receptor (CAR), and optionally the lymphocyte is a B cell or a T cell (CAR-T cell), and optionally the lymphocyte is a tumor infiltrating lymphocyte (TIL), and optionally the microbe is genetically engineered to substantially decrease, reduce or eliminate the microbe's toxicity, and optionally the microbe is genetically engineered to comprise a kill switch so the microbe can be rendered non-vital after administration of an appropriate trigger or signal, and optionally the microbe is genetically engineered to secrete anti-inflammatory compositions or have an anti-inflammatory effect, and optionally the genetically engineered cell is administered or delivered before administration of, simultaneously with, and/or after administration or delivery of the formulation.

In alternative embodiments, provided are formulations or pharmaceutical compositions comprising:

(a) a combination of microbes as set forth in Tables 15 to 16;

(b) a combination of microbes as used in a method as provided herein or as provided herein; and/or (c) at least two different species or genera (or types) of non-pathogenic bacteria, wherein each of the non-pathogenic bacteria comprise (or are in the form of) a plurality of non-pathogenic colony forming live bacteria, a plurality of non-pathogenic germinable non-pathogenic bacterial spores, or a combination thereof, and the formulation comprises at least one (or any one, several, or all of) non-pathogenic bacteria or spore of the family or genus (or class): Agathobaculum (TaxID: 2048137), *Alistipes* (TaxID: 239759), Anaeromassilibacillus (TaxID: 1924093), *Anaerostipes* (TaxID: 207244), *Asaccharobacter* (TaxID: 553372), *Bacteroides* (TaxID: 816), *Barnesiella* (TaxID: 397864), *Bifidobacterium* (TaxID: 1678), *Blautia* (TaxID: 572511), *Butyricicoccus* (TaxID: 580596), *Clostridium* (TaxID: 1485), *Collinsella* (TaxID: 102106), *Coprococcus* (TaxID: 33042), *Dorea* (TaxID: 189330), *Eubacterium* (TaxID: 1730), *Faecalibacterium* (TaxID: 216851), *Fusicatenibacter* (TaxID: 1407607), *Gemmiger* (TaxID: 204475), *Gordonibacter* (TaxID: 644652), Lachnoclostridium (TaxID: 1506553), *Methanobrevibacter* (TaxID: 2172), *Parabacteroides* (TaxID: 375288), Romboutsia (TaxID: 1501226), *Roseburia* (TaxID: 841), *Ruminococcus* (TaxID: 1263), Erysipelotrichaceae (TaxID: 128827), *Coprobacillus* (TaxID: 100883), Erysipelatoclostridium sp. SNUG30099 (TaxID: 1982626), Erysipelatoclostridium (TaxID: 1505663), Acetatifactor (TaxID: 1427378), *Adlercreutzia* (TaxID: 447020), Agathobacter (TaxID: 1766253), *Anaerotruncus* (TaxID: 244127), Bariatricus (TaxID: 1924081), *Butyrivibrio* (TaxID: 830), Christensenellaceae (TaxID: 990719), Clostridiales (TaxID: 186802), *Dialister* (TaxID: 39948), Drancourtella (TaxID: 1903506), *Eggerthella* (TaxID: 84111), Eisenbergiella (TaxID: 1432051), Enterocloster (TaxID: 2719313), *Enterococcus* (TaxID: 1350), Intestinibacter (TaxID: 1505657), *Lachnospira* (TaxID: 28050), Lachnospiraceae (TaxID: 186803), Mediterraneibacter (TaxID: 2316020), Negativibacillus (TaxID: 1980693), *Oscillibacter* (TaxID: 459786), *Phocaeicola* (TaxID: 909656), *Pseudobutyrivibrio* (TaxID: 46205), *Pseudoflavonifractor* (TaxID: 1017280), Ruminococcaceae (TaxID: 541000), Sellimonas (TaxID: 1769710), *Solobacterium* (TaxID: 123375), Terrisporobacter (TaxID: 1505652), Tidjanibacter (TaxID: 1929083), *Veillonella* (TaxID: 29465), or a combination thereof.

In alternative embodiments, of formulations or pharmaceutical compositions as provided herein, or methods as provided herein:

the wherein the formulation comprises at least one (or any one, several, or all of) non-pathogenic bacteria or spore form thereof as set forth in Tables 1, 5, 10, 11, or 12, or included in the combination of non-pathogenic bacteria and/or spores thereof (or spore derived from) as set forth in Table 15 or 16;

the formulation comprises an inner core surrounded by an outer layer of polymeric material enveloping the inner core, wherein the non-pathogenic bacteria or the non-pathogenic germinable bacterial spores are substantially in the inner core, and optionally the polymeric material comprises a natural polymeric material;

the plurality of non-pathogenic colony forming live bacteria are substantially dormant colony forming live bacteria, or the plurality of non-pathogenic colony forming live bacteria or the plurality of non-pathogenic germinable bacterial spores are lyophilized, wherein optionally the non-pathogenic dormant colony forming live bacteria comprise live vegetative bacterial cells that have been rendered dormant by lyophilization or freeze drying;

the formulation comprises at least $1 \times 10^4$ colony forming units (CFUs), or between about $1 \times 10^2$ and $1 \times 10^8$ CFUs, $1 \times 10^3$ and $1 \times 10^7$ CFUs, or $1 \times 10^4$ and $1 \times 10^6$ CFUs, of live non-pathogenic bacteria and/or non-pathogenic germinable bacterial spores;

the formulation or pharmaceutical composition comprises water, saline, a pharmaceutically acceptable preservative, a carrier, a buffer, a diluent, an adjuvant or a combination thereof;

the formulation or pharmaceutical composition is formulated for administration orally or rectally, or is formulated as a liquid, a food, a gel, a geltab, a candy, a lozenge, a tablet, pill or capsule, or a suppository;

the formulation or pharmaceutical composition further comprises: a biofilm disrupting or dissolving agent, an antibiotic, an inhibitor of an inhibitory immune checkpoint molecule and/or a stimulatory immune checkpoint molecule (or any composition for use in checkpoint blockade immunotherapy);

the inhibitor of an inhibitory immune checkpoint molecule comprises a protein or polypeptide that binds to an inhibitory immune checkpoint protein, and optionally the inhibitor of the inhibitory immune checkpoint molecule is an antibody or an antigen binding fragment thereof that binds to an inhibitory immune checkpoint protein;

the inhibitor of an inhibitory immune checkpoint molecule targets a compound or protein comprising: CTLA4 or CTLA-4 (cytotoxic T-lymphocyte-associated protein 4, also known as CD152, or cluster of differentiation 152); Programmed cell Death protein 1, also known as PD-1 or CD279; Programmed Death-Ligand 1 (PD-L1), also known as cluster of differentiation 274 (CD274) or B7 homolog 1 (B7-H1)); PD-L2; A2AR (adenosine $A_{2A}$ receptor, also known as ADORA2A); B7-H3; B7-H4; BTLA (B- and T-lymphocyte attenuator protein); KIR (Killer-cell Immunoglobulin-like Receptor); IDO (Indoleamine-pyrrole 2,3-dioxygenase); LAG3 (Lymphocyte-Activation Gene 3 protein); TIM-3; VISTA (V-domain Ig suppressor of T cell activation protein) or any combination thereof;

the inhibitor of an inhibitory immune checkpoint molecule comprises: ipilimumab or YERVOY®; pembrolizumab or KEYTRUDA®; nivolumab or OPDIVO®; atezolizumab or TECENTRIQ®; avelumab or BAVENCIO®; durvalumab or IMFINZI®; AMP-224 (MedImmune), AMP-514 (an anti-programmed cell death 1 (PD-1) monoclonal antibody (mAb) (MedImmune)), PDR001 (a humanized mAb that targets PD-1), STI-A1110 or STI-A1010 (Sorrento Therapeutics), BMS-936559 (Bristol-Myers Squibb), BMS-986016 (Bristol-Myers Squibb), TSR-042 (Tesaro), JNJ-61610588 (Janssen Research & Development), MSB-0020718C, AUR-012, enoblituzumab (also known as MGA271) (MacroGenics, Inc.), MBG453, LAG525 (Novartis), BMS-986015 (Bristol-Myers Squibb), cemiplimab (or LIBTAYO®) (Regeneron), or any combination thereof; and/or the stimulatory immune checkpoint molecule comprises a member of the tumor necrosis factor (TNF) receptor superfamily, optionally CD27, CD40, OX40, GITR (a glucocorticoid-Induced TNFR family Related gene protein) or CD137, or comprises a member of the B7-CD28 superfamily, optionally CD28 or Inducible T-cell co-stimulator (ICOS).

In alternative embodiments, provided are kits or products of manufacture comprising a formulation or pharmaceutical composition as provided herein, wherein optionally the product of manufacture is an implant.

In alternative embodiments, provided are uses of a formulation or pharmaceutical composition as provided herein, or a kit or product of manufacture as provided herein, for controlling, ameliorating, preventing or treating a cancer in an individual in need thereof.

In alternative embodiments, provided are uses of a formulation or a pharmaceutical composition as provided herein in the manufacture of a medicament for controlling, ameliorating, preventing or treating a cancer in an individual in need thereof.

In alternative embodiments, provided are formulations or pharmaceutical compositions as provided herein, or a kit as provided herein, for use in controlling, ameliorating, preventing or treating a cancer in an individual in need thereof. In alternative embodiments, the cancer is melanoma, advanced melanoma, cutaneous or intraocular melanoma, primary neuroendocrine carcinoma of the skin, breast cancer, a cancer of the head and neck, uterine cancer, rectal and colorectal cancer, a cancer of the head and neck, cancer of the small intestine, a colon cancer, a cancer of the anal region, a stomach cancer, lung cancer, brain cancer, non-small-cell lung cancer, ovarian cancer, angiosarcoma, bone cancer, osteosarcoma, prostate cancer; cancer of the bladder; cancer of the kidney or ureter or renal cell carcinoma, or carcinoma of the renal pelvis; a neoplasm of the central nervous system (CNS) or renal cell carcinoma.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of exemplary embodiments provided herein and are not meant to limit the scope of the invention as encompassed by the claims.

FIG. 16 illustrates Table 2, as discussed in Example 7, below.

FIG. 17 illustrates Table 3, as discussed in Example 9, below.

FIG. 18 illustrates Table 4, as discussed in Example 9, below.

FIG. 19 illustrates Table 8, as discussed in Example 10, below.

FIG. 20 illustrates Table 9, as discussed in Example 10, below.

FIG. 22 illustrate Table 13, as discussed in Example 10, below.

FIG. 23 illustrate Table 14, as discussed in Example 10, below.

Like reference symbols in the various drawings indicate like elements.

DETAILED DESCRIPTION

Figure 1:
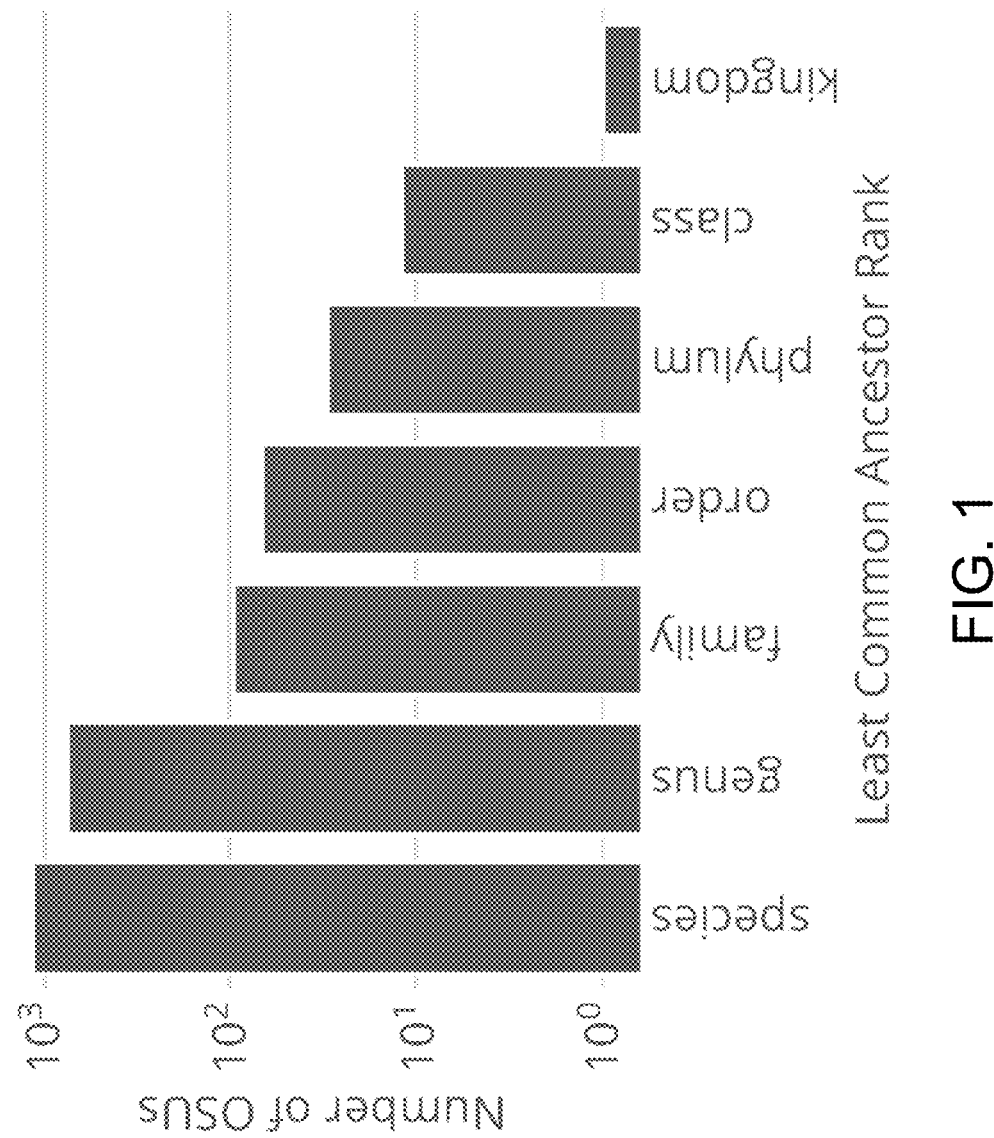
FIG. 1 graphically summarizes the classification level of least common ancestors for each cluster. Microbial genome assemblies from NCBI RefSeq are classified into operational species units by clustering similar genome assemblies together. The least common ancestor in the NCBI hierarchy for the assemblies in each operational species unit (OSU) cluster is determined. For OSU's containing more than one microbial assembly, the rank of the least common ancestor is displayed. Most OSU's have a least common ancestor at the species or genus level, demonstrating consistency between the assigned OSU's and the pre-existing NCBI taxonomic tree, as described in Example 9, below.

In alternative embodiments, provided are compositions, including products of manufacture and kits, and methods, comprising novel combinations of microbes, also called live biotherapeutic compositions such as non-pathogenic, live (optionally dormant) bacteria and/or bacterial spores, e.g., such as the exemplary combinations of microbes as listed in Tables 15 and 16, Example 10. In alternative embodiments, the compositions, products of manufacture, kits and methods as provided herein are used as a therapy (e.g., as a monotherapy or as a co-therapy, or co-treatment) for the control, amelioration, prevention and/or treatment of a disease or condition, for example, a cancer. In alternative embodiments, the compositions, products of manufacture, kits and/or methods as provided herein are administered to an individual receiving a drug, e.g., a cancer therapy, thereby resulting in a modification or modulation of the patient's gut microfloral population(s), thus resulting in an enhancement of the drug therapy, for example, lowering the dosage or amount of drug needed for effective therapy, or the frequency with which a drug must be administered to be effective. In alternative embodiments, by modulating or modifying the individual's gut microbial population(s) using compositions, products of manufacture and methods as provided herein, the pharmacodynamics of a drug administered to the patient is altered, for example, the pharmacodynamics of the drug is enhanced, e.g., the individual's ability to absorb a drug is modified (e.g., accelerated or slowed, or enhanced), or the dose efficacy of a drug is increased (e.g., resulting in needing a lower dose of drug for an intended effect), or the gut microbes act orthogonally on the drug target (e.g., resulting in the presence of the microbe being essential for the drug to have the intended effect). For example, in alternative embodiments, by modulating or modifying the patient's gut microbial population(s) using compositions, products of manufacture and methods as provided herein the dose efficacy of a cancer drug is increased, thereby enhancing the control or treatment of that cancer.

In alternative embodiments, the amount, identity, presence, and/or ratio of gut microbiota in a subject is manipulated to facilitate a mono-therapy or one or more co-treatments; for example, in alternative embodiments, combinations of microbes as provided herein are administered with (e.g., concurrent with, or before and/or after) a chemotherapy, a radiation therapy, an immune checkpoint inhibitor, a Chimeric Antigen Receptor (CAR) T-cell therapy (CAR-T) or other immunotherapy or cancer treatment.

Described here for the first time are novel combinations of specific microbes, for example, bacteria, including for example microbes found in a human gut or recombinantly engineered or cultured microbes, which can be administered as a mono-therapy or as a co-therapy for, in alternative embodiments, cancer or autoimmune patients, where in alternative embodiments the cancer patients are undergoing immune checkpoint inhibitor treatment, or are undergoing a chemotherapy, a radiation therapy, an immune checkpoint inhibitor, a Chimeric Antigen Receptor (CAR) T-cell therapy (CAR-T) or other immunotherapy or cancer treatment.

As described in the Examples, below, we demonstrated a correlation between these combinations of microbes and the metabolic functions associated with them, and the efficacy of treatment in both human patients and mouse cancer models. In alternative embodiments, administering combinations of microbes as provided herein to cancerous mice improves the fraction of animals that show significant tumor size reduction as compared to mice given the same drug but not having their gut microbiome altered using compositions or methods as provided herein.

In alternative embodiments, the chemotherapy, radiation therapy, Chimeric Antigen Receptor (CAR) T-cell therapy (CAR-T) or other immunotherapy or cancer treatment, for example, the immune checkpoint inhibitors (or inhibitors of an inhibitory immune checkpoint molecule) and/or stimulatory immune checkpoint molecules (or more accurately, stimulatory immune molecules), are administered with (e.g., are administered concurrently or sequentially), or formulated with, the combinations of microbes as provided herein, e.g., administered or formulated with non-pathogenic bacteria and/or non-pathogenic germination-competent bacterial spores as provided herein.

The immune checkpoint inhibitors (also described as an inhibitor of an inhibitory immune checkpoint molecule) can function by interfering with regulatory pathways that naturally exist to prevent T cell proliferation. In the tumor microenvironment these inhibitory pathways are highly active, so T cells are often driven to an ineffective state. Checkpoint inhibitors bind to particular proteins in these regulatory pathways associated with inhibition of T cell activation, such as cytotoxic T lymphocyte-associated protein 4 (CTLA-4), programmed cell death protein 1 (PD-1), or programmed cell death ligand 1 (PD-L1), thereby allowing excitatory T cell response to tumor antigens. Thus, in alternative embodiments, an inhibitor of an inhibitory immune checkpoint molecule is a molecule that can directly (or specifically) bind to CTLA-4, PD-1, PD-L1, or other component of the inhibitory immune checkpoint to prevent proper binding to its natural corresponding receptor or ligand.

In alternative embodiments, a stimulatory immune checkpoint molecule—which can also be, or more accurately is, described as a stimulatory immune molecule potentiates excitation and activation of T cells, either by enhancing the action of a checkpoint inhibitor or by an independent mechanism.

In alternative embodiments, provided are therapeutic compositions, including formulations and pharmaceutical compositions, comprising non-pathogenic (optionally dormant) live microbes such as bacteria and/or germination-competent bacterial spores, which can be used for the prevention or treatment of a cancer or the side effects of a cancer therapy, e.g., a drug therapy, or can be used or administered with a chemotherapy, a radiation therapy, an immune checkpoint inhibitor, a Chimeric Antigen Receptor (CAR) T-cell therapy (CAR-T) or other immunotherapy or cancer treatment.

In alternative embodiments, therapeutic compositions, formulations or pharmaceutical compositions as provided herein, or used to practice methods as provided herein, comprise colony forming (optionally dormant) live bacteria and/or germinable bacterial spores which can be used in mono- or co-therapies, for example, as an adjuvant to an antineoplastic treatment administered to a cancer patient, or administered with or as a supplement to a chemotherapy, a radiation therapy, an immune checkpoint inhibitor, a Chimeric Antigen Receptor (CAR) T-cell therapy (CAR-T) or other immunotherapy or cancer treatment.

In some embodiments, a therapeutic composition as provided herein acts or is used as a probiotic composition which can be administered with, before and/or after a chemotherapy, a radiation therapy, an immune checkpoint inhibitor, a Chimeric Antigen Receptor (CAR) T-cell therapy (CAR-T) or other immunotherapy or cancer treatment. In alternative embodiments, therapeutic compositions (e.g., the formulations) as provided herein, comprise the bacteria and/or spores and an antineoplastic active agent such as an immune checkpoint inhibitor.

In alternative embodiments, therapeutic compositions, formulations or pharmaceutical compositions as provided herein, or used to practice methods as provided herein, comprise colony forming (optionally dormant) live bacteria and/or germinable bacterial spores for use as a mono-therapy or in combination with (e.g., as a co-therapy) or supplementary to a drug (which can be a small molecule or a protein, e.g., a therapeutic antibody) blocking an immune checkpoint for inducing immuno-stimulation in a cancer patient. The therapeutic composition as provided herein and the drug (e.g., an antibody) can be administered separately or together, or at different time points or at the same time, or can be administered sequentially or concurrently.

In alternative embodiments, therapeutic compositions, formulations or pharmaceutical compositions as provided herein comprise colony forming (optionally dormant) live bacteria and/or germinable bacterial spores which can be used as an adjuvant to an anti-cancer or antineoplastic treatment, for example, an immune checkpoint treatment, administered to a cancer patient. In alternative embodiments, the therapeutic composition comprises the antineoplastic or immune checkpoint active agents. In alternative embodiments, the therapeutic composition, formulations or pharmaceutical compositions as provided herein are administered with or after, or both with and after, administration of the antineoplastic or immune checkpoint active agent.

In alternative embodiments, the formulation or pharmaceutical composition further comprises, or is manufactured with, an outer layer of polymeric material (e.g., natural polymeric material) enveloping, or surrounding, a core that comprises the combination of microbes as provided herein.

In alternative embodiments, therapeutic compositions, formulations or pharmaceutical compositions as provided herein, or used to practice methods as provided herein, can comprise a pharmaceutically acceptable carrier, diluent, and/or adjuvant. In other embodiments a pharmaceutically acceptable preservative is present. In yet other embodiments, a pharmaceutically acceptable germinate is present. In still other embodiments the therapeutic composition contains, or further comprises, a prebiotic nutrient at an effective dose of 0.005, 0.05, 0.5, 5.0 milligrams per kilogram body weight.

In alternative embodiments, therapeutic compositions, formulations or pharmaceutical compositions as provided herein, or used to practice methods as provided herein, are in the form of a tablet, geltab or capsule, e.g., a polymer capsule such as a gelatin or a hydroxypropyl methylcellulose (HPMC, or hypromellose) capsule (e.g., VCAPS PLUS™ (Capsugel, Lonza)). In other embodiments, the therapeutic compositions, formulations or pharmaceutical compositions are in or are manufactured as a food or drink, e.g., an ice, candy, lolly or lozenge, or any liquid, e.g., in a beverage.

In alternative embodiments, therapeutic compositions, formulations or pharmaceutical compositions as provided herein, or used to practice methods as provided herein, comprise at least one bacterial type that is not detectable, of low natural abundance, or not naturally found, in a healthy or normal subject's (e.g., human) gastrointestinal tract. In alternative embodiments, the gastrointestinal tract refers to the stomach, the small intestine, the large intestine and the rectum, or combinations thereof.

In alternative embodiments, provided are methods of ameliorating, preventing or treating cancer and/or at least one symptom resulting from a cancer therapy or of a condition of the gastrointestinal tract.

In alternative embodiments, by administration of a therapeutic composition, formulation or pharmaceutical composition as provided herein to a subject, or practicing a method as provided herein, the microbiome population or composition of the subject is modulated or altered.

In alternative embodiments, the term "microbiome" encompasses the communities of microbes that can live sustainably and/or transiently in and on a subject's body, e.g., in the gut of a human, including bacteria, viruses and bacterial viruses, archaea, and eukaryotes. In alternative embodiments, the term "microbiome" encompasses the "genetic content" of those communities of microbes, which includes the genomic DNA, RNA (ribosomal-, messenger-, and transfer-RNA), the epigenome, plasmids, and all other types of genetic information.

In alternative embodiments, the term "subject" refers to any animal subject including humans, laboratory animals (e.g., primates, rats, mice), livestock (e.g., cows, sheep, goats, pigs, turkeys, and chickens), and household pets (e.g., dogs, cats, and rodents). The subject may be suffering from a disease, e.g., a cancer.

In alternative embodiments, the term "type" or "types" when used in conjunction with "bacteria" or "bacterial" refers to bacteria differentiated at the genus level, the species level, the sub-species level, the strain level, or by any other taxonomic method known in the art.

In alternative embodiments, the phrase "dormant live bacteria" refers to live vegetative bacterial cells that have been rendered dormant by lyophilization or freeze drying. Such dormant live vegetative bacterial cells are capable of resuming growth and reproduction immediately upon resuscitation.

In alternative embodiments, the term "spore" also includes "endospore", and these terms can refer to any bacterial entity which is in a dormant, non-vegetative and non-reproductive stage, including spores that are resistant to environmental stress such as desiccation, temperature variation, nutrient deprivation, radiation, and chemical disinfectants. In alternative embodiments, "spore germination" refers to the dormant spore beginning active metabolism and developing into a fully functional vegetative bacterial cell capable of reproduction and colony formation. In alternative embodiments, "germinant" is a material, composition, and/or physical-chemical process capable of inducing vegetative growth of a dormant bacterial spore in a host organism or in vitro, either directly or indirectly.

In alternative embodiments, the term "colony forming" refers to a vegetative bacterium that is capable of forming a colony of viable bacteria or a spore that is capable of germinating and forming a colony of viable bacteria.

In alternative embodiments, the term "natural polymeric material" comprises a naturally occurring polymer that is not easily digestible by human enzymes so that it passes through most of the human digestive system essentially intact until it reaches the large or small intestine.

In alternative embodiments, therapeutic compositions, formulations or pharmaceutical compositions as provided herein comprise population(s) of non-pathogenic dormant live bacteria and/or bacterial spores. The dormant live bacteria can be capable of colony formation and, in the case of spores, germination and colony formation. Thus, in alternative embodiments, compositions are useful for altering a subject's gastrointestinal biome, e.g., by increasing the population of those bacterial types or microorganisms, or are capable of altering the microenvironment of the gastrointestinal biome, e.g., by changing the chemical microenvironment or disrupting or degrading intestinal mucin or biofilm, thereby providing treatment of cancer, gastrointestinal conditions, and symptoms resulting from cancer therapy, ultimately increasing the health of the subject to whom they are administered.

In alternative embodiments, the terms "purify," "purified," and "purifying" are used interchangeably to describe a population's known or unknown composition of bacterial type(s), amount of that bacterial type(s), and/or concentration of the bacterial type(s); a purified population does not have any undesired attributes or activities, or if any are present, they can be below an acceptable amount or level. In alternative embodiments, the various populations of bacterial types are purified, and the terms "purified," "purify," and "purifying" refer to a population of desired bacteria and/or bacterial spores that have undergone at least one process of purification; for example, a process comprising screening of individual colonies derived from fecal matter for a desired phenotype, such as their effectiveness in enhancing the pharmacodynamics of a drug (such as a cancer drug, e.g., a drug inhibitory to an immune checkpoint), e.g., the individual's ability to absorb a drug is modified (e.g., accelerated or slowed, or enhanced), or the dose efficacy of a drug is increased (e.g., resulting in needing a lower dose of drug for an intended effect), or the immune system is primed for improved drug efficacy, or a selection or enrichment of the desired bacterial types.

Enrichment can be accomplished by increasing the amount and/or concentration of the bacterial types, such as by culturing in a media that selectively favors the growth of certain types of microbes, by screening pure microbial isolates for the desired genotype, or by a removal or reduction in unwanted bacterial types.

In alternative embodiments, bacteria used to practice compositions and methods provided herein are derived from fecal material donors that are in good health, have microbial biomes associated with good health, and are typically free from antibiotic administration during the collection period and for a period of time prior to the collection period such that no antibiotic remains in the donor's system. In alternative embodiments, the donor subjects do not suffer from and have no family history of renal cancer, bladder cancer, breast cancer, prostate cancer, lymphoma, leukemia, autoimmune disease. In alternative embodiments, donor subjects are free from irritable bowel disease, irritable bowel syndrome, celiac disease, Crohn's disease, colorectal cancer, anal cancer, stomach cancer, sarcomas, any other type of cancer, or a family history of these diseases. In alternative embodiments, donor subjects do not have and have no family history of mental illness, such as anxiety disorder, depression, bipolar disorder, autism spectrum disorders, panic disorders, obsessive-compulsive disorder, attention-deficit disorders, eating disorders (e.g. bulimia, anorexia), mood disorder or schizophrenia. In yet other embodiments the donor subjects have no knowledge or history of food allergies or sensitivities.

In alternative embodiments, the health of fecal matter donors is screened prior to the collection of fecal matter, such as at 1, 2, 3, 4, 8, 16, 20, 24, 28, 32, 36, 40, 44, 48, or 52 weeks pre-collection. In alternative embodiments, fecal matter donors are also screened post-collection, such as at 1, 2, 3, 4, 8, 16, 20, 24, 28, 32, 36, 40, 44, 48, or 52 weeks post-collection. Pre- and post-screening can be conducted daily, weekly, bi-weekly, monthly, or yearly. In alternative embodiments, individuals who do not test positive for pathogenic bacteria and/or viruses (e.g. HIV, hepatitis, polio, adeno-associated virus, pox, coxsackievirus, etc.) pre- and post-collection are considered verified donors.

In alternative embodiments, to purify bacteria and/or bacterial spores, fecal matter is collected from donor subjects and placed in an anaerobic chamber within a short time after elimination, such as no more than 1 minute, 5 minutes, 10 minutes, 15 minutes, 20 minutes, 25 minutes, 30 minutes, 35 minutes, 40 minutes, 45 minutes, 50 minutes, 55 minutes, or 60 minutes or more after elimination. In alternative embodiments, fecal matter is collected from donor subjects are placed in an anaerobic chamber within between about 1 minute and 48 hours, or more, after elimination from the donor.

Bacteria from a sample of the collected fecal matter can be collected in several ways. For example, the sample can be mixed with anoxic nutrient broth, dilutions of the resulting mixture conducted, and bacteria present in the dilutions grown on solid anoxic media. Alternatively, bacteria can be isolated by streaking a sample of the collected material directly on anoxic solid media for growth of isolated colonies. In alternative embodiments, to increase the ease of isolating bacteria from fecal samples mixed with anoxic nutrient broth, the resulting mixture can be shaken, vortexed, blended, filtered, and centrifuged to break up and/or remove large non-bacterial matter.

In alternative embodiments, purification of the isolated bacteria and/or bacterial spores by any means known in the art, for example, contamination by undesirable bacterial types, host cells, and/or elements from the host microbial environment can be eliminated by reiterative streaking to single colonies on solid media until at least two replicate streaks from serial single colonies show only a single colony morphology. Purification can also be accomplished by reiterative serial dilutions to obtain a single cell, for example, by conducting multiple 10-fold serial dilutions to achieve an ultimate dilution of $10^{-2}$, $10^{-3}$, $10^{-4}$, $10^{-5}$, $10^{-6}$, $10^{-7}$, $10^{-8}$, $10^{-9}$ or greater. Any methods known to those of skill in the art can also be applied. Confirmation of the presence of only a single bacterial type can be confirmed in multiple ways such as, gram staining, PCR, DNA sequencing, enzymatic analysis, metabolic profiling/analysis, antigen analysis, and flow cytometry using appropriate distinguishing reagents.

In alternative embodiments, purified population(s) of vegetative bacteria that are incorporated into therapeutic bacterial compositions as provided herein, or used to practice methods as provided herein, are fermented in growth media.

Suitable growth media include Nutrient Broth (Thermo Scientific™ Oxoid™), Anaerobe Basal Broth (Thermo Scientific™ Oxoid™), Reinforced Clostridial Medium (Thermo Scientific™ Oxoid™), Schaedler Anaerobic Broth (Thermo Scientific™ Oxoid™), MRS Broth Vegitone *Actinomyces* Broth (Millipore-Sigma™), Vegitone Infusion Broth (Millipore-Sigma™), Vegitone Casein Soya Broth (Millipore-Sigma™), or one of the following media available from Anaerobe Systems: Brain Heart Infusion Broth (BHI), *Campylobacter*-Thioglycollate Broth (CAMPY-THIO), Chopped Meat Broth (CM), Chopped Meat Carbohydrate Broth (CMC), Chopped Meat Glucose Broth (CMG), Cycloserine Cefoxitin Mannitol Broth with Taurocholate Lysozyme Cysteine (CCMB-TAL), Oral Treponeme Enrichment Broth (OTEB), MTGE-Anaerobic Enrichment Broth (MTGE), Thioglycollate Broth with Hemin, Vit. K, without indicator, (THIO), Thioglycollate Broth with Hemin, Vit. K, without indicator, (THIO), Lactobacilli-MRS Broth (LMRS), *Brucella* Broth (BRU-BROTH), Peptone Yeast Extract Broth (PY), PY Glucose (PYG), PY Arabinose, PY Adonitol, PY Arginine, PY Amygdalin, PYG Bile, PY Cellobiose, PY DL-Threonine, PY Dulcitol, PY Erythritol, PY Esculin, PYG Formate/Fumarate for FA/GLCf, PY Fructose, PY Galactose, PYG Gelatin, PY Glycerol, Indole-Nitrate Broth, PY Inositol, PY Inulin, PY Lactate for FA/GLCf, PY Lactose, PY Maltose, PY Mannitol, PY Mannose, PY Melezitose, PY Melibiose, PY Pyruvic Acid, PY Raffinose, PY Rhamnose, PY Ribose, PY Salicin, PY Sorbitol, PY Starch, PY Sucrose, PY Trehalose, PY Xylan, PY Xylose, Reinforced Clostridial Broth (RCB), Yeast Casitone Fatty Acids Broth with Carbohydrates (YCFAC Broth). In alternative embodiments, growth media includes or is supplemented with reducing agents such as L-cysteine, dithiothreitol, sodium thioglycolate, and sodium sulfide. In alternative embodiments, fermentation is conducted in stirred-tank fermentation vessels, performed in either batch or fed-batch mode, with nitrogen sparging to maintain anaerobic conditions. pH is controlled by the addition of concentrated base, such as $NH_4OH$ or NaOH. In the case of fed-batch mode, the feed is a primary carbon source for growth of the microorganisms, such as glucose. In alternative embodiments, the post-fermentation broth is collected, and/or the bacteria isolated by ultrafiltration or centrifugation and lyophilized or freeze dried prior to formulation.

In alternative embodiments, purified and isolated vegetative bacterial cells used in therapeutic bacterial compositions as provided herein, or used to practice methods as provided herein, have been made dormant; noting that bacterial spores are already in a dormancy state. Dormancy of the vegetative bacterial cells can be accomplished by, for example, incubating and maintaining the bacteria at temperatures of less than 4° C., freezing and/or lyophilization of the bacteria. Lyophilization can be accomplished according to normal bacterial freeze-drying procedures as used by those of skill in the art, such as those reported by the American Type Culture Collection (ATCC) on the ATCC website (see, e.g., (https://www.atcc.org).

In alternative embodiments, the purified population of dormant live bacteria and/or bacterial spores has undetectable levels of pathogenic activities, such as the ability to cause infection and/or inflammation, toxicity, an autoimmune response, an undesirable metabolic response (e.g. diarrhea), or a neurological response.

In alternative embodiments, all of the types of dormant live bacteria or bacterial spores present in a purified population are obtained from fecal material treated as described herein or as otherwise known to those of skill in the art. In other embodiments, one or more of the types of dormant live bacteria or bacterial spores present in a purified population is generated individually in culture and combined with one or more types obtained from fecal material. In alternative embodiments, all of the types of dormant live bacteria or bacterial spores present in a purified population are generated individually in culture. In still other embodiments, one or all of the types of dormant live bacteria and/or bacterial spores present in a purified population are non-naturally occurring or engineered. In yet other embodiments, non-naturally occurring or engineered non-bacterial microorganisms are present, with or without dormant live bacteria and/or bacterial spores.

In alternative embodiments, bacterial compositions used in compositions as provided herein, or to practice methods as provided herein, comprise combinations of different bacteria, e.g., comprising at least 2, 3, 4, 5, 6, 7, 8, 9, 10 or more bacterial types, or more than 20 bacterial types, or between about 2 and 30 bacterial types.

In alternative embodiments, the bacterial compositions comprise at least about $10^2$, $10^3$, $10^4$, $10^5$, $10^6$, $10^7$, $10^8$, $10^9$, $10^{10}$, $10^{11}$, $10^{12}$, $10^{13}$, $10^{14}$, or more (or between about $10^2$ to $10^{15}$) microbes, for example, dormant live bacteria and/or bacterial spores. In some embodiments each bacterial type is equally represented in the total number of dormant live bacteria and/or bacterial spores. In other embodiments, at least one bacterial type is represented in a higher amount than the other bacterial type(s) found in the composition.

In alternative embodiments, a population of different bacterial types used in compositions as provided herein, or to practice methods as provided herein, can increase microbe populations found in the subject's gastrointestinal tract by at least about 10%, 20%, 30%, 40%, 50%, 60%, 70%, 80%, 90%, 100%, 200%, 300%, 400%, 500%, 600%, 700%, 800%, 900% or 1000%, or between about 5% and 2000%, as compared to the subject's microbiome gastrointestinal population prior to treatment.

In alternative embodiments, the combination of microbes, e.g., combination of bacterial cells and/or spores, used in compositions as provided herein, or to practice methods as provided herein, are mixed with pharmaceutically acceptable excipients, such as diluents, carriers, adjuvants, binders, fillers, salts, lubricants, glidants, disintegrants, coatings, coloring agents, etc. Examples of such excipients are acacia, alginate, alginic acid, aluminum acetate, benzyl alcohol, butyl paraben, butylated hydroxy toluene, citric acid, calcium carbonate, candelilla wax, croscarmellose sodium, confectioner sugar, colloidal silicone dioxide, cellulose, plain or anhydrous calcium phosphate, carnuba wax, corn starch, carboxymethylcellulose calcium, calcium stearate, calcium disodium EDTA, copolyvidone, calcium hydrogen phosphate dihydrate, cetylpyridine chloride, cysteine HCL, crospovidone, calcium phosphate di or tri basic, dibasic calcium phosphate, disodium hydrogen phosphate, dimethicone, erythrosine sodium, ethyl cellulose, gelatin, glyceryl monooleate, glycerin, glycine, glyceryl monostearate, glyceryl behenate, hydroxy propyl cellulose, hydroxyl propyl methyl cellulose, hypromellose, HPMC phthalate, iron oxides or ferric oxide, iron oxide yellow, iron oxide red or ferric oxide, lactose hydrous or anhydrous or monohydrate or spray dried, magnesium stearate, microcrystalline cellulose, mannitol, methyl cellulose, magnesium carbonate, mineral oil, methacrylic acid copolymer, magnesium oxide, methyl paraben, providone or PVP, PEG, polysorbate 80, propylene glycol, polyethylene oxide, propylene paraben, polaxamer 407 or 188, potassium bicarbonate, potassium sorbate, potato starch, phosphoric acid, polyoxy 140 stearate, sodium starch glycolate, starch pregelatinized, sodium carmellose, sodium lauryl sulfate, starch, silicon dioxide, sodium benzoate, stearic acid, sucrose, sorbic acid, sodium carbonate, saccharin sodium, sodium alginate, silica gel, sorbiton monooleate, sodium stearyl fumarate, sodium chloride, sodium metabisulfite, sodium citrate dihydrate, sodium starch, sodium carboxy methyl cellulose, succinic acid, sodium propionate, titanium dioxide, talc, triacetin, and triethyl citrate.

In alternative embodiments, the combinations of microbes, e.g., combination of bacterial cells and/or spores, used in compositions as provided herein, or to practice methods as provided herein, are fabricated as colonic or microflora-triggered delivery systems, as described for example, in Basit et al, J. Drug Targeting, 17:1, 64-71; Kotla, Int J Nanomedicine. 2016; 11: 1089-1095; Bansai et al, Polim Med. 2014 April-June; 44(2):109-18; or, Shah et al, Expert Opin Drug Deliv. 2011 June; 8(6):779-96.

In alternative embodiments, combinations of microbes, e.g., combination of bacterial cells and/or spores, used in compositions as provided herein, or to practice methods as provided herein, are encapsulated in at least one polymeric material, e.g., a natural polymeric material, such that there is a core of bacterial cells and/or spores surrounded by a layer of the polymeric material, e.g., a polysaccharide. Examples of suitable polymeric materials are those that have been demonstrated to remain intact through the GI tract until reaching the small or large intestine, where they are degraded by microbial enzymes in the intestines. Exemplary natural polymeric materials can include, but are not restricted to, chitosan, inulin, guar gum, xanthan gum, amylose, alginates, dextran, pectin, khava, and albizia gum (Dafe et al. (2017) Int J Biol Macromol; Kofla et al. (2016) Int J Nanomedicine 11:1089-1095).

In alternative embodiments, compositions provided herein are suitable for therapeutic administration to a human or other mammal in need thereof. In alternative embodiments the compositions are produced by a process comprising, e.g.: (a) obtaining fecal material from a mammalian donor subject, (b) subjecting the fecal material to at least one purification treatment under conditions that produce a single bacterial type population of bacteria and/or bacterial spores, or a combination of bacterial types and/or bacterial spores, (c) optionally combining the purified population with another purified population obtained from the same or different fecal material, from cultured conditions, or from a genetic stock center such as ATCC or DSMZ, (d) if the microbes, e.g., bacterial cells, are not dormant, then treating the purified population(s) under conditions that cause vegetative bacterial cells to become dormant, and (e) placing the dormant bacteria and/or bacterial spores in a vehicle for administration.

In alternative embodiments, formulations and pharmaceutical compositions, and microbes, e.g., bacterial cells and/or spores, used in compositions as provided herein or to practice methods as provided herein, are formulated for oral or gastric administration to a mammalian subject. In particular embodiments, the composition is formulated for oral administration as a solid, semi-solid, gel or liquid form, such as in the form of a pill, tablet, capsule, lozenge, food, extract or beverage. Examples of suitable foods are those that require little mastication, such as yogurt, puddings, gelatins, and ice cream. Examples of extracts include crude and processed pomegranate juice, strawberry, raspberry and blackberry. Examples of suitable beverages include cold beverages, such as juices (pomegranate, raspberry, blackberry, blueberry, cranberry, acai, cloudberry, etc., and combinations thereof) and teas (green, black, etc.) and oaked wine.

In alternative embodiments, formulations and pharmaceutical compositions further comprise, or methods as provided herein further comprise administration of, at least one antibiotic, e.g., a doxycycline, chlortetracycline, tetracycline hydrochloride, oxytetracycline, demeclocycline, methacycline, minocycline, penicillin, amoxycillin, erythromycin, vancomycin, clarithromycin, roxithromycin, azithromycin, spiramycin, oleandomycin, josamycin, kitasamycin, flurithromycin, nalidixic acid, oxolinic acid, norfloxacin, pefloxacin, amifloxacin, ofloxacin, ciprofloxacin, sparfloxacin, levofloxacin, rifabutin, rifampicin, rifapentine, sulfisoxazole, sulfamethoxazole, sulfadiazine, sulfadoxine, sulfasalazine, sulfaphenazole, dapsone, sulfacytidine, linezolid or any combination thereof. In alternative embodiments, the antibiotic or a combination of antibiotics are administered before, during and/or after administration of formulations and pharmaceutical compositions as provided herein.

Gradual or Delayed Release Formulations

In alternative embodiments, exemplary formulations comprise, contain or are coated by an enteric coating to protect a microbe, e.g., a bacteria, in a formulation and pharmaceutical compositions as provided herein to allow it to pass through the stomach and small intestine (e.g., protect the administered combination of microbes such that a substantial majority of the microbes remain viable), although spores are typically resistant to the stomach and small intestines.

In alternative embodiments, compositions and formulations as provided herein, and compositions and formulations used to practice methods as provided herein, are formulated with a delayed release composition or formulation, coating or encapsulation. In alternative embodiments, compositions and formulations as provided herein, and compositions and formulations used to practice methods as provided herein, are designed or formulated for implantation of living microbes, e.g., bacteria or spores, into the gut, including the intestine and/or the distal small bowel and/or the colon. In this embodiment the living microbes, e.g., bacteria pass the areas of danger, e.g., stomach acid and pancreatic enzymes and bile, and reach the intestine substantially undamaged to be viable and implanted in the GI tract.

In alternative embodiments, a formulation or pharmaceutical preparation, or the combination of microbes contained therein, is liquid, frozen or freeze-dried. In alternative embodiments, e.g., for an encapsulated formulation, all are in powdered form. In alternative embodiments, if a formulation or pharmaceutical preparation as provided herein is in a powdered, lyophilate or freeze-dried form, the powder, lyophilate or freeze-dried form can be in a container such as a bottle, cartridge, packet or packette, or sachet, and the powder, lyophilate or freeze-dried form can be hydrated or reconstituted by a liquid, for example by adding water, saline, juice, milk and the like to the powder, lyophilate or freeze-dried form, for example, the powdered, lyophilate or freeze-dried form can be added to the liquid. In alternative embodiments, a powdered, lyophilate or freeze-dried form as provided herein is in a bottle or container, and the liquid is added to the bottle or container, and this mixture can be consumed by an individual in need thereof. In alternative embodiments, a powdered, lyophilate or freeze-dried form as provided herein is in a cartridge that can be part of a container or bottle, and the powdered, lyophilate or freeze-dried form can be mixed with the liquid, e.g., as described in U.S. Pat. No. 8,590,753. In alternative embodiments, a powdered, lyophilate or freeze-dried form as provided herein can be contained in or can be added to a container or bottle as described e.g., in U.S. Pat. Nos. 10,315,815; 10,315,803; 10,281,317; 10,183,116; 9,809,374; 9,345,831; 9,173,999; 7,874,420.

In alternative embodiments, compositions and formulations as provided herein, and compositions and formulations used to practice methods as provided herein, are formulated for delayed or gradual enteric release using cellulose acetate (CA) and polyethylene glycol (PEG), e.g., as described by Defang et al. (2005) Drug Develop. & Indust. Pharm. 31:677-685, who used CA and PEG with sodium carbonate in a wet granulation production process.

In alternative embodiments, compositions and formulations as provided herein, and compositions and formulations used to practice methods as provided herein, are formulated for delayed or gradual enteric release using a hydroxypropylmethylcellulose (HPMC), a microcrystalline cellulose (MCC) and magnesium stearate, as described e.g., in Huang et al. (2004) European J. of Pharm. & Biopharm. 58: 607-614).

In alternative embodiments, compositions and formulations as provided herein, and compositions and formulations used to practice methods as provided herein, are formulated for delayed or gradual enteric release using e.g., a poly (meth)acrylate, e.g. a methacrylic acid copolymer B, a methyl methacrylate and/or a methacrylic acid ester, a polyvinylpyrrolidone (PVP) or a PVP-K90 and a EUDRAGIT® RL PO™, as described e.g., in Kuksal et al. (2006) AAPS Pharm. 7(1), article 1, E1 to E9.

In alternative embodiments, compositions and formulations as provided herein, and compositions and formulations used to practice methods as provided herein, are formulated for delayed or gradual enteric release as described in U.S. Pat. App. Pub. 20100239667. In alternative embodiments, the composition comprises a solid inner layer sandwiched between two outer layers. The solid inner layer can comprise the non-pathogenic bacteria and/or spores, and one or more disintegrants and/or exploding agents, or one or more effervescent agents or a mixture. Each outer layer can comprise a substantially water soluble and/or crystalline polymer or a mixture of substantially water soluble and/or crystalline polymers, e.g., a polyglycol. These can be adjusted to achieve delivery of the living components to the intestine.

In alternative embodiments, compositions and formulations as provided herein, and compositions and formulations used to practice methods as provided herein, are formulated for delayed or gradual enteric release as described in U.S. Pat. App. Pub. 20120183612, which describes stable pharmaceutical formulations comprising active agents in a non-swellable diffusion matrix. In alternative embodiments, compositions and formulations as provided herein, and compositions and formulations used to practice methods as provided herein, are released from a matrix in a sustained, invariant and, if several active agents are present, independent manner and the matrix is determined with respect to its substantial release characteristics by ethylcellulose and at least one fatty alcohol to deliver bacteria distally.

In alternative embodiments, compositions and formulations as provided herein, and compositions and formulations used to practice methods as provided herein, are formulated for delayed or gradual enteric release as described in U.S. Pat. No. 6,284,274, which describes a bilayer tablet containing an active agent (e.g., an opiate analgesic), a polyalkylene oxide, a polyvinylpyrrolidone and a lubricant in the first layer and a second osmotic push layer containing polyethylene oxide or carboxymethylcellulose.

In alternative embodiments, compositions and formulations as provided herein, and compositions and formulations used to practice methods as provided herein, are formulated for delayed or gradual enteric release as described in U.S. Pat. App. Pub. No. 20030092724, which describes sustained release dosage forms in which a nonopioid analgesic and opioid analgesic are combined in a sustained release layer and in an immediate release layer, sustained release formulations comprising microcrystalline cellulose, EUDRAGIT RSPO™, CAB-O-SIL™, sodium lauryl sulfate, povidone and magnesium stearate.

In alternative embodiments, compositions and formulations as provided herein, and compositions and formulations used to practice methods as provided herein, are formulated for delayed or gradual enteric release as described in U.S. Pat. App. Pub. 20080299197, describing a multi-layered tablet for a triple combination release of active agents to an environment of use, e.g., in the GI tract. In alternative embodiments, a multi-layered tablet is used, and it can comprise two external drug-containing layers in stacked arrangement with respect to and on opposite sides of an oral dosage form that provides a triple combination release of at least one active agent. In one embodiment the dosage form is an osmotic device, or a gastro-resistant coated core, or a matrix tablet, or a hard capsule. In these alternative embodiments, the external layers may contain biofilm dissolving agents and internal layers can comprise viable/living bacteria, for example, a formulation comprising at least two different species or genera (or types) of non-pathogenic bacteria as used to practice methods as provided herein.

In alternative embodiments, compositions and formulations as provided herein, and compositions and formulations used to practice methods as provided herein, are formulated as multiple layer tablet forms, e.g., where a first layer provides an immediate release of a formulation or pharmaceutical preparation as provided herein and a second layer provides a controlled-release of another (or the same) bacteria or drug, or another active agent, e.g., as described e.g., in U.S. Pat. No. 6,514,531 (disclosing a coated trilayer immediate/prolonged release tablet), U.S. Pat. No. 6,087,386 (disclosing a trilayer tablet), U.S. Pat. No. 5,213,807 (disclosing an oral trilayer tablet with a core comprising an active agent and an intermediate coating comprising a substantially impervious/impermeable material to the passage of the first active agent), and U.S. Pat. No. 6,926,907 (disclosing a trilayer tablet that separates a first active agent contained in a film coat from a core comprising a controlled-release second active agent formulated using excipients which control the drug release, the film coat can be an enteric coating configured to delay the release of the active agent until the dosage form reaches an environment where the pH is above four).

In alternative embodiments, compositions and formulations as provided herein, and compositions and formulations used to practice methods as provided herein, are formulated for delayed or gradual enteric release as described in U.S. Pat. App. Pub. 20120064133, which describes a release-retarding matrix material such as: an acrylic polymer, a cellulose, a wax, a fatty acid, shellac, zein, hydrogenated vegetable oil, hydrogenated castor oil, polyvinylpyrrolidine, a vinyl acetate copolymer, a vinyl alcohol copolymer, polyethylene oxide, an acrylic acid and methacrylic acid copolymer, a methyl methacrylate copolymer, an ethoxyethyl methacrylate polymer, a cyanoethyl methacrylate polymer, an aminoalkyl methacrylate copolymer, a poly(acrylic acid), a poly(methacrylic acid), a methacrylic acid alkylamide copolymer, a poly(methyl methacrylate), a poly(methacrylic acid anhydride), a methyl methacrylate polymer, a polymethacrylate, a poly(methyl methacrylate) copolymer, a polyacrylamide, an aminoalkyl methacrylate copolymer, a glycidyl methacrylate copolymer, a methyl cellulose, an ethylcellulose, a carboxymethylcellulose, a hydroxypropyl-methylcellulose, a hydroxymethyl cellulose, a hydroxyethyl cellulose, a hydroxypropyl cellulose, a crosslinked sodium carboxymethylcellulose, a crosslinked hydroxypropylcellulose, a natural wax, a synthetic wax, a fatty alcohol, a fatty acid, a fatty acid ester, a fatty acid glyceride, a hydrogenated fat, a hydrocarbon wax, stearic acid, stearyl alcohol, beeswax, glycowax, castor wax, carnauba wax, a polylactic acid, polyglycolic acid, a copolymer of lactic and glycolic acid, carboxymethyl starch, potassium methacrylate/divinylbenzene copolymer, crosslinked polyvinylpyrrolidone, polyvinylalcohols, polyvinylalcohol copolymers, polyethylene glycols, non-crosslinked polyvinylpyrrolidone, polyvinylacetates, polyvinylacetate copolymers or any combination thereof. In alternative embodiments, spherical pellets are prepared using an extrusion/spheronization technique, of which many are well known in the pharmaceutical art. The pellets can comprise one or more formulations or pharmaceutical preparations as provided herein.

In alternative embodiments, compositions and formulations as provided herein, and compositions and formulations used to practice methods as provided herein, are formulated for delayed or gradual enteric release as described in U.S. Pat. App. Pub. 20110218216, which describes an extended release pharmaceutical composition for oral administration, and uses a hydrophilic polymer, a hydrophobic material and a hydrophobic polymer or a mixture thereof, with a microenvironment pH modifier. The hydrophobic polymer can be ethylcellulose, cellulose acetate, cellulose propionate, cellulose butyrate, methacrylic acid-acrylic acid copolymers or a mixture thereof. The hydrophilic polymer can be polyvinylpyrrolidone, hydroxypropylcellulose, methylcellulose, hydroxypropylmethyl cellulose, polyethylene oxide, acrylic acid copolymers or a mixture thereof. The hydrophobic material can be a hydrogenated vegetable oil, hydrogenated castor oil, carnauba wax, candellia wax, beeswax, paraffin wax, stearic acid, glyceryl behenate, cetyl alcohol, cetostearyl alcohol or and a mixture thereof. The microenvironment pH modifier can be an inorganic acid, an amino acid, an organic acid or a mixture thereof. Alternatively, the microenvironment pH modifier can be lauric acid, myristic acid, acetic acid, benzoic acid, palmitic acid, stearic acid, oxalic acid, malonic acid, succinic acid, adipic acid, sebacic acid, fumaric acid, maleic acid; glycolic acid, lactic acid, malic acid, tartaric acid, citric acid, sodium dihydrogen citrate, gluconic acid, a salicylic acid, tosylic acid, mesylic acid or malic acid or a mixture thereof.

In alternative embodiments, therapeutic combinations or formulations, or pharmaceuticals or the pharmaceutical preparations as provided herein, or as used in methods as provided herein, are formulated as a delayed or gradual enteric release composition or formulation, and optionally the formulation comprises a gastro-resistant coating designed to dissolve at a pH of 7 in the terminal ileum, for example, an active ingredient is coated with an acrylic based resin or equivalent, for example, a poly(meth)acrylate, for example a methacrylic acid copolymer B, NF, which dissolves at pH 7 or greater, for example, comprises a multimatrix (MMX) formulation. In alternative embodiments, compositions and formulations as provided herein, and compositions and formulations used to practice methods as provided herein, are powders that can be included into a suitable carrier, e.g., such as a liquid, a tablet or a suppository. In alternative embodiments, compositions and formulations as provided herein, and compositions and formulations used to practice methods as provided herein, are 'powders for reconstitution' as a liquid to be drunk, placed down a naso-duodenal tube or used as an enema for patients to take home and self-administer enemas. In alternative embodiments, compositions and formulations as provided herein, and compositions and formulations used to practice methods as provided herein, are micro-encapsulated, formed into tablets and/or placed into capsules, especially enteric-coated capsules. In alternative embodiments, compositions as provided herein are formulated to be effective in a given mammalian subject in a single administration or over multiple administrations. In some embodiments, a substrate or prebiotic required by the bacterial type in a formulation as provided herein is administered for a period of time in advance of the administration of the combination of microbes, e.g., bacterial compositions, as provided herein. Such administration (e.g., of prebiotics) pre-loads the gastrointestinal tract with the substrates needed by the bacterial types of the composition and increases the potential for the bacterial composition to have adequate resources to perform the required metabolic reactions. In other embodiments, the composition is administered simultaneously with the substrates required by the bacterial types a formulation as provided herein. In still other embodiments the substrate or prebiotic is administered alone. In alternative embodiments, efficacy is measured by an increase in the population of those bacterial types in the subject's intestinal tract, or an increase in the population of those bacterial types originally found in the subject's intestinal tract before treatment.

In alternative embodiments, compositions as provided herein comprise, further comprise, or have added to: at least one probiotic or prebiotic, wherein optionally the prebiotic comprises an inulin, lactulose, extracts of artichoke, chicory root, oats, barley, various legumes, garlic, kale, beans or flacks or an herb, wherein optionally the probiotic comprises a cultured or stool-extracted microorganism or bacteria, or a bacterial component, and optionally the bacteria or bacterial component comprises or is derived from a Bacteroidetes, a Firmicutes, a Lactobacilli, a Bifidobacteria, an *E. coli*, a *Streptococcus faecalis* and equivalents.

In alternative embodiments, compositions as provided herein comprise, further comprise, or have added to: at least one congealing agent, wherein optionally the congealing agent comprises an arrowroot or a plant starch, a powdered flour, a powdered potato or potato starch, an absorbent polymer, an Absorbable Modified Polymer, and/or a corn flour or a corn starch; or, further comprise an additive selected from one or more of a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent and/or coloring agent, vitamin, mineral and/or dietary supplement, or a prebiotic nutrient; or, further comprise, or have added to: at least one Biofilm Disrupting Compound, wherein optionally the biofilm disrupting compound comprises an enzyme, a deoxyribonuclease (DNase), N-acetyl-cysteine, an auranofin, an alginate lyase, glycoside hydrolase dispersin B; a Quorum-sensing inhibitor, a ribonucleic acid III inhibiting peptide, *Salvadora persica* extracts, Competence-stimulating peptide, Patulin and penicillic acid; peptides—cathelicidin-derived peptides, small lytic peptide, PTP-7, nitric oxide, neo-emulsions; ozone, lytic bacteriophages, lactoferrin, xylitol hydrogel, synthetic iron chelators, a statin (optionally lovastatin (optionally MEVACOR™), simvastatin (optionally ZOCOR™), atorvastatin (optionally LIPITOR™), pravastatin (optionally PRAVACHOL™), fluvastain (optionally LESCOL™) or rosuvastatin (optionally CRESTOR™)), cranberry components, curcumin, silver nanoparticles, Acetyl-11-keto-β-boswellic acid (AKBA), barley coffee components, probiotics, sinefungin, S-adenosylmethionine, S-adenosyl-homocysteine, Delisea furanones, N-sulfonyl homoserine lactones or any combination thereof.

In alternative embodiments, compositions as provided herein comprise, further comprise, or have added to: a flavoring or a sweetening agent, an aspartamine, a *stevia*, monk fruit, a sucralose, a saccharin, a cyclamate, a xylitol, a vanilla, an artificial vanilla or chocolate or strawberry flavor, an artificial chocolate essence, or a mixture or combination thereof.

Products of Manufacture and Kits

Provided are products of manufacture, e.g., implants or pharmaceuticals, and kits, containing components for practicing methods as provided herein, e.g., including a formulation comprising a combination of microbes as provided herein, such as e.g., freshly isolated microbes, cultured microbes, or genetically engineered microbes, or at least two different species or genera (or types) of non-pathogenic bacteria, wherein each of the non-pathogenic bacteria comprise (or are in the form of) a plurality of non-pathogenic colony forming live bacteria, a plurality of non-pathogenic germinable bacterial spores, or a combination thereof, and optionally including instructions for practicing methods as provided herein.

Companion Diagnostics and Patient Biomarkers

Provided are biomarkers indicative of patient response or non-response to a composition or method as provided herein, including e.g., a chemotherapy, a radiation therapy, an immune checkpoint inhibitor (e.g., a checkpoint inhibitor therapy), a Chimeric Antigen Receptor (CAR) T-cell therapy (CAR-T) or other immunotherapy or cancer treatment. These biomarkers may be in the form of microbial species abundance in the gut (or abundance in the colon), microbial gene expression or protein expression, or abundance of a metabolite in a stool sample or a sample of bacteria taken from the gut. Alternatively, the biomarkers may be metabolite concentration, cytokine profile, or protein expression in the blood. These biomarkers are used to develop a diagnostic screen to predict in advance whether a patient will naturally respond to therapy or will require microbial intervention to enable the composition or method as provided herein, e.g., checkpoint inhibitors or CAR-T therapy, to function efficaciously or more efficaciously as compared to their effectiveness in the patient if a composition or method as provided herein had not been administered.

Genetic Modification of Microbial Therapeutics

In alternative embodiments, microbes, e.g., bacteria, used in compositions as provided herein, or used to practice methods as provided herein, are genetically engineered. In alternative embodiments, microbes are genetically engineered to increase their efficacy, e.g., to increase the efficacy of a chemotherapy, a radiation therapy, an immune checkpoint inhibitor (e.g., a checkpoint inhibitor therapy), a Chimeric Antigen Receptor (CAR) T-cell therapy (CAR-T) or other immunotherapy or cancer treatment. In alternative embodiments, one several or all of a combination of microbes as provided herein, or used to practice methods as provided herein, are genetically engineered. In alternative embodiments, microbes are genetically engineered to substantially decrease, reduce or eliminate their toxicity. In alternative embodiments, microbes are genetically engineered to comprise a kill switch so they can be rendered non-vital after administration of an appropriate trigger or signal. In alternative embodiments, microbes are genetically engineered to secrete anti-inflammatory compositions or have an anti-inflammatory effect. In alternative embodiments, microbes are genetically engineered to secrete an anti-cancer sub stance.

Microbes, e.g., bacteria, used in compositions as provided herein, or used to practice methods as provided herein, can be genetically engineered using any method known in the art, e.g., as discussed in the Examples, below. For example, one or more gene sequence(s) and/or gene cassette(s) may be expressed on a high-copy plasmid, a low-copy plasmid, or a chromosome. In some embodiments, expression from the plasmid is used to increase expression of an inserted, e.g., heterologous nucleic acid, e.g., a gene or protein encoding sequence or an inhibitory nucleic acid such as an antisense or siRNA-encoding nucleic acid. The inserted nucleic acid of interest can be inserted into a bacterial chromosome at one or more integration sites.

For example, in alternative embodiments, microbes are genetically engineered to comprise one or more gene sequence(s) and/or gene cassette(s) for producing a non-native anti-inflammation and/or gut barrier function enhancer molecule. In alternative embodiments, the anti-inflammation and/or gut barrier function enhancer molecule comprises a short-chain fatty acid, butyrate, propionate, acetate, IL-2, IL-22, superoxide dismutase (SOD), GLP-2, GLP-1, IL-10, IL-27, TGF-.beta.1, TGF-.beta.2, N-acylphosphatidylethanolamines (NAPES), elafin (also known as peptidase inhibitor 3 or SKALP), trefoil factor, melatonin, $PGD_2$, kynurenic acid, and kynurenine. A molecule may be primarily anti-inflammatory, e.g., IL-10, or primarily gut barrier function enhancing, e.g., GLP-2. In alternative embodiments, microbes are genetically engineered to comprise one or more gene sequence(s) and/or gene cassette(s) that are inhibitory to the activity of, or substantially or completely inhibit expression of, bacterial virulence factors, toxins, or antibiotic resistance functions.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (1989) Molecular Cloning: A Laboratory Manual, Second Edition, Cold Spring Harbor Laboratory Press, N.Y. and in Volumes 1 and 2 of Ausubel et al. (1994) Current Protocols in Molecular Biology, Current Protocols, USA. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

The following Examples describe methods and compositions for practicing embodiments as provided herein, including methods for making and using compositions comprising non-pathogenic bacteria and non-pathogenic germinable bacterial spores used to practice methods as provide herein.

Example 1: Anaerobic Culture Conditions

Preparation of Anaerobic Growth Medium

Exemplary bacterial strains described herein are obligate anaerobes that require anaerobic conditions for culture. Growth media suitable for culture of anaerobic bacteria include reducing agents such as L-cysteine, sodium thioglycolate, and dithiothreitol, for the purpose of scavenging and removing oxygen. Appropriate commercially available anaerobic growth media include but are not limited to Anaerobe Basal Broth (Oxoid/Thermo Scientific), Reinforced Clostridial Medium (Oxoid/Thermo Scientific), Wilkins-Chalgren Anaerobe Broth (Oxoid/Thermo Scientific), Schaedler Anaerobe Broth (Oxoid/Thermo Scientific), and Brain Heart Infusion Broth (Oxoid/Thermo Scientific). Animal free medium for anaerobic culture include but are not limited to Vegitone *Actinomyces* Broth (Millipore-Sigma), MRS Broth (Millipore-Sigma), Vegitone Infusion Broth (Millipore-Sigma), and Vegitone Casein Soya Broth (Millipore-Sigma).

One liter of Anaerobic growth medium is prepared by combining the manufacturer's recommended amount in grams of dry growth medium powder with 800 ml Reagent Grade Water (NERL™) along with 1 ml 2.5 mg/ml resazurin (ACROS Organics™) in a 2 liter beaker and stirred on a heated stir plate until dissolved. The volume is adjusted to 1 liter by addition of additional Reagent Grade Water, then the volume is brought to a boil while stirring until the red color imbued by the resazurin becomes colorless, indicating removal of oxygen from the solution. The volume is then removed from the stir plate to cool for 10 minutes on the benchtop before further manipulation.

From the 1-liter volume, 900 ml is transferred to a 1 liter anaerobic media bottle (Chemglass Life Sciences) and then placed back on the heated stir plate to remove any oxygen introduced in the transfer, as indicated by the color of the added resazurin. The anaerobic media bottle is then stoppered with a butyl rubber bung that is secured by a crimped aluminum collar, and then brought into the anaerobic chamber (Coy Lab Type A Vinyl Anaerobic Chamber, Coy Laboratory Products, Grass Lake, MI). The butyl rubber bung is removed to open the bottle within the anaerobic chamber to equilibrate with the anoxic atmosphere while cooling to ambient temperature. The bottle is resealed with a fresh butyl rubber bung and crimped aluminum collar, brought out of the chamber, then sterilized by autoclaving for 20 minutes followed by slow exhaust.

Alternatively, the 1-liter volume can be aliquoted into smaller 50 ml volumes in 100 ml serum bottles (Chemglass Life Sciences, Vineland New Jersey). The boiled 1-liter volume is transferred to a one-liter screwcap bottle, which is placed back on the heated stir plate to drive off any oxygen introduced by the transfer. The bottle cap is then securely tightened, and the bottle is immediately brought into the anaerobic chamber, where the cap is loosened to allow the volume to equilibrate with the anoxic atmosphere and to cool for 1 hour. The volume is then transferred in 50 ml aliquots to 100 ml serum bottles using a serological pipette, then the liquid contents cooled to ambient temperature. The bottles are sealed with butyl rubber bungs and crimped aluminum collars, brought out of the chamber, then sterilized by autoclaving for 20 minutes followed by slow exhaust.

Alternatively, the 1-liter volume can be aliquoted into smaller 10 ml volumes in sealed Hungate tubes (Chemglass Life Sciences, Vineland New Jersey) as follows. The boiled 1-liter volume is transferred to a one-liter screwcap bottle, which is placed back on the heated stir plate to drive off any oxygen introduced by the transfer. The bottle cap is then securely tightened, and the bottle is immediately brought into the anaerobic chamber, where the cap is loosened to allow the volume to equilibrate with the anoxic atmosphere and to cool for 1 hour. The volume is then transferred in 10 ml aliquots to fill racked Hungate tubes, then allowed to cool to ambient temperature, followed by securely capping and sealing each tube with screwcaps with butyl rubber septa. The sealed Hungate tube aliquots are removed from the anaerobic chamber and then sterilized by autoclaving for 20 minutes followed by slow exhaust.

Alternatively, the 1 liter volume can be combined with 15 grams Agar (Thermo Scientific™) to make solid media in culture plates as follows: The boiled 1 liter volume is poured into a 1 liter screwcap bottle, followed by replacement on a heated stir plate to remove any oxygen introduced by the transfer as indicated by the colorless resazurin oxygen indicator. The bottle is loosely capped and then autoclaved for 20 minutes followed by slow exhaust. Immediately after autoclaving, the cap of the bottle is tightened prior to bringing the bottle into the anaerobic chamber. Once in the anaerobic chamber, the cap is loosened and the contents cooled for 30 minutes, then 25 ml volumes are poured into culture plates and allowed to cool until solidified. The plates are then allowed to dry in the anaerobic chamber for 24 hours prior to use.

Live Cryostorage of Anaerobic Microbes

Individual microbes of interest are prepared for long-term cryogenic live storage by inoculating a pure colony isolate grown on anaerobic solid medium into a prepared Hungate tube containing liquid anaerobic growth medium previously determined to be optimal for the species. The inoculated Hungate tube is then incubated at 37° C. until turbidity evident of exponential growth is observed. The Hungate culture is brought into the anaerobic chamber, and 1 ml is transferred by pipette into a 2 ml screwcap cryotube containing anoxic 1 ml Biobank Buffer (Phosphate Buffered Saline (PBS) plus 2% trehalose plus 10% dimethyl sulfoxide, filter sterilized and bubbled with nitrogen gas to remove oxygen). The resulting 2 ml volume is thoroughly mixed by pipetting, securely tightened, then placed for long-term storage in the gaseous phase of a liquid nitrogen Dewar or in a −80° C. freezer.

Microbes in fecal matter can be cryogenically preserved for later revival and new strain discovery as follows. Freshly obtained fecal material is brought into the anaerobic chamber and 1 gram is weighed and mixed in a 15 ml conical tube with a solution consisting of 5 ml Anaerobe Basal Broth (ABB) and 5 ml Biobank Buffer. The tube is tightly capped, and the fecal matter is thoroughly suspended in the solution by vortexing for 20 minutes, followed by incubation upright on ice to allow large particles to settle. One ml aliquots of the fecal suspension are then transferred by pipette to a 2 ml screwcap cryotube, securely tightened, then placed for long-term storage in the gaseous phase of a liquid nitrogen Dewar or in a −80° C. freezer.

Example 2: Fecal Matter Collection from Patients and Processing

Fecal matter donations are acquired from healthy volunteers as well as individuals exhibiting disease symptoms. Donors can be cancer patients being administered approved therapies or participating in clinical trials testing various cancer treatment regimens. Donors can be healthy volunteers that do not exhibit disease symptoms.

Donors receive a stool sampling kit by mail sent to the contact address provided or by their physician. Stool samples are collected by the subject at home, or with necessary assistance if hospitalized. Stool sampling kits consist of the following: gloves, instructions for stool collection, welcome card, freezer pack, Styrofoam container, plastic bracket and plastic commode to aid in stool collection, Bristol stool chart, FedEx shipping labels, and stickers to seal kit prior to shipping. Subjects receive a freezer pack for chilling the samples and are instructed to place it in their freezer overnight upon receipt of the sampling kit. The stool sampling kit also includes a plastic commode that can be placed safely and securely on a toilet seat, allowing the subject to defecate directly into a plastic container. The subject is instructed to use the commode to capture a stool sample, then seal the sample container with a provided snap-cap lid. Subjects are instructed to wear the gloves provided in the kit before removing the sample container from the toilet. The subject is instructed to seal the plastic container inside a specimen bag and remove gloves. The subject is then instructed to remove the ice pack from their home freezer and place it inside the Styrofoam cooler box along with the bagged and sealed stool sample, and the graded Bristol Stool card (form indicating stool collection date/time and consistency). The subject is instructed to close the lid on the foam container and then close the box, sealing with the packing sticker. The subject is instructed to schedule a FedEx pickup at their home within 24 hours of stool collection or drop it off at the nearest FedEx location. Under these conditions the stool has been demonstrated to remain chilled during shipment for as long as 48 hours.

Once received, the stool sample receptacle is given a unique alphanumeric identifier that is used subsequently for sample tracking. The stool is unpacked from the shipping box in a laboratory setting, homogenized, and divided into enough individual aliquots for all projected analyses prior to freezing and storage at −80° C., as described below. All aliquots also bear an alphanumeric identifier corresponding to the subject donor. Any remaining stool after the aliquots are taken is disposed as biohazardous waste.

Preparation of Fecal Matter Samples for Analysis

Fecal matter received from donors can be processed using any method known in the art, for example, as described in U.S. Pat. Nos. 10,493,111; 10,471,107; 10,286,012; 10,314,863; 9,623,056.

For example, received fecal matter in its receptacle is placed on ice and then brought into the anaerobic chamber. The receptacle is opened and approximately 40 g stool is weighed into a tared specimen cup. 15 ml sterile anoxic PBS is then added, and the mixture is homogenized by a hand-held homogenizer to achieve a smooth consistency.

The homogenized fecal matter is then processed and aliquoted for cryopreservation for several different analyses as follows:

1) For Genomic and Transcriptomic Analyses: homogenized fecal matter is weighed and then an equal volume to weight amount of RNAlater® (Thermo Fisher Scientific) solution is added. The tube is capped tightly and then vortexed for 20 seconds and then placed on ice. A pipette is used to transfer 1 ml aliquots into 2 ml Eppendorf tubes. Aliquoted samples are frozen on dry ice and then stored at −80° C.

2) Live Cryopreservation for Fecal Microbiome Transfer (FMT) Experiments in Mice: Homogenized fecal matter is combined with FMT Buffer (Phosphate Buffered Saline plus 1% L-Cysteine plus 2% Trehalose plus 30% glycerol). The tube is then vortexed for 20 seconds and then placed on ice. A pipette is used to transfer 1 ml aliquots into 2 ml cryotubes that are then tightly capped. Aliquoted samples are frozen on dry ice and then stored at −80° C.

3) Live Cryopreservation for Isolation and Discovery of Microbes: Homogenized fecal matter is combined in a conical tube with Anaerobe Basal Broth and Biobank Buffer (Phosphate Buffered Saline plus 2% Trehalose plus 10% dimethyl sulfoxide), tightly capped and vortexed for 20 seconds, then put on ice upright and allowed to settle for 10 minutes. Using a pipette, 1 ml aliquots are added to 2 ml cryotubes, which are then tightly capped. Aliquoted samples are frozen on dry ice and then stored at −80° C.

For Genomic and Metabolomic Analyses: Homogenized fecal matter is added to a plastic bag. About 1 cm of the tip end of the bag is cut off with scissors, then aliquots are made by manually squeezing 1 ml of the bag contents into 2 ml Eppendorf tubes. Aliquoted samples are frozen on dry ice and then stored at −80° C.

Example 3: Isolation and Characterization of Pure Microbial Strains from Fecal Matter In alternative embodiments, microbes used in compositions as provided herein, or used to practice methods as provided herein, are isolated from fecal matter, and can be used on the form of a pure microbial strain isolated from fecal matter.

Individual bacterial strains can be isolated and cultured from fecal matter material for further study and for assembly of therapeutic biologicals, i.e. for manufacturing combinations of microbes as provided herein. The majority of live bacteria that inhabit fecal matter tend to be obligate anaerobes so care must be taken to perform all culture and isolation work in the anaerobic chamber to prevent their exposure to oxygen, and to use various anaerobic growth media that includes reductant compounds as described in Example 1. Growth media that favor growth of target bacteria can be used to improve the ability to find and isolate them as pure living cultures. Different anaerobic growth media are used to enable growth of different subsets of microbes to improve overall ability to isolate and purify an inclusive number of unique bacterial species from each individual fecal material sample.

To begin a microbial isolation and characterization campaign, one cryotube containing cryogenically preserved fecal matter is removed from storage in the liquid nitrogen Dewar, brought into the anaerobic chamber, and then allowed to thaw gently on ice. The entire 1 ml contents are added to 10 ml of Anaerobe Basal Broth (ABB) or another suitable anaerobic growth medium to establish a 1/10 dilution. Successive 10-fold serial dilutions are then performed in ABB to establish 1/100, 1/1000, 1/10000, 1/100000, 1/1000000 dilutions of the fecal matter. From each of the 1/10000, 1/100000, and 1,1000000 dilutions, four 0.1 ml volumes are removed and then added to and spread over solid anaerobic growth medium of choice. The platings are incubated at 37° C. for 1, 2, 3, 4, 5, 6, 7, 8, 9, 10, 11, 12 days to allow for a wide variety of bacterial colonies to grow. Platings are made from several liquid dilutions of fecal matter to ensure that there will be ones that have numerous yet non-overlapping colonies for efficient colony picking.

Colonies are manually picked from plates using sterile pipette tips. Colonies may also be picked by an automated colony picking machine that is enclosed in an anaerobic chamber. Colonies are picked in multiples of 96 to accommodate subsequent 96-well-based genomic DNA isolation steps and large-scale cryogenic storage steps. The individual picked colonies are then struck on solid anaerobic growth medium of choice to isolate single purified colonies from each picked colony, and then incubated at 37° C. for 1, 2, 3, 4, 5, 6, 7, 8, 9, 10, 11, 12 days to allow for visible colony growth to arise. After visible colonies are evident on the streak, single colonies are picked and then each inoculated into an individual well of a 2 ml 96-well deep well block, each well with 1 ml liquid anaerobic growth medium of choice. Once all wells of the deep-well block have been inoculated with different picked colonies, the deep well block is covered with an adhesive gas-permeable seal and then incubated at 37° C. in an incubator within the anaerobic chamber for 1, 2, 3, 4, 5, 6, 7, 8, 9, 10, 11, 12 days to allow for liquid growth from each isolated colony.

After turbid growth is apparent in all wells, the gas-permeable seal is removed from the 96-well deep well block and a viable stock representation is made by transferring 0.1 ml culture from each well to the corresponding wells of a second 96-well deep-well block, each well containing 0.4 ml of the same anaerobic growth medium plus 0.5 ml Biobank Buffer (Phosphate Buffered Saline plus 2% Trehalose plus 10% dimethyl sulfoxide. The volumes in each well are thoroughly mixed by pipetting up and down several times, then the deep-well block is sealed with an impermeable foil seal rated for −80° C. storage, then stored in a −80° C. freezer.

Sequence and Computational Characterization of Isolated Fecal Bacteria

The remaining 0.9 ml culture in the original 96-well deep-well plate is then used for whole genome sequence determination of the isolated strain as follows: The deep-well block is subjected to centrifugation for 20 minutes at 6000 g to pellet the cells. After centrifugation, 0.8 ml supernatant is carefully removed by pipette, leaving 0.1 ml pellet and medium for gDNA processing. Total genomic DNA is extracted from the cell pellet using the MagAttract PowerMicrobiome DNA/RNA EP kit (Qiagen). Genomic DNA is then prepared for Whole Genome Sequencing analysis using the sparQ DNA Frag & Library Prep kit (Quantabio). Sequencing analysis is conducted on the Illumina platform using paired-end 150 bp reads.

Sequencing data is processed to remove low quality reads and adapter contamination using Trim Galore, a wrapper for cutadapt (https://journal.embnet.org/index.php/embnetjournal/article/view/200).

The high-quality reads for each isolate are compared against each bacterial or archaeal assembly in NCBI RefSeq using mash (https://genomebiology.biomedcentral.com/articles/10.1186/s13059-016-0997-x). This identifies the most similar organism in the RefSeq database to each isolate at the species and strain level. If the distance reported by mash is below 0.01, the isolate is assumed to be the same strain as the reference strain. If the distance is less than 0.04, the isolate is assumed to be of the same species as the reference strain. If the distance is greater than 0.04, the isolate is assumed to be of a potentially novel species; these isolates are handled on a case-by-case basis.

Further analysis is performed on isolates of interest by assembling with SPAdes (https://www.ncbi.nlm.nih.gov/pmc/articles/PMC3342519/) and using mummer (https://journals.plos.org/ploscompbiol/article?id=10.1371/journal.pcbi.1005944) to align the reference genome and isolate genome against each other.

Complete genomes are generated for organisms of special interest using long-read sequencing. High molecular weight genomic DNA is prepared from organisms of interest using a commercially available kit e.g. Genomic-tip (Qiagen). Library preparation on genomic DNA is performed using the Ligation Sequencing Kit (Oxford Nanopore) and sequencing is performed on a MinION (Oxford Nanopore). Reads are filtered and trimmed for quality and assembly is performed using the assembler Flye (Kolmogorov et al. (2019) Nature Biotechnology 37:540-546). The resulting assembly is polished using multiple rounds of pilon (Walker et al. (2014) PLOS ONE 9:e112963) with short reads to correct for errors inherent in long read sequencing. Genes are predicted on the polished genome using prodigal (Hyatt et al. (2010) BMC Bioinformatics 11:119) or the NCBI Prokaryotic Gene Annotation Pipeline (Tatusova et al. (2016) Nucleic Acids Research 44(14):6614-24). Results of this analysis on isolates collected so far are provided in Table 1.

TABLE 1

Exemplary bacterial strains isolated from human fecal material that can be used alone to practice methods as provided herein, or in making or using combinations of microbe compositions as provided herein.

| Strain ID | Screening Medium | NCBI Taxonomy ID | NCBI Organism Name[a] | NCBI Infraspecific Name | Distance from Reference Assembly (mash) |
|---|---|---|---|---|---|
| 1 | ABB | 742722 | Collinsella sp. 4_8_47FAA | 4_8_47FAA | 0.0473307 |
| 2 | ABB | 2292944 | Bacteroides sp. AM25-34 | AM25-34 | 0.00558143 |
| 3 | ABB | 1073351 | Bacteroides stercoris CC31F | CC31F | 0.0198874 |
| 4 | ABB | 1339345 | Parabacteroides distasonis str. 3999B T(B) 6 | 3999B T(B) 6 | 0.00787841 |
| 5 | ABB | 1073351 | Bacteroides stercoris CC31F | CC31F | 0.021248 |
| 6 | ABB | 1335613 | Gordonibacter urolithinfaciens | DSM 27213T | 0.00456858 |
| 7 | ABB | 2292910 | Alistipes sp. AF14-19 | AF14-19 | 0.0168764 |
| 8 | ABB | 742722 | Collinsella sp. 4_8_47FAA | 4_8_47FAA | 0.0417882 |
| 9 | ABB | 47678 | Bacteroides caccae | OM05-21BH | 0.05067 |
| 10 | ABB | 47678 | Bacteroides caccae | OM05-21BH | 0.0121561 |
| 11 | ABB | 2292944 | Bacteroides sp. AM25-34 | AM25-34 | 0.00593905 |
| 12 | ABB | 2292944 | Bacteroides sp. AM25-34 | AM25-34 | 0.00583101 |
| 13 | ABB | 2292316 | Collinsella sp. AM34-10 | AM34-10 | 0.0529596 |
| 14 | ABB | 471875 | Ruminococcus lactaris ATCC 29176 | ATCC 29176 | 0.0131398 |
| 15 | ABB | 28116 | Bacteroides ovatus | AM40-4 | 0.0117158 |
| 16 | ABB | 997891 | Bacteroides vulgatus CL09T03C04 | CL09T03C04 | 0.0141644 |
| 17 | ABB | 742722 | Collinsella sp. 4_8_47FAA | 4_8_47FAA | 0.0447107 |
| 18 | ABB | 2292316 | Collinsella sp. AM34-10 | AM34-10 | 0.0538719 |
| 19 | ABB | 1680 | Bifidobacterium adolescentiss | 2789STDY5608862 | 0.0147396 |
| 20 | ABB | 1339345 | Parabacteroides distasonis str. 3999BT(B) 6 | 3999B T(B) 6 | 0.00817721 |

TABLE 1-continued

Exemplary bacterial strains isolated from human fecal material that can be used alone to practice methods
as provided herein, or in making or using combinations of microbe compositions as provided herein.

| Strain ID | Screening Medium | NCBI Taxonomy ID | NCBI Organism Name[a] | NCBI Infraspecific Name | Distance from Reference Assembly (mash) |
|---|---|---|---|---|---|
| 21 | ABB | 2292236 | *Odoribacter* sp. AF15-53 | AF15-53 | 0.011787 |
| 22 | ABB | 46503 | *Parabacteroides merdae* | AM48-24BH | 0.0113184 |
| 23 | ABB | 88431 | *Dorea longicatena* | AF17-8AC | 0.0165507 |
| 24 | ABB | 2292944 | *Bacteroides* sp. AM25-34 | AM25-34 | 0.00946265 |
| 25 | ABB | 1681 | *Bifidobacterium bifidum* | 2789STDY5608877 | 0.160172 |
| 26 | ABB | 2292944 | *Bacteroides* sp. AM25-34 | AM25-34 | 0.116478 |
| 27 | ABB | 454154 | *Paraprevotella clara* | AF15-8 | 0.0236678 |
| 28 | ABB | 742722 | *Collinsella* sp. 4_8_47FAA | 4_8_47FAA | 0.0439329 |
| 29 | ABB | 997891 | *Bacteroides vulgatus* CL09T03C04 | CL09T03C04 | 0.0125382 |
| 30 | ABB | 821 | *Bacteroides vulgatus* | AM39-10 | 0.0105456 |
| 31 | ABB | 997891 | *Bacteroides vulgatus* CL09T03C04 | CL09T03C04 | 0.0126174 |
| 32 | ABB | 2292303 | *Clostridium* sp. AM30-24 | AM30-24 | 0.0326468 |
| 33 | ABB | 2292316 | *Collinsella* sp. AM34-10 | AM34-10 | 0.0537876 |
| 34 | ABB | 2109334 | *Blautia* sp. SG-772 | SG-772 | 0.0332125 |
| 35 | ABB | 454154 | *Paraprevotella clara* | AF15-8 | 0.0238471 |
| 36 | ABB | 2109334 | *Blautia* sp. SG-772 | SG-772 | 0.0255631 |
| 37 | ABB | 2292944 | *Bacteroides* sp. AM25-34 | AM25-34 | 0.0114769 |
| 38 | ABB | 33039 | [*Ruminococcus*] *torques* | 2789STDY5608867 | 0.0279573 |
| 39 | ABB | 1160721 | *Ruminococcus bicirculans* | 80/3 | 0.0243949 |
| 40 | ABB | 2109686 | *Butyricicoccus* sp. GAM44 | GAM44 | 0.0264344 |
| 41 | ABB | 2109334 | *Blautia* sp. SG-772 | SG-772 | 0.0246868 |
| 42 | ABB | 2293190 | *Ruminococcus* sp. AM26-12LB | AM26-12LB | 0.0196594 |
| 43 | ABB | 820 | *Bacteroides uniformis* | DSM 6597 | 0.0115705 |
| 44 | ABB | 411485 | *Faecalibacterium prausnitzii* M21/2 | M21/2 | 0.0299116 |
| 45 | ABB | 39491 | [*Eubacterium*] *rectale* | T1-815 | 0.0237145 |
| 46 | ABB | 28116 | *Bacteroides ovatus* | AF04-46 | 0.0211933 |
| 47 | ABB | 742722 | *Collinsella* sp. 4_8_47FAA | 4_8_47FAA | 0.0448295 |
| 48 | ABB | 39488 | *Anaerobutyricum hallii* | | 0.0309762 |
| 49 | ABB | 2292372 | *Ruminococcus* sp. AM42-11 | AM42-11 | 0.0259854 |
| 50 | ABB | 88431 | *Dorea longicatena* | 2789STDY5608851 | 0.015968 |
| 51 | ABB | 216816 | *Bifidobacterium longum* | DPC6320 | 0.0151441 |
| 52 | ABB | 216816 | *Bifidobacterium longum* | DPC6320 | 0.203899 |
| 53 | ABB | 649756 | *Anaerostipes hadrus* | 2789STDY5834860 | 0.0183835 |
| 54 | ABB | 216816 | *Bifidobacterium longum* | DPC6320 | 0.0143493 |
| 55 | ABB | 2292976 | *Blautia* sp. AM42-2 | AM42-2 | 0.0212548 |
| 56 | ABB | 818 | *Bacteroides thetaiotaomicron* | NLAE-zl-C579 | 0.0111348 |
| 57 | ABB | 2292944 | *Bacteroides* sp. AM25-34 | AM25-34 | 0.0058836 |
| 58 | ABB | 1504823 | bacterium LF-3 | | 0.0156336 |
| 59 | ABB | 1520805 | *Blautia* sp. SF-50 | SF-50 | 0.0184835 |
| 60 | ABB | 39491 | [*Eubacterium*] *rectale* | T1-815 | 0.0231774 |
| 61 | ABB | 28116 | *Bacteroides ovatus* | AF29-12 | 0.00552489 |
| 62 | ABB | 47678 | *Bacteroides caccae* | OM05-21BH | 0.0123645 |
| 63 | ABB | 47678 | *Bacteroides caccae* | OM05-21BH | 0.0127433 |
| 64 | ABB | 88431 | *Dorea longicatena* | 2789STDY5608851 | 0.0155486 |
| 65 | ABB | 1547 | *Erysipelatoclostridium ramosum* | OF04-4AC | 0.059652 |
| 66 | ABB | 1138888 | *Enterococcus faecium* EnGen0015 | E1007 | 0.0076997 |
| 67 | ABB | 997891 | *Bacteroides vulgatus* CL09T03C04 | CL09T03C04 | 0.0126509 |
| 68 | ABB | 1138888 | *Enterococcus faecium* EnGen0015 | E1007 | 0.00801624 |
| 69 | ABB | 1073351 | *Bacteroides stercoris* CC31F | CC31F | 0.0211864 |
| 70 | ABB | 997891 | *Bacteroides vulgatus* CL09T03C04 | CL09T03C04 | 0.0132351 |
| 71 | ABB | 820 | *Bacteroides uniformis* | DSM 6597 | 0.012262 |
| 72 | ABB | 410072 | *Coprococcus comes* | 2789STDY5608832 | 0.0177664 |
| 73 | YCFACB | 39485 | [*Eubacterium*] *eligens* | AF41-18 | 0.0460076 |
| 74 | YCFACB | 88431 | *Dorea longicatena* | 2789STDY5608851 | 0.0481542 |
| 75 | YCFACB | 2292357 | *Faecalibacterium* sp. OM04-11BH | OM04-11BH | 0.0598966 |
| 76 | YCFACB | 1350472 | *Bifidobacterium longum* subsp. *longum* 7-1B | 7-1B | 0.0517639 |
| 76 | YCFACB | 748224 | *Faecalibacterium* cf. *prausnitzii* KLE1255 | KLE1255 | 0.0426093 |
| 77 | YCFACB | 88431 | *Dorea longicatena* | 2789STDY5608851 | 0.0471561 |
| 78 | YCFACB | 88431 | *Dorea longicatena* | 2789STDY5608851 | 0.0471561 |
| 79 | YCFACB | 1073376 | *Ruminococcus lactaris* CC59_002D | CC59002D | 0.0436095 |
| 80 | YCFACB | 1917876 | *Blautia* sp. Marseille-P3087 | Marseille-P3087 | 0.0581289 |
| 81 | YCFACB | 2086273 | *Subdoligranulum* sp. APC924/74 | APC924/74 | 0.0631331 |
| 82 | YCFACB | 2086273 | *Subdoligranulum* sp. APC924/74 | APC924/74 | 0.0585937 |
| 83 | YCFACB | 39491 | [*Eubacterium*] *rectale* | 2789STDY5608860 | 0.0551094 |
| 117 | ABB+RF | 33039 | [*Ruminococcus*] *torques* | 2789STDY5608867 | 0.0201569 |
| 85 | YCFACB | 2086273 | *Subdoligranulum* sp. APC924/74 | APC924/74 | 0.0549626 |
| 85 | YCFACB | 2292357 | *Faecalibacterium* sp. OM04-11BH | OM04-11BH | 0.0625862 |
| 86 | YCFACB | 39485 | [*Eubacterium*] *eligens* | AF41-18 | 0.0480639 |
| 87 | YCFACB | 748224 | *Faecalibacterium* cf. *prausnitzii* KLE1255 | KLE1255 | 0.0647989 |
| 88 | YCFACB | 1073376 | *Ruminococcus lactaris* CC59_002D | CC59002D | 0.0563141 |
| 89 | YCFACB | 39485 | [*Eubacterium*] *eligens* | AF41-18 | 0.0565927 |
| 90 | YCFACB | 515619 | [*Eubacterium*] *rectale* ATCC 33656 | ATCC 33656 | 0.0641779 |
| 91 | ABB + RF | 2292969 | *Blautia* sp. AM16-16B | AM16-16B | 0.207695 |

TABLE 1-continued

Exemplary bacterial strains isolated from human fecal material that can be used alone to practice methods
as provided herein, or in making or using combinations of microbe compositions as provided herein.

| Strain ID | Screening Medium | NCBI Taxonomy ID | NCBI Organism Name[a] | NCBI Infraspecific Name | Distance from Reference Assembly (mash) |
|---|---|---|---|---|---|
| 92 | ABB + RF | 1907658 | *Bacteroides ilei* | Marseille-P3208 | 0.168518 |
| 95 | ABB + RF | 214856 | *Alistipes finegoldii* | 2789STDY5608890 | 0.0243467 |
| 110 | ABB + RF | 2153227 | *Lactobacillus* sp. DS22_6 | DS22_6 | 0.00438886 |
| 93 | ABB + RF | 214856 | *Alistipes finegoldii* | 2789STDY5608890 | 0.0317272 |
| 94 | ABB + RF | 214856 | *Alistipes finegoldii* | 2789STDY5608890 | 0.0445532 |
| 96 | ABB + RF | 820 | *Bacteroides uniformis* | OM07-9 | 0.0172799 |
| 97 | ABB + RF | 357276 | *Bacteroides dorei* | An16 | 0.0141874 |
| 98 | ABB + RF | 214856 | *Alistipes finegoldii* | 2789STDY5608890 | 0.015699 |
| 99 | ABB + RF | 2292910 | *Alistipes* sp. AF14-19 | AF14-19 | 0.0155836 |
| 100 | ABB + RF | 74426 | *Collinsella aerofaciens* | 2789STDY5608842 | 0.0424285 |
| 101 | ABB + RF | 214856 | *Alistipes finegoldii* | 2789STDY5608890 | 0.0116057 |
| 102 | ABB + RF | 28118 | *Odoribacter splanchnicus* | AF36-2 | 0.00844432 |
| 103 | ABB + RF | 74426 | *Collinsella aerofaciens* | 2789STDY5608842 | 0.0432902 |
| 104 | ABB + RF | 717959 | *Alistipes shahii* WAL 8301 | WAL 8301 | 0.0166515 |
| 105 | ABB + RF | 2109688 | Clostridiales bacterium CCNA10 | CCNA10 | 0.114893 |
| 106 | ABB + RF | 2293194 | *Ruminococcus* sp. AM28-13 | AM28-13 | 0.0253257 |
| 107 | ABB + RF | 28118 | *Odoribacter splanchnicus* | AF36-2 | 0.00863912 |
| 108 | ABB + RF | 1871021 | *Lachnoclostridium phocaeense* | Marseille-P3177 | 0.0176872 |
| 109 | ABB + RF | 411471 | *Subdoligranulum variabile* DSM 15176 | DSM 15176 | 0.0987184 |
| 111 | ABB + RF | 28116 | *Bacteroides ovatus* | AF20-9LB | 0.0209153 |
| 112 | ABB + RF | 214856 | *Alistipes finegoldii* | 2789STDY5608890 | 0.011059 |
| 113 | ABB + RF | 2292910 | *Alistipes* sp. AF14-19 | AF14-19 | 0.0149744 |
| 114 | ABB + RF | 357276 | *Bacteroides dorei* | An16 | 0.0129382 |
| 115 | ABB + RF | 28116 | *Bacteroides ovatus* | AF24-28LB | 0.00894456 |
| 116 | ABB + RF | 357276 | *Bacteroides dorei* | An16 | 0.012209 |
| 118 | ABB + RF | 93975 | *Bacteroides* sp. AR29 | AR29 | 0.00583626 |
| 119 | ABB + RF | 357276 | *Bacteroides dorei* | An16 | 0.0121318 |
| 120 | ABB + RF | 537012 | *Bacteroides cellulosilyticus* DSM14838 | DSM 14838 | 0.0196531 |
| 121 | ABB + RF | 457415 | *Synergistes* sp. 3_1_syn1 | 3_1_syn1 | 0.0177098 |
| 122 | ABB + RF | 33039 | [*Ruminococcus*] *torques* | AM22-16 | 0.0983271 |
| 123 | ABB + RF | 214856 | *Alistipes finegoldii* | 2789STDY5608890 | 0.0109684 |
| 124 | ABB + RF | 1605 | *Lactobacillus animalis* | P38 | 0.038387 |
| 125 | ABB + RF | 2108523 | *Lawsonibacter asaccharolyticus* | 3BBH22 | 0.0167368 |
| 126 | ABB + RF | 40520 | *Blautia obeum* | 2789STDY5834861 | 0.0656918 |
| 127 | ABB + RF | 40520 | *Blautia obeum* | 2789STDY5834861 | 0.0698723 |
| 128 | ABB + RF | 820 | *Bacteroides uniformis* | OM07-9 | 0.0156336 |
| 129 | ABB + RF | 46503 | *Parabacteroides merdae* | AM26-6AC | 0.0107148 |
| 130 | ABB + RF | 1871021 | *Lachnoclostridium phocaeense* | Marseille-P3177 | 0.0176477 |
| 131 | ABB + RF | 871324 | *Bacteroides stercorirosoris* | OF03-9BH | 0.0133266 |
| 132 | ABB + RF | 1339343 | *Parabacteroides distasonis* str. 3776 D15iv | 3776 D15 iv | 0.0123851 |
| 133 | ABB + RF | 1339343 | *Parabacteroides distasonis* str. 3776 D15iv | 3776 D15 iv | 0.012998 |
| 134 | ABB + RF | 820 | *Bacteroides uniformis* | OM07-9 | 0.0152174 |
| 135 | ABB + RF | 2153227 | *Lactobacillus* sp. DS22_6 | DS22_6 | 0.00381963 |
| 136 | ABB + RF | 216816 | *Bifidobacterium longum* | APC1472 | 0.0129809 |
| 137 | ABB + RF | 216816 | *Bifidobacterium longum* | APC1472 | 0.0133747 |
| 138 | ABB + RF | 2153227 | *Lactobacillus* sp. DS22_6 | DS22_6 | 0.0021922 |
| 139 | ABB + RF | 84112 | *Eggerthella lenta* | CC8/6 D5 4 | 0.051842 |
| 141 | ABB + RF | 46503 | *Parabacteroides merdae* | AF33-34 | 0.0418058 |
| 141 | ABB + RF | 40520 | *Blautia obeum* | 2789STDY5834957 | 0.0215309 |
| 143 | ABB + RF | 40520 | *Blautia obeum* | 2789STDY5834957 | 0.0421419 |
| 146 | ABB + RF | 40520 | *Blautia obeum* | 2789STDY5834957 | 0.0479964 |
| 147 | ABB + RF | 2292330 | *Collinsella* sp. TF05-9AC | TF05-9AC | 0.0755452 |
| 148 | ABB + RF | 357276 | *Bacteroides dorei* | OF04-10BH | 0.0311421 |
| 151 | ABB + RF | 2305245 | Clostridiaceae bacterium TF01-6 | TF01-6 | 0.0354795 |
| 152 | ABB + RF | 46503 | *Parabacteroides merdae* | AF33-34 | 0.00811509 |
| 153 | ABB + RF | 47678 | *Bacteroides caccae* | AM16-49B | 0.0324692 |
| 154 | ABB + RF | 2292271 | Lachnospiraceae bacterium AM48-27BH | AM48-27BH | 0.115114 |
| 155 | ABB + RF | 2109334 | *Blautia* sp. SG-772 | SG-772 | 0.0491926 |
| 157 | ABB + RF | 2109334 | *Blautia* sp. SG-772 | SG-772 | 0.0500057 |
| 158 | ABB + RF | 2293120 | *Parabacteroides* sp. AM25-14 | AM25-14 | 0.0330546 |
| 160 | ABB + RF | 476272 | *Blautia hydrogenotrophica* DSM10507 | DSM 10507 | 0.0320835 |
| 161 | ABB + RF | 40520 | *Blautia obeum* | 2789STDY5834957 | 0.0213648 |
| 162 | ABB + RF | 33039 | [*Ruminococcus*] *torques* | 2789STDY5608833 | 0.0616729 |
| 163 | ABB + RF | 357276 | *Bacteroides dorei* | OF04-10BH | 0.0166462 |
| 165 | ABB + RF | 2292372 | *Ruminococcus* sp. AM42-11 | AM42-11 | 0.0625862 |
| 166 | ABB + RF | 2292041 | *Dorea* sp. AF36-15AT | AF36-15AT | 0.0479066 |
| 167 | ABB + RF | 649756 | *Anaerostipes hadrus* | 2789STDY5608868 | 0.0381896 |
| 169 | ABB + RF | 291644 | *Bacteroides salyersiae* | 2789STDY5608871 | 0.0128024 |
| 170 | ABB + RF | 33039 | [*Ruminococcus*] *torques* | 2789STDY5608833 | 0.0440096 |
| 171 | ABB + RF | 2292316 | *Collinsella* sp. AM34-10 | AM34-10 | 0.0316248 |
| 172 | ABB + RF | 2026190 | *Bacillus mobilis* | 0711P9-1 | 0.0365402 |
| 173 | ABB + RF | 47678 | *Bacteroides caccae* | ATCC 43185 | 0.0133309 |
| 174 | ABB + RF | 2292041 | *Dorea* sp. AF36-15AT | AF36-15AT | 0.0604284 |

TABLE 1-continued

Exemplary bacterial strains isolated from human fecal material that can be used alone to practice methods
as provided herein, or in making or using combinations of microbe compositions as provided herein.

| Strain ID | Screening Medium | NCBI Taxonomy ID | NCBI Organism Name[a] | NCBI Infraspecific Name | Distance from Reference Assembly (mash) |
|---|---|---|---|---|---|
| 175 | ABB + RF | 47678 | *Bacteroides caccae* | AM16-49B | 0.0423206 |
| 176 | ABB + RF | 357276 | *Bacteroides dorei* | OF04-10BH | 0.031968 |
| 177 | ABB + RF | 47678 | *Bacteroides caccae* | AM16-49B | 0.0296094 |
| 178 | ABB + RF | 39486 | *Dorea formicigenerans* | AF36-1BH | 0.0394151 |
| 179 | ABB + RF | 291644 | *Bacteroides salyersiae* | 2789STDY5608871 | 0.0250827 |
| 180 | ABB + RF | 33039 | *[Ruminococcus] torques* | 2789STDY5608833 | 0.0187091 |
| 181 | ABB + RF | 357276 | *Bacteroides dorei* | OF04-10BH | 0.0179373 |
| 182 | ABB + RF | 40520 | *Blautia obeum* | AM18-2AC | 0.0393356 |
| 183 | ABB + RF | 33039 | *[Ruminococcus] torques* | 2789STDY5608833 | 0.0186138 |
| 184 | ABB + RF | 2292992 | *Catenibacterium* sp. AM22-6LB | AM22-6LB | 0.063331 |
| 185 | ABB + RF | 742738 | *Flavonifractor plautii* 1__3__50AFAA | 1__3__50AFAA | 0.0462584 |
| 186 | ABB + RF | 476272 | *Blautia hydrogenotrophica* DSM10507 | DSM 10507 | 0.0312646 |
| 187 | ABB + RF | 2292041 | *Dorea* sp. AF36-15AT | AF36-15AT | 0.0644247 |
| 188 | ABB + RF | 476272 | *Blautia hydrogenotrophica* DSM10507 | DSM 10507 | 0.00299106 |
| 189 | ABB + RF | 1339350 | *Bacteroides vulgatus* str. 3775 SL(B) 10 (iv) | 3775 SL(B) 10 (iv) | 0.0288871 |
| 190 | ABB + RF | 476272 | *Blautia hydrogenotrophica* DSM10507 | DSM 10507 | 0.00287005 |
| 191 | ABB + RF | 357276 | *Bacteroides dorei* | OF04-10BH | 0.00672075 |
| 192 | ABB + RF | 33039 | *[Ruminococcus] torques* | 2789STDY5608833 | 0.0189436 |
| 193 | ABB + RF | 33039 | *[Ruminococcus] torques* | 2789STDY5608833 | 0.0195966 |
| 194 | ABB + RF | 291644 | *Bacteroides salyersiae* | 2789STDY5608871 | 0.0308224 |
| 195 | ABB + RF | 2292041 | *Dorea* sp. AF36-15AT | AF36-15AT | 0.0641779 |
| 196 | ABB + RF | 2292271 | Lachnospiraceae bacterium AM48-27BH | AM48-27BH | 0.0957194 |
| 197 | ABB + RF | 33039 | *[Ruminococcus] torques* | 2789STDY5608833 | 0.0197225 |
| 198 | ABB + RF | 40520 | *Blautia obeum* | 2789STDY5834957 | 0.0243949 |
| 199 | ABB + RF | 997890 | *Bacteroides uniformis* CL03T12C37 | CL03T12C37 | 0.0228174 |
| 200 | ABB + RF | 2292330 | *Collinsella* sp. TF05-9AC | TF05-9AC | 0.0741211 |
| 201 | ABB + RF | 292800 | *Flavonifractor plautii* | 2789STDY5834932 | 0.0427185 |
| 202 | ABB + RF | 997890 | *Bacteroides uniformis* CL03T12C37 | CL03T12C37 | 0.0075679 |
| 203 | ABB + RF | 33039 | *[Ruminococcus] torques* | 2789STDY5608833 | 0.0182258 |
| 204 | ABB + RF | 40520 | *Blautia obeum* | OM06-11AA | 0.0550506 |
| 205 | ABB + RF | 33039 | *[Ruminococcus] torques* | 2789STDY5608833 | 0.0194467 |
| 206 | ABB + RF | 2292372 | *Ruminococcus* sp. AM42-11 | AM42-11 | 0.0486105 |
| 207 | ABB + RF | 357276 | *Bacteroides dorei* | OF04-10BH | 0.0219313 |
| 208 | ABB + RF | 2292330 | *Collinsella* sp. TF05-9AC | TF05-9AC | 0.0388799 |
| 209 | ABB + RF | 357276 | *Bacteroides dorei* | OF04-10BH | 0.0270028 |
| 210 | ABB + RF | 2292330 | *Collinsella* sp. TF05-9AC | TF05-9AC | 0.0396229 |
| 211 | ABB + RF | 649756 | *Anaerostipes hadrus* | 2789STDY5608868 | 0.0577367 |
| 212 | ABB + RF | 357276 | *Bacteroides dorei* | OF04-10BH | 0.00644046 |
| 213 | ABB + RF | 649756 | *Anaerostipes hadrus* | 2789STDY5608868 | 0.0187271 |
| 215 | ABB + RF | 88431 | *Dorea longicatena* | OM02-16 | 0.041336 |
| 216 | ABB + RF | 28116 | *Bacteroides ovatus* | AM32-14LB | 0.0215518 |
| 220 | ABB + RF | 2293220 | *Ruminococcus* sp. AM46-18 | AM46-18 | 0.0498603 |
| 221 | ABB + RF | 40520 | *Blautia obeum* | APC942/31-1 | 0.045432 |
| 222 | ABB + RF | 84112 | *Eggerthella lenta* | CC8/6 D5 4 | 0.0316362 |
| 223 | ABB + RF | 821 | *Bacteroides vulgatus* | AF28-7 | 0.0382047 |
| 227 | ABB + RF | 40520 | *Blautia obeum* | AF21-24 | 0.0354526 |
| 228 | ABB + RF | 665950 | Lachnospiraceae bacterium 3__1__46FAA | 3__1__46FAA | 0.0556449 |
| 229 | ABB + RF | 226186 | *Bacteroides thetaiotaomicron* VPI-5482 | VPI-5482 | 0.0228025 |
| 230 | ABB + RF | 471189 | *Gordonibacter pamelaeae* | 3C | 0.0276437 |
| 231 | ABB + RF | 84112 | *Eggerthella lenta* | CC8/6 D5 4 | 0.0280918 |
| 232 | ABB + RF | 665950 | Lachnospiraceae bacterium 3__1__46FAA | 3__1__46FAA | 0.0579648 |
| 233 | ABB + RF | 821 | *Bacteroides vulgatus* | AF28-7 | 0.0405226 |
| 234 | ABB + RF | 742738 | *Flavonifractor plautii* 1__3__50AFAA | 1__3__50AFAA | 0.0337178 |
| 235 | ABB + RF | 742738 | *Flavonifractor plautii* 1__3__50AFAA | 1__3__50AFAA | 0.0297444 |
| 236 | ABB + RF | 74426 | *Collinsella aerofaciens* | 2789STDY5608842 | 0.0768508 |
| 237 | ABB + RF | 74426 | *Collinsella aerofaciens* | 2789STDY5608823 | 0.0661271 |
| 238 | ABB + RF | 1720194 | *Clostridium* sp. AT4 | AT5 | 0.0475507 |
| 239 | ABB + RF | 471189 | *Gordonibacter pamelaeae* | 3C | 0.0393992 |
| 240 | ABB + RF | 411462 | *Dorea longicatena* DSM13814 | DSM 13814 | 0.0575426 |
| 241 | RCM | 1504823 | bacterium LF-3 | | 0.0156336 |
| 242 | RCM | 33038 | *[Ruminococcus] gnavus* | RJX1120 | 0.022603 |
| 243 | RCM | 33039 | *[Ruminococcus] torques* | 2789STDY5608867 | 0.0235981 |
| 244 | RCM | 33039 | *[Ruminococcus] torques* | 2789STDY5608867 | 0.0273626 |
| 245 | RCM | 33039 | *[Ruminococcus] torques* | 2789STDY5608833 | 0.0309541 |
| 246 | RCM | 33039 | *[Ruminococcus] torques* | 2789STDY5608833 | 0.0267663 |
| 247 | RCM | 33039 | *[Ruminococcus] torques* | 2789STDY5608833 | 0.0285595 |
| 248 | RCM | 39488 | *Anaerobutyricum hallii* | | 0.0430304 |
| 249 | RCM | 39488 | *Anaerobutyricum hallii* | AF45-14BH | 0.0321067 |
| 250 | RCM | 1532 | *Blautia coccoides* | NCTC11035 | 0.022559 |
| 251 | RCM | 476272 | *Blautia hydrogenotrophica* DSM10507 | DSM 10507 | 0.108521 |
| 252 | RCM | 476272 | *Blautia hydrogenotrophica* DSM10507 | DSM 10507 | 0.0213993 |
| 253 | RCM | 40520 | *Blautia obeum* | 2789STDY5608837 | 0.0222102 |
| 254 | RCM | 40520 | *Blautia obeum* | AM37-4AC | 0.0291893 |

TABLE 1-continued

Exemplary bacterial strains isolated from human fecal material that can be used alone to practice methods as provided herein, or in making or using combinations of microbe compositions as provided herein.

| Strain ID | Screening Medium | NCBI Taxonomy ID | NCBI Organism Name[a] | NCBI Infraspecific Name | Distance from Reference Assembly (mash) |
|---|---|---|---|---|---|
| 255 | RCM | 40520 | *Blautia obeum* | OF03-14 | 0.0315342 |
| 256 | RCM | 410072 | *Coprococcus comes* | 2789STDY5834962 | 0.0318186 |
| 257 | RCM | 410072 | *Coprococcus comes* | 2789STDY5608832 | 0.0375188 |
| 258 | RCM | 410072 | *Coprococcus comes* | 2789STDY5834962 | 0.0339433 |
| 259 | RCM | 410072 | *Coprococcus comes* | 2789STDY5608832 | 0.0324692 |
| 260 | RCM | 39486 | *Dorea formicigenerans* | AF19-13 | 0.0283927 |
| 261 | RCM | 39486 | *Dorea formicigenerans* | AF19-13 | 0.0245322 |
| 262 | RCM | 39486 | *Dorea formicigenerans* | AF19-13 | 0.0306047 |
| 263 | RCM | 39486 | *Dorea formicigenerans* | TF12-1 | 0.0844968 |
| 264 | RCM | 39486 | *Dorea formicigenerans* | TF12-1 | 0.013909 |
| 265 | RCM | 39486 | *Dorea formicigenerans* | TF12-1 | 0.0367526 |
| 266 | RCM | 88431 | *Dorea longicatena* | 2789STDY5608851 | 0.0210911 |
| 267 | RCM | 88431 | *Dorea longicatena* | 2789STDY5608851 | 0.026948 |
| 268 | RCM | 88431 | *Dorea longicatena* | OM02-16 | 0.0378742 |
| 269 | RCM | 88431 | *Dorea longicatena* | 2789STDY5834914 | 0.0338178 |
| 270 | RCM | 88431 | *Dorea longicatena* | OM02-16 | 0.037681 |
| 271 | RCM | 88431 | *Dorea longicatena* | OM02-16 | 0.0381896 |
| 272 | RCM | 88431 | *Dorea longicatena* | 2789STDY5608851 | 0.0314102 |
| 273 | RCM | 411462 | *Dorea longicatena* DSM13814 | DSM 13814 | 0.0304105 |
| 274 | RCM | 2292041 | *Dorea* sp. AF36-15AT | AF36-15AT | 0.035887 |
| 275 | RCM | 2292041 | *Dorea* sp. AF36-15AT | AF36-15AT | 0.0313653 |
| 276 | RCM | 28052 | *Lachnospira pectinoschiza* | 2789STDY5834886 | 0.0345299 |
| 277 | RCM | 1160721 | *Ruminococcus bicirculans* | 80/3 | 0.0394469 |
| 278 | RCM | 2293190 | *Ruminococcus* sp. AM26-12LB | AM26-12LB | 0.0238706 |
| 279 | RCM | 2292372 | *Ruminococcus* sp. AM42-11 | AM42-11 | 0.0346335 |
| 280 | RCM | 2292372 | *Ruminococcus* sp. AM42-11 | AM42-11 | 0.0305938 |
| 281 | RCM | 2292372 | *Ruminococcus* sp. AM42-11 | AM42-11 | 0.0353051 |
| 282 | RCM | 2292372 | *Ruminococcus* sp. AM42-11 | AM42-11 | 0.0292401 |
| 283 | ActVeg | 457422 | Erysipelotrichaceae bacterium 2_2_44A | 2_2_44A | 0.0120469 |
| 284 | ActVeg | 1597 | *Lactobacillus* paracasei | 1316.rep1_LPAR | 0.0122212 |
| 285 | ActVeg | 573236 | *Bifidobacterium animalis* subsp. *lactis* V9 | V9 | 0.0122825 |
| 286 | ActVeg | 1522 | [*Clostridium*] *innocuum* | AF18-35LB | 0.0163194 |
| 287 | ActVeg | 457422 | Erysipelotrichaceae bacterium 2_2_44A | 2_2_44A | 0.0170934 |
| 288 | ActVeg | 84112 | *Eggerthella lenta* | CC8/6 D5 4 | 0.0177777 |
| 289 | ActVeg | 649756 | *Anaerostipes hadrus* | 2789STDY5608868 | 0.0237534 |
| 290 | ActVeg | 39486 | *Dorea formicigenerans* | TF12-1 | 0.0244433 |
| 291 | ActVeg | 410072 | *Coprococcus comes* | 2789STDY5834962 | 0.0245972 |
| 292 | ActVeg | 410072 | *Coprococcus comes* | 2789STDY5834962 | 0.0252752 |
| 293 | ActVeg | 33035 | *Blautia producta* | DSM 3507 | 0.0263101 |
| 294 | ActVeg | 2293194 | *Ruminococcus* sp. AM28-13 | AM28-13 | 0.0269024 |
| 295 | ActVeg | 410072 | *Coprococcus comes* | 2789STDY5834962 | 0.0277667 |
| 296 | ActVeg | 457412 | *Ruminococcus* sp. 5_1_39BFAA | 5_1_39BFAA | 0.0293319 |
| 297 | ActVeg | 100884 | *Coprobacillus cateniformis* | OM02-34 | 0.0320488 |
| 298 | ActVeg | 39486 | *Dorea formicigenerans* | AF36-1BH | 0.0344011 |
| 299 | ActVeg | 2293184 | *Ruminococcus* sp. AM16-34 | AM16-34 | 0.0374015 |
| 300 | ActVeg | 1870991 | *Massilioclostridium coli* | Marseille-P2976 | 0.0377106 |
| 301 | ActVeg | 665951 | Lachnospiraceae bacterium 8_1_57FAA | 8_1_57FAA | 0.0377551 |
| 302 | ActVeg | 665950 | Lachnospiraceae bacterium 3_1_46FAA | 3_1_46FAA | 0.0381292 |
| 303 | ActVeg | 2302976 | Erysipelotrichaceae bacterium AF19-24AC | AF19-24AC | 0.0434587 |
| 304 | ActVeg | 649724 | *Clostridium* sp. ATCCBAA-442 | ATCC BAA-442 | 0.0446515 |
| 305 | ActVeg | 74426 | *Collinsella aerofaciens* | 2789STDY5608823 | 0.0474845 |
| 306 | ActVeg | 74426 | *Collinsella aerofaciens* | 2789STDY5608842 | 0.0479739 |
| 307 | ActVeg | 665950 | Lachnospiraceae bacterium 3_1_46FAA | 3_1_46FAA | 0.0516344 |
| 308 | ActVeg | 649756 | *Anaerostipes hadrus* | 2789STDY5608868 | 0.0525015 |
| 309 | ActVeg | 1965564 | *Massilimicrobiota* sp. An142 | An142 | 0.0530685 |
| 310 | ActVeg | 2292330 | *Collinsella* sp. TF05-9AC | TF05-9AC | 0.0557352 |
| 311 | ActVeg | 1737424 | *Blautia massiliensis* | GD9 | 0.0581948 |
| 312 | ActVeg | 2292330 | *Collinsella* sp. TF05-9AC | TF05-9AC | 0.0649247 |
| 313 | ActVeg | 2292330 | *Collinsella* sp. TF05-9AC | TF05-9AC | 0.0649247 |
| 314 | ActVeg | 2292227 | *Collinsella* sp. AF28-5AC | AF28-5AC | 0.0929879 |
| 315 | ActVeg | 552398 | Ruminococcaceae bacterium D16 | D16 | 0.0957194 |
| 316 | ActVeg | 208479 | [*Clostridium*] *bolteae* | AM35-14 | 0.0989821 |
| 317 | ActVeg | 33039 | [*Ruminococcus*] *torques* | AM22-16 | 0.109435 |
| 318 | ActVeg | 2086584 | *Mordavella* sp. Marseille-P3756 | Marseille-P3756 | 0.112966 |
| 319 | ActVeg | 457412 | *Ruminococcus* sp. 5_1_39BFAA | 5_1_39BFAA | 0.114022 |
| 320 | ActVeg | 1121115 | *Blautia wexlerae* DSM 19850 | DSM 19850 | 0.129179 |
| 321 | ActVeg | 2293156 | *Ruminococcus* sp. AF18-29 | AF18-29 | 0.130966 |
| 322 | ActVeg | 2292372 | *Ruminococcus* sp. AM42-11 | AM42-11 | 0.134052 |
| 323 | ActVeg | 552398 | Ruminococcaceae bacterium D16 | D16 | 0.13446 |
| 324 | ActVeg | 1965654 | *Lachnoclostridium* sp. An76 | An76 | 0.13446 |
| 325 | ActVeg | 1965654 | *Lachnoclostridium* sp. An76 | An76 | 0.138386 |
| 326 | ActVeg | 33039 | [*Ruminococcus*] *torques* | AM22-16 | 0.139328 |
| 327 | ActVeg | 552398 | Ruminococcaceae bacterium D16 | D16 | 0.139328 |

TABLE 1-continued

Exemplary bacterial strains isolated from human fecal material that can be used alone to practice methods
as provided herein, or in making or using combinations of microbe compositions as provided herein.

| Strain ID | Screening Medium | NCBI Taxonomy ID | NCBI Organism Name[a] | NCBI Infraspecific Name | Distance from Reference Assembly (mash) |
|---|---|---|---|---|---|
| 328 | ActVeg | 2292376 | *Ruminococcus* sp. OM08-7 | OM08-7 | 0.142336 |
| 329 | ActVeg | 116085 | *Coprococcus catus* | AF45-17 | 0.148079 |
| 330 | ActVeg | 2292970 | *Blautia* sp. AM22-22LB | AM22-22LB | 0.150025 |
| 331 | ActVeg | 2292970 | *Blautia* sp. AM22-22LB | AM22-22LB | 0.163053 |
| 332 | ActVeg | 2293138 | *Roseburia* sp. AM59-24XD | AM59-24XD | 0.164074 |
| 333 | ActVeg | 1235835 | *Anaerotruncus* sp. G3(2012) | G3 | 0.166219 |
| 334 | ActVeg | 29348 | [*Clostridium*] *spiroforme* | OM02-6 | 0.172308 |
| 335 | ActVeg | 2292376 | *Ruminococcus* sp. OM08-7 | OM08-7 | 0.176605 |
| 336 | ActVeg | 2293138 | *Roseburia* sp. AM59-24XD | AM59-24XD | 0.183409 |

[a] Listed are the closest genome/species matches for each strain, determined by the analysis described in the text.

Antibiotic Resistance Characterization of Isolated Strains from Fecal Matter

The complete genome sequence of each organism is screened to ensure it contains no genes or pathogenicity island gene clusters encoding known virulence factors, toxins, or antibiotic resistance functions, using publicly available databases such as DBETH55 (for example, see Chakraborty A, et al. (2012) *Nucleic Acids Res.* 40:615-620) and VFDB56 (Chen L, et al. (2005) *Nucleic Acids Res.* 33:325-328). Each organism is tested by standard antibiotic sensitivity profile techniques such as broth microdilution susceptibility panels or plate-based methods such as disk diffusion method and antimicrobial gradient method (James H. Jorgensen and Mary Jane Ferraro 2009 Clinical Infectious Diseases 49:1749-1755). Such tests determine the minimal inhibitory concentration (MIC) of an antibiotic on microbial growth. Antibiotics tested include but are not limited to amoxicillin, amoxicillin/clavulanic acid, carbapenem, methicillin, ampicillin, gentamicin, metronidazole, and neomycin. MIC determinations of novel microbes are compared to published values for both sensitive and resistant related strains to make an assessment on sensitivity (CLSI Guideline M45: Methods for Antimicrobial Dilution and Disk Susceptibility Testing of Infrequently Isolated or Fastidious Bacteria. Wayne, PA; 2015) to type strains of related microbes to determine possible relative increases in antibiotic resistance.

Example 4: Isolation and Characterization of Pure Microbial Strains from Endospores Purified from Fecal Matter In alternative embodiments, microbes used in compositions as provided herein, or used to practice methods as provided herein, are derived from, or are cultured as, pure microbial strains derived from endospores purified or derived from fecal matter.

Individual spore-forming bacterial strains can be preferentially isolated and cultured from endospores purified from fecal matter using a protocol adapted from Kearney et al 2018 ISME J. 12:2403-2416. Purified endospores are spread on solid anaerobic medium plates and allowed to germinate and form colonies that can be further characterized. Vegetative cells in the fecal matter are rendered non-viable during the endospore purification process, and thus any resulting colonies are restricted to spore-forming bacteria. Endospores are purified from fecal matter as follows:

Fecal samples are collected and processed in an anaerobic chamber within 30 minutes of defecation. Samples (5 g) are suspended in 20 mL of 1% sodium hexametaphosphate solution (a flocculant) in order to bring biomass into suspension. The suspension is bump vortexed with glass beads to homogenize and centrifuged at 50×g for 5 min at room temperature to sediment particulate matter and beads. Quadruplicate 1 mL aliquots of the supernatant liquid is transferred into cryovials and stored at –80° C. until processing.

The frozen supernatant liquid samples are thawed at 4° C., centrifuged at 4° C. and 10,000×g for 5 minutes, washed and then resuspended in 1 mL Tris-EDTA pH 7.6. The samples are heated at 65° C. for 30 minutes with shaking at 100 rpm and then cooled on ice for 5 minutes. Lysozyme (10 mg/mL) is added to a final concentration of 2 mg/mL and the samples are incubated at 37° C. for 30 minutes with shaking at 100 rpm. At 30 minutes, 50 μL Proteinase K (>600 mAU/ml) (Qiagen) is added and the samples incubated for an additional 30 minutes at 37° C. 200 μL 6% SDS, 0.3N NaOH solution is added to each sample and incubated for 1 hour at room temperature with shaking at 100 rpm. Samples are then centrifuged at 10,000 rpm for 30 minutes. At this step, a pellet containing resistant endospores is visible, and the pellet is washed three times at 10,000×g with 1 mL chilled sterile ddH2O. The pellet containing endospores is stored at –20° C. until required.

To germinate and resuscitate spore-forming bacterial colonies from the purified endospores, the endospore pellet is brought into the anaerobic chamber, thawed and then suspended in 1.0 ml reduced ABB. Successive 10-fold serial dilutions of the suspended spores are then performed in ABB to establish 1/10, 1/100, 1/1000, 1/10000, 1/100000, 1/1000000 dilutions of the endospore preparation. From each 10-fold serial dilution, four 0.1 ml volumes are removed and then added to and spread over Reinforced Clostridial Medium Agar (Oxoid), with 0.1% intestinal bile salts (taurocholate, cholate, glycocholate) to stimulate endospore germination. The platings are incubated at 37° C. for 2, 3, 4, 5, 6, 7, 8, 9, 10, 11, 12 days to allow for the endospores to germinate and grow as single colonies. These colonies are then manually picked, individually cultivated, and the subjected to identification by whole genome sequencing analysis as described in Example 3.

Example 5: Stability Testing

In alternative embodiments, microbes used in compositions as provided herein, or used to practice methods as provided herein, comprise or can be derived from any one of family or genus (or class): Agathobaculum (TaxID: 2048137), *Alistipes* (TaxID: 239759), Anaeromassilibacillus (TaxID: 1924093), *Anaerostipes* (TaxID: 207244), *Asaccharobacter* (TaxID: 553372), *Bacteroides* (TaxID: 816), *Barnesiella* (TaxID: 397864), *Bifidobacterium* (TaxID: 1678), *Blautia* (TaxID: 572511), *Butyricicoccus* (TaxID: 580596), *Clostridium* (TaxID: 1485), *Collinsella* (TaxID: 102106), *Coprococcus* (TaxID: 33042), *Dorea* (TaxID: 189330), *Eubacterium* (TaxID: 1730), *Faecalibacterium* (TaxID: 216851), *Fusicatenibacter* (TaxID: 1407607), *Gemmiger* (TaxID: 204475), *Gordonibacter* (TaxID: 644652), Lachnoclostridium (TaxID: 1506553), *Methanobrevibacter* (TaxID: 2172), *Parabacteroides* (TaxID: 375288), Romboutsia (TaxID: 1501226), *Roseburia* (TaxID: 841), *Ruminococcus* (TaxID: 1263), Erysipelotrichaceae (TaxID: 128827), *Coprobacillus* (TaxID: 100883), Erysipelatoclostridium sp. SNUG30099 (TaxID: 1982626), Erysipelatoclostridium (TaxID: 1505663), Acetatifactor (TaxID: 1427378), *Adlercreutzia* (TaxID: 447020), Agathobacter (TaxID: 1766253), *Anaerotruncus* (TaxID: 244127), Bariatricus (TaxID: 1924081), *Butyrivibrio* (TaxID: 830), Christensenellaceae (TaxID: 990719), Clostridiales (TaxID: 186802), *Dialister* (TaxID: 39948), Drancourtella (TaxID: 1903506), *Eggerthella* (TaxID: 84111), Eisenbergiella (TaxID: 1432051), Enterocloster (TaxID: 2719313), *Enterococcus* (TaxID: 1350), Intestinibacter (TaxID: 1505657), *Lachnospira* (TaxID: 28050), Lachnospiraceae (TaxID: 186803), Mediterraneibacter (TaxID: 2316020), Negativibacillus (TaxID: 1980693), *Oscillibacter* (TaxID: 459786), *Phocaeicola* (TaxID: 909656), *Pseudobutyrivibrio* (TaxID: 46205), *Pseudoflavonifractor* (TaxID: 1017280), Ruminococcaceae (TaxID: 541000), Sellimonas (TaxID: 1769710), *Solobacterium* (TaxID: 123375), Terrisporobacter (TaxID: 1505652), Tidjanibacter (TaxID: 1929083), *Veillonella* (TaxID: 29465), for any combination thereof.

In alternative embodiments, any microbe used in a composition as provided herein, or used to practice methods as provided herein, for example, including a microbe as listed above, can be stored in a sealed container, e.g., at 25° C. or 4° C. and the container can be placed in an atmosphere having 30%, 40%, 50%, 60%, 70%, 75%, 80%, 90% or 95% relative humidity, or between about 20% and 99% relative humidity. In alternative embodiments, after 1 month, 2 months, 3 months, 6 months, 1 year, 1.5 years, 2 years, 2.5 years or 3 years, at least 50%, 60%, 70%, 80% or 90% of the bacterial strain shall remain as measured in colony forming units determined by standard protocols.

Example 6—in Silico Modeling to Discover
Microbe-Microbe Interactions

Microbe-microbe interactions are determined to exploit and manipulate metabolic reactions present in the gut microbiome using compositions and methods as provided herein for, e.g., increasing the efficacy of a chemotherapy, a radiation therapy, an immune checkpoint inhibitor (e.g., a checkpoint inhibitor therapy), a Chimeric Antigen Receptor (CAR) T-cell therapy (CAR-T) or other immunotherapy or cancer treatment.

Genome scale metabolic modeling is used as a tool to explore the diversity of metabolic reactions present in the gut microbiome, interpret the omics data described here in the framework of cellular metabolism, and evaluate interspecies interactions. A set of 773 different organism-specific metabolic models have been created (Magnusdottir et al. Nature Biotechnology 2017, 35(1):85-89) and are used in this work. Models are used individually to predict the metabolic capabilities of each organism and combined to enable multispecies simulations that predict how these organisms interact when supplied with a nutrient mix mimicking the typical Western human diet or variations thereof. Simulations are performed using the COBRA™ package v2.0™ (Schellenberger et al., Nature Protocols 2011, 6:1290-1307) or updated versions thereof. Commensal relationships among the organisms result when one or more species consume a compound that another species produces and can be detected by an increased maximum predicted growth rate of each species when growing together than when each is grown separately. In the cases where commensalism is not predicted in the live biotherapeutics provided, simulations are used to identify a suitable microbial partner that can be included in the live biotherapeutic product, thus improving the ability of the active microbes to grow in the gut ecosystem. Similarly, simulations are used to identify prebiotic compounds to be supplemented that can be utilized by the active species as a carbon or energy source.

Metabolic models are downloaded from the Thiele lab website (https://wwwen.uni.lu/lcsb/research/mol_systems_physiology/in_silico_models) for the following organisms: *Coprococcus comes, Dorea formicigenerans, Anaerostipes hadrus, Dorea longicatena, Coprococcus eutactus, Ruminococcus lactaris, Coprococcus catus, Fusicatenibacter saccharivorans,* Lachnoclostridium sp. SNUG30099, *Clostridium sporogenes, Eubacterium ventriosum, Blautia obeum,* Erysipelotrichaceae bacterium GAM147, *Akkermansia Faecalibacterium prausnitzii, Ruminococcus torques, Ruminococcus gnavus, Eubacterium hallii, Blautia obeum,* and *Clostridium scindens.* The models are then used for simulations in the COBRA v2.0™ package (Schellenberger et al., Nature Protocols 2011, 6:1290-1307). Cell metabolism is simulated by defining nutrient uptake rates (mmol/gDCW-hr) and optimizing for growth of each organism ($hr^{-1}$). Oxygen uptake rate is set to zero, to simulate anaerobic conditions. Values for each nutrient uptake rate are obtained from (Magnusdottir et al. Nature Biotechnology 2017, 35(1):85-89, Supplemental Table 12), as estimated for a typical Western diet. To simulate the gut ecosystem comprising of multiple bacterial species, each organism model is treated as a separate compartment, with the extracellular space in the gut considered an additional compartment. Nutrients can enter and exit the extracellular space freely, to simulate food uptake and waste excretion. Nutrients can enter and exit each microbial species based on the specific transporters present in the respective model. The objective function to be maximized is defined to be the total biomass of all species; i.e., the sum of all individual growth rates. The minimum growth rate of each species is set at $0.001\ hr^{-1}$.

The consortia of gut microbe metabolic models are used as a framework for interpreting genomic, transcriptomic, and metabolomic data obtained from the mouse and human studies. Enriched genes or pathways at the genomic or transcriptomic level are mapped to the source organism model to determine the metabolic functions these represent and how they connect with the rest of metabolism in that organism, as well as in the gut ecosystem. Enrichments also in metabolic intermediates or end products of these pathways provide further evidence for these pathways' contribution to checkpoint inhibitor function.

Example 7: In Silico Simulation of Relevant
Microbial Species

Models were downloaded for the following organisms: *Akkermansia Faecalibacterium prausnitzii, Ruminococcus torques, Ruminococcus gnavus, Ruminococcus lactaris,*

*Eubacterium hallii, Blautia obeum, Anaerostipes hadrus, Dorea formicigenerans, Coprococcus comes, Coprocuccus catus,* Erysipelotrichaceae sp., and *Clostridium scindens.* The models are then used for simulations in the COBRA package v2.0 (Schellenberger et al., Nature Protocols 2011, 6:1290-1307). Cell metabolism was simulated by defining nutrient uptake rates (mmol/gDCW-hr) and optimizing for growth rate of each organism (hr$^{-1}$). Oxygen uptake rate was set to zero, to simulate anaerobic conditions.

First, simulations were performed to determine the minimal growth substrate requirements of each organism. Starting with all substrate uptake fluxes open, allowing utilization of any nutrient, simulations were performed as nutrient uptake fluxes are systematically removed. This was continued for each organism until a minimal set of carbon sources remained, the removal of any of which would result in zero predicted growth. Normally, this resulted in a single sugar compound (often glucose) and one or more other nutrients such as amino acids, nucleotides, vitamins, or lipids. These other compounds are considered auxotrophic requirements of the organism. Next, the substrate utilization range of the organism was determined. The uptake flux of the primary growth substrate (generally, a sugar) was set to zero, and growth was evaluated with different carbon sources one at a time. The predicted ability to grow using each carbon source was documented. The ability to co-utilize organic acid carbon sources was also evaluated. These compounds generally cannot be used as a sole growth substrate during anaerobic growth but can be taken up in conjunction with a sugar. Simulations were run with the uptake rate of each compound constrained to a non-zero value, while maintaining the uptake of the primary sugar source. If an increase was observed in the predicted growth rate over the use of the sugar alone, then co-utilization is considered to be feasible.

The capability of each strain to produce various fermentation products was evaluated using the models. Some products were predicted to naturally form during the carbon source simulations above, as fermentation products are needed to balance redox in anaerobic conditions. These products were noted. For other compounds, the model was constrained to make each one by setting the output flux to a non-zero value. If the simulation gave a feasible solution, then the organism was considered capable of making this product.

Table 2 (illustrated as FIG. 16). Simulation of selected organisms with constraint-based modeling.

$^a$ 1 indicates predicted growth on substrate; 0 indicates predicted no growth $^b$ 1 indicates compound is predicted to be used as a supplemental carbon source; 0 indicates it cannot be consumed $^c$ 1 indicates that model predicts production of fermentation product is feasible; 0 indicates it is not feasible $^d$ Compounds that must be supplied in the growth media are indicated by X

Example 8: Laboratory-Scale Fermentation of Isolated Anaerobic Microorganisms In alternative embodiments, microbes used in compositions as provided herein, or used to practice methods as provided herein, comprise use of isolated anaerobic microorganisms, for example, anaerobic bacteria isolated from a fecal sample, e.g., from a donor.

A laboratory-scale fermentation is performed using a Sartorius BIOSTAT A™ bioreactor with 2-liter (L) vessel, using the growth media described in Example 1. While still in the anaerobic chamber, 1 L media is transferred to a sterile feed bottle, which has two ports with tubing leading blocked by pinch clamps and covered in foil to maintain sterility.

The fermentation vessel is sterilized by autoclaving, then flushed with a continuous purge of sterile nitrogen gas with oxygen catalytically removed. Two inlet ports are fitted with tubing leading to a connector blocked with a pinch clamp, and the sampling port fitted with tubing leading to a syringe. The vessel is also fitted with a dissolved oxygen probe, a pH probe, and a thermowell containing a temperature probe. Once anaerobic conditions are ensured, the media is removed from the anaerobic chamber and connected to one of the inlet ports. The other feed bottle port is connected to sterile nitrogen purge. The pinch clamp is removed, and media transferred into the fermentation vessel by peristaltic pump or just by the nitrogen pressure. Once the transfer is complete, both lines are sealed again by the pinch clamps, the feed bottle removed, and returned to the anaerobic chamber.

A 50 mL seed culture of one or more bacteria from the following genera (any one of which are used to practice compositions or methods as provided herein), Agathobaculum (TaxID: 2048137), *Alistipes* (TaxID: 239759), Anaeromassilibacillus (TaxID: 1924093), *Anaerostipes* (TaxID: 207244), *Asaccharobacter* (TaxID: 553372), *Bacteroides* (TaxID: 816), *Barnesiella* (TaxID: 397864), *Bifidobacterium* (TaxID: 1678), *Blautia* (TaxID: 572511), *Butyricicoccus* (TaxID: 580596), *Clostridium* (TaxID: 1485), *Collinsella* (TaxID: 102106), *Coprococcus* (TaxID: 33042), *Dorea* (TaxID: 189330), *Eubacterium* (TaxID: 1730), *Faecalibacterium* (TaxID: 216851), *Fusicatenibacter* (TaxID: 1407607), *Gemmiger* (TaxID: 204475), *Gordonibacter* (TaxID: 644652), Lachnoclostridium (TaxID: 1506553), *Methanobrevibacter* (TaxID: 2172), *Parabacteroides* (TaxID: 375288), Romboutsia (TaxID: 1501226), *Roseburia* (TaxID: 841), *Ruminococcus* (TaxID: 1263), Erysipelotrichaceae (TaxID: 128827), *Coprobacillus* (TaxID: 100883), Erysipelatoclostridium sp. SNUG30099 (TaxID: 1982626), Erysipelatoclostridium (TaxID: 1505663), are grown to mid-exponential phase in a sealed culture bottle using the same media composition as above, and are transferred into the feed bottle in the anaerobic chamber. Repeating the above transfer procedure, this time with the culture, the fermenter is inoculated.

5 M ammonium hydroxide is prepared in another feed bottle. One port is connected to sterile nitrogen, and the bottle is purged for 5 minutes to remove all oxygen. The outlet tubing is then blocked by a pinch clamp and attached to the other inlet port in the fermentation vessel. This tubing is then threaded into a peristaltic pump head, and the pinch clamp removed. Using the software built into the Biostat A™ unit, this pump is controlled to maintain pH at 7.0.

During growth of the culture, temperature is maintained at 37° C. using a temperature controller and heating blanket on the vessel. Nitrogen purge is set at 0.5 L/min to maintain anaerobic conditions and positive pressure in the vessel, and agitation is set at 500 rpm to keep the culture well mixed. Periodic samples are taken using the syringe attached to the sample port. For each sample, optical density is measured at 600 nm wavelength using a spectrophotometer.

Example 9: Patient Data Collection from Clinical Trials and Machine Learning and Data Analysis on the Same Eligible patients were selected based on current health condition, cancer status (current or in remission), and treatment program. Prior patient medical history was also collected and analyzed when available. This includes but is not limited to prior cancer history, diabetes, autoimmune disease, neurodegenerative disease, heart disease, metabolic syndrome, digestive disease, psychological disorders, HIV, and allergies. In addition, lifestyle and dietary habits were collected, including diet regimen, exercise routine, alcohol, nicotine, and caffeine intake, medical as well as recreational drug use, recent courses of antibiotics, vitamins, and probiotics. In some cases, information and data collected from wearable devices that monitor but is not limited to heart rate, calories burned, steps walked, blood pressure, biochemical release, time spent exercising and seizures. This data was assembled and used as input to the machine learning algorithms with the goal of determining correlations between patient history, wearable devices and treatment efficacy. In addition, relationships between this data and the results of sample analysis described below were elucidated.

For current cancer patients, tumor size and cancer progression are tracked over time and are classified based on radiographic assessment using the Response Criteria in Solid Tumors version 1.1 (Schwartz et al. Eur. J. Cancer 2016, 62:132-137) criteria. This is based on longitudinal measurements of lesions in cancer tissue, given a strict set of guidelines for lesion selection and measurement techniques. Responders to checkpoint inhibitor treatment are defined as patients that were cured or had stable disease lasting at least 6 months, while non-responders are defined as those whose cancer progressed or was stable for less than 6 months.

Each patient provided stool samples using the procedures as outlined in Example 2 and buccal swabs of the oral biome. In some cases, Urine, Blood and plasma samples were also taken by healthcare personnel within 1-2 days of the stool samples. Stool, urine and buccal samples were kept on ice or at 4° C. until processed. Whole blood was collected into an EDTA tube. Plasma was isolated from the blood by centrifugation at 1000×g for 10 minutes, followed by centrifugation at 2000×g for 10 minutes. At least three timepoints were taken for each patient, roughly every 6 to 8 weeks.

Flow Cytometry Analysis of Peripheral Blood

Flow cytometry analysis of peripheral blood can provide a non-invasive immune profile of the patients on study (Showe et al. Cancer Res. 2009 Dec. 15; 69(24): 9202-9210). The peripheral blood immuno-profile evaluation was performed on blood samples collected from patients on study. Phenotypic markers of lymphocyte subpopulations and regulatory T cells (Tregs) was evaluated using flow cytometry with populations gated to include CD3, CD4, CD8, CD11b, CD14, CD15, CD25, CD45, CD56, HLA-DR and FoxP3-expressing cells using antibodies to each cell type (BD Biosciences). Peripheral blood cells were stained with Live/Dead violet dye (Invitrogen, Carlsbad, CA) to gate on live cells. Data was acquired on an LSR II™ flow cytometer (BD Biosciences) and analyzed with FLOWJO™ software (TreeStar, Ashland, OR).

Peripheral Blood Mononuclear Cell (PBMC) Preparation and CyTOF® Analysis

Peripheral blood mononuclear cells (PBMC's) are isolated from subject blood using a standard kit and stored in liquid nitrogen at $1\times10^6$ cells/mL until use. Prior to storage, PBMC's may be processed using flow sorting or an antibody spin separation kit to select for a certain purified lymphocyte subpopulation, such as T cells. To characterize the immune profile of the PBMCs, single cell proteomics analysis (CyTOF®) is applied. This work is conducted by the Bioanalytical and Single-Cell Facility at the University of Texas, San Antonio, and entails a comprehensive panel of 29 different immune markers, allowing for deep interrogation of cellular phenotype and function (https://www.fluidigm.com/products/helios). To complement these results, RNA sequencing is applied to the entire population of the PBMCs, sorted populations, and also to single cells. Single cell RNAseq is applied using the method developed by 10× Genomics (https://www.10xgenomics.com/solutions/single-cell/). Finally, cytokine levels are determined using the Human Cytokine 30-Plex Luminex assay (https://www.thermofisher.com/order/catalog/product/LHC6003M).

Reassignment of Microbial Genomes into Operational Species Units

Because of the limitations of the NCBI taxonomy tree, and the necessity of including proprietary microbial genome assemblies into the reference alignment sequence database, it is necessary to generate a new taxonomy of microbes. Previous work (e.g., see Jain et al. (2018) Nature CommunicaGtabletions 9(1):5114) shows that species are a biologically relevant construction, with the average genomic distance (1-average nucleotide identity) between strains of a species being less than 0.04. Using this as an inspiration, all microbial assemblies from the NCBI RefSeq (Pruitt et al. (2006) Nucleic Acids Research 35 (suppl_1):D61-D65) were assigned into operational species units (OSUs) based on a clustering in which microbial assemblies within a genomic distance of 0.04 are assigned to the same OSU.

All microbial assemblies belonging to bacteria and archaea were acquired from the NCBI RefSeq database. All pairwise distances were calculated between assemblies using mash (Ondov et al. (2016) Genome Biology 17(1): 132). Clustering is performed using DBSCAN (Ester et al. (1996) KDD-96 96:226-231) with an epsilon parameter of 0.04. Identified clusters were denoted as operational species units (OSUs). Proprietary microbial assemblies were seamlessly included in this procedure as well.

For each OSU, an integer cluster label was created, and a new taxonomic ID created that is unique from any existing NCBI taxonomic identification numbers. The least common ancestor of each OSU was calculated using the original NCBI taxonomy IDs of its member assemblies, and each OSU taxonomic ID was inserted into the NCBI tree under its least common ancestor. Each OSU is also named using its most common species and label number (e.g. *Bifidobacterium adolescentis* C0001).

Figure 2:
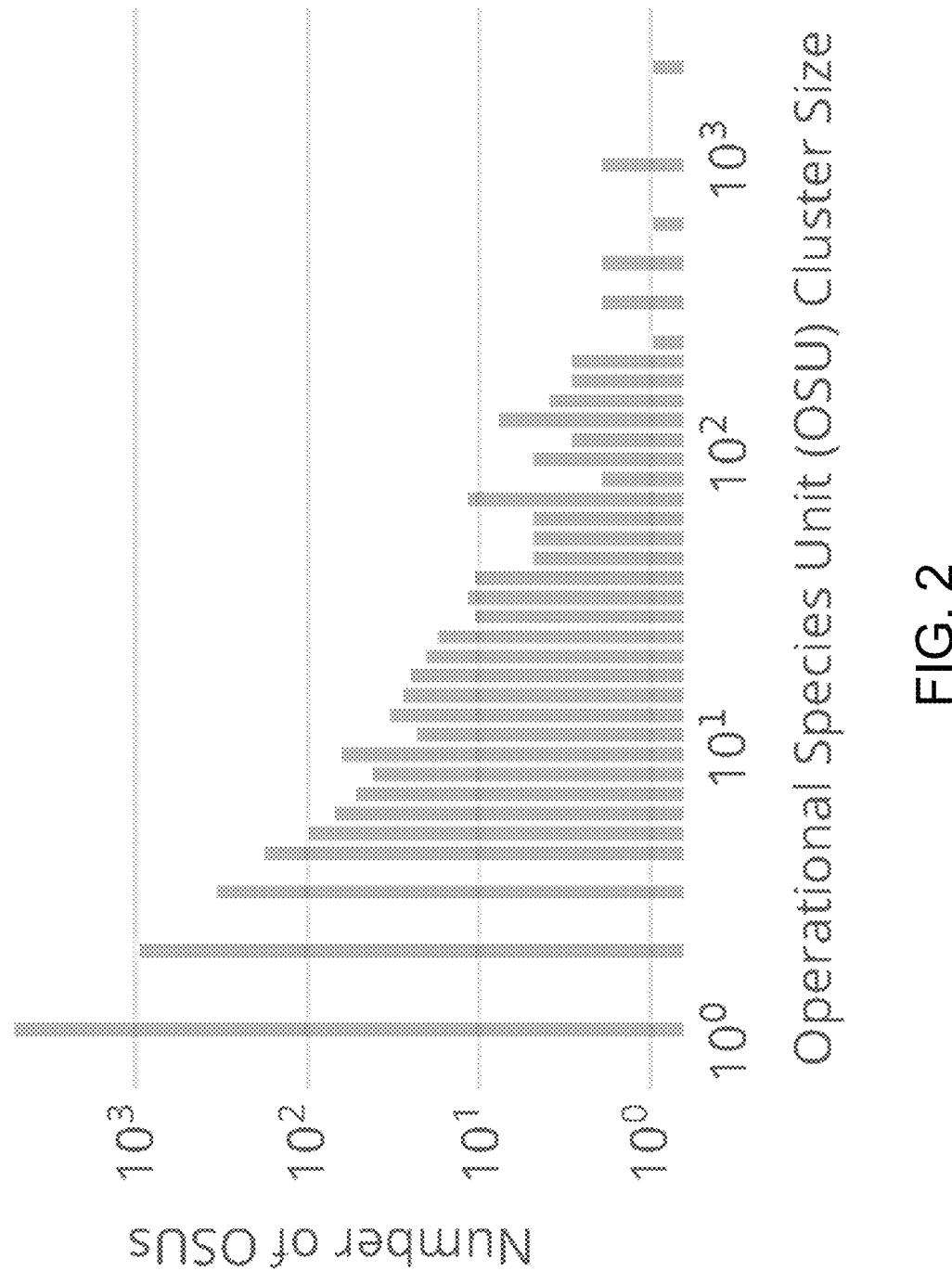
FIG. 2 graphically shows the distribution of OSU cluster sizes. Microbial genome assemblies from NCBI RefSeq are classified into operational species units by clustering similar genome assemblies together. The cluster size distribution is visualized, as described in Example 9, below.

In FIG. 1, the ranks of the least common ancestor of each OSU that contains more than one assembly are displayed. Most OSUs are consistent with pre-existing NCBI taxonomy, with a least common ancestor at the species or genus level. However, for 207 out of 2,112 non-singleton OSUs, the least common ancestor is at the family level or higher. The chart in FIG. 2 demonstrates that the frequency of OSUs decreases as the cluster size increases in a log-log fashion.

The new names, reference sequences, and taxonomy were used to generate a new reference database for the alignment program centrifuge (Kim et al. (2016) Genome Research 26:1721-1729). The centrifuge program classifies sequencing reads from a metagenomic fecal sample to reference sequences and uses an expectation-maximization method to estimate relative abundance of the taxa present in the sample. The estimated relative abundances for each OSU are carried into downstream analyses, such as machine learning or differential abundance analysis.

In addition to the method for re-assigning taxonomy described, pre-built databases that use the Genome Taxonomy Database (GTDB) were directly used for centrifuge classification (Parks et al. (2019) bioRxiv 771964, Meric et al. (2019) bioRxiv 712166).

Whole Genome Sequencing of Patient Fecal Samples

Whole genome sequencing was performed as previously described in Example 3 on a total of 450 fecal samples. Of the 450 samples, 322 samples were from cancer patients, 96 were from control subjects, and 32 were from subjects in remission. The results were classified, and abundance was estimated for each sample using centrifuge, using either a reference database built in-house consisting of operational species units (OSUs) or the publicly available GTDB database (Parks et al. (2019) bioRxiv 771964, Meric et al. (2019) bioRxiv 712166).

Figure 3:
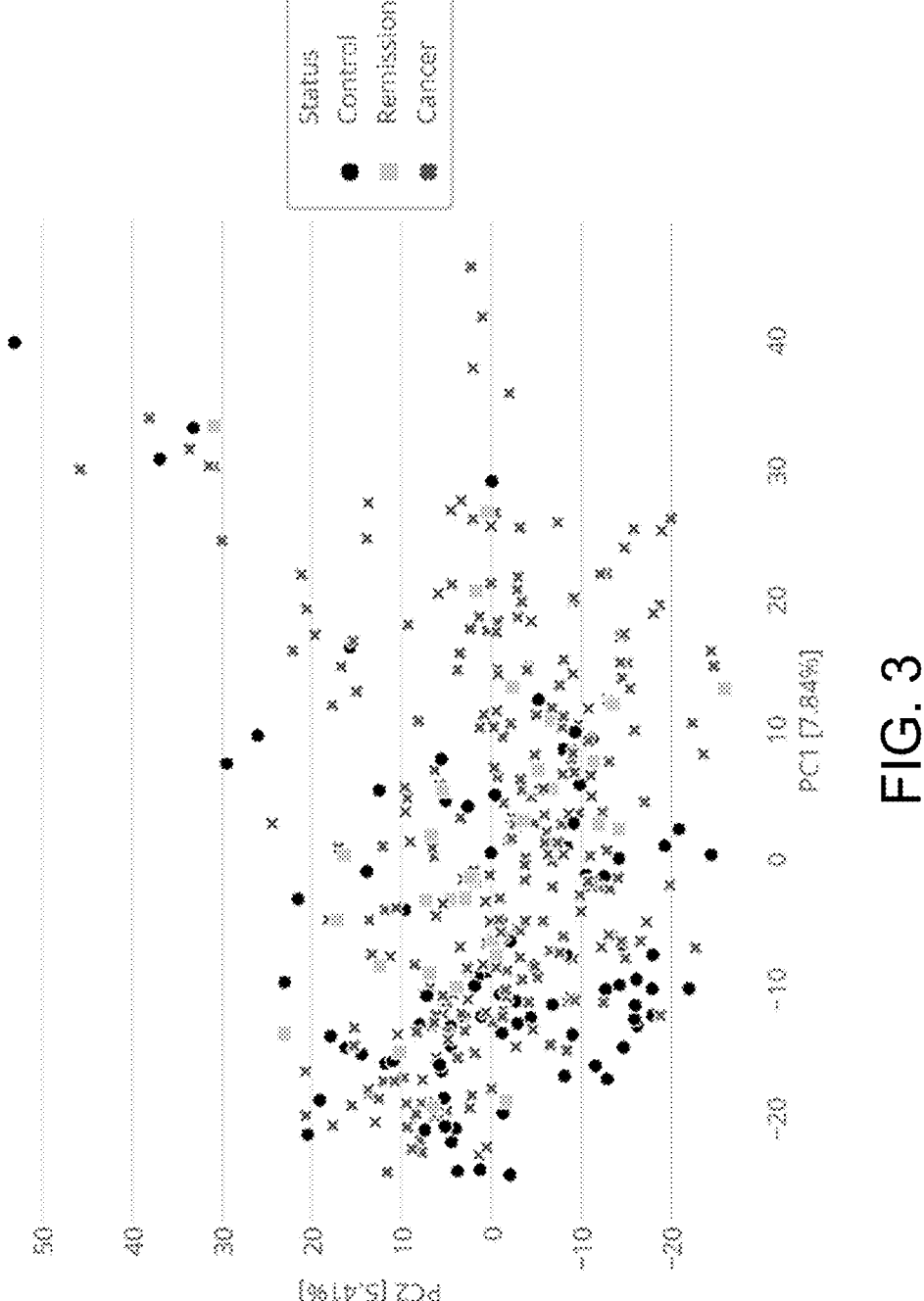
FIG. 3 graphically illustrates a principal component analysis (PCA) of microbiome composition obtained from fecal samples. Whole genome sequencing is performed on fecal samples from subjects with and without cancer as well as in remission. The reads are classified, and abundance of each operational species unit is estimated computationally. PCA is performed on centered-log-ratio transformed abundances, and the first two principal coordinates are plotted for cancer, remission, and control sample cohorts, as described in Example 9, below.
Figure 4:
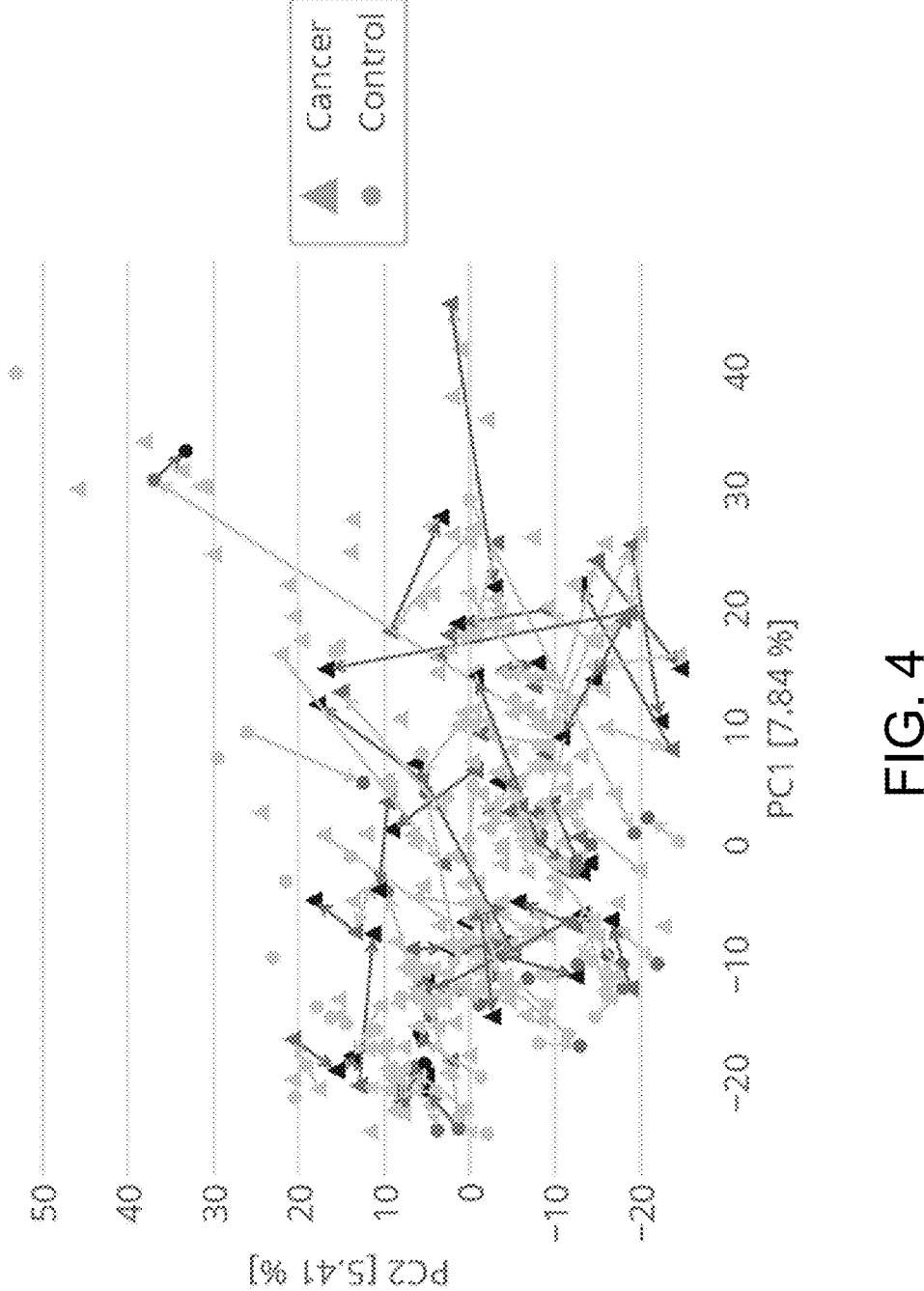
FIG. 4 graphically illustrates a PCA plot showing the relationship between longitudinal samples of the same patient. Whole genome sequencing is performed on fecal samples from subjects with and without cancer as well as in remission. The reads are classified and abundance of each operational species unit is estimated computationally. PCA is performed on centered-log-ratio transformed abundances, and the first two principal coordinates are plotted for cancer and control sample cohorts, with longitudinal samples being connected by arrows. Later samples from the same subject are colored darker, as described in Example 9, below.
Figure 5:
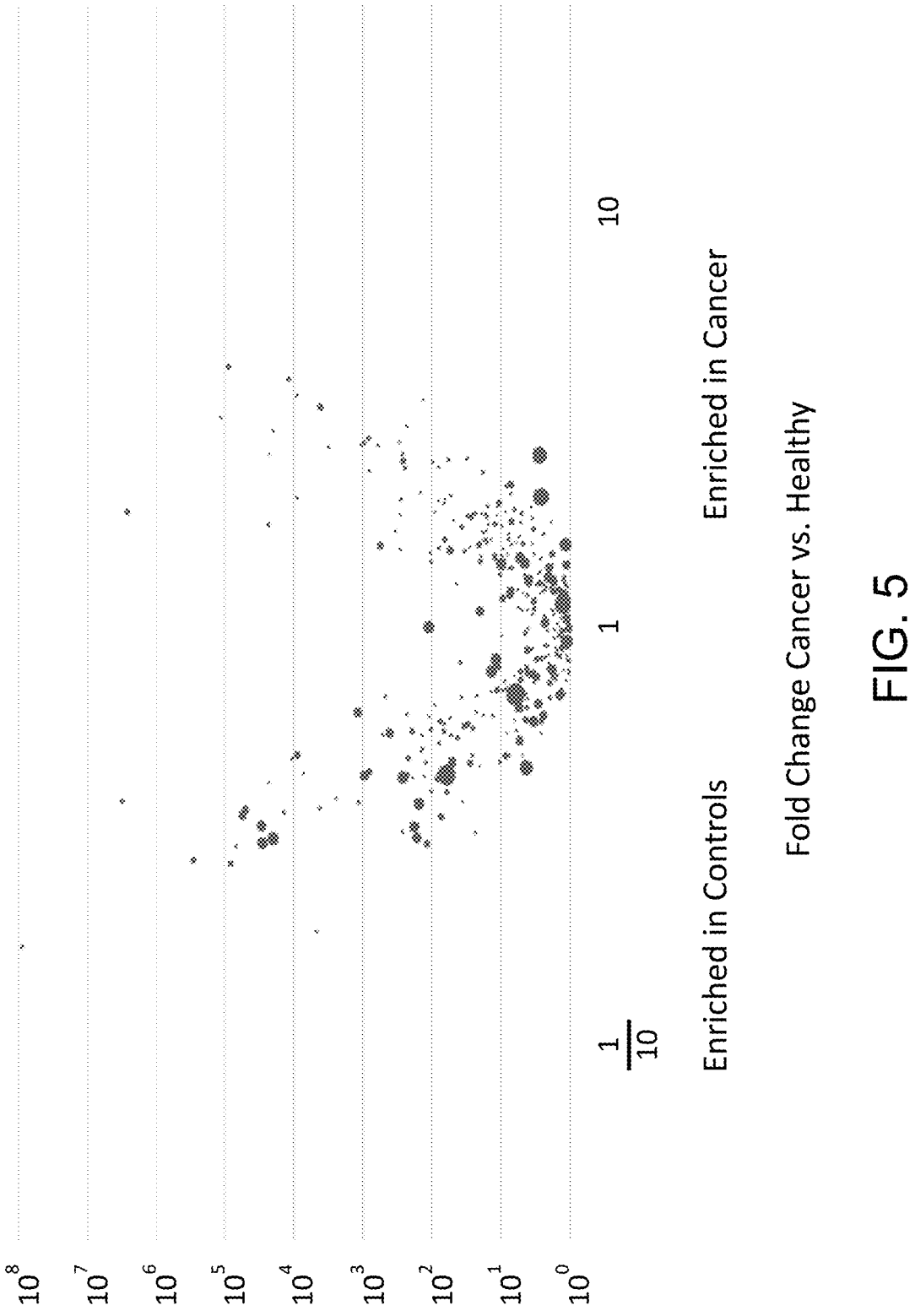
FIG. 5 graphically illustrates a volcano plot showing the differential abundance of species in cancer and control cohorts. Whole genome sequencing is performed on fecal samples from subjects with and without cancer and the reads are classified and abundance of each operational species unit is estimated computationally. The fold change difference and statistical significance (inverse p value, Mann Whitney U test) is calculated for abundances between cancer and control sample cohorts. The results are displayed on a volcano plot. Each point is an operational species unit, and the area of each point corresponds to the average abundance of that operational species unit across all samples, as described in Example 9, below.
Figure 6:
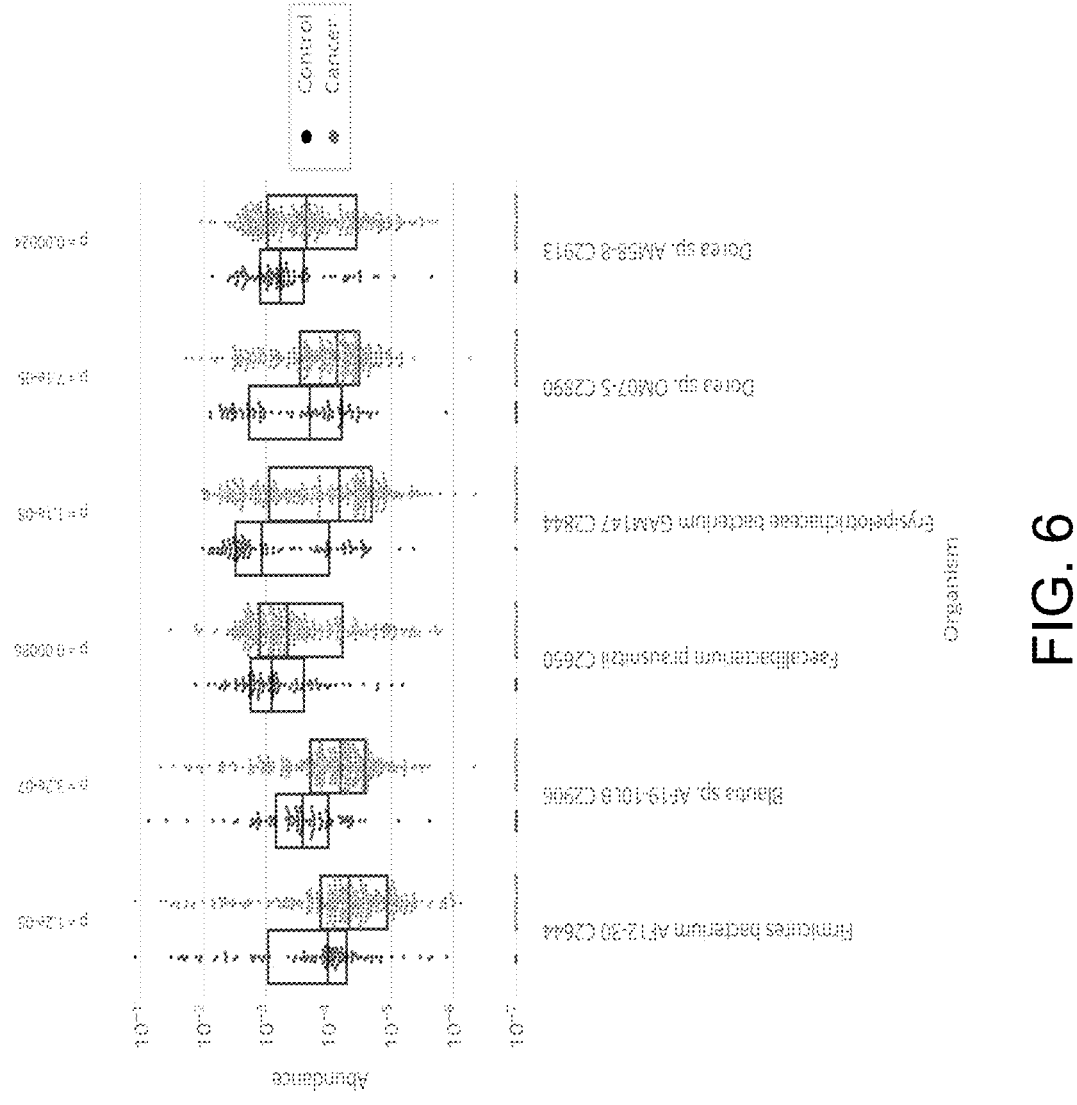
FIG. 6 shows the distribution of abundances of specific organisms among the different patient samples in each cohort. Whole genome sequencing is performed on fecal samples from subjects with and without cancer and the reads are classified and abundance of each operational species unit is estimated computationally. Operational species units with significant differences between cancer and control are displayed, as described in Example 9, below.
Figure 7:
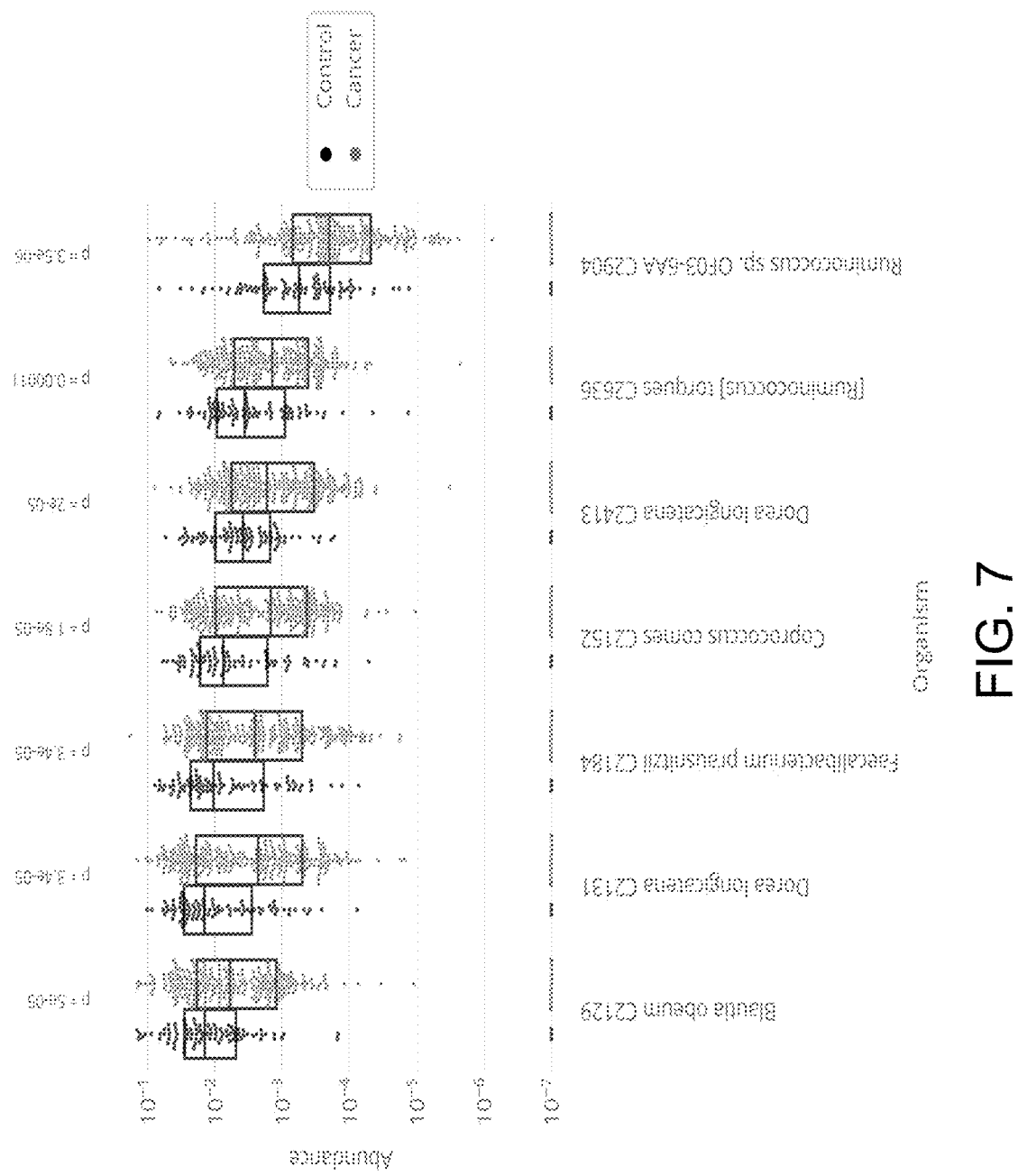
FIG. 7 graphically illustrates the distribution of abundances of additional specific organisms among the different patient samples in each cohort, plotted as in FIG. 6.

The results were analyzed for differential relative abundance of organisms (classified as OSUs) between cancer and control cohorts, as well as correlations between relative abundance of organisms and immune markers, as measured by flow cytometry. Principal component analysis was performed to visualize the structure of the data (FIG. 3 and FIG. 4) and exhibited a partial separation between cancer and control samples. This separation is driven by a specific subset of microbes that have differential abundance between the two cohorts (FIGS. 5-7 and Table 3). Microbes were ranked based on the magnitude and significance of this difference. Additionally, machine learning was performed to train a model capable of discriminating between a subject with cancer and a control subject.

Metagenomic sequences are also scanned to identify novel CRISPR sequences using a scoring algorithm such as that described in (Moreno-Mateos et al. (2015) Nat. Met. 12:982-988), and for predicted natural product gene clusters using the antiSMASH routine (Medema et al. (2011) Nuc. Acids Res. 39:W339-W346).

Table 3, illustrated as FIG. 17. Whole genome sequencing was performed on fecal samples from subjects with and without cancer and the reads were classified and abundance of each operational species unit (OSU) was estimated computationally. The fold change difference and statistical significance (inverse p value, Mann Whitney U test) was calculated for abundances between cancer and control sample cohorts. For OSUs with a mean relative abundance of at least 0.05%, p-values were filtered using an adjusted p-value computed using a two-stage Benjamini-Hochberg procedure. OSUs passing the threshold are reported.

Table 4, illustrated as FIG. 18. Whole genome sequencing was performed on fecal samples from subjects with and without cancer and the reads were classified using the GTDB database and abundance of each species was estimated computationally (Centrifuge). For classified hits with a mean relative abundance of at least 0.005%, The fold change difference and statistical significance (inverse p value, Mann Whitney U test) was calculated for abundances between cancer and control sample cohorts.

Figure 8:
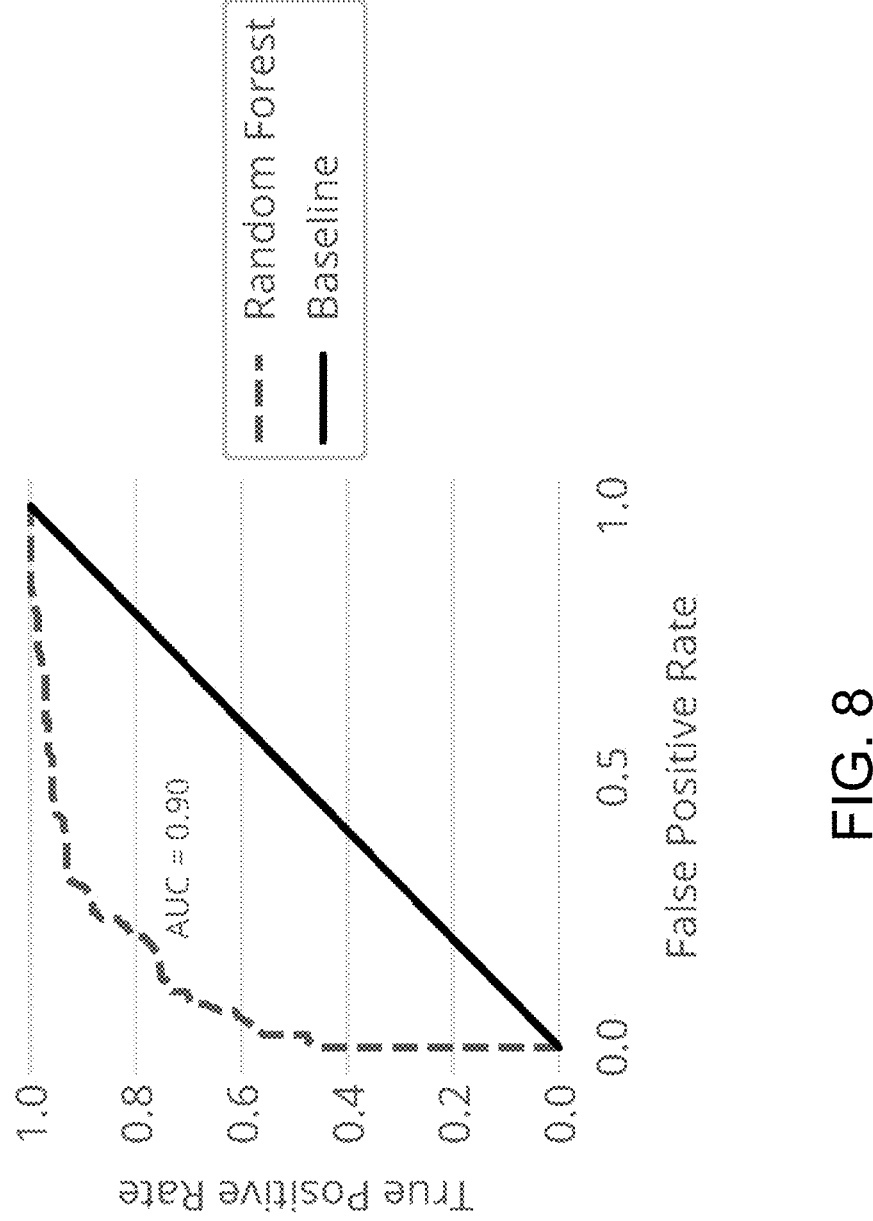
FIG. 8 graphically illustrates a receiver operating characteristic (ROC) curve of the classifier developed based on stool species distribution. A random forest classifier is trained to classify operational species unit abundances for a sample as corresponding to cancer or control. An ROC curve is generated on 145 cancer samples and 88 control samples using leave-one-out cross validation. No hyperparameter optimization was performed, as described in Example 10, below.

Example 10: Data Driven and Machine Learning Approaches for Therapeutic Design Whole genome sequencing and flow cytometry analysis were performed on human fecal and blood samples, respectively, as described in Example 9. A machine learning model was fit to discriminate cancer and control samples, using all fecal data collected to date. The model was validated using leave-one-out cross-validation, and performance evaluated using a receiver operating characteristic curve (FIG. 8 and Table 5). Alternatively, the model developed using the GTDB database was validated using Stratified Group K-Fold Cross Validation (Tables 6 to 7).

TABLE 5

A random forest classifier was trained to classify operational species unit abundances for a sample as corresponding to cancer or control. An ROC curve was generated on 145 cancer samples and 88 control samples using leave-one-out cross validation. Following validation, the model was trained on all the samples and feature importance values are reported.

| Feature Importance (Random Forest) | log 10 of Fold Change (Control vs Cancer) | Organism Name (Operational Species Unit) |
|---|---|---|
| 0.016501858 | 0.415683892 | *Blautia* sp. AF19-10LB C2906 |
| 0.013518985 | 0.764382216 | Erysipelotrichaceae bacterium GAM147 C2844 |
| 0.010943304 | 0.280259145 | *Flavonifractor plautii* C2284 |
| 0.009899023 | −0.565340143 | *Firmicutes* bacterium AF12-30 C2644 |
| 0.009291084 | −0.557690435 | *Ruminococcus* sp. OF03-6AA C2904 |
| 0.008763332 | −0.52436559 | *Coprobacillus* sp. 8_1_38FAA C2606 |
| 0.008543128 | −0.370730577 | *Eubacterium ramulus* C2852 |
| 0.008185491 | 0.314786908 | [*Clostridium*] *symbiosum* C2238 |
| 0.00777239 | −0.449283525 | *Coprococcus comes* C2152 |
| 0.007387547 | −0.432405099 | *Dorea* sp. AM58-8 C2913 |
| 0.007370147 | 0.386220508 | *Streptococcus vestibularis* C7338 |
| 0.00712668 | −0.436129729 | *Dorea longicatena* C2413 |
| 0.006857525 | 0.266781049 | *Catenibacterium* sp. AM22-15 C2888 |
| 0.00606504 | 0.249321416 | [*Clostridium*] *bolteae* C2137 |
| 0.006038427 | 0.629434999 | [*Clostridium*] *scindens* C2143 |
| 0.005741584 | 0.559795019 | *Blautia* sp. N6H1-15 C2865 |
| 0.005164589 | −0.516206872 | *Dorea longicatena* C2131 |
| 0.005038218 | 0.440453628 | Clostridiales bacterium TF09-2AC C2150 |
| 0.004962784 | 0.089210304 | *Parabacteroides merdae* C0130 |
| 0.00488605 | −0.442770588 | *Dorea* sp. OM07-5 C2890 |
| 0.00482885 | −0.353929055 | *Anaerostipes hadrus* C2144 |
| 0.004801012 | 0.531527103 | *Anaerostipes hadrus* C3044 |
| 0.004709165 | 0.446480902 | *Anaerostipes caccae* C2134 |
| 0.004700494 | 0.204253574 | *Alistipes senegalensis* C0284 |
| 0.004668466 | 0.189644361 | *Hungatella hathewayi* C2175 |
| 0.004549795 | 0.246863312 | *Alistipes* sp. An66 C0846 |

TABLE 5-continued

A random forest classifier was trained to classify operational species
unit abundances for a sample as corresponding to cancer or control. An
ROC curve was generated on 145 cancer samples and 88 control samples using
leave-one-out cross validation. Following validation, the model was trained
on all the samples and feature importance values are reported.

| Feature Importance (Random Forest) | log 10 of Fold Change (Control vs Cancer) | Organism Name (Operational Species Unit) |
|---|---|---|
| 0.004488856 | −0.201826507 | *Fusicatenibacter saccharivorans* C2643 |
| 0.004384083 | −0.504914016 | *Blautia obeum* C2129 |
| 0.004369678 | 0.341085636 | *Lactobacillus fermentum* C3433 |
| 0.004361877 | 0.198581902 | *Oscillibacter* sp. PEA192 C2443 |
| 0.00430547 | −0.486272557 | *Phascolarctobacterium succinatutens* YIT 12067 C2237 |
| 0.00427777 | −0.490502377 | *Bifidobacterium catenulatum* C0014 |
| 0.004249632 | 0.185525714 | *Angelakisella massiliensis* C3120 |
| 0.004222488 | −0.352856347 | *Ruminococcus callidus* C2440 |
| 0.004185622 | 0.324033352 | *Bifidobacterium dentium* C0003 |
| 0.004155963 | 0.253779907 | *Extibacter muris* C2915 |
| 0.004044015 | 0.507281373 | [*Clostridium*] *clostridioforme* AGR2157 C2412 |
| 0.004017688 | 0.47474479 | [*Clostridium*] *lavalense* C2843 |
| 0.004004597 | −0.163492912 | *Clostridium* sp. AM18-55 C2845 |
| 0.003953855 | 0.181627961 | Clostridia bacterium UC5.1-1D1 C2633 |
| 0.003917395 | 0.231236234 | *Streptococcus parasanguinis* C4037 |
| 0.003901166 | 0.40868596 | *Streptococcus mutans* C3345 |
| 0.003875451 | −0.421426117 | *Anaerobutyricum hallii* C2206 |
| 0.003867169 | 0.259650758 | *Erysipelatoclostridium ramosum* C2142 |
| 0.003761301 | 0.375605827 | *Paraprevotella clara* C0224 |
| 0.003659752 | 0.400215198 | Eubacteriaceae bacterium CHKCI004 C2759 |
| 0.003549486 | −0.727951095 | *Collinsella* sp. AM34-10 C1986 |
| 0.003509696 | 0.195100824 | *Flavonifractor* sp. An9 C2755 |
| 0.003494686 | −0.348031554 | *Ruminococcus* sp. AF46-10NS C2926 |
| 0.003477621 | 0.206071101 | *Clostridium* sp. OM02-18AC C2931 |
| 0.003447056 | 0.457446985 | *Dorea* sp. Marseille-P4003 C3269 |
| 0.003386838 | 0.440006771 | *Blautia producta* C2356 |
| 0.00337533 | −0.305064647 | Firmicutes bacterium TM09-10 C2909 |
| 0.003362471 | 0.273578745 | *Phocea massiliensis* C2631 |
| 0.003322609 | 0.009697135 | *Merdibacter massiliensis* C3221 |
| 0.003256256 | −0.247491324 | *Oscillibacter* sp. ER4 C2580 |
| 0.003236909 | 0.547982486 | Clostridiales bacterium VE202-09 C2460 |
| 0.003178005 | 0.309883036 | *Harryflintia acetispora* C2880 |
| 0.003172428 | 0.224781595 | *Flavonifractor* sp. An82 C2757 |
| 0.00315518 | 0.405385756 | *Streptococcus* sp. HS1SS2 C4629 |
| 0.003153913 | 0.185518308 | *Eisenbergiella massiliensis* C2435 |
| 0.003099824 | 0.309145503 | *Clostridium* sp. SN20 C3256 |
| 0.003032509 | 0.190748088 | *Butyricicoccus porcorum* C2752 |
| 0.002974263 | 0.21217243 | *Bifidobacterium scardovii* C0042 |
| 0.002943309 | −0.183114283 | Firmicutes bacterium AM10-47 C2889 |
| 0.002906076 | −0.344627962 | *Blautia* sp. TF11-31AT C2841 |
| 0.0029012 | 0.069794378 | *Bacteroides clarus* C0195 |
| 0.0028804 | 0.218206762 | *Lachnoclostridium* sp. An14 C2775 |
| 0.00287576 | −0.103576385 | *Bacteroides uniformis* C0132 |
| 0.002848749 | −0.167126002 | Firmicutes bacterium AF36-3BH C2905 |
| 0.002824076 | 0.309520673 | Clostridiales bacterium CCNA10 C2953 |
| 0.002809724 | 0.314889985 | *Dorea* sp. 5-2 C2378 |
| 0.002808948 | 0.251398969 | *Clostridium* sp. AT4 C2666 |
| 0.002808102 | −0.399757353 | *Christensenella minuta* C2682 |
| 0.002796624 | 0.40212407 | *Acidaminococcus intestini* C2208 |
| 0.00277314 | −0.349179114 | *Massilioclostridium coli* C3076 |
| 0.002759323 | 0.447842365 | *Streptococcus gordonii* C3645 |
| 0.002718198 | −0.312636412 | *Ruminococcus* sp. AF14-10 C2897 |
| 0.00270911 | −0.304912298 | *Odoribacter* sp. AF21-41 C0847 |
| 0.002652152 | 0.136177714 | *Anaeromassilibacillus* sp. An200 C2765 |
| 0.002620021 | 0.243049812 | *Anaerostipes hadrus* C2161 |
| 0.002615116 | 0.233225815 | *Lachnoclostridium* sp. An298 C2760 |
| 0.002611426 | −0.032159744 | *Roseburia faecis* C2648 |
| 0.002606658 | −0.304525941 | [*Ruminococcus*] *torques* C2636 |
| 0.002587424 | 0.352092737 | *Dialister pneumosintes* C2708 |
| 0.002576223 | 0.155095629 | *Bacteroides caccae* C0156 |
| 0.002573354 | 0.192538373 | *Butyricimonas* sp. Marseille-P4593 C1362 |
| 0.002552093 | −0.244156505 | Clostridiales bacterium VE202-01 C2458 |
| 0.002548102 | 0.361035514 | *Blautia* sp. An249 C2761 |
| 0.002517171 | −0.394453097 | *Turicibacter sanguinis* C2220 |
| 0.002506636 | 0.277784722 | *Enorma massiliensis* C1943 |
| 0.002501752 | 0.275045721 | *Streptococcus* sp. HSISM1 C4627 |
| 0.00249105 | −0.534927741 | *Raoultibacter massiliensis* C2013 |
| 0.002478591 | 0.165198022 | Ruminococcaceae bacterium AM07-15 C2928 |
| 0.002471317 | −0.392581823 | *Clostridium* sp. AF36-4 C2893 |

TABLE 5-continued

A random forest classifier was trained to classify operational species
unit abundances for a sample as corresponding to cancer or control. An
ROC curve was generated on 145 cancer samples and 88 control samples using
leave-one-out cross validation. Following validation, the model was trained
on all the samples and feature importance values are reported.

| Feature Importance (Random Forest) | log 10 of Fold Change (Control vs Cancer) | Organism Name (Operational Species Unit) |
|---|---|---|
| 0.002468113 | 0.175364006 | *Eubacterium* sp. 3__1__31 C2186 |
| 0.002461251 | −0.215314373 | Clostridiales bacterium AM23-16LB C2886 |
| 0.002456084 | 0.016078272 | *Tyzzerella nexilis* C2155 |
| 0.002443061 | 0.267120144 | *Sellimonas intestinalis* C2461 |
| 0.002440381 | −0.295779942 | *Butyricicoccus* sp. AM29-23AC C2943 |
| 0.002429933 | −0.160088535 | *Alistipes putredinis* DSM17216 C0133 |
| 0.002403414 | −0.34579043 | Firmicutes bacterium AF25-13AC C2695 |
| 0.002389793 | 0.233921669 | [*Clostridium*] *citroniae* C2272 |
| 0.002388663 | −0.287905997 | *Faecalibacterium prausnitzii* C2809 |
| 0.002377287 | 0.265105676 | *Collinsella intestinalis* C1929 |
| 0.002371557 | 0.325006666 | *Lachnoclostridium* sp. An196 C2766 |
| 0.002331412 | 0.161011335 | *Ruthenibacterium lactatiformans* C2282 |
| 0.00232152 | −0.257009611 | *Ruminococcus* sp. AF21-42 C2938 |
| 0.002321468 | −0.069789147 | *Butyrivibrio crossotus* DSM2876 C2154 |
| 0.002319772 | 0.003128369 | *Bacteroides vulgatus* C0099 |
| 0.00229641 | 0.091890638 | *Bacteroides acidifaciens* C0604 |
| 0.002277453 | 0.195676439 | *Flavonifractor* sp. An10 C2786 |
| 0.002276704 | −0.046379748 | *Drancourtella* sp. An177 C2763 |
| 0.002272041 | 0.160264471 | *Anaerotruncus colihominis* C2145 |
| 0.00225912 | −0.120363782 | *Pseudoflavonifractor capillosus* ATCC 29799 C2198 |
| 0.002256141 | −0.517722756 | *Bifidobacterium bifidum* C0005 |
| 0.002250462 | −0.094755491 | *Anaeromassilibacillus* sp. Marseille-P3876 C2925 |
| 0.002249251 | 0.292298556 | *Coprobacter fastidiosus* C0231 |
| 0.002245262 | 0.338335356 | *Bariatricus massiliensis* C3067 |
| 0.002237507 | 0.162776529 | *Coprococcus* sp. AF21-14LB C2900 |
| 0.002226962 | −0.408971832 | Clostridiaceae bacterium OM08-6BH C2949 |
| 0.002218309 | −0.002771039 | [*Bacteroides*] *pectinophilus* ATCC 43243 C2151 |
| 0.002217958 | 0.25729072 | *Pseudoflavonifractor* sp. An184 C2770 |
| 0.002200796 | −0.200989635 | *Eubacterium* sp. AM18-26 C2923 |
| 0.00218927 | −0.081898577 | *Parabacteroides* sp. AF18-52 C1227 |
| 0.002187486 | −0.123209619 | *Coprococcus eutactus* C2642 |
| 0.002161484 | 0.30195464 | *Phascolarctobacterium faecium* C2862 |
| 0.002158572 | −0.087502084 | Lachnospiraceae bacterium OM04-12BH C2952 |
| 0.002148262 | 0.047074352 | *Parabacteroides distasonis* C0100 |
| 0.002142893 | −0.255666512 | *Faecalibacterium* sp. AF28-13AC C2810 |
| 0.002134925 | −0.158568078 | *Bacteroides stercoris* C0134 |
| 0.002114346 | −0.355662173 | Firmicutes bacterium AM41-11 C2946 |
| 0.002110017 | −0.165551333 | [*Clostridium*] *amygdalinum* C2887 |
| 0.00210878 | 0.250557414 | *Anaerotignum lactatifermentans* C2790 |
| 0.002107104 | 0.436062031 | [*Clostridium*] *aldenense* C2884 |
| 0.002095506 | 0.084877313 | *Intestinimonas timonensis* C3301 |
| 0.002094298 | 0.256448208 | *Alistipes finegoldii* C0177 |
| 0.002084535 | 0.058630203 | *Mordavella* sp. Marseille-P3756 C3280 |
| 0.002082758 | 0.128186268 | *Streptococcus oralis* subsp. *tigurinus* C6034 |
| 0.002078318 | 0.085608213 | *Prevotella* sp. P3-92 C0874 |
| 0.002078069 | 0.213972847 | *Alterileibacterium massiliense* C3118 |
| 0.002056041 | −0.041470873 | *Coprococcus eutactus* C2140 |
| 0.00205311 | 0.306957134 | *Fusobacterium nucleatum* C2028 |
| 0.002052465 | −0.248224092 | *Massilimaliae massiliensis* C3228 |
| 0.00204697 | −0.360378609 | *Clostridium* sp. AM33-3 C2947 |
| 0.00204635 | −0.169578698 | Firmicutes bacterium AM29-6AC C2940 |
| 0.002030614 | 0.14595452 | *Hungatella hathewayi* C2351 |
| 0.00202297 | −0.251539605 | *Blautia luti* C2436 |
| 0.001993254 | −0.189503492 | *Holdemanella biformis* C2160 |
| 0.001989672 | −0.240687636 | *Anaerobutyricum hallii* C3263 |
| 0.001971269 | 0.089118345 | *Alistipes shahii* C0199 |
| 0.001965797 | 0.274298289 | *Odoribacter laneus* YIT 12061 C0239 |
| 0.001965483 | 0.078208985 | *Peptoniphilus lacrimalis* C2213 |
| 0.00194357 | 0.120085576 | *Streptococcus constellatus* C4635 |
| 0.001936923 | −0.130171095 | *Eubacterium* sp. AF15-50 C2941 |
| 0.001934746 | 0.058661303 | Clostridiales bacterium CHKCI006 C3057 |
| 0.00193182 | 0.157031233 | *Alistipes onderdonkii* C0322 |
| 0.001930949 | 0.599613718 | *Lactobacillus salivarius* C3392 |
| 0.001892559 | 0.121653741 | *Neglecta timonensis* C3059 |
| 0.001887608 | 0.232534892 | *Clostridium* sp. 1001271st1 H5 C3046 |
| 0.001866112 | 0.045627845 | *Prevotellamassilia timonensis* C1705 |
| 0.001865236 | 0.16241841 | *Slackia exigua* C1932 |
| 0.001854461 | −0.219463054 | *Bacteroides finegoldii* C0138 |
| 0.001852121 | −0.224535064 | *Barnesiella intestinihominis* C0275 |

TABLE 5-continued

A random forest classifier was trained to classify operational species
unit abundances for a sample as corresponding to cancer or control. An
ROC curve was generated on 145 cancer samples and 88 control samples using
leave-one-out cross validation. Following validation, the model was trained
on all the samples and feature importance values are reported.

| Feature Importance (Random Forest) | log 10 of Fold Change (Control vs Cancer) | Organism Name (Operational Species Unit) |
|---|---|---|
| 0.001841628 | −0.224153342 | *Eubacterium ventriosum* C2128 |
| 0.001839575 | 0.14243286 | *Streptococcus anginosus* C4636 |
| 0.001839422 | 0.049603186 | *Prevotella* sp. BCRC 81118 C1221 |
| 0.001838081 | 0.080289666 | *Akkermansia* sp. aa__0143 C1922 |
| 0.001836116 | 0.387030309 | *Blautia* sp. Marseille-P3201T C3179 |
| 0.001832526 | −0.319221468 | *Ruminococcus lactaris* C2149 |
| 0.001830134 | −0.187587381 | *Eubacterium* sp. AF34-35BH C2902 |
| 0.001829468 | 0.227277401 | *Paraprevotella xylaniphila* C0198 |
| 0.001821326 | −0.005377338 | *Alistipes* sp. 5CPEGH6 C1580 |
| 0.001819158 | −0.045467144 | *Eubacterium* sp. TM06-47 C2917 |
| 0.001812327 | −0.36246911 | *Faecalibacterium prausnitzii* C2651 |
| 0.001807702 | 0.407496562 | *Lachnoclostridium* sp. An118 C2782 |
| 0.001804296 | 0.162945863 | *Bacteroides* sp. AM10-21B C1214 |
| 0.001801377 | −0.612948492 | *Collinsella aerofaciens* C1977 |
| 0.001799781 | 0.200783717 | Ruminococcaceae bacterium D16 C2214 |
| 0.001795815 | −0.230812001 | *Dorea formicigenerans* C2197 |
| 0.001782118 | 0.050805612 | *[Clostridium] leptum* C2136 |
| 0.001769616 | 0.255735482 | *Parabacteroides johnsonii* C0139 |
| 0.001757969 | 0.335044837 | *[Clostridium] methylpentosum* DSM 5476 C2167 |
| 0.001748845 | 0.137798554 | *Parabacteroides* sp. SN4 C1840 |
| 0.001732845 | −0.088799912 | *Clostridium* sp. YH-panp20 C2971 |
| 0.001730465 | 0.187542345 | *[Ruminococcus] gnavus* C2199 |
| 0.001721291 | 0.245585432 | *Holdemania* sp. Marseille-P2844 C3176 |
| 0.001711469 | 0.326189698 | *[Clostridium] asparagiforme* C2165 |
| 0.001709265 | −0.32340108 | *Ruminococcus* sp. AM42-11 C2945 |
| 0.001708751 | −0.211956107 | *Blautia* sp. OF03-15BH C2912 |
| 0.001705071 | −0.326716726 | *Subdoligranulum* sp. APC924/74 C2870 |
| 0.001704797 | −0.391815999 | *Romboutsia timonensis* C3123 |
| 0.001697621 | 0.114228311 | *Streptococcus oralis* C5466 |
| 0.0016965 | −0.048932599 | *Clostridium* sp. AF34-13 C2653 |
| 0.001691772 | 0.20344874 | *Dialister invisus* DSM 15470 C2174 |
| 0.001689134 | 0.095511852 | *Olsenella uli* C1928 |
| 0.001673536 | −0.100055999 | *[Eubacterium] siraeum* C2135 |
| 0.001662325 | 0.122632002 | *Akkermansia muciniphila* C1917 |
| 0.001656155 | 0.214252057 | *Faecalimonas umbilicata* C2244 |
| 0.001642083 | 0.182409993 | Clostridiales bacterium Marseille-P5551 C3291 |
| 0.001637493 | 0.004280452 | Ruminococcaceae bacterium C2861 |
| 0.001634056 | 0.134322164 | *Lactonifactor longoviformis* C2830 |
| 0.0016262656 | 0.485421565 | *Lactobacillus rhamnosus* C3457 |
| 0.001625673 | 0.273598423 | Coriobacteriaceae bacterium CHKCI002 C1973 |
| 0.001624111 | −0.011206269 | *Anaerofilum* sp. An201 C2764 |
| 0.001623073 | 0.072560155 | *Bacteroides stercorirosoris* C0463 |
| 0.001622251 | −0.202159024 | *Alistipes* sp. CHKCI003 C1653 |
| 0.001620599 | 0.174483602 | *Anaeromassilibacillus* sp. Marseille-P3371 C2632 |
| 0.001619706 | 0.30918881 | *Bacteroides* sp. HF-5092 C1596 |
| 0.001619395 | 0.147450868 | *Bacteroides coprocola* C0136 |
| 0.001617633 | −0.087543931 | *Blautia obeum* C2901 |
| 0.001614518 | 0.34599988 | *Evtepia gabavorous* C2876 |
| 0.001613136 | −0.161787704 | *Ruminococcus* sp. AF31-8BH C2903 |
| 0.001603563 | 0.123138967 | *Anaerococcus* sp. HMSC068A02 C2185 |
| 0.001598053 | 0.202218832 | *Lactobacillus plantarum* C3798 |
| 0.001594311 | −0.488328224 | *Allisonella histaminiformans* C3105 |
| 0.001586576 | −0.098634411 | *Roseburia intestinalis* C2158 |
| 0.001584302 | −0.452532206 | *Bifidobacterium pseudocatenulatum* C0013 |
| 0.001572828 | −0.061735341 | *Alistipes* sp. 5CBH24 C0283 |
| 0.001570429 | 0.116445939 | *Streptococcus salivarius* C4352 |
| 0.001563761 | −0.1456938 | *Gordonibacter pamelaeae* C1937 |
| 0.001552982 | −0.476696467 | *Collinsella aerofaciens* C1933 |
| 0.001550017 | 0.146736525 | *Flavonifractor* sp. An92 C2753 |
| 0.001546685 | −0.312675608 | *Clostridium* sp. OF10-22XD C2132 |
| 0.001544022 | 0.143206979 | *Haemophilus parainfluenzae* T3T1 C4194 |
| 0.001541656 | 0.177526741 | *Streptococcus gallolyticus* C3902 |
| 0.001538447 | −0.306056064 | *Bacteroides heparinolyticus* C1005 |
| 0.00153663 | −0.11819143 | *Eubacterium* sp. OM08-24 C2896 |
| 0.001535096 | −0.242001524 | *Faecalibacterium prausnitzii* C2863 |
| 0.001532366 | −0.074691634 | *Bacteroides nordii* C0263 |
| 0.00153067 | −0.077986369 | *Marvinbryantia formatexigens* C2205 |
| 0.00152307 | 0.128955058 | Lachnospiraceae bacterium 1__4__56FAA C2258 |
| 0.001515629 | 0.100560583 | *Roseburia* sp. OF03-24 C2911 |

TABLE 5-continued

A random forest classifier was trained to classify operational species
unit abundances for a sample as corresponding to cancer or control. An
ROC curve was generated on 145 cancer samples and 88 control samples using
leave-one-out cross validation. Following validation, the model was trained
on all the samples and feature importance values are reported.

| Feature Importance (Random Forest) | log 10 of Fold Change (Control vs Cancer) | Organism Name (Operational Species Unit) |
|---|---|---|
| 0.001515375 | −0.070429456 | Lachnospiraceae bacterium AM48-27BH C2935 |
| 0.00151401 | 0.209874419 | Fusobacterium nucleatum C2027 |
| 0.001504779 | −0.142905059 | Clostridium sp. OF09-36 C2944 |
| 0.001497974 | 0.032287603 | Peptostreptococcus anaerobius C2217 |
| 0.00149702 | −0.090219746 | Leuconostoc mesenteroides C3570 |
| 0.001495408 | 0.419154573 | Blautia producta C2581 |
| 0.001489385 | 0.10891937 | Bacteroides cellulosilyticus C0143 |
| 0.001487732 | −0.474788291 | Faecalibacterium prausnitzii C2184 |
| 0.00147645 | 0.378916316 | Lachnoclostridium sp. An181 C2771 |
| 0.001467508 | −0.26283664 | Clostridium sp. AM49-4BH C2934 |
| 0.001467098 | 0.000605824 | Clostridium sp. ATCC 29733 C2438 |
| 0.0014621 | −0.322415354 | Blautia sp. KGMB01111 C3003 |
| 0.001454853 | 0.095997825 | Clostridioides difficile C2074 |
| 0.001447136 | −0.061440984 | Parvimonas micra C2139 |
| 0.001444928 | 0.212594053 | Megasphaera sp. DISK 18 C2433 |
| 0.001443122 | 0.285426008 | Bacteroides salyersiae C0264 |
| 0.001438622 | −0.046750403 | Lactobacillus paracasei C3573 |
| 0.00143852 | −0.082129699 | Eggerthella timonensis C2011 |
| 0.001425959 | −0.114661776 | Bifidobacterium animalis C0002 |
| 0.001416675 | 0.280368137 | Klebsiella variicola C3709 |
| 0.001414944 | −0.246601387 | Agathobaculum butyriciproducens C2850 |
| 0.001405704 | 0.074907434 | Anaeromassilibacillus sp. An250 C2762 |
| 0.001402711 | −0.081852178 | Ruminococcus sp. AF24-32LB C2894 |
| 0.001385668 | −0.358288898 | Faecalibacterium prausnitzii C2138 |
| 0.001385102 | −0.035320328 | Streptococcus mitis NCTC 12261 C4004 |
| 0.001379637 | 0.168782631 | Prevotella sp. AM23-5 C0872 |
| 0.001378158 | 0.138984788 | Collinsella tanakaei C2458 |
| 0.001375186 | 0.128316545 | Intestinimonas butyriciproducens C2577 |
| 0.001357814 | −0.130545436 | Gemmiger formicilis C3234 |
| 0.001356921 | 0.099487524 | Culturomica massiliensis C1230 |
| 0.001349152 | −0.028077053 | Roseburia sp. AM51-8 C2924 |
| 0.001346043 | 0.172383478 | Eubacterium sp. Anil C2784 |
| 0.001345379 | 0.067714209 | Hungatella hathewayi C2462 |
| 0.001342127 | 0.190693108 | Bacteroides rodentium JCM 16496 C0461 |
| 0.001325512 | −0.073609518 | Clostridium sp. TM06-18 C2922 |
| 0.001314021 | −0.14364999 | Clostridium sp. AF27-2AA C2937 |
| 0.001303967 | −0.118957311 | Parabacteroides sp. TM07-1AC C1229 |
| 0.001301855 | 0.049387119 | Butyricimonas sp. Marseille-P2440 C0330 |
| 0.001297003 | −0.022569114 | Neobitarella massiliensis C3275 |
| 0.001291043 | −0.159405658 | Clostridium sp. AM30-24 C2942 |
| 0.001276208 | −0.060522193 | Prevotella sp. Marseille-P4119 C1902 |
| 0.001268369 | 0.116021978 | Clostridium perfringens C2078 |
| 0.001264612 | −0.0200892 | Bacteroides sp. An19 C0842 |
| 0.001263236 | 0.301353216 | Klebsiella pneumoniae C3423 |
| 0.001260612 | −0.160766973 | Alistipes timonensis C0271 |
| 0.001256742 | 0.252094618 | Salmonella enterica C3329 |
| 0.001253605 | 0.178630171 | Intestinimonas massiliensis C2614 |
| 0.001252735 | 0.470799178 | Cuneatibacter caecimuris C3008 |
| 0.001241543 | 0.105626404 | Eubacterium brachy ATCC 33089 C2452 |
| 0.001233195 | −0.111096287 | Eisenbergiella tayi C2259 |
| 0.001231803 | 0.203084745 | Akkermansia muciniphila C1923 |
| 0.001229663 | 0.07528375 | Akkermansia muciniphila C1921 |
| 0.001227806 | 0.316271739 | Metaprevotella massiliensis C1901 |
| 0.001223817 | 0.103266649 | Streptococcus intermedius C4476 |
| 0.001223003 | −0.009215998 | Desulfovibrio piger C7227 |
| 0.001210017 | −0.103823837 | Eubacterium ramulus C2442 |
| 0.001208958 | −0.066912759 | Clostridium sp. OM07-10AC C2948 |
| 0.001208297 | −0.011533879 | Faecalicatena fissicatena C2241 |
| 0.001206301 | −0.14769711 | Clostridium sp. AF23-8 C2908 |
| 0.001201907 | 0.087391156 | Klebsiella michiganensis C4315 |
| 0.001201625 | 0.090163662 | Collinsella sp. AF08-23 C1987 |
| 0.001199225 | 0.047629461 | Megasphaera cerevisiae C2604 |
| 0.00119489 | 0.157003749 | Lachnoclostridium sp. An138 C2776 |
| 0.001192374 | 0.346071847 | Eubacterium limosum C2659 |
| 0.001183998 | 0.163715553 | Streptococcus pneumoniae C3327 |
| 0.001173126 | 0.161269394 | Eubacterium callanderi C2127 |
| 0.001161929 | −0.321742198 | Ruminococcus champanellensis C2249 |
| 0.001157051 | −0.04739511 | Catenibacterium mitsuokai DSM 15897 C2204 |
| 0.001154034 | 0.069882758 | Streptococcus sanguinis C3561 |

TABLE 5-continued

A random forest classifier was trained to classify operational species
unit abundances for a sample as corresponding to cancer or control. An
ROC curve was generated on 145 cancer samples and 88 control samples using
leave-one-out cross validation. Following validation, the model was trained
on all the samples and feature importance values are reported.

| Feature Importance (Random Forest) | log 10 of Fold Change (Control vs Cancer) | Organism Name (Operational Species Unit) |
| --- | --- | --- |
| 0.001152159 | −0.229970619 | Firmicutes bacterium AF22-6AC C2933 |
| 0.001149193 | −0.093698754 | Roseburia sp. OM04-15AA C2892 |
| 0.001148872 | −0.136898288 | Holdemania massiliensis AP2 C2339 |
| 0.00114848 | −0.143597792 | Olsenella sp. AF21-51 C1985 |
| 0.001145605 | 0.041391195 | Bacteroides ovatus C0131 |
| 0.001144548 | 0.310613625 | Eggerthella sp. YY7918 C1941 |
| 0.001142328 | 0.294636274 | Lachnospiraceae bacterium 2_1_46FAA C2247 |
| 0.001139964 | −0.109907027 | Anaerostipes sp. 992a C2729 |
| 0.001136248 | 0.071917201 | Eggerthella lenta C1927 |
| 0.001127673 | −0.035851608 | Streptococcus sp. ChDC B345 C6537 |
| 0.00112536 | 0.235371201 | Ruminococcus sp. AF18-22 C2662 |
| 0.001124558 | 0.22935135 | Blautia sp. An81 C2788 |
| 0.001120621 | −0.502954606 | Ruminococcus sp. KGMB03662 C2557 |
| 0.001117895 | −0.016216198 | Bacteroides sp. OF04-15BH C1226 |
| 0.001117113 | −0.317608637 | Eubacterium sp. AF22-8LB C2898 |
| 0.001116776 | −0.13214399 | Candidatus Borkfalkia ceftriaxoniphila C3005 |
| 0.001115975 | −0.245958899 | Gordonibacter urolithinfaciens C1971 |
| 0.001114616 | −0.335185925 | Bifidobacterium adolescentis C0001 |
| 0.001114192 | 0.083292114 | Eubacterium pyruvativorans C3098 |
| 0.001113405 | −0.113942218 | Massilimaliae timonensis C3250 |
| 0.001111358 | −0.321124776 | Clostridium disporicum C2479 |
| 0.001108373 | 0.416260181 | Bacteroides zoogleoformans C1004 |
| 0.001099862 | 0.103183512 | Bacteroides sartorii C0346 |
| 0.001096801 | 0.127258668 | Finegoldia magna C2170 |
| 0.001096565 | 0.053902093 | Burkholderiales bacterium YL45 C5482 |
| 0.001090767 | −0.25222383 | Bacteroides mediterraneensis C1791 |
| 0.001089194 | −0.192935162 | Clostridium sp. AF46-9NS C2891 |
| 0.001085672 | −0.022510129 | Bacteroides faecis C0221 |
| 0.001084937 | 0.183744827 | Enteroscipio rubneri C1978 |
| 0.001080288 | 0.217242623 | Streptococcus agalactiae C3342 |
| 0.001077696 | 0.014956563 | Oscillibacter ruminantium GH1 C2321 |
| 0.001071923 | 0.226961129 | Bacteroides coprophilus C0141 |
| 0.001070282 | −0.085202725 | Prevotella sp. 885 C0883 |
| 0.001068757 | 0.41779361 | Blautia hominis C2806 |
| 0.00106737 | 0.227560508 | Fusobacterium nucleatum C2023 |
| 0.001063571 | −0.005996163 | Alistipes sp. Marseille-P2431 C1656 |
| 0.001046414 | −0.131247999 | Christensenella sp. Marseille-P3954 C3290 |
| 0.001046021 | 0.073482048 | Blautia hydrogenotrophica C2163 |
| 0.001034582 | 0.033741303 | Escherichia coli C6189 |
| 0.001034232 | 0.000419447 | Bacteroides plebeius C0183 |
| 0.001033161 | 0.037947008 | Eubacterium limosum C2585 |
| 0.001031559 | 0.231894983 | Bacteroides sp. NM69_E16B C1512 |
| 0.00102259 | −0.332512425 | Olsenella sp. Marseille-P4518 C1983 |
| 0.001019694 | −0.164199636 | Lachnoanaerobaculum saburreum C2233 |
| 0.001017125 | −0.206044424 | Clostridium sp. AF20-17LB C2921 |
| 0.001013385 | −0.159145062 | Bifidobacterium angulatum C0006 |
| 0.001011242 | −0.124685694 | Coprococcus sp. OM04-5BH C2951 |
| 0.001010502 | 0.199924075 | Bacteroides caecimuris C0768 |
| 0.001005476 | −0.054514013 | Paramuribaculum intestinale C1027 |
| 0.001002001 | 0.065282268 | Bacteroides eggerthii C0137 |
| 0.001001469 | −0.069431173 | Pseudoflavonifractor sp. An44 C2769 |
| 0.00100062 | 0.224179803 | Bacteroides togonis C1815 |
| 0.000998879 | −0.079349954 | Enterorhabdus caecimuris C1946 |
| 0.000996811 | −0.035659589 | Butyricicoccus pullicaecorum C2367 |
| 0.000996394 | 0.119454752 | Lachnospiraceae bacterium KGMB03038 C3054 |
| 0.000988689 | −0.095646493 | Clostridium sp. SY8519 C2300 |
| 0.00098773 | −0.244190108 | Bifidobacterium ruminantium C0033 |
| 0.000983787 | 0.167974308 | Veillonella dispar C2172 |
| 0.000981089 | 0.009434997 | Faecalibacterium sp. An122 C2768 |
| 0.000971714 | −0.078320362 | Paraeggerthella hongkongensis C1991 |
| 0.000970657 | −0.061838315 | Bacteroides faecichinchillae C0462 |
| 0.000970589 | −0.100958093 | Veillonella seminalis C2333 |
| 0.000966201 | −0.203389419 | Anaerofustis stercorihominis C3043 |
| 0.000965329 | −0.127606155 | Gabonia massiliensis C0573 |
| 0.000958921 | 0.097531327 | Lachnospiraceae bacterium C7401 |
| 0.000955835 | 0.220644706 | Clostridia bacterium UC5.1-1D10 C2630 |
| 0.000946293 | −0.119032203 | Parabacteroides acidifaciens C1178 |
| 0.000939111 | −0.491867958 | Collinsella sp. TM05-38 C1984 |
| 0.000937568 | 0.238492033 | Veillonella parvula C2108 |

TABLE 5-continued

A random forest classifier was trained to classify operational species
unit abundances for a sample as corresponding to cancer or control. An
ROC curve was generated on 145 cancer samples and 88 control samples using
leave-one-out cross validation. Following validation, the model was trained
on all the samples and feature importance values are reported.

| Feature Importance (Random Forest) | log 10 of Fold Change (Control vs Cancer) | Organism Name (Operational Species Unit) |
|---|---|---|
| 0.000932801 | 0.088210302 | *Gemmiger* sp. An50 C2791 |
| 0.000932461 | 0.080276705 | *Bacteroides pyogenes* C0391 |
| 0.000932048 | 0.20638792 | *Lachnoclostridium* sp. An76 C2789 |
| 0.000931273 | −0.417870861 | *Faecalibacterium prausnitzii* C2650 |
| 0.00093091 | 0.034378724 | *Drancourtella* sp. An57 C2780 |
| 0.000930578 | −0.057174001 | *Desulfovibrio* sp. G11 C3781 |
| 0.000927044 | 0.214918452 | *Faecalicatena orotica* C2855 |
| 0.000926301 | 0.080750766 | *[Ruminococcus] torques* C2130 |
| 0.000924352 | −0.052296196 | *Coprobacillus cateniformis* C2235 |
| 0.000924235 | −0.30548312 | *Prevotella stercorea* C0227 |
| 0.000922776 | 0.214718723 | *Enterobacter asburiae* C4744 |
| 0.000921102 | 0.275685331 | *Streptococcus lutetiensis* C4617 |
| 0.000908652 | −0.209498347 | *Bacteroides massiliensis* C0310 |
| 0.000902209 | 0.024387818 | *Anaerofustis stercorihominis* C2147 |
| 0.000897276 | −0.417096051 | *Senegalimassilia anaerobia* C1940 |
| 0.000895988 | 0.122269666 | *Clostridium cadaveris* C2409 |
| 0.000894405 | −0.129710456 | *Eubacterium coprostanoligenes* C3232 |
| 0.000892552 | 0.092455818 | *Streptococcus infantarius* subsp. *infantarius* CJ18 C4334 |
| 0.000889081 | −0.157473973 | Clostridiales bacterium Marseille-P2846 C3254 |
| 0.000885777 | 0.084144866 | *Lachnoclostridium* sp. An169 C2774 |
| 0.000885709 | −0.011837149 | *Bacteroides fragilis* C0096 |
| 0.000885092 | −0.096838499 | *Intestinibacter bartlettii* C2141 |
| 0.000884226 | 0.102943242 | *Absiella dolichum* C2133 |
| 0.000879993 | 0.276721768 | *Bacteroides intestinalis* C1222 |
| 0.000874022 | −0.176033978 | Lachnospiraceae bacterium OF09-6 C2885 |
| 0.000871852 | 0.11799681 | *Lachnoclostridium edouardi* C3267 |
| 0.000867157 | 0.03000888 | *Bacteroides timonensis* C0434 |
| 0.000859738 | −0.191448288 | *[Clostridium] spiroforme* C2146 |
| 0.000854106 | 0.032964866 | *Streptococcus* sp. I-G2 C4650 |
| 0.000852642 | 0.193752289 | *[Clostridium] clostridioforme* C2275 |
| 0.000850375 | −0.107533876 | *Alistipes ihumii* API 1 C0292 |
| 0.00084566 | 0.029668283 | *[Clostridium] innocuum* C2230 |
| 0.000841331 | −0.182746209 | *Leuconostoc lactis* C5492 |
| 0.000837107 | −0.148687377 | *Lactococcus lactis* C3409 |
| 0.000833791 | 0.075233896 | *Bifidobacterium gallinarum* C0040 |
| 0.000832892 | −0.052348168 | *Lachnospira pectinoschiza* C2649 |
| 0.000819471 | 0.044124824 | *Clostridium tertium* C2166 |
| 0.000818078 | 0.013262705 | *Bacteroides gallinarum* C0320 |
| 0.000816004 | −0.007624252 | *Gardnerella vaginalis* C0077 |
| 0.000814064 | 0.124276378 | *Candidatus Stoquefichus* sp. KLE1796 C2685 |
| 0.000810143 | −0.077567242 | *Megamonas funiformis* C2294 |
| 0.000806911 | −0.216211462 | *Eubacterium* sp. TM05-53 C2895 |
| 0.000805937 | −0.10501558 | *Roseburia hominis* C2266 |
| 0.00080548 | 0.160289033 | *Actinomyces naeslundii* C5308 |
| 0.00080031 | −0.040410654 | *Clostridium* sp. M62/1 C2168 |
| 0.000794225 | 0.016679858 | Lachnospiraceae bacterium OF09-33XD C2950 |
| 0.000784244 | 0.025757522 | *Mediterranea massiliensis* C1792 |
| 0.000783028 | −0.473565196 | *Collinsella bouchesdurhonensis* C1956 |
| 0.000780365 | 0.18073776 | *Parabacteroides distasonis* C1282 |
| 0.000776777 | −0.066719417 | *Alistipes* sp. cv1 C1225 |
| 0.000775056 | 0.215608385 | *Lactobacillus paragasseri* C5843 |
| 0.000774821 | 0.106290282 | *Enterococcus faecalis* C3356 |
| 0.000770822 | 0.044316403 | *Emergencia timonensis* C2919 |
| 0.000770705 | 0.007621492 | *Muribaculum* sp. An287 C0841 |
| 0.000765772 | −0.039039051 | *Candidatus Stoquefichus* sp. SB1 C2613 |
| 0.000764151 | 0.149737605 | *Haemophilus parainfluenzae* C6724 |
| 0.000758758 | −0.139580633 | *Acidaminococcus fermentans* C2110 |
| 0.000758604 | 0.014886565 | *Streptococcus* sp. A12 C5358 |
| 0.000757928 | 0.103430739 | *Ruminococcus* sp. JE7A12 C3041 |
| 0.000757477 | 0.124922464 | *Anaeroglobus geminatus* F0357 C2283 |
| 0.000752717 | 0.201105928 | *Bacteroides* sp. An322 C0849 |
| 0.000750886 | 0.092991853 | *Klebsiella aerogenes* C4223 |
| 0.00074905 | −0.151453151 | Firmicutes bacterium AM43-11BH C2910 |
| 0.00074725 | 0.319641701 | *Citrobacter freundii* C4862 |
| 0.000746863 | 0.019294667 | Lachnospiraceae bacterium C2825 |
| 0.000744408 | 0.024367545 | *Collinsella stercoris* DSM 13279 C1930 |
| 0.000742398 | −0.069413745 | *Alistipes inops* C0554 |
| 0.000740749 | 0.074724867 | *Staphylococcus aureus* C3394 |
| 0.000737647 | 0.166740913 | *Pseudoflavonifractor* sp. AF19-9AC C2939 |

TABLE 5-continued

A random forest classifier was trained to classify operational species
unit abundances for a sample as corresponding to cancer or control. An
ROC curve was generated on 145 cancer samples and 88 control samples using
leave-one-out cross validation. Following validation, the model was trained
on all the samples and feature importance values are reported.

| Feature Importance (Random Forest) | log 10 of Fold Change (Control vs Cancer) | Organism Name (Operational Species Unit) |
|---|---|---|
| 0.000734243 | 0.047494987 | *Bifidobacterium breve* C0007 |
| 0.000733278 | −0.106066732 | *Asaccharobacter celatus* C1952 |
| 0.000733193 | 0.200658318 | *Bacteroides thetaiotaomicron* C0098 |
| 0.000732128 | 0.006225001 | *Streptococcus mitis* C5142 |
| 0.000731863 | −0.123724955 | *Lactobacillus acidophilus* C3484 |
| 0.000727884 | −0.197342794 | *Subdoligranulum variabile* DSM 15176 C2162 |
| 0.000725883 | −0.32980633 | *Turicibacter sanguinis* C2647 |
| 0.000724945 | 0.024395901 | *Lactobacillus curvatus* C5454 |
| 0.000721941 | −0.116696596 | *Roseburia inulinivorans* C2207 |
| 0.000719454 | 0.14576632 | *Agathobaculum desmolans* ATCC 43058 C2531 |
| 0.000719137 | 0.061521208 | *Eisenbergiella* sp. OF01-20 C2932 |
| 0.000717609 | −0.008006904 | *Lawsonibacter asaccharolyticus* C2612 |
| 0.000716353 | −0.27637531 | *Coprococcus catus* C2881 |
| 0.000714658 | −0.235792289 | *Faecalibacterium prausnitzii* C2864 |
| 0.000713496 | 0.044440911 | *Bacteroides fluxus* YIT 12057 C0196 |
| 0.000709063 | 0.057843542 | Ruminococcaceae bacterium Marseille-P2935 C3117 |
| 0.000708861 | 0.132034289 | *Lactobacillus casei* C4934 |
| 0.000706391 | −0.223572419 | *Faecalibacterium prausnitzii* C2191 |
| 0.00070492 | 0.178244024 | *Escherichia coli* C3313 |
| 0.000702873 | −0.053059381 | *Prevotella lascolaii* C1655 |
| 0.000699434 | −0.068127523 | *Christensenella timonensis* C3068 |
| 0.000695606 | −0.191454148 | *Streptococcus thermophilus* C3480 |
| 0.00068995 | −0.007031037 | *Dielma fastidiosa* C2331 |
| 0.000689289 | 0.054494897 | *Faecalitalea* sp. Marseille-P3755 C3257 |
| 0.000689111 | −0.231345103 | *Dialister succinatiphilus* YIT 11850 C2287 |
| 0.000687764 | −0.101689367 | *Chitinophaga* sp. K20C18050901 C1205 |
| 0.000683105 | −0.18109626 | *Bifidobacterium longum* C0000 |
| 0.000681336 | 0.121849135 | *Streptococcus australis* C7313 |
| 0.000680574 | −0.255797065 | *Clostridium cuniculi* C3022 |
| 0.000675816 | −0.101093017 | Clostridiales bacterium KA00274 C2670 |
| 0.0006733 | 0.066007328 | *Erysipelatoclostridium* sp. An173 C2772 |
| 0.000667452 | 0.055143325 | *Pseudoflavonifractor* sp. Marseille-P3106 C3237 |
| 0.000666343 | 0.27979269 | *Lachnoclostridium* sp. An131 C2777 |
| 0.000663042 | −0.127290782 | *Ruminococcus* sp. AF41-9 C2929 |
| 0.000659973 | 0.094285428 | *Shuttleworthia* sp. MSX8B C2176 |
| 0.00065507 | 0.110634228 | *Methanobrevibacter smithii* C3636 |
| 0.000649624 | −0.078446486 | *Butyricimonas faecihominis* C1324 |
| 0.000647276 | 0.05887023 | *Massilimicrobiota timonensis* C2778 |
| 0.000646901 | 0.137638451 | *Bacteroides barnesiae* C0323 |
| 0.0006433 | −0.134246508 | Victivallales bacterium CCUG 44730 C6246 |
| 0.000640184 | 0.122380223 | *Haemophilus parainfluenzae* C6455 |
| 0.000636883 | 0.064289399 | *Akkermansia muciniphila* C1920 |
| 0.000632492 | −0.308227618 | *Catabacter hongkongensis* C2600 |
| 0.000630493 | −0.363573867 | *Bacteroides bouchesdurhonensis* C1842 |
| 0.000622319 | 0.014535125 | *Prevotella* sp. P3-122 C0877 |
| 0.000619871 | 0.0165477 | *Roseburia* sp. 831b C2726 |
| 0.000615916 | −0.163514198 | *Sutterella megalosphaeroides* C6522 |
| 0.000614283 | −0.082835345 | Erysipelotrichaceae bacterium 3_1_53 C2188 |
| 0.000614281 | 0.013021903 | *Holdemania filiformis* C2164 |
| 0.000613954 | 0.059841271 | *Alistipes* sp. Marseille-P5997 C0839 |
| 0.00060878 | 0.148711311 | *Blautia coccoides* C2701 |
| 0.000597168 | −0.02417881 | *Clostridium* sp. BSD2780061688st1 E8 C3045 |
| 0.000594817 | −0.17197938 | *Mogibacterium diversum* C2838 |
| 0.000591669 | 0.038151561 | *Fusobacterium ulcerans* C2030 |
| 0.000588198 | 0.24254803 | *Enterobacter cloacae* C3869 |
| 0.000587106 | 0.027112536 | *Monoglobus pectinilyticus* C2823 |
| 0.000581387 | 0.090800994 | *Prevotella oris* C0118 |
| 0.000576756 | 0.144277974 | *Veillonella tobetsuensis* C2607 |
| 0.000574411 | −0.155129298 | *Kandleria vitulina* C2503 |
| 0.00057406 | 0.021398815 | *Negativibacillus massiliensis* C3220 |
| 0.0005648 | −0.270611264 | *[Eubacterium] eligens* C2123 |
| 0.000561479 | −0.00147982 | *Fournierella massiliensis* C2661 |
| 0.000557105 | 0.017814008 | *Agathobacter ruminis* C2528 |
| 0.000554427 | 0.126947262 | *Acetitomaculum ruminis* DSM 5522 C3147 |
| 0.000551557 | −0.119643009 | *Parolsenella catena* C1992 |
| 0.000546323 | 0.093101738 | *Alistipes* sp. An31A C0840 |
| 0.000544823 | 0.100984449 | *Slackia piriformis* YIT12062 C1942 |
| 0.000542329 | 0.084136379 | *Pseudoflavonifractor* sp. An85 C2787 |
| 0.000541822 | 0.150927143 | *Enterococcus faecium* C4060 |

TABLE 5-continued

A random forest classifier was trained to classify operational species
unit abundances for a sample as corresponding to cancer or control. An
ROC curve was generated on 145 cancer samples and 88 control samples using
leave-one-out cross validation. Following validation, the model was trained
on all the samples and feature importance values are reported.

| Feature Importance (Random Forest) | log 10 of Fold Change (Control vs Cancer) | Organism Name (Operational Species Unit) |
|---|---|---|
| 0.000536091 | −0.257161011 | *Faecalitalea cylindroides* C2250 |
| 0.000528743 | −0.065393049 | *Lactobacillus sanfranciscensis* TMW 1.1304 C4264 |
| 0.000525582 | −0.129615434 | *Absiella* sp. AM22-9 C2879 |
| 0.000524183 | 0.15556154 | *Streptococcus mitis* C5322 |
| 0.00052379 | −0.131464448 | *Streptococcus mitis* C3901 |
| 0.000521696 | −0.005526656 | *Butyricimonas virosa* C0441 |
| 0.000521234 | 0.161136825 | *Agathobaculum* sp. Marseille-P7918 C3297 |
| 0.000520468 | 0.079408986 | *Bacteroides intestinalis* C0161 |
| 0.000517736 | −0.007357649 | *Senegalimassilia* sp. KGMB04484 C1994 |
| 0.000515789 | 0.116997696 | *Anaeromassilibacillus* sp. An172 C2773 |
| 0.000513282 | −0.22188977 | *Anaeromassilibacillus* sp. Marseille-P4683 C3061 |
| 0.000507316 | −0.160416981 | *Clostridium* sp. Marseille-P3244 C3177 |
| 0.00050396 | 0.078131194 | *Rothia mucilaginosa* C3456 |
| 0.000501417 | 0.027192943 | *Candidatus Methanomassiliicoccus intestinalis* Issoire-Mx1 C4599 |
| 0.000499738 | 0.0174744 | *Anaerostipes* sp. 494a C2731 |
| 0.000498341 | −0.029178099 | *Paraeggerthella hongkongensis* C1982 |
| 0.000496569 | −0.032045271 | *Lactococcus garvieae* C6016 |
| 0.000494032 | 0.057726242 | *Eubacterium* sp. AF19-12LB C2907 |
| 0.000491168 | 0.033329345 | Lachnospiraceae bacterium oral taxon 096 C2846 |
| 0.000491138 | −0.14106364 | *Prevotella intermedia* C0255 |
| 0.000483914 | 0.076399152 | *Bacteroides* sp. OM05-12 C1216 |
| 0.000478931 | −0.12999452 | *Propionibacterium freudenreichii* C3941 |
| 0.000478583 | −0.216633597 | *Oxalobacter formigenes* C5820 |
| 0.000473254 | 0.13675923 | *Eubacterium* sp. ER2 C2579 |
| 0.000472977 | −0.15732306 | *Alistipes indistinctus* C0222 |
| 0.00047013 | −0.01796799 | *Traorella massiliensis* C3119 |
| 0.000463894 | −0.134877322 | *Weissella cibaria* C5172 |
| 0.000461977 | 0.043780038 | *Prevotella pleuritidis* C0414 |
| 0.000461965 | 0.379126295 | *Citrobacter* sp. FDAARGOS__156 C5320 |
| 0.000458829 | −0.103085248 | [*Collinsella*] *massiliensis* C1944 |
| 0.000455848 | −0.216482839 | *Alloscardovia omnicolens* C0021 |
| 0.000454098 | −0.101700886 | *Bacteroides ilei* C1793 |
| 0.000452132 | 0.27056853 | *Dialister* sp. Marseille-P5638 C3282 |
| 0.000447852 | 0.21438821 | *Christensenella massiliensis* C3223 |
| 0.000446473 | 0.089598965 | *Bacteroides cutis* C1215 |
| 0.000442533 | −0.125406142 | *Prevotella* sp. P4-51 C0876 |
| 0.0004413 | 0.013913335 | *Bacteroides coprosuis* DSM 18011 C0203 |
| 0.000440392 | 0.228587525 | *Lachnoclostridium phocaeense* C3180 |
| 0.000438656 | 0.057515059 | *Ruminococcus bromii* C2818 |
| 0.000435684 | 0.170474597 | *Prevotella copri* C0142 |
| 0.000434472 | 0.278015777 | *Enterobacter kohei* C4431 |
| 0.000430769 | 0.15735214 | *Clostridioides difficile* C2586 |
| 0.000429829 | 0.275828056 | *Collinsella phocaeensis* C2002 |
| 0.000427367 | 0.069690121 | Muribaculaceae bacterium Isolate-102 (HZI) C1306 |
| 0.000425447 | 0.254830162 | [*Clostridium*] *scindens* C2446 |
| 0.000425124 | 0.07985737 | *Enterobacter roggenkampii* C4889 |
| 0.000424989 | 0.039030901 | *Erysipelatoclostridium* sp. AM42-17 C2927 |
| 0.000422993 | −0.009708183 | *Weissella confusa* C6837 |
| 0.000421896 | −0.083440639 | *Bacteroides fragilis* C0140 |
| 0.000421212 | 0.151608309 | *Anaerotruncus massiliensis* C2969 |
| 0.00041345 | −0.066234762 | *Parabacteroides goldsteinii* C0282 |
| 0.000409746 | −0.008970984 | *Anaerotruncus* sp. AF02-27 C2916 |
| 0.000408594 | −0.076490222 | *Akkermansia* sp. KLE1605 C1918 |
| 0.000408035 | −0.013734886 | *Butyricimonas* sp. Marseille-P3923 C1885 |
| 0.000404935 | −0.12049091 | *Prevotella buccalis* C0169 |
| 0.00040246 | 0.105160049 | *Merdimonas faecis* C2715 |
| 0.000402431 | −0.118683458 | *Streptococcus suis* C3679 |
| 0.000399456 | 0.167898284 | *Klebsiella oxytoca* C5296 |
| 0.00039537 | 0.140861068 | *Colibacter massiliensis* C3075 |
| 0.000394389 | −0.099002939 | *Leclercia* sp. W6 C6193 |
| 0.000389717 | 0.047195465 | *Bifidobacterium pseudolongum* C0023 |
| 0.000385746 | 0.137224213 | Clostridiaceae bacterium OM02-2AC C2883 |
| 0.000376658 | −0.006154069 | *Odoribacter splanchnicus* C0185 |
| 0.000376547 | 0.132471129 | *Lactobacillus crispatus* C3942 |
| 0.000372155 | 0.077170538 | *Clostridium liquoris* C2835 |
| 0.000371344 | −0.013289801 | *Prevotella shahii* C0456 |
| 0.000369066 | 0.058668971 | *Prevotella buccae* C0148 |
| 0.000368916 | −0.151810317 | *Carnobacterium divergens* C5502 |

TABLE 5-continued

A random forest classifier was trained to classify operational species
unit abundances for a sample as corresponding to cancer or control. An
ROC curve was generated on 145 cancer samples and 88 control samples using
leave-one-out cross validation. Following validation, the model was trained
on all the samples and feature importance values are reported.

| Feature Importance (Random Forest) | log 10 of Fold Change (Control vs Cancer) | Organism Name (Operational Species Unit) |
| --- | --- | --- |
| 0.000365348 | 0.037280739 | *Intestinimonas massiliensis* C3302 |
| 0.000362723 | 0.096694087 | *Megasphaera* sp. MJR8396C C2669 |
| 0.000362664 | −0.209757142 | *Lactococcus lactis* C3326 |
| 0.000359275 | 0.013743499 | *Ruminococcus gauvreauii* DSM 19829 C2421 |
| 0.000354446 | −0.067786957 | *Megasphaera* sp. NM10 C2382 |
| 0.000354236 | −0.101587608 | *Lactobacillus sakei* C3886 |
| 0.000349708 | 0.052923252 | *Fusobacterium varium* C2031 |
| 0.000349377 | 0.12801912 | *Raoultella ornithinolytica* C4582 |
| 0.000342204 | −0.224210946 | *Clostridium* sp. CL-2 C2570 |
| 0.000339415 | −0.018984193 | *Schaalia odontolytica* C6913 |
| 0.000336634 | 0.085134208 | [*Clostridium*] *aminophilum* C2554 |
| 0.000318155 | 0.079087407 | *Escherichia* sp. E4742 C6917 |
| 0.000317742 | −0.111845972 | *Porphyromonas* sp. COT-290 OH860 C0549 |
| 0.000316438 | −0.129465239 | *Criibacterium bergeronii* C2703 |
| 0.00031524 | −0.151761323 | *Gardnerella vaginalis* C0008 |
| 0.000313466 | 0.093860399 | *Citrobacter freundii* complex sp. CFNIH3 C5883 |
| 0.00031154 | −0.030174898 | *Veillonella* sp. S13053-19 C2226 |
| 0.000305314 | −0.019154943 | *Enterococcus casseliflavus* C4021 |
| 0.000301412 | −0.028685455 | *Clostridium paraputrificum* C2404 |
| 0.000301347 | 0.135067509 | *Citrobacter amalonaticus* C5315 |
| 0.000299201 | 0.056396549 | *Peptoniphilus harei* C2229 |
| 0.000295876 | 0.105606587 | *Lactobacillus reuteri* C3427 |
| 0.00029558 | −0.087470002 | *Prevotella bivia* C0170 |
| 0.00029533 | 0.2944697 | *Massilimicrobiota* sp. An134 C2756 |
| 0.000292461 | −0.16360222 | *Clostridium celatum* DSM 1785 C2336 |
| 0.000290231 | −0.107393237 | *Eubacterium saphenum* ATCC 49989 C2183 |
| 0.000289466 | 0.098825501 | *Caproiciproducens galactitolivorans* C3034 |
| 0.000283388 | 0.088913554 | *Peptococcus niger* C3096 |
| 0.000281338 | −0.199624188 | *Bacteroides* sp. Marseille-P3684 C1903 |
| 0.000280597 | −0.35259961 | [*Eubacterium*] *rectale* C2102 |
| 0.000278229 | −0.123327354 | *Hungatella hathewayi* C2277 |
| 0.000275274 | 0.032280996 | *Raoultibacter timonensis* C2015 |
| 0.000274761 | 0.026049476 | *Bifidobacterium minimum* C0024 |
| 0.000274208 | −0.250305123 | *Slackia isoflavoniconvertens* C1981 |
| 0.000272806 | −0.148295608 | *Prevotella* sp. 109 C0642 |
| 0.000271138 | 0.085385438 | *Bacteroides ndongoniae* C1721 |
| 0.000270351 | 0.096334331 | *Sanguibacteroides justesenii* C0594 |
| 0.000268105 | −0.092100556 | *Enterococcus* sp. M190262 C4628 |
| 0.000264389 | 0.028275689 | *Candidatus Soleaferrea massiliensis* AP7 C2589 |
| 0.000258394 | 0.095952069 | *Fusobacterium mortiferum* C2024 |
| 0.000257776 | −0.123638868 | *Mitsuokella jalaludinii* C2546 |
| 0.000256938 | −0.044689114 | *Haemophilus pittmaniae* C7263 |
| 0.000256376 | 0.057471563 | *Citrobacter koseri* C3675 |
| 0.000255931 | 0.098498867 | *Staphylococcus epidermidis* C3349 |
| 0.000255753 | −0.157103426 | *Lachnotalea* sp. AF33-28 C2930 |
| 0.000249354 | 0.103829306 | *Streptococcus troglodytae* C6006 |
| 0.000247989 | −0.04348123 | *Eubacterium nodatum* ATCC 33099 C2463 |
| 0.000237849 | 0.136436955 | *Bacteroides acidifaciens* C0454 |
| 0.000235895 | 0.025076982 | *Cloacibacillus porcorum* C5498 |
| 0.000234449 | 0.207586523 | *Desulfovibrio fairfieldensis* C5303 |
| 0.000232439 | 0.06389105 | *Citrobacter amalonaticus* Y19 C5026 |
| 0.000231523 | 0.21351164 | *Frisingicoccus caecimuris* C3012 |
| 0.000229189 | 0.116831596 | *Streptococcus equinus* C4630 |
| 0.000224376 | −0.071274749 | *Enterobacter ludwigii* C4314 |
| 0.000223221 | −0.001425117 | *Lachnospira multipara* C2406 |
| 0.000219577 | −0.252448758 | *Comamonas kerstersii* C5 760 |
| 0.000215028 | −0.201289125 | *Odoribacter* sp. AF15-53 C1228 |
| 0.000212884 | 0.129978944 | *Clostridium ventriculi* C2645 |
| 0.000212879 | 0.012267554 | *Prevotella denticola* C0190 |
| 0.00021254 | −0.090029408 | *Acidaminococcus timonensis*C3121 |
| 0.000209014 | 0.081821172 | *Pediococcus acidilactici* C5564 |
| 0.00020599 | −0.091958501 | *Parabacteroides gordonii* C0394 |
| 0.000204627 | −0.03219179 | *Salmonella bongori* C4344 |
| 0.000201044 | 0.046058989 | *Corynebacterium argentoratense* DSM 44202 C4728 |
| 0.000195048 | −0.148177716 | *Ruminococcus* sp. Marseille-P6503 C3293 |
| 0.000193863 | 0.115675916 | *Veillonella atypica* C2224 |
| 0.000191688 | 0.075560921 | *Clostridium neonatale* C2656 |
| 0.000191566 | 0.059627079 | *Hafnia paralvei* C5321 |
| 0.000187799 | 0.004958554 | *Ruminococcus bromii* C3091 |

TABLE 5-continued

A random forest classifier was trained to classify operational species
unit abundances for a sample as corresponding to cancer or control. An
ROC curve was generated on 145 cancer samples and 88 control samples using
leave-one-out cross validation. Following validation, the model was trained
on all the samples and feature importance values are reported.

| Feature Importance (Random Forest) | log 10 of Fold Change (Control vs Cancer) | Organism Name (Operational Species Unit) |
|---|---|---|
| 0.000187592 | 0.108114105 | *Megasphaera micronuciformis* F0359 C2190 |
| 0.000185989 | 0.049809679 | *Hafnia alvei* C4732 |
| 0.000184299 | 0.072305952 | *Clostridium* sp. Marseille-P8228 C3298 |
| 0.000182455 | 0.081144244 | *Salmonella enterica* C3691 |
| 0.000182401 | 0.040354086 | *Prevotella maculosa* C0236 |
| 0.000180958 | 0.045550681 | *Tetragenococcus halophilus* C4414 |
| 0.000180446 | 0.155453018 | *[Clostridium] cocleatum* C2817 |
| 0.000175141 | 0.003197966 | *Ruminococcus flavefaciens* C3174 |
| 0.000175125 | 0.088990805 | *Clostridium* sp. CL-6 C2568 |
| 0.000173291 | −0.017099749 | *Prevotella* sp. P5-125 C0597 |
| 0.000169963 | −0.057233209 | *Pseudomonas fragi* C5503 |
| 0.00016916 | −0.248823705 | *Leuconostoc gelidum* JB7 C4451 |
| 0.00016589 | 0.065183802 | *Cronobacter sakazakii* C3665 |
| 0.00016331 | −0.208923621 | *Megasphaera elsdenii* C2304 |
| 0.000161384 | 0.067558754 | *Klebsiella oxytoca* C5056 |
| 0.000161379 | 0.13837813 | *Lactobacillus helveticus* C3606 |
| 0.000159676 | −0.003463017 | *Pediococcus pentosaceus* C35 72 |
| 0.000157298 | 0.144136167 | *Enterobacter hormaechei* C4773 |
| 0.000155828 | −0.260724092 | *Roseburia* sp. AM59-24XD C2936 |
| 0.000151336 | −0.292938975 | *Lactobacillus delbrueckii* C3568 |
| 0.000141557 | 0.076327611 | *Prevotella salivae* C0180 |
| 0.000131281 | 0.143665959 | *Lactobacillus amylovorus* C4089 |
| 0.000130941 | −0.047422488 | *Lactobacillus ruminis* ATCC 27782 C4263 |
| 0.000130595 | −0.04481037 | *Paraclostridium bifermentans* C2432 |
| 0.000129911 | 0.167682779 | *Escherichia albertii* C4681 |
| 0.000127495 | 0.04633969 | *Enterococcus durans* C5114 |
| 0.000127484 | 0.072529092 | *Cellulosilyticum* sp. WCF-2 C2221 |
| 0.000123473 | 0.173686087 | Clostridiales bacterium S5-A14a C2574 |
| 0.000122727 | −0.074297589 | *Blautia wexlerae* C2171 |
| 0.000121299 | −0.053122344 | *Methanosphaera stadtmanae* DSM 3091 C3505 |
| 0.000120188 | 0.119050783 | *Clostridium* sp. MSTE9 C2303 |
| 0.000120039 | −0.052843577 | *Clostridium disporicum* C2646 |
| 0.000116659 | 0.080030593 | *Lactobacillus johnsonii* C3366 |
| 0.000113997 | 0.104093107 | *Serratia marcescens* C4687 |
| 0.000113245 | −0.00308721 | *Prevotella amnii* C0171 |
| 0.000107199 | −0.022568473 | *Cronobacter condimenti* 1330 C5129 |
| 0.000104701 | 0.000252647 | Ruminococcaceae bacterium CPB6 C2750 |
| 0.000104084 | 0.066800683 | *Veillonella ratti* C2991 |
| 0.000102394 | 0.152599321 | *Bacteroides paurosaccharolyticus* JCM15092 C0457 |
| 9.37347E−05 | 0.174241239 | *Lactobacillus gasseri* C3569 |
| 8.56015E−05 | 0.059945469 | *[Clostridium] hylemonae* C2157 |
| 7.75294E−05 | 0.1191171 | *Citrobacter amalonaticus* C5318 |
| 7.55257E−05 | 0.068345197 | *Bacteroides* sp. KCTC 15687 C1337 |
| 6.75319E−05 | 0.006391049 | *Lactococcus garvieae* C4388 |
| 6.59076E−05 | 0.120223702 | *Faecalicoccus pleomorphus* C2383 |
| 6.45031E−05 | 0.097753343 | *Lactobacillus animalis* C6895 |
| 5.21062E−05 | 0.149698537 | *Anaerostipes rhamnosivorans* C3039 |
| 4.42633E−05 | −0.007497948 | *Enterobacter bugandensis* C5325 |
| 4.37847E−05 | 0.032643624 | *Lactobacillus mucosae* LM1 C4338 |
| 4.32409E−05 | 0.065872962 | *Bacteroides propionicifaciens* C0324 |
| 0 | 0.078372213 | *Streptococcus sobrinus* C6344 |
| 0 | −0.064034551 | Ruminococcaceae bacterium D5 C3161 |
| 0 | 0.015908673 | *Ruminococcus albus* C3136 |
| 0 | 0.070235779 | *Selenomonas noxia* C2179 |
| 0 | 0.102015151 | *Citrobacter werkmanii* C4750 |
| 0 | 0.106931981 | *Providencia rettgeri* C6875 |
| 0 | −0.08278651 | *Anaerococcus lactolyticus* C2159 |
| 0 | 0.026978526 | *Ruminococcus* sp. FC2018 C2499 |
| 0 | 0.040473615 | *Robinsoniella peoriensis* C2512 |
| 0 | −0.153859627 | *Megasphaera hexanoica* C2664 |
| 0 | 0.005437415 | *Atlantibacter hermannii* C7332 |
| 0 | −0.050219427 | *Megasphaera* sp. AM44-1BH C2918 |
| 0 | 0.013360056 | *Clostridium* sp. 12(A) C2475 |
| 0 | −0.075062059 | *Eggerthella sinensis* Cl979 |
| 0 | 0.029503909 | *Proteus vulgaris* C6084 |
| 0 | 0.020972769 | *Plautia stali symbiont* C4087 |
| 0 | −0.009219528 | *Bacteroides graminisolvens* C0392 |
| 0 | 0.034902834 | *Providencia rettgeri* C4489 |
| 0 | −0.072959896 | *Candidatus Ishikawaella capsulata* Mpkobe C4922 |

TABLE 5-continued

A random forest classifier was trained to classify operational species
unit abundances for a sample as corresponding to cancer or control. An
ROC curve was generated on 145 cancer samples and 88 control samples using
leave-one-out cross validation. Following validation, the model was trained
on all the samples and feature importance values are reported.

| Feature Importance (Random Forest) | log 10 of Fold Change (Control vs Cancer) | Organism Name (Operational Species Unit) |
|---|---|---|
| 0 | −0.060674729 | secondary endosymbiont of *Ctenarytaina eucalypti* C4438 |
| 0 | 0.000740595 | *Shimwellia blattae* C4368 |
| 0 | 0.042068637 | *Bacteroides reticulotermitis* JCM 10512 C0437 |
| 0 | 0.134402606 | *Proteus mirabilis* C3929 |
| 0 | 0.085291723 | *Peptoclostridium* sp. AF21-18 C2156 |
| 0 | 0.071303376 | Bacteroidales bacterium KA00251 C0708 |
| 0 | 0.044896419 | *Klebsiella* sp. PO552 C5864 |
| 0 | −0.020350527 | *Cronobacter universalis* NCTC 9529 C5126 |
| 0 | 0.042060758 | *Lelliottia jeotgali* C5960 |
| 0 | 0.010010498 | *Pseudomonas balearica* DSM 6083 C4912 |
| 0 | 0.069859304 | *Fusobacterium nucleatum* C2036 |
| 0 | −0.098855648 | *Mitsuokella* sp. AF21-1AC C2899 |

TABLE 6

A logistic regression classifier was trained to classify samples
as corresponding to cancer or control on samples with a mean
relative abundance of at least 0.005% using the GTDB database.
An ROC curve was generated on 322 cancer samples and 92 control
samples using Stratified Group K-Fold Cross Validation (AUC =
0.79). Following validation, the model was trained on all
the samples and feature importance values are reported.

| Feature Importance (Logistic Regression) | Organism Name |
|---|---|
| 0.514417994 | *Collinsella* sp900548935 |
| 0.486287437 | *Clostridium* sp900539375 |
| 0.381613445 | UBA1191 sp900545775 |
| 0.310730798 | *Raoultibacter massiliensis* |
| 0.289945387 | *Christensenella minuta* |
| 0.283774901 | CAG-145 sp900540145 |
| 0.27456207 | *Bacteroides stercoris* |
| 0.26468198 | *Erysipelatoclostridium* sp90054443. |
| 0.263480075 | *Phocaeicola salanitronis* |
| 0.250041885 | *Marvinbryantia* sp900066075 |
| 0.249755758 | *Odoribacter* sp900544025 |
| 0.216103903 | UBA738 sp003522945 |
| 0.207027879 | An200 sp900550095 |
| 0.195934646 | *Mediterraneibacter faecis* |
| 0.185692545 | CAG-170 sp000436735 |
| 0.179847461 | *Megasphaera elsdenii* |
| 0.162281593 | *Methanosphaera stadtmanae* |
| 0.159663737 | UMGS1611 sp900553435 |
| 0.157611925 | CAG-177 sp003538135 |
| 0.157485555 | UBA6398 sp003150315 |
| 0.155329072 | CAG-492 sp000434015 |
| 0.153100473 | *Dorea* sp000433215 |
| 0.151760426 | *Evtepia* sp004556345 |
| 0.14588862 | UMGS1071 sp900542375 |
| 0.145040782 | *Collinsella* sp900554585 |
| 0.136236542 | *Clostridium*_Q sp003024715 |
| 0.131388743 | CAG-460sp900544625 |
| 0.130605804 | *Blautia*_A sp900551715 |
| 0.12874627 | *Niameybacter* sp900549765 |
| 0.127187848 | CAG-45 sp002299665 |
| 0.098447454 | *Mailhella* sp900541395 |
| 0.092072207 | SFFH01 sp900548125 |
| 0.080714744 | *Dorea longicatena* |
| 0.079070946 | *Sutterella wadsworthensis*_A |
| 0.076582096 | *Negativibacillus* sp000435195 |
| 0.073355953 | UMGS1590 sp900552455 |
| 0.061020643 | *Coprococcus*_A sp900548825 |
| 0.059560254 | *Blautia*_A sp900066335 |
| 0.058625801 | *Eubacterium*_I sp900557275 |
| 0.048160806 | Firm-11 sp900540045 |

TABLE 6-continued

A logistic regression classifier was trained to classify samples
as corresponding to cancer or control on samples with a mean
relative abundance of at least 0.005% using the GTDB database.
An ROC curve was generated on 322 cancer samples and 92 control
samples using Stratified Group K-Fold Cross Validation (AUC =
0.79). Following validation, the model was trained on all
the samples and feature importance values are reported.

| Feature Importance (Logistic Regression) | Organism Name |
|---|---|
| 0.0465729 | *Dorea longicatena*_B |
| 0.045683691 | UMGS1491 sp900554775 |
| 0.044846674 | UMGS1241 sp900549955 |
| 0.044173983 | CAG-1427 sp000436075 |
| 0.040847644 | *Alistipes* sp900541585 |
| 0.040245741 | *Gemmiger variabilis* |
| 0.039602886 | CAG-495 sp000432275 |
| 0.036058062 | *Bariatricus comes* |
| 0.035781984 | *Oxalobacter formigenes* |
| 0.03030392 | *Frisingicoccus caecimuris* |
| 0.025478979 | CAG-314 sp000437915 |
| 0.023104086 | QALW01 sp003150515 |
| 0.021151433 | *Collinsella* sp900554325 |
| 0.020407288 | CAG-485 sp900541835 |
| 0.020130762 | CAG-452 sp000434035 |
| 0.017010213 | *Agathobacter* sp900546625 |
| 0.016426446 | UBA5394 sp003150565 |
| 0.005947673 | *Blautia*_A obeum_B |
| 0.004390397 | *Coprobacillus cateniformis* |
| 0.002233086 | *Akkermansia* sp004167605 |
| 0.00152013 | *Anaerostipes hadrus*_A |
| −0.001234426 | *Limosilactobacillus fermentum*_A |
| −0.003827343 | CAG-115 sp003531585 |
| −0.008153089 | *Fusobacterium*_B sp900541465 |
| −0.014246241 | *Prevotella* sp900552515 |
| −0.016286555 | *Collinsella* sp900551665 |
| −0.021479219 | *Anaerotignum lactatifermentans* |
| −0.023122468 | UMGS1781 sp900553695 |
| −0.024041329 | *Odoribacter laneus* |
| −0.034455465 | UBA11471 sp000434215 |
| −0.037849311 | *Prevotellamassilia* sp000437675 |
| −0.039128417 | *Angelakisella* sp900547385 |
| −0.039646845 | *Agathobaculum* sp900291975 |
| −0.041056608 | *Eubacterium*_R sp000434995 |
| −0.04266878 | *Eubacterium*_F sp900539115 |
| −0.044059805 | *Alistipes* sp000434235 |
| −0.050522202 | UMGS1590 sp900553245 |
| −0.051836169 | UMGS1688 sp900554085 |
| −0.057847833 | *Butyricimonas faecalis* |
| −0.066253286 | *Akkermansia muciniphila*_A |

TABLE 6-continued

A logistic regression classifier was trained to classify samples
as corresponding to cancer or control on samples with a mean
relative abundance of at least 0.005% using the GTDB database.
An ROC curve was generated on 322 cancer samples and 92 control
samples using Stratified Group K-Fold Cross Validation (AUC =
0.79). Following validation, the model was trained on all
the samples and feature importance values are reported.

| Feature Importance (Logistic Regression) | Organism Name |
|---|---|
| −0.067189759 | *Coprobacter fastidiosus* |
| −0.067646141 | CAG-83 sp900550585 |
| −0.083533993 | *Prevotella* sp900554045 |
| −0.085318406 | *Intestinimonas butyriciproducens* |
| −0.093860595 | *Eubacterium_F* sp000434115 |
| −0.103834319 | *Eubacterium_R* sp900540305 |
| −0.106144597 | *Desulfovibrio fairfieldensis* |
| −0.113985815 | *Lachnospira* sp900316325 |
| −0.117390396 | *Porphyromonas* sp000768875 |
| −0.122672447 | *Acidaminococcus intestini* |
| −0.126358887 | CAG-303 sp000437755 |
| −0.127237507 | *Bacteroides caccae* |
| −0.136509832 | *Prevotella* sp900548745 |
| −0.136915786 | *Dorea* sp000433535 |
| −0.137055372 | *Ligilactobacillus salivarius* |
| −0.151411951 | *Blautia_A* sp900551465 |
| −0.174551647 | CAG-83 sp000431575 |
| −0.182703866 | *Streptococcus vestibularis* |
| −0.188088114 | CAG-302 sp900543825 |
| −0.191528797 | *Butyricimonas virosa* |
| −0.207519696 | *Dialister* sp900343095 |
| −0.208796646 | *Streptococcus* sp000314795 |
| −0.21979495 | QANA01 sp900554725 |
| −0.220254926 | *Enterococcus_B faecium* |
| −0.249373565 | COE1 sp001916965 |
| −0.249871731 | *Mailhella* sp003150275 |
| −0.251086664 | *Lachnospira eligens* |
| −0.299023203 | *Catenibacterium* sp000437715 |
| −0.303053041 | GCA-900066755 sp900066755 |
| −0.30357643 | CAG-1031 sp000431215 |
| −0.306860922 | UBA1691 sp900544375 |
| −0.318039896 | CAG-495 sp001917125 |
| −0.32832744 | AM07-15 sp003477405 |
| −0.387480395 | *Ruthenibacterium* sp003149955 |
| −0.441806113 | *Parabacteroides johnsonii* |
| −0.513157387 | *Bariatricus massiliensis* |

TABLE 7

A logistic regression classifier was trained to classify samples
as corresponding to cancer (non-responder) or control on samples
with a mean relative abundance of at least 0.005% using the GTDB
database. An ROC curve was generated on 43 non-responder samples
and 92 control samples using Stratified Group K-Fold Cross Validation
(AUC = 0.71). Following validation, the model was trained
on all the samples and feature importance values are reported.

| Feature Importance (Logistic Regression) | Organism Name |
|---|---|
| 0.568597444 | CAG-170 sp000436735 |
| 0.543705645 | *Coprobacillus cateniformis* |
| 0.509426281 | *Mailhella* sp900541395 |
| 0.482820632 | *Blautia_A* sp003474435 |
| 0.471483202 | UMGS1611 sp900553435 |
| 0.244782119 | UMGS911 sp900557415 |
| 0.184527891 | CAG-354 sp900553015 |
| 0.174892874 | *Blautia_A massiliensis* |
| 0.158545809 | *Agathobacter* sp900317585 |
| 0.140717769 | *Negativibacillus* sp000435195 |
| 0.127151205 | *Prevotella* sp002251385 |
| 0.122995374 | *Coprococcus_A* sp900548825 |
| 0.118746116 | *Alistipes_A indistinctus* |
| 0.118323236 | UMGS1071 sp900542375 |

TABLE 7-continued

A logistic regression classifier was trained to classify samples
as corresponding to cancer (non-responder) or control on samples
with a mean relative abundance of at least 0.005% using the GTDB
database. An ROC curve was generated on 43 non-responder samples
and 92 control samples using Stratified Group K-Fold Cross Validation
(AUC = 0.71). Following validation, the model was trained
on all the samples and feature importance values are reported.

| Feature Importance (Logistic Regression) | Organism Name |
|---|---|
| 0.115663494 | *Erysipelatoclostridium* sp900544435 |
| 0.10338765 | *Collinsella* sp900547285 |
| 0.102410987 | *Prevotella* sp900556825 |
| 0.094993875 | UMGS172 sp900539855 |
| 0.06348916 | *Phocaeicola* sp900551445 |
| 0.061539232 | *Agathobacter rectalis* |
| 0.056113717 | *Anaerobutyricum hallii* |
| 0.053598211 | *Blautia_A* sp900066335 |
| 0.053249701 | *Anaerostipes hadrus_A* |
| 0.045497159 | *Clostridium* sp001916075 |
| 0.037406556 | *Holdemanella* sp003458715 |
| 0.021590668 | *Christensenella minuta* |
| 0.002218293 | *Collinsella* sp900541725 |
| 4.2957E−05 | *Phascolarctobacterium faecium* |
| −0.004703489 | *Bacteroides togonis* |
| −0.008809374 | *Paraprevotella clara* |
| −0.03119867 | *Holdemania* sp900120005 |
| −0.031492474 | AM51-8 sp900546435 |
| −0.035434119 | Phil1 sp001940855 |
| −0.038913964 | *Schaedlerella* sp004556565 |
| −0.044020829 | *Lachnospira* sp900552795 |
| −0.047515072 | *Muricomes* sp900604355 |
| −0.052967481 | *Prevotella buccae* |
| −0.071596115 | *Longicatena* sp003433845 |
| −0.0796651 | *Desulfovibrio fairfieldensis* |
| −0.100975915 | *Lachnospira* sp003537285 |
| −0.115966192 | *Butyricimonas faecihominis* |
| −0.172472377 | *Blautia_A* sp900551465 |
| −0.187868969 | *Anaerotruncus massiliensis* |
| −0.19109635 | *Anaerofustis stercorihominis* |
| −0.206509093 | UMGS1688 sp900544575 |
| −0.210914586 | *Bifidobacterium dentium* |
| −0.228226067 | *Bacteroides cutis* |
| −0.241407669 | F23-B02 sp001916715 |
| −0.247678711 | COE1 sp001916965 |
| −0.267182222 | *Ruminococcus_E bromii_B* |
| −0.286160011 | *Porphyromonas* sp001552775 |
| −0.323514014 | UBA1691sp900544715 |
| −0.335225188 | GCA-900066755 sp900066755 |
| −0.340598662 | *Eubacterium_G* sp900548465 |
| −0.35989301 | *Limosilactobacillus fermentum_A* |
| −0.460367032 | *Mesosutterella massiliensis* |
| −0.475293296 | *Escherichia flexneri* |
| −0.542914883 | *Enterococcus_B faecium* |
| −0.599141069 | CAG-521 sp000437635 |
| −0.675358406 | *Phocaeicola* sp000436795 |
| −0.774574761 | CAG-83 sp900550585 |

Figure 9:
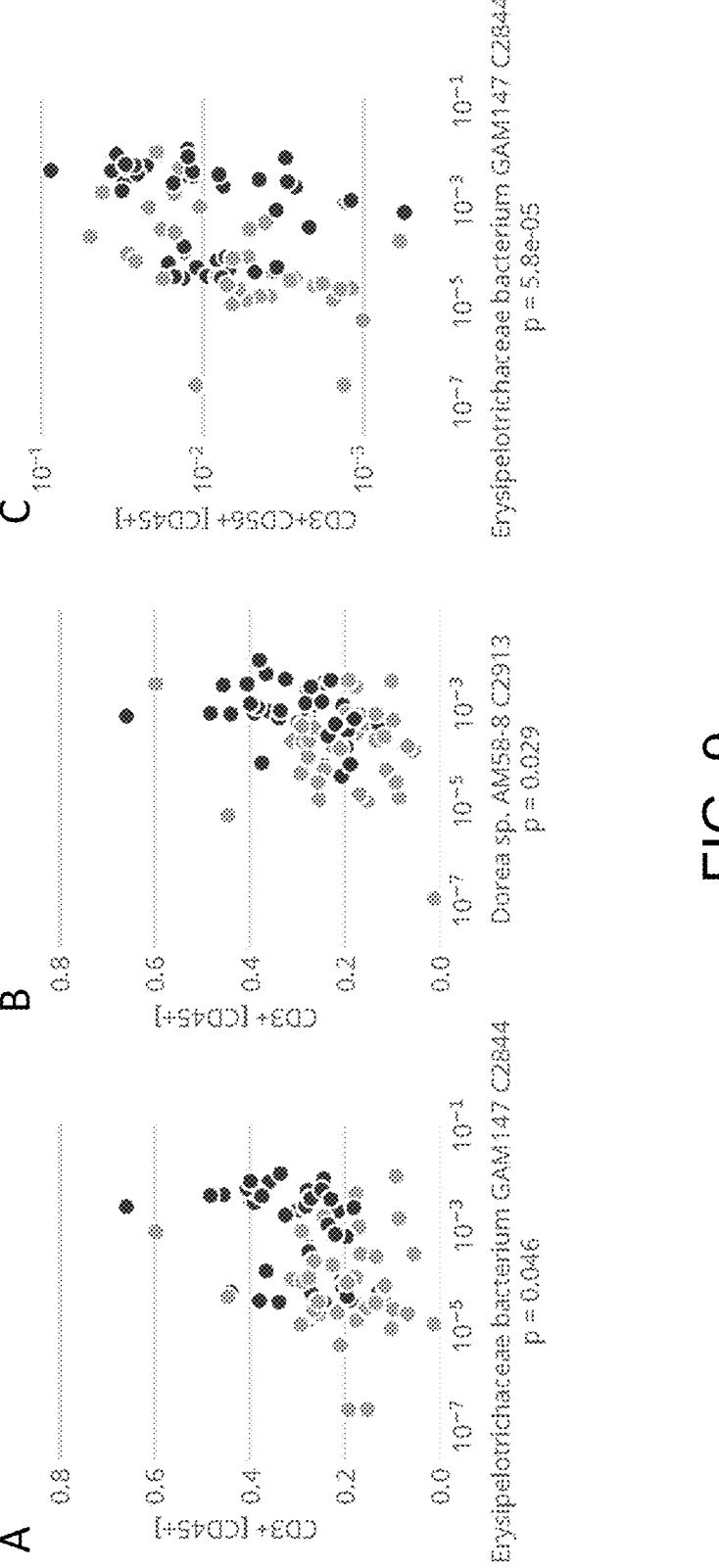
FIG. 9 graphically illustrates correlations of species abundance with immune markers obtained from blood analysis. Immune markers with significant correlations to operational species unit relative abundances are plotted. P values are generated by a linear mixed model fit that model immune marker proportions as being linearly related to the logarithm of OSU abundance, with a random effect accounting for cancer and control groups. For CD3+CD56+, the logarithm of the immune marker proportion is used as the output of the mixed model. (a) positive correlations; (b) negative correlations, as described in Example 10, below.
Figure 9:
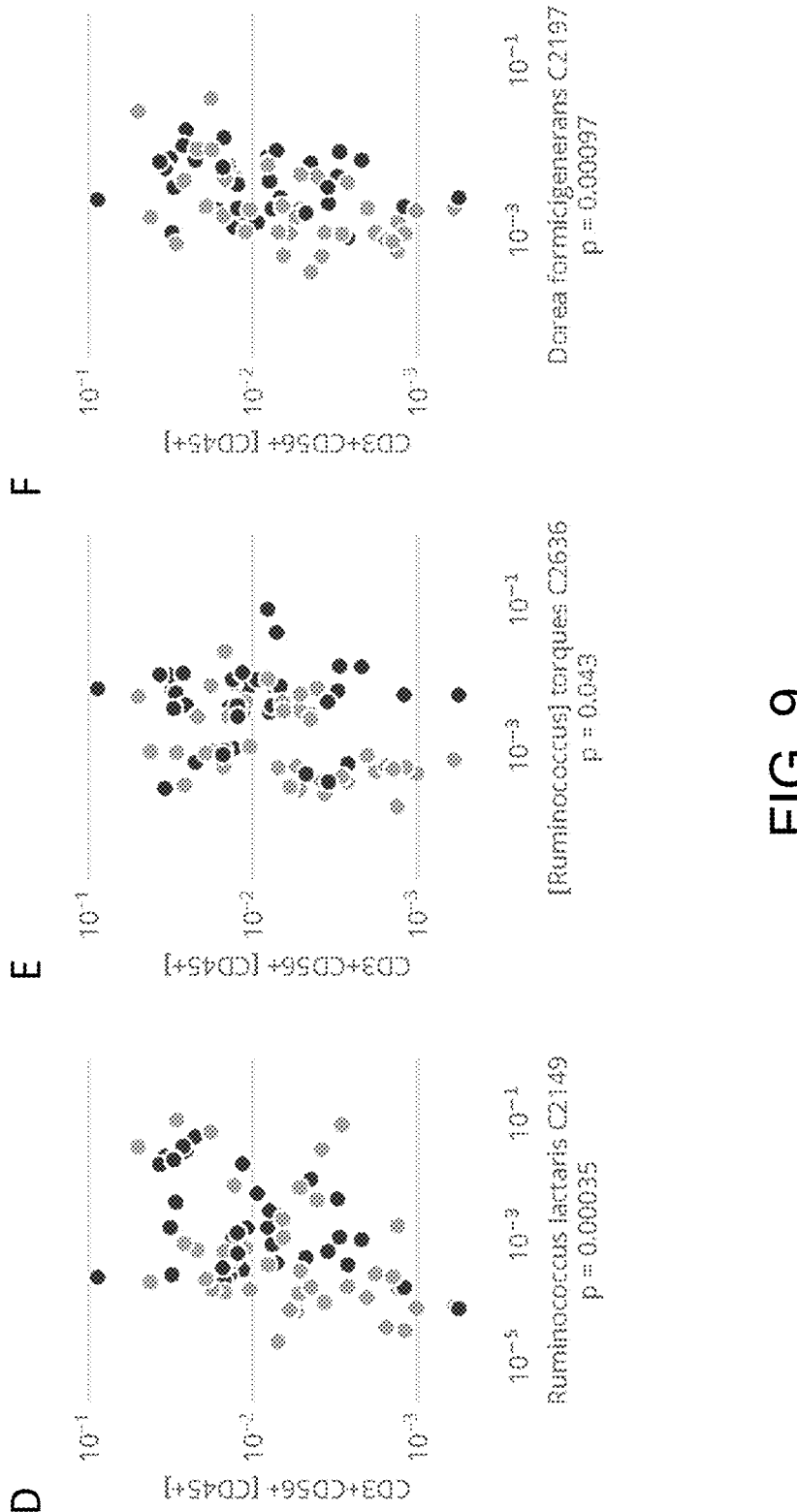
Figure 10:
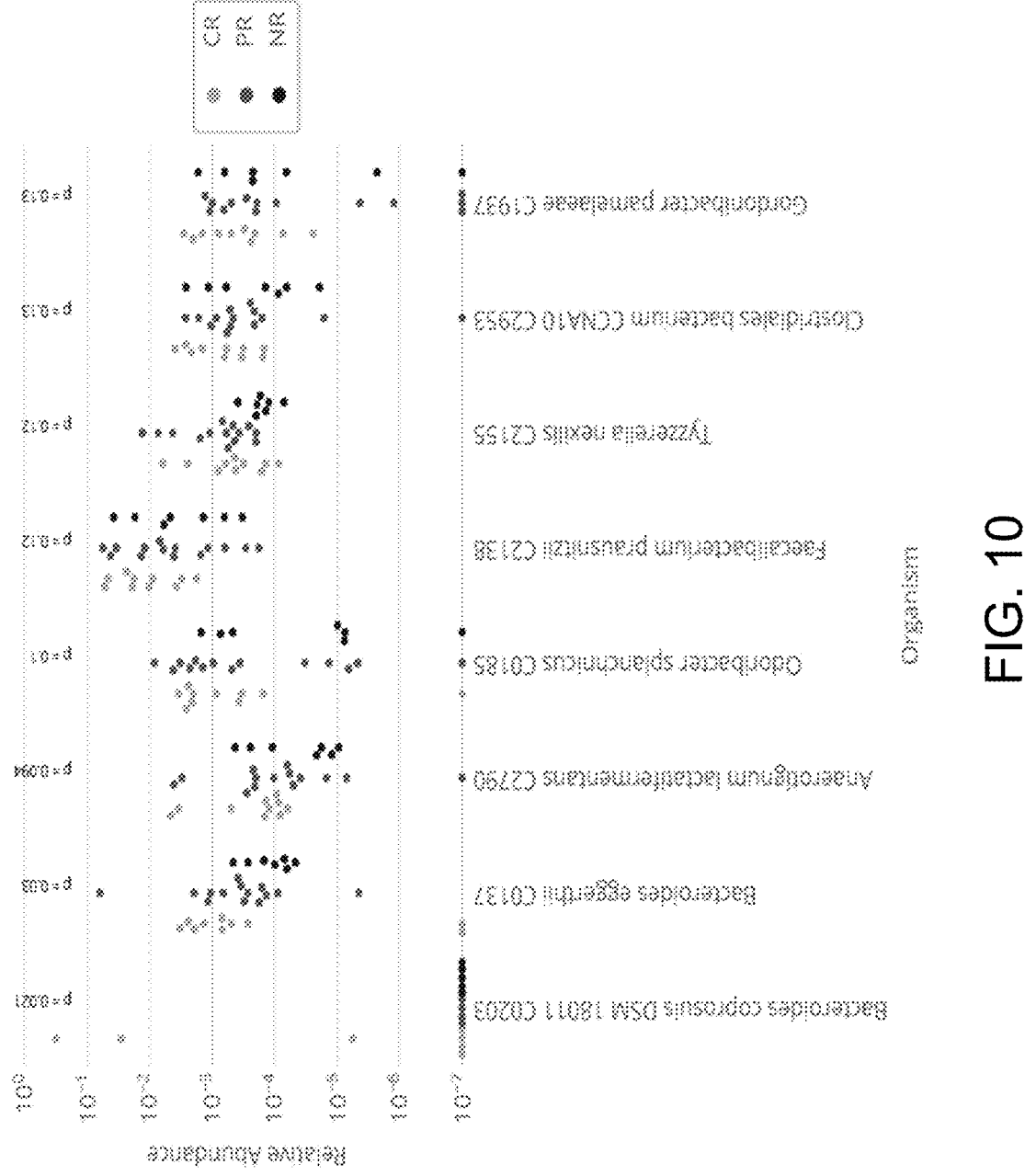
FIG. 10 graphically illustrates the distribution of abundances of specific organisms in complete responders (CR), partial responders (PR), and non-responders (NR). Whole genome sequencing is performed on the initial time point fecal samples from subjects undergoing cancer immunotherapy and the reads are classified and abundance of each operational species unit is estimated computationally. Operational species unit abundances are correlated to response to therapy using a score of 2 for complete response, 1 for partial response, 0 for no response, using the Spearman rank correlation. Operational species unit abundances for several notable OSUs are displayed with the corresponding Spearman p values, as described in Example 10, below.

Flow cytometry was performed on cancer and control blood samples as described in Example 9, and correlations between immune markers and organism abundances in the corresponding stool samples were determined (FIG. 9 and Tables 8 and 9). The organisms were also ranked according to differential abundance between responder and non-responder patients (FIG. 10 and Table 10). In addition, linear discriminant analysis (LDA) effect size method (LEfSe) was used to classify microbes identified using the GTDB database enriched in cancer or control (Table 11).

Table 8, illustrated as FIG. 18. Flow cytometry was performed on 38 cancer blood samples and 38 control blood samples, along with corresponding whole genome sequencing and classification. All operational species unit (OSU) abundances were correlated against a suite of immune markers (CD11b+, CD14+CD15−, CD14−CD15+, CD15+ CD14−, CD15−CD14+, CD3+, CD3+CD56+, CD3+ HLADR+, CD3−CD56+, CD3−HLA-DR+, CD3-HLA-DR-low, CD4+, CD4+HLA-DR+, CD8+, CD8+HLA-DR+, Foxp3+). Correlations and p values were computed on all the samples, or on a subset of samples consisting of just control samples or just cancer samples. The p values obtained from all the samples were filtered using a two-stage Benjamini-Hochberg procedure and correlated with an adjusted p value below 0.15 are reported.

Table 9, illustrated in FIG. 19. Flow cytometry was performed on 38 cancer blood samples and 38 control blood samples, along with corresponding whole genome sequencing and classification. All operational species units (OSUs) were correlated against the CD3+ and CD3+CD56+ immune markers (as a subset of CD45+) using a Spearman rank correlation. Adjusted p values were computed using a two-stage Benjamini-Hochberg procedure for each immune marker, and correlations with an adjusted p value below 0.2 are retained. The retained correlations were further vetted using a linear mixed model that accounts for a random effect induced by group (cancer vs. control). The logarithm of the OSU abundance was used as the input to the model. For CD3+CD56+, the logarithm of the immune marker proportion was used as the output of the mixed model. The mixed model p values and coefficients are reported.

TABLE 10

Whole genome sequencing was performed on the initial time point fecal samples from subjects undergoing cancer immunotherapy and the reads were classified and abundance of each operational species unit was estimated computationally. Operational species unit abundances were correlated to response to therapy using a score of 2 for complete response, 1 for partial response, 0 for no response, using the Spearman rank correlation. Correlations with a p value below 0.15 are reported.

| Mean Abundance (All Samples) | p value (Spearman rank) | Spearman Correlation | Organism (Operational Species Unit) | Adjusted p value (Two Stage BH) |
|---|---|---|---|---|
| 0.004824863 | 0.009065354 | −0.460919277 | *Bacteroides barnesiae* C0323 | 0.50270646 |
| 0.001854242 | 0.011550331 | −0.447714196 | *Streptococcus mutans* C3345 | 0.50270646 |
| 0.002592642 | 0.013008588 | −0.441044685 | *Lactobacillus fermentum* C3433 | 0.50270646 |
| 0.003900899 | 0.01697159 | −0.425648294 | *Bacteroides heparinolyticus* C1005 | 0.50270646 |
| 0.011114361 | 0.020991328 | 0.412834447 | *Bacteroides coprosuis* DSM 18011 C0203 | 0.50270646 |
| 0.001347612 | 0.021974899 | −0.410011686 | *Blautia obeum* C2901 | 0.50270646 |
| 0.005138808 | 0.022206972 | −0.409360874 | *Streptococcus vestibularis* C7338 | 0.50270646 |
| 0.004109069 | 0.028915901 | −0.392598094 | *Streptococcus thermophilus* C3480 | 0.50270646 |
| 0.002625559 | 0.029553117 | 0.391177567 | *Bacteroides eggerthii* C0137 | 0.50270646 |
| 0.00180933 | 0.029570968 | −0.391138132 | *Streptococcus* sp. HSISS2 C4629 | 0.50270646 |
| 0.006421035 | 0.045485127 | −0.361828833 | *Bacteroides coprocola* C0136 | 0.702951961 |
| 0.00479161 | 0.066985005 | −0.333215846 | *Lachnospira pectinoschiza* C2649 | 0.884186581 |
| 0.001357573 | 0.067614268 | −0.332494913 | *Lactobacillus paragasseri* C5843 | 0.884186581 |
| 0.002942156 | 0.074018907 | −0.325438908 | *Escherichia coli* C3313 | 0.894382098 |
| 0.001499661 | 0.089187848 | −0.310437419 | *Intestinibacter bartlettii* C2141 | 0.894382098 |
| 0.001315245 | 0.090931568 | −0.308841524 | *Lactococcus lactis* C3409 | 0.894382098 |
| 0.000593797 | 0.093500218 | 0.306532546 | *Anaerotignum lactatifermentans* C2790 | 0.894382098 |
| 0.001096895 | 0.100936329 | −0.300108932 | *Bifidobacterium dentium* C0003 | 0.894382098 |
| 0.001297862 | 0.101670448 | 0.2994944 | *Odoribacter splanchnicus* C0185 | 0.894382098 |
| 0.002123253 | 0.113189533 | −0.290262241 | *Faecalimonas umbilicata* C2244 | 0.894382098 |
| 0.014086171 | 0.120986249 | 0.284404931 | *Faecalibacterium prausnitzii* C2138 | 0.894382098 |
| 0.001420926 | 0.123671567 | 0.282452495 | *Tyzzerella nexilis* C2155 | 0.894382098 |
| 0.000841219 | 0.131047516 | 0.277245997 | Clostridiales bacterium CCNA10 C2953 | 0.894382098 |
| 0.001049951 | 0.132465355 | −0.276270029 | *Clostridium disporicum* C2479 | 0.894382098 |
| 0.000534773 | 0.1330099 | 0.275897229 | *Gordonibacter pamelaeae* C1937 | 0.894382098 |

TABLE 11

Linear discriminant analysis (LDA) effect size method (LEfSe) was used to classify microbes (GTDB database) enriched in cancer or control. Analysis was conducted on 322 cancer samples and 96 control samples. LEfSe first identifies features that are statistically different among various populations using the non-parametric factorial Kruskal-Wallis (KW) sum-rank test; It then performs additional pairwise tests to assess whether these differences are consistent with respect to population subclasses using the unpaired Wilcoxon rank-sum test. Lastly, LEfSe uses LDA to estimate the effect size of each differentially abundant feature. A total of 135 species were enriched in cancer patients and 189 species were enriched in healthy individuals.

| taxID | Organism Name | Enrichment Group | LDA score (log10) | p-value (Kruskal-Wallis test) |
|---|---|---|---|---|
| 17568 | *Blautia_A sp900120195* | Cancer | 2.13760 | 0.0010911377336 |
| 17532 | *Blautia coccoides* | Cancer | 2.39200 | 0.000968237855956 |
| 17534 | *Blautia hansenii* | Cancer | 2.61227 | 0.0216950428348 |
| 17535 | *Blautia hominis* | Cancer | 2.00955 | 0.0132436138036 |
| 17536 | *Blautia sp000432195* | Cancer | 2.64642 | 6.48111804063e−05 |
| 38844 | *Streptococcus mutans* | Cancer | 2.19809 | 0.000766810025194 |
| 21762 | *Eisenbergiella tayi* | Cancer | 2.09239 | 0.0257014664011 |
| 18508 | CAG-273 sp000437855 | Cancer | 2.19293 | 0.00149432368338 |

TABLE 11-continued

Linear discriminant analysis (LDA) effect size method (LEfSe) was used to classify
microbes (GTDB database) enriched in cancer or control. Analysis was conducted on
322 cancer samples and 96 control samples. LEfSe first identifies features that are
statistically different among various populations using the non-parametric factorial
Kruskal-Wallis (KW) sum-rank test; It then performs additional pairwise tests to assess
whether these differences are consistent with respect to population subclasses using
the unpaired Wilcoxon rank-sum test. Lastly, LEfSe uses LDA to estimate the effect
size of each differentially abundant feature. A total of 135 species were enriched
in cancer patients and 189 species were enriched in healthy individuals.

| taxID | Organism Name | Enrichment Group | LDA score (log10) | p-value (Kruskal-Wallis test) |
|---|---|---|---|---|
| 22144 | *Escherichia* sp000208585 | Cancer | 2.24534 | 0.000447045218029 |
| 20468 | *Coprococcus eutactus* | Cancer | 2.35758 | 0.00917122961097 |
| 17540 | *Blautia* sp003287895 | Cancer | 2.62746 | 1.36005693245e−05 |
| 17547 | *Blautia* sp900556555 | Cancer | 2.05367 | 0.0264114231619 |
| 17148 | *Bacteroides bouchesdurhonensis* | Cancer | 2.10570 | 0.00282381576978 |
| 15906 | *Anaerostipes* sp000508985 | Cancer | 2.01922 | 0.00114807012388 |
| 14115 | 43-108 sp001915545 | Cancer | 2.64298 | 1.11878531695e−06 |
| 36509 | *Ruminococcus*_H sp900549945 | Cancer | 2.33650 | 0.00895450765663 |
| 15832 | *Anaerobutyricum hallii*_A | Cancer | 2.23321 | 0.0225920389673 |
| 36428 | *Ruminococcus*_A sp000432335 | Cancer | 2.53016 | 0.00139750682718 |
| 25300 | *Hungatella* sp005845265 | Cancer | 2.20734 | 2.41051912452e−07 |
| 31012 | *Oscillibacter welbionis* | Cancer | 2.97773 | 0.000181598180603 |
| 23244 | *Fusobacterium*_B sp900541465 | Cancer | 2.05886 | 0.00968800303448 |
| 21884 | *Enterocloster aldenensis* | Cancer | 2.53945 | 6.46879345659e−10 |
| 26966 | *Longicatena innocuum* | Cancer | 2.62342 | 0.000826173225832 |
| 38939 | *Streptococcus* sp000187445 | Cancer | 2.54944 | 0.000251671138383 |
| 20690 | *Cronobacter sakazakii* | Cancer | 2.00001 | 0.00176581732956 |
| 20055 | *Clostridium*_Q *symbiosum* | Cancer | 2.60684 | 4.89158492686e−09 |
| 15178 | *Agathobacter* sp000434275 | Cancer | 2.00539 | 0.0481413837296 |
| 21731 | *Eggerthella lenta* | Cancer | 2.94523 | 0.006101347123 |
| 38891 | *Streptococcus parasanguinis*_D | Cancer | 2.42213 | 2.6511957776e−05 |
| 38889 | *Streptococcus parasanguinis*_B | Cancer | 2.56043 | 0.000319467593934 |
| 38888 | *Streptococcus parasanguinis*_A | Cancer | 2.33233 | 9.51509478653e−05 |
| 38887 | *Streptococcus parasanguinis* | Cancer | 2.35117 | 0.00071108799438 |
| 22512 | *Faecalimonas* sp900556835 | Cancer | 2.23748 | 0.012095387025 |
| 19869 | *Citrobacter freundii* | Cancer | 2.07185 | 0.00906080909617 |
| 23068 | *Flavonifractor* sp000508885 | Cancer | 2.96730 | 2.14986779138e−09 |
| 33819 | *Providencia rettgeri*_D | Cancer | 2.20376 | 0.00955245042142 |
| 17543 | *Blautia* sp900541955 | Cancer | 2.50204 | 0.0173404800143 |
| 32690 | *Phocaeicola dorei* | Cancer | 3.66861 | 0.000216406212684 |
| 32695 | *Phocaeicola plebeius* | Cancer | 2.44370 | 0.00392932331679 |
| 32699 | *Phocaeicola sartorii* | Cancer | 2.18940 | 0.00108006311504 |
| 18772 | CAG-83 sp001916855 | Cancer | 2.01482 | 0.00380931699685 |
| 17198 | *Bacteroides* sp900557355 | Cancer | 2.48723 | 0.0172953376659 |
| 17196 | *Bacteroides* sp900556215 | Cancer | 2.44481 | 0.00508686372198 |
| 17191 | *Bacteroides* sp900066265 | Cancer | 2.18952 | 4.52735545739e−05 |
| 44733 | *Veillonella atypica* | Cancer | 2.18847 | 0.0402708440438 |
| 27993 | *Mediterraneibacter torques* | Cancer | 3.55674 | 0.0496897855081 |
| 38890 | *Streptococcus parasanguinis*_C | Cancer | 2.20714 | 0.000599054128583 |
| 21757 | *Eisenbergiella* sp900539715 | Cancer | 2.18135 | 0.00915828126624 |
| 17157 | *Bacteroides faecis* | Cancer | 2.61898 | 0.000484436396227 |
| 15918 | *Anaerotruncus colihominis* | Cancer | 2.22604 | 0.00133142885356 |
| 38951 | *Streptococcus* sp001556435 | Cancer | 2.92682 | 0.00217861964326 |
| 18579 | CAG-45 sp900066395 | Cancer | 2.49950 | 0.00574455333834 |
| 17554 | *Blautia*_A sp000433815 | Cancer | 3.19213 | 2.23528859735e−06 |
| 21497 | *Dorea scindens* | Cancer | 2.79558 | 2.09572874651e−05 |
| 26866 | *LimosiLactobacillus fermentum* | Cancer | 2.34117 | 0.0103155939811 |
| 17205 | *Bacteroides xylanisolvens* | Cancer | 3.21745 | 0.00012372735459 |
| 21888 | *Enterocloster clostridioformis* | Cancer | 3.08276 | 3.13138339085e−12 |
| 21886 | *Enterocloster bolteae* | Cancer | 2.81644 | 2.15012098387e−11 |
| 18199 | *Butyricimonas faecihominis* | Cancer | 2.14057 | 4.33439876776e−05 |
| 41906 | UBA1691 sp900544375 | Cancer | 3.44725 | 2.33522633211e−10 |
| 25980 | *Klebsiella variicola* | Cancer | 2.09542 | 0.0155919157839 |
| 21889 | *Enterocloster clostridioformis*_A | Cancer | 2.54158 | 2.41667650124e−07 |
| 36521 | *Ruthenibacterium lactatiformans* | Cancer | 2.77271 | 8.80361828788e−05 |
| 26241 | *Lachnospira* sp000436535 | Cancer | 2.04108 | 0.0461403001471 |
| 15835 | *Anaerobutyricum* sp900016875 | Cancer | 2.11887 | 0.0181255372277 |
| 21501 | *Dorea* sp000433535 | Cancer | 3.18022 | 8.50501585649e−07 |
| 15033 | *Acutalibacter* sp900543555 | Cancer | 2.20583 | 2.07942112135e−05 |
| 17156 | *Bacteroides faecichinchillae* | Cancer | 2.00310 | 0.00578699520994 |
| 17150 | *Bacteroides caecimuris* | Cancer | 2.30080 | 1.18027718738e−06 |
| 44095 | UBA9502 sp900538475 | Cancer | 2.56934 | 0.000419156172297 |
| 32688 | *Phocaeicola coprocola* | Cancer | 3.05308 | 0.0168486380976 |
| 39618 | *Succiniclasticum* sp900544275 | Cancer | 2.14647 | 0.0262474166286 |
| 17197 | *Bacteroides* sp900556625 | Cancer | 2.67332 | 0.0181020544302 |
| 18198 | *Butyricimonas faecalis* | Cancer | 2.54767 | 2.02297766283e−06 |

TABLE 11-continued

Linear discriminant analysis (LDA) effect size method (LEfSe) was used to classify
microbes (GTDB database) enriched in cancer or control. Analysis was conducted on
322 cancer samples and 96 control samples. LEfSe first identifies features that are
statistically different among various populations using the non-parametric factorial
Kruskal-Wallis (KW) sum-rank test; It then performs additional pairwise tests to assess
whether these differences are consistent with respect to population subclasses using
the unpaired Wilcoxon rank-sum test. Lastly, LEfSe uses LDA to estimate the effect
size of each differentially abundant feature. A total of 135 species were enriched
in cancer patients and 189 species were enriched in healthy individuals.

| taxID | Organism Name | Enrichment Group | LDA score (log10) | p-value (Kruskal-Wallis test) |
|---|---|---|---|---|
| 36434 | Ruminococcus_B gnavus | Cancer | 3.40611 | 0.00343207293924 |
| 36436 | Ruminococcus_C callidus | Cancer | 2.59013 | 3.11571237196e−06 |
| 37769 | Sellimonas intestinalis | Cancer | 2.90188 | 0.0010421172501 |
| 14650 | Acidaminococcus intestini | Cancer | 2.84483 | 5.37086074804e−06 |
| 38929 | Streptococcus salivarius | Cancer | 2.93889 | 0.0133708816272 |
| 31909 | Parabacteroides distasonis | Cancer | 3.49346 | 0.00845055659135 |
| 26428 | Lawsonibacter sp900066825 | Cancer | 2.27921 | 0.00119563602136 |
| 15902 | Anaerostipes caccae | Cancer | 2.59029 | 1.32175359294e−05 |
| 22142 | Escherichia flexneri | Cancer | 3.07841 | 0.000448573849446 |
| 39003 | Streptococcus vestibularis | Cancer | 2.91268 | 1.23303428895e−06 |
| 17204 | Bacteroides uniformis | Cancer | 3.76744 | 0.00767040878452 |
| 22082 | Erysipelatoclostridium ramosum | Cancer | 3.10882 | 4.49001877438e−05 |
| 17179 | Bacteroides rodentium | Cancer | 2.36982 | 0.000809140186422 |
| 25979 | Klebsiella quasivariicola | Cancer | 2.50337 | 0.0209044295048 |
| 38737 | Streptococcus anginosus_C | Cancer | 2.56735 | 0.0450278679091 |
| 19879 | Citrobacter youngae | Cancer | 2.10125 | 0.0268286601359 |
| 32689 | Phocaeicola coprophilus | Cancer | 2.39012 | 8.788249368e−06 |
| 33237 | Prevotella sp000257925 | Cancer | 2.05312 | 0.00100376799716 |
| 23067 | Flavonifractor plautii | Cancer | 2.95190 | 2.03840497779e−09 |
| 22140 | Escherichia dysenteriae | Cancer | 2.72638 | 0.000178346031215 |
| 21898 | Enterocloster sp900541315 | Cancer | 2.07701 | 0.0133349033913 |
| 21890 | Enterocloster lavalensis | Cancer | 2.05837 | 5.58379720897e−08 |
| 17201 | Bacteroides thetaiotaomicron | Cancer | 3.50101 | 0.0235802219915 |
| 38946 | Streptococcus sp000448565 | Cancer | 2.35186 | 3.7304387141e−05 |
| 26964 | Longicatena caecimuris | Cancer | 2.71146 | 0.000140435878 |
| 31921 | Parabacteroides sp900155425 | Cancer | 2.04037 | 0.000627513743016 |
| 21401 | Dialister sp900343095 | Cancer | 2.42134 | 0.0326132648947 |
| 18336 | CAG-103 sp900543625 | Cancer | 2.23674 | 0.000902041176381 |
| 17180 | Bacteroides salyersiae | Cancer | 2.66579 | 2.13189055395e−05 |
| 18337 | CAG-1031 sp000431215 | Cancer | 2.57987 | 0.000146355127079 |
| 21512 | Dorea sp900543415 | Cancer | 2.70565 | 3.39380545885e−10 |
| 32682 | Phil12 sp002633275 | Cancer | 2.31286 | 0.00199992224058 |
| 22509 | Faecalimonas sp900550975 | Cancer | 2.27491 | 0.0151214093109 |
| 22186 | Eubacterium_G ventriosum | Cancer | 2.14863 | 0.000467276332765 |
| 22513 | Faecalimonas umbilicata | Cancer | 2.77402 | 0.0436444293568 |
| 32208 | Parasutterella sp000980495 | Cancer | 2.31846 | 0.0356205438601 |
| 32727 | Phocaeicola vulgatus | Cancer | 3.87915 | 0.0142224019801 |
| 18334 | CAG-103 sp900317855 | Cancer | 2.18662 | 0.0252397542571 |
| 26805 | Ligilactobacillus salivarius | Cancer | 2.50862 | 0.000565702472295 |
| 17147 | Bacteroides acidifaciens | Cancer | 2.02458 | 0.000193059075288 |
| 33256 | Prevotella sp001275135 | Cancer | 2.00053 | 0.0228785615692 |
| 32637 | Phascolarctobacterium faecium | Cancer | 3.07562 | 0.00859527040104 |
| 19917 | Clostridioides difficile | Cancer | 2.14826 | 0.000396856053418 |
| 17574 | Blautia_A sp900547615 | Cancer | 2.00426 | 0.00105097878926 |
| 18469 | CAG-217 sp900547275 | Cancer | 2.17756 | 0.0150594036026 |
| 18461 | CAG-194 sp000432915 | Cancer | 2.41211 | 0.0114380924628 |
| 17578 | Blautia_A sp900551465 | Cancer | 2.09782 | 8.7672215879e−05 |
| 31913 | Parabacteroides johnsonii | Cancer | 2.32757 | 7.57370993477e−07 |
| 36435 | Ruminococcus_B sp900544395 | Cancer | 2.32731 | 0.000138031227462 |
| 17188 | Bacteroides sp003545565 | Cancer | 2.09073 | 0.00116767135794 |
| 18649 | CAG-492 sp000434335 | Cancer | 2.02629 | 0.000100614508133 |
| 41907 | UBA1691 sp900544715 | Cancer | 2.86541 | 7.87326411749e−07 |
| 17160 | Bacteroides fragilis | Cancer | 2.62172 | 0.0152421440534 |
| 31910 | Parabacteroides distasonis_A | Cancer | 2.20437 | 0.0138650485607 |
| 17186 | Bacteroides sp002491635 | Cancer | 2.21447 | 0.00117561051251 |
| 17189 | Bacteroides sp003865075 | Cancer | 2.61541 | 4.67903060213e−07 |
| 20471 | Coprococcus sp000433075 | Cancer | 2.05457 | 8.85142109464e−08 |
| 17167 | Bacteroides intestinalis | Cancer | 2.99981 | 0.0304061339071 |
| 17168 | Bacteroides intestinalis_A | Cancer | 2.49123 | 0.011609802117 |
| 21894 | Enterocloster sp001517625 | Cancer | 2.40734 | 0.00141864996401 |
| 17154 | Bacteroides cutis | Cancer | 2.12726 | 0.038819131362 |
| 36679 | SFFH01 sp900542445 | Control | 2.41059 | 3.30021813163e−06 |
| 36440 | Ruminococcus_C sp000980705 | Control | 3.20407 | 1.2103932064e−08 |
| 41347 | UBA11524 sp000437595 | Control | 2.03222 | 0.00829874351407 |
| 20338 | Collinsella sp900556415 | Control | 2.08313 | 1.11217975236e−08 |
| 22089 | Erysipelatoclostridium sp900544435 | Control | 2.42399 | 1.1132866617e−06 |

TABLE 11-continued

Linear discriminant analysis (LDA) effect size method (LEfSe) was used to classify
microbes (GTDB database) enriched in cancer or control. Analysis was conducted on
322 cancer samples and 96 control samples. LEfSe first identifies features that are
statistically different among various populations using the non-parametric factorial
Kruskal-Wallis (KW) sum-rank test; It then performs additional pairwise tests to assess
whether these differences are consistent with respect to population subclasses using
the unpaired Wilcoxon rank-sum test. Lastly, LEfSe uses LDA to estimate the effect
size of each differentially abundant feature. A total of 135 species were enriched
in cancer patients and 189 species were enriched in healthy individuals.

| taxID | Organism Name | Enrichment Group | LDA score (log10) | p-value (Kruskal-Wallis test) |
|---|---|---|---|---|
| 22087 | Erysipelatoclostridium sp003024675 | Control | 2.25783 | 2.64720533759e−10 |
| 20324 | Collinsella sp900554905 | Control | 2.21598 | 1.04125747668e−08 |
| 22085 | Erysipelatoclostridium sp000752095 | Control | 2.96769 | 4.21528595137e−11 |
| 20321 | Collinsella sp900554645 | Control | 2.00425 | 0.000781585095622 |
| 36447 | Ruminococcus_D bicirculans | Control | 3.39071 | 6.09724921548e−06 |
| 18401 | CAG-1427 sp000435675 | Control | 2.05861 | 0.000239442448034 |
| 15198 | Agathobaculum sp900625105 | Control | 2.45929 | 0.00687534588514 |
| 17538 | Blautia sp001304935 | Control | 2.76252 | 0.00021477069236 |
| 44369 | UMGS1241 sp900549955 | Control | 2.48651 | 0.000229158432302 |
| 26970 | Longicatena sp900411325 | Control | 2.04471 | 0.0253206102387 |
| 15193 | Agathobaculum sp003481705 | Control | 2.72460 | 2.55177393509e−06 |
| 22497 | Faecalibacterium sp900539885 | Control | 2.45021 | 0.00114034752317 |
| 15191 | Agathobaculum butyriciproducens | Control | 2.40050 | 9.30926345453e−05 |
| 18588 | CAG-460 sp900544625 | Control | 2.45197 | 0.00302957091049 |
| 36473 | Ruminococcus_E sp003438075 | Control | 2.36465 | 0.0116416270466 |
| 25246 | Holdemanella sp900551285 | Control | 2.39373 | 5.39071908999e−06 |
| 25245 | Holdemanella sp900547815 | Control | 2.13257 | 0.010514300225 |
| 25244 | Holdemanella sp003458715 | Control | 2.16423 | 0.000129153396687 |
| 18402 | CAG-1427 sp000436075 | Control | 2.02925 | 0.00989909203149 |
| 20131 | Collinsella aerofaciens_G | Control | 2.50700 | 9.18497857285e−06 |
| 22491 | Faecalibacterium prausnitzii_J | Control | 2.61316 | 1.05261675827e−06 |
| 17200 | Bacteroides stercoris | Control | 3.05136 | 0.042749136853 |
| 18416 | CAG-1427 sp900556585 | Control | 2.27099 | 0.0267898981999 |
| 41454 | UBA1191 sp900545775 | Control | 2.21447 | 9.43642971559e−06 |
| 22490 | Faecalibacterium prausnitzii | Control | 2.65573 | 1.19439741311e−05 |
| 20339 | Collinsella sp900556445 | Control | 2.31396 | 1.12520743428e−05 |
| 23770 | GCA-900066135 sp900543575 | Control | 2.13602 | 2.91176542674e−08 |
| 17575 | Blautia_A sp900548245 | Control | 2.61892 | 1.33647845585e−07 |
| 18784 | CAG-83 sp900547745 | Control | 2.05677 | 0.000783754622785 |
| 17344 | Bifidobacterium adolescentis | Control | 3.89216 | 0.0472240909999 |
| 25848 | KLE1615 sp900066985 | Control | 2.60806 | 1.08359063226e−05 |
| 17562 | Blautia_A sp900066145 | Control | 2.06312 | 0.000228185017914 |
| 18450 | CAG-180 sp000432435 | Control | 3.28508 | 0.00107407122157 |
| 32723 | Phocaeicola sp900553715 | Control | 2.61412 | 0.032610595599 |
| 41455 | UBA1191 sp900549125 | Control | 2.50874 | 8.12599169877e−05 |
| 21661 | ER4 sp000765235 | Control | 2.34673 | 0.000662818789913 |
| 18331 | CAG-103 sp000432375 | Control | 2.87783 | 5.58314397621e−07 |
| 37771 | Sellimonas sp002161525 | Control | 2.51538 | 0.0307760188802 |
| 18338 | CAG-110 sp000434635 | Control | 2.74437 | 6.44929544018e−05 |
| 24117 | Gemmiger sp900539695 | Control | 2.05341 | 4.66989314069e−05 |
| 24112 | Gemmiger formicilis | Control | 2.44504 | 0.00333770203037 |
| 33197 | Prevotella copri_A | Control | 2.65431 | 0.0283791459871 |
| 24118 | Gemmiger sp900540595 | Control | 2.16137 | 1.2620604518e−05 |
| 44359 | UMGS1071 sp900542375 | Control | 2.09882 | 0.000974900001284 |
| 21409 | Dialister sp900555245 | Control | 2.63436 | 0.00333770203037 |
| 22173 | Eubacterium_F sp003491505 | Control | 2.36858 | 3.51840365919e−05 |
| 21500 | Dorea sp000433215 | Control | 2.33715 | 1.97114808776e−08 |
| 19946 | Clostridium saudiense | Control | 2.17730 | 0.0230705246422 |
| 19949 | Clostridium sp000435835 | Control | 2.05791 | 0.00616715858917 |
| 17560 | Blautia_A sp003478765 | Control | 2.33260 | 2.52783279408e−06 |
| 17563 | Blautia_A sp900066165 | Control | 2.88048 | 0.00298338599418 |
| 17566 | Blautia_A sp900066355 | Control | 2.55805 | 5.85243145116e−06 |
| 41419 | UBA11774 sp003507655 | Control | 2.48337 | 0.0450169284476 |
| 17559 | Blautia_A sp003477525 | Control | 2.26051 | 0.00340034813393 |
| 21493 | Dorea longicatena | Control | 3.31604 | 5.28875486139e−09 |
| 17565 | Blautia_A sp900066335 | Control | 2.75595 | 9.24085724755e−11 |
| 18785 | CAG-83 sp900548615 | Control | 2.00739 | 0.00287952903975 |
| 18783 | CAG-83 sp900545585 | Control | 2.51557 | 4.66505048711e−06 |
| 17413 | Bifidobacterium sp002742445 | Control | 2.50849 | 0.00126433385994 |
| 15188 | Agathobacter sp900550845 | Control | 2.36342 | 0.000411600171088 |
| 15183 | Agathobacter sp900546625 | Control | 2.45178 | 0.00017678701388 |
| 15181 | Agathobacter sp900317585 | Control | 2.82123 | 0.000142395876762 |
| 15186 | Agathobacter sp900549895 | Control | 2.34044 | 0.0348666029549 |
| 18651 | CAG-492 sp900553225 | Control | 2.53389 | 0.000269274517967 |
| 19908 | Cloacibacillus porcorum | Control | 2.01540 | 0.0327228894077 |
| 18241 | Butyrivibrio_A crossotus | Control | 2.37277I | 0.00126177720823 |

TABLE 11-continued

Linear discriminant analysis (LDA) effect size method (LEfSe) was used to classify
microbes (GTDB database) enriched in cancer or control. Analysis was conducted on
322 cancer samples and 96 control samples. LEfSe first identifies features that are
statistically different among various populations using the non-parametric factorial
Kruskal-Wallis (KW) sum-rank test; It then performs additional pairwise tests to assess
whether these differences are consistent with respect to population subclasses using
the unpaired Wilcoxon rank-sum test. Lastly, LEfSe uses LDA to estimate the effect
size of each differentially abundant feature. A total of 135 species were enriched
in cancer patients and 189 species were enriched in healthy individuals.

| taxID | Organism Name | Enrichment Group | LDA score (log10) | p-value (Kruskal-Wallis test) |
|---|---|---|---|---|
| 18243 | *Butyrivibrio_A* sp900543865 | Control | 2.29993 | 0.000757328088867 |
| 20287 | *Collinsella* sp900551365 | Control | 2.10823 | 5.77069184548e−06 |
| 44382 | UMGS1375 sp900066615 | Control | 2.31480 | 0.00204908177496 |
| 14550 | *Acetatifactor* sp900066365 | Control | 2.28979 | 0.00350713933387 |
| 17230 | *Barnesiella intestinihominis* | Control | 2.45687 | 0.00109479017124 |
| 17558 | *Blautia_A* sp003474435 | Control | 2.11266 | 1.13585564617e−09 |
| 27982 | *Mediterraneibacter faecis* | Control | 3.12051 | 3.79965372336e−09 |
| 44383 | UMGS1375 sp900551235 | Control | 2.10198 | 1.99431838413e−06 |
| 17549 | *Blautia_A massiliensis* | Control | 3.35483 | 9.0678522457e−06 |
| 44304 | UCG-010 sp003150115 | Control | 2.07626 | 1.93454349489e−08 |
| 40350 | *Terrisporobacter* sp900557165 | Control | 2.27319 | 0.0201956139629 |
| 17555 | *Blautia_A* sp000436615 | Control | 2.77455 | 1.50755393035e−07 |
| 17550 | *Blautia_A obeum* | Control | 3.28966 | 5.87804863778e−05 |
| 17551 | *Blautia_A obeum_B* | Control | 2.10105 | 0.00117560721128 |
| 18491 | CAG-269 sp003525075 | Control | 2.94816 | 1.10382253131e−06 |
| 30848 | *Odoribacter laneus* | Control | 2.42804 | 0.02830176635 |
| 17564 | *Blautia_A* sp900066205 | Control | 2.57852 | 3.49087257679e−11 |
| 15043 | *Adlercreutzia celatus_A* | Control | 2.07439 | 0.0164550857066 |
| 36088 | *Roseburia inulinivorans* | Control | 2.43035 | 0.0265096583225 |
| 20185 | *Collinsella* sp900541475 | Control | 2.45893 | 1.78086972764e−07 |
| 22483 | *Faecalibacterium prausnitzii_A* | Control | 2.53717 | 1.48409829345e−07 |
| 14374 | AM51-8 sp003478275 | Control | 2.04747 | 0.001001970988 |
| 21494 | *Dorea longicatena_B* | Control | 3.01526 | 4.84949138423e−07 |
| 18771 | CAG-83 sp000435975 | Control | 2.58227 | 0.00441888019065 |
| 18673 | CAG-533 sp000434495 | Control | 2.22485 | 0.00514615742321 |
| 18475 | CAG-245 sp000435175 | Control | 2.22165 | 0.0435372051499 |
| 15831 | *Anaerobutyricum hallii* | Control | 3.09528 | 0.00014746116909 |
| 15836 | *Anaerobutyricum* sp900554965 | Control | 2.70371 | 0.000916439523968 |
| 22482 | *Faecalibacterium prausnitzii* | Control | 3.19093 | 2.18287972068e−06 |
| 20276 | *Collinsella* sp900550185 | Control | 2.08412 | 7.91309114891e−05 |
| 20272 | *Collinsella* sp900549455 | Control | 2.49443 | 1.41645935111e−08 |
| 24122 | *Gemmiger* sp900554145 | Control | 2.36155 | 4.05221257543e−06 |
| 44754 | *Veillonella* sp900556785 | Control | 2.24720 | 0.0330231957551 |
| 36477 | *Ruminococcus_E* sp003526955 | Control | 3.37778 | 0.0144137210572 |
| 21892 | *Enterocloster* sp000431375 | Control | 2.38993 | 0.00857107906373 |
| 18445 | CAG-177 sp003538135 | Control | 2.07697 | 0.000716445637701 |
| 40005 | TF01-11 sp001414325 | Control | 2.66655 | 0.000363496777214 |
| 17366 | *Bifidobacterium catenulatum* | Control | 2.20765 | 0.0114038100379 |
| 26235 | *Lachnospira eligens_B* | Control | 2.56502 | 0.0154865827583 |
| 36087 | *Roseburia intestinalis* | Control | 3.09407 | 0.0279857822864 |
| 23215 | *Fusicatenibacter saccharivorans* | Control | 3.44159 | 2.62500713715e−06 |
| 19959 | *Clostridium* sp900540255 | Control | 2.64288 | 0.000134946507533 |
| 30930 | *Olsenella_E* sp003150175 | Control | 2.10495 | 9.32929729361e−05 |
| 18510 | CAG-273 sp003507395 | Control | 3.10648 | 7.55800913874e−06 |
| 36438 | *Ruminococcus_C* sp000437175 | Control | 2.50387 | 0.00215829381827 |
| 17579 | *Blautia_A* sp900551715 | Control | 2.07825 | 5.77555977528e−12 |
| 18631 | CAG-485 sp900541835 | Control | 2.21771 | 0.00687270499319 |
| 20052 | *Clostridium_Q* sp003024715 | Control | 2.13420 | 5.46070638709e−05 |
| 18846 | CAG-964 sp000435335 | Control | 2.16784 | 0.0427477385672 |
| 21907 | *Enterococcus faecalis* | Control | 2.55268 | 0.000973238270192 |
| 17233 | *Barnesiella* sp003150885 | Control | 2.22322 | 0.00884314924177 |
| 17404 | *Bifidobacterium ruminantium* | Control | 2.66841 | 0.00855402261808 |
| 29933 | *Negativibacillus* sp900435195 | Control | 2.17199 | 0.0422015141754 |
| 18346 | CAG-110 sp003525905 | Control | 2.33171 | 0.00175739825879 |
| 20478 | *Coprococcus_A* sp900548825 | Control | 2.31292 | 1.03016482881e−08 |
| 40012 | TF01-11 sp003529475 | Control | 2.55554 | 2.41121115527e−06 |
| 18426 | CAG-170 sp000432135 | Control | 2.41207 | 0.000193772855899 |
| 22237 | *Eubacterium_R* sp000433975 | Control | 2.42086 | 0.00209914829707 |
| 22498 | *Faecalibacterium* sp900539945 | Control | 2.93189 | 8.29721553513e−07 |
| 22499 | *Faecalibacterium* sp900540455 | Control | 2.40470 | 0.000272278325887 |
| 22484 | *Faecalibacterium prausnitzii_C* | Control | 3.14427 | 3.49956264954e−06 |
| 44737 | *Veillonella dispar_A* | Control | 2.58590 | 0.011756073445 |
| 22199 | *Eubacterium_I ramulus* | Control | 2.44993 | 0.000781473771325 |
| 20133 | *Collinsella aerofaciens_I* | Control | 2.42591 | 4.45271353249e−07 |
| 23216 | *Fusicatenibacter* sp900543115 | Control | 2.62476 | 0.00684254308783 |
| 18577 | CAG-45 sp000438375 | Control | 2.02767 | 0.0318370090133 |

TABLE 11-continued

Linear discriminant analysis (LDA) effect size method (LEfSe) was used to classify
microbes (GTDB database) enriched in cancer or control. Analysis was conducted on
322 cancer samples and 96 control samples. LEfSe first identifies features that are
statistically different among various populations using the non-parametric factorial
Kruskal-Wallis (KW) sum-rank test; It then performs additional pairwise tests to assess
whether these differences are consistent with respect to population subclasses using
the unpaired Wilcoxon rank-sum test. Lastly, LEfSe uses LDA to estimate the effect
size of each differentially abundant feature. A total of 135 species were enriched
in cancer patients and 189 species were enriched in healthy individuals.

| taxID | Organism Name | Enrichment Group | LDA score (log10) | p-value (Kruskal-Wallis test) |
|---|---|---|---|---|
| 36437 | *Ruminococcus_C* sp000433635 | Control | 2.14431 | 8.48212740565e−05 |
| 30995 | *Oscillibacter* sp001916835 | Control | 2.10314 | 0.000287891879703 |
| 18843 | CAG-95 sp900066375 | Control | 2.50108 | 0.00140687944173 |
| 18482 | CAG-269 sp000437215 | Control | 2.72572 | 0.028711054205 |
| 15903 | *Anaerostipes hadrus* | Control | 3.45161 | 4.07263251646e−05 |
| 44517 | UMGS743 sp900545085 | Control | 2.14080 | 0.00458547437347 |
| 36674 | SFEL01 sp004557245 | Control | 2.08035 | 1.95437989749e−05 |
| 15904 | *Anaerostipes hadrus_A* | Control | 3.04152 | 7.21486613455e−09 |
| 44405 | UMGS1491 sp900554775 | Control | 2.24642 | 0.000330918704025 |
| 36508 | *Ruminococcus_H* sp003531055 | Control | 2.95780 | 0.000800746402152 |
| 15468 | *Alistipes* sp000434235 | Control | 2.30490 | 0.0124196560779 |
| 18511 | CAG-273 sp003534295 | Control | 2.70758 | 0.0159319228906 |
| 20477 | *Coprococcus_A catus* | Control | 2.29379 | 1.01475697641e−06 |
| 20167 | *Collinsella* sp900540895 | Control | 2.39447 | 9.35633056563e−09 |
| 36429 | *Ruminococcus_A* sp000437095 | Control | 2.42518 | 7.23070236119e−05 |
| 20473 | *Coprococcus* sp900066115 | Control | 2.25740 | 1.14391166168e−08 |
| 25571 | *Intestinibacter* sp900540355 | Control | 2.27861 | 0.0497710656561 |
| 17226 | *Bariatricus comes* | Control | 3.17691 | 4.0099294784e−10 |
| 36096 | *Roseburia* sp900552665 | Control | 2.24323 | 0.0231106169811 |
| 24113 | *Gemmiger qucibialis* | Control | 3.16098 | 2.99842836046e−05 |
| 22496 | *Faecalibacterium* sp003449675 | Control | 2.23613 | 1.90744603181e−07 |
| 43535 | UBA7182 sp003481535 | Control | 2.09576 | 1.84717329358e−07 |
| 24119 | *Gemmiger* sp900540775 | Control | 2.56966 | 1.80894410074e−07 |
| 36431 | *Ruminococcus_A* sp003011855 | Control | 2.66427 | 5.49451308118e−08 |
| 18480 | CAG-269 sp000431335 | Control | 3.04994 | 6.96985807634e−06 |
| 18484 | CAG-269 sp001915995 | Control | 2.01969 | 0.025830997993 |
| 18485 | CAG-269 sp001916005 | Control | 2.10988 | 3.25915762025e−07 |
| 18648 | CAG-492 sp000434015 | Control | 2.21000 | 1.30539446398e−07 |
| 26240 | *Lachnospira* sp000436475 | Control | 2.55618 | 0.000628363206244 |
| 18679 | CAG-536 sp000434355 | Control | 2.82212 | 0.00456621092046 |
| 15176 | *Agathobacter rectalis* | Control | 3.41921 | 0.000310178035846 |
| 21491 | *Dorea formicigenerans* | Control | 2.80870 | 5.93297276419e−06 |
| 26245 | *Lachnospira* sp003451515 | Control | 2.56136 | 0.0023267608224 |
| 18509 | CAG-273 sp000438355 | Control | 2.76462 | 0.0305438756183 |
| 20345 | *Collinsella* sp900557455 | Control | 2.00151 | 2.5548792017e−07 |
| 20342 | *Collinsella* sp900556605 | Control | 3.12583 | 9.53488707721e−05 |
| 25241 | *Holdemanella biformis* | Control | 2.52660 | 0.00128748752692 |
| 36078 | *Romboutsia timonensis* | Control | 2.47361 | 0.000416035368085 |
| 18438 | CAG-170 sp900556635 | Control | 2.15669 | 2.45053105973e−05 |
| 28004 | *Megasphaera* sp000417505 | Control | 2.70507 | 0.0488599018113 |
| 22488 | *Faecalibacterium prausnitzii_G* | Control | 2.98235 | 1.81752622445e−05 |
| 22489 | *Faecalibacterium prausnitzii_H* | Control | 2.77389 | 3.98763445095e−06 |
| 18433 | CAG-170 sp900545925 | Control | 2.09412 | 1.07072435143e−06 |
| 20469 | *Coprococcus eutactus_A* | Control | 2.96335 | 0.00490028391811 |
| 19952 | *Clostridium* sp001916075 | Control | 2.47249 | 9.76605249819e−06 |
| 33438 | *Prevotella* sp900551275 | Control | 2.63503 | 0.0105872123676 |
| 27983 | *Mediterraneibacter lactaris* | Control | 2.82901 | 3.28992544736e−05 |
| 17358 | *Bifidobacterium bifidum* | Control | 2.90693 | 0.00395513293096 |
| 22277 | *Evtepia* sp004556345 | Control | 2.09867 | 0.000584164019016 |
| 40011 | TF01-11 sp003524945 | Control | 2.99299 | 0.0106460099673 |
| 22486 | *Faecalibacterium prausnitzii_E* | Control | 2.31452 | 6.15296343593e−06 |
| 26247 | *Lachnospira* sp900316325 | Control | 2.63101 | 0.0141817065492 |

A composite score was then assigned to each organism, accounting for both their correlations to immune markers and fold change between cancer and control cohorts (Tables 12, 13, and 14). The score is defined as the geometric mean of three metrics: fold change between cancer and control samples, CD3+ correlation, and CD3+CD56+ correlation.

TABLE 12

Operational species units (OSUs) with a mean abundance of at least 0.05% with significant differences between cancer and control cohorts for inclusion into the therapeutic. For each OSU, CD3+ and CD3+CD56+ correlations are included in the table as per the linear mixed model analysis or set to zero if the mixed model correlation is negative or if the Spearman correlation was not significant enough to necessitate mixed model analysis. The cancer and control fold change, CD3+ correlation, and CD3+CD56+ correlation for each OSU were converted to percentile scores, and a combined score for each OSU was generated as the geometric mean of each of the three percentiles.

| p value Control vs Cancer (Mann Whitney U) | log10 Fold Change (Cancer/Control) | Organism Name (Operational Species Unit) | CD3+ Correlation (Spearman, if significant) | CD3+CD56+ Correlation (Spearman, if significant) | Total Score |
|---|---|---|---|---|---|
| 1.13356E−08 | −0.764382216 | Erysipelotrichaceae bacterium GAM147 C2844 | 0.417881066 | 0.481640465 | 99.3759725 |
| 0.000236114 | −0.432405099 | Dorea sp. AM58-8 C2913 | 0.395242652 | 0.415256323 | 94.53854775 |
| 0.000111496 | −0.304525941 | [Ruminococcus] torques C2636 | 0.282433356 | 0.290799727 | 81.68743735 |
| 4.96202E−05 | −0.504914016 | Blautia obeum C2129 | 0.441968558 | 0 | 75.35264806 |
| 1.19211E−05 | −0.565340143 | Firmicutes bacterium AF12-30 C2644 | 0.279890636 | 0 | 73.10872098 |
| 3.1747E−07 | −0.415683892 | Blautia sp. AF19-10LB C2906 | 0.3738098 | 0 | 71.5962122 |
| 0.016231058 | −0.392581823 | Clostridium sp. AF36-4 C2893 | 0.39447635 | 0 | 71.56015136 |
| 3.36506E−05 | −0.474788291 | Faecalibacterium prausnitzii C2184 | 0.277732589 | 0 | 71.19231957 |
| 3.45381E−06 | −0.557690435 | Ruminococcus sp. OF03-6AA C2904 | 0.246561859 | 0 | 69.34836951 |
| 1.9624E−05 | −0.436129729 | Dorea longicatena C2413 | 0.268680793 | 0 | 69.18884624 |
| 0.013509112 | −0.452532206 | Bifidobacterium pseudocatenulatum C0013 | 0.256499594 | 0 | 69.12262094 |
| 0.008426878 | −0.517722756 | Bifidobacterium bifidum C0005 | 0.239694858 | 0 | 68.55170178 |
| 1.77058E−05 | −0.449283525 | Coprococcus comes C2152 | 0.245550239 | 0 | 67.24353586 |
| 0.006074794 | −0.502954606 | Ruminococcus sp. KGMB03662 C2557 | 0.219878468 | 0 | 66.11567283 |
| 0.00457584 | −0.312675608 | Clostridium sp. OF10-22XD C2132 | 0.320929597 | 0 | 65.97044298 |
| 0.003783812 | −0.358288898 | Faecalibacterium prausnitzii C2138 | 0.249514696 | 0 | 65.6229349 |
| 0.015331343 | −0.34579043 | Firmicutes bacterium AF25-13AC C2695 | 0.257170198 | 0 | 65.61067466 |
| 0.01271148 | −0.27637531 | Coprococcus catus C2881 | 0.35595352 | 0 | 65.4138845 |
| 0.000860995 | −0.417870861 | Faecalibacterium prausnitzii C2650 | 0.237566644 | 0 | 65.21900583 |
| 0.51444269 | −0.130545436 | Gemmiger formicilis C3234 | 0.27442242 | 0.283691046 | 64.00839092 |
| 0.014929144 | −0.247491324 | Oscillibacter sp. ER4 C2580 | 0.362077922 | 0 | 63.36416394 |
| 0.001048844 | −0.353929055 | Anaerostipes hadrus C2144 | 0.224716336 | 0 | 63.19608844 |
| 0.019540986 | −0.319221468 | Ruminococcus lactaris C2149 | 0 | 0.37621326 | 61.28393922 |
| 0.013186687 | −0.224153342 | Eubacterium ventriosum C2128 | 0.32683527 | 0 | 59.96015726 |
| 0.002439804 | −0.251539605 | Blautia luti C2436 | 0.251838688 | 0 | 59.70580459 |
| 0.039249769 | −0.240687636 | Anaerobutyricum hallii C3263 | 0.255775803 | 0 | 58.66605169 |
| 0.018826044 | −0.257161011 | Faecalitalea cylindroides C2250 | 0 | 0.322093794 | 58.53674188 |
| 0.03257254 | −0.230812001 | Dorea formicigenerans C2197 | 0 | 0.383267259 | 56.61344825 |
| 0.29746277 | −0.106066732 | Asaccharobacter celatus C1952 | 0.219961719 | 0.298085866 | 55.95335448 |
| 0.386245537 | −0.224535064 | Barnesiella intestinihominis C0275 | 0.239107807 | 0 | 55.71314544 |
| 0.717556152 | −0.160088535 | Alistipes putredinis DSM 17216 C0133 | 0.306064417 | 0 | 53.10583588 |
| 3.44484E−05 | −0.516206872 | Dorea longicatena C2131 | 0 | 0 | 52.8235779 |
| 0.005503739 | −0.476696467 | Collinsella aerofaciens C1933 | 0 | 0 | 52.30053782 |
| 7.0925E−05 | −0.442770588 | Dorea sp. OM07-5 C2890 | 0 | 0 | 51.58644796 |
| 0.08814635 | −0.14769711 | Clostridium sp. AF23-8 C2908 | 0.272672591 | 0 | 51.08317009 |
| 0.00646676 | −0.421426117 | Anaerobutyricum hallii C2206 | 0 | 0 | 51.03761433 |
| 0.026898361 | −0.165551333 | [Clostridium] amygdalinum C2887 | 0 | 0.37771702 | 50.67666817 |
| 0.577485114 | −0.11819143 | Eubacterium sp. OM08-24 C2896 | 0.285831465 | 0 | 50.55687075 |
| 0.009817398 | −0.391815999 | Romboutsia timonensis C3123 | 0 | 0 | 50.28695213 |
| 0.011792583 | −0.36246911 | Faecalibacterium prausnitzii C2651 | 0 | 0 | 50.09574515 |
| 0.004344805 | −0.352856347 | Ruminococcus callidus C2440 | 0 | 0 | 49.51318366 |
| 0.016312939 | −0.35259961 | [Eubacterium] rectale C2102 | 0 | 0 | 49.31591789 |
| 0.001239483 | −0.344627962 | Blautia sp.TF11-31AT C2841 | 0 | 0 | 48.91658119 |
| 0.233152423 | −0.335185925 | Bifidobacterium adolescentis C0001 | 0 | 0 | 48.71444425 |
| 0.019421399 | −0.326716726 | Subdoligranulum sp. APC924/74 C2870 | 0 | 0 | 48.51061574 |
| 0.035937114 | −0.32340108 | Ruminococcus sp. AM42-11 C2945 | 0 | 0 | 48.30505982 |
| 0.00812493 | −0.322415354 | Blautia sp. KGMB01111 C3003 | 0 | 0 | 48.09773941 |
| 0.097361497 | −0.321124776 | Clostridium disporicum C2479 | 0 | 0 | 47.88861616 |
| 0.117266616 | −0.306056064 | Bacteroides heparinolyticus C1005 | 0 | 0 | 47.25002508 |
| 0.038561827 | −0.305064647 | Firmicutes bacterium TM09-10 C2909 | 0 | 0 | 47.0332788 |
| 0.269625863 | −0.114661776 | Bifidobacterium animalis C0002 | 0.248008991 | 0 | 47.00940403 |
| 0.188811422 | −0.270611264 | [Eubacterium] eligens C2123 | 0 | 0 | 46.37075 |
| 0.023532312 | −0.26283664 | Clostridium sp. AM49-4BH C2934 | 0 | 0 | 46.14564573 |
| 0.555562154 | −0.10501558 | Roseburia hominis C2266 | 0.267204375 | 0 | 46.03382224 |
| 0.187155428 | 0.260724092 | Roseburia sp. AM59-24XD C2936 | 0 | 0 | 45.91832359 |
| 0.326490078 | −0.116696596 | Roseburia inulinivorans C2207 | 0 | 0.286753247 | 45.8451976 |
| 0.001936194 | −0.255666512 | Faecalibacterium sp. AF28-13AC C2810 | 0 | 0 | 45.45680166 |
| 0.005147868 | −0.246601387 | Agathobaculum butyriciproducens C2850 | 0 | 0 | 44.74642259 |
| 0.009668016 | −0.242001524 | Faecalibacterium prausnitzii C2863 | 0 | 0 | 44.50454531 |
| 0.23748252 | −0.094755491 | Anaeromassilibacillus sp. Marseille-P3816 C2925 | 0.353693881 | 0 | 44.32727446 |
| 0.553126103 | −0.098634411 | Roseburia intestinalis C2158 | 0.270102529 | 0 | 44.05697948 |
| 0.028683688 | −0.235792289 | Faecalibacterium prausnitzii C2864 | 0 | 0 | 44.01274212 |
| 0.01512723 | −0.229970619 | Firmicutes bacterium AF22-6AC C2933 | 0 | 0 | 43.5096953 |
| 0.299408337 | −0.223572419 | Faecalibacterium prausnitzii C2191 | 0 | 0 | 42.73256973 |
| 0.230520123 | −0.219463054 | Bacteroides finegoldii C0138 | 0 | 0 | 42.46714319 |
| 0.07671217 | −0.209757142 | Lactococcus lactis C3326 | 0 | 0 | 42.1983566 |
| 0.412393028 | −0.209498347 | Bacteroides massiliensis C0310 | 0 | 0 | 41.92610156 |
| 0.004324117 | −0.206044424 | Clostridium sp. AF20-17LB C2921 | 0 | 0 | 41.65026396 |

TABLE 12-continued

Operational species units (OSUs) with a mean abundance of at least 0.05% with significant differences between cancer
and control cohorts for inclusion into the therapeutic. For each OSU, CD3+ and CD3+CD56+ correlations
are included in the table as per the linear mixed model analysis or set to zero if the mixed model correlation
is negative or if the Spearman correlation was not significant enough to necessitate mixed model analysis. The
cancer and control fold change, CD3+ correlation, and CD3+CD56+ correlation for each OSU were converted
to percentile scores, and a combined score for each OSU was generated as the geometric mean of each of the three percentiles.

| p value Control vs Cancer (Mann Whitney U) | log10 Fold Change (Cancer/ Control) | Organism Name (Operational Species Unit) | CD3+ Correlation (Spearman, if significant) | CD3+CD56+ Correlation (Spearman, if significant) | Total Score |
|---|---|---|---|---|---|
| 0.000839149 | −0.201826507 | *Fusicatenibacter saccharivorans* C2643 | 0 | 0 | 41.37072356 |
| 0.171446365 | −0.192935162 | *Clostridium* sp. AF46-9NS C2891 | 0 | 0 | 41.08735355 |
| 0.190921078 | −0.191454148 | *Streptococcus thermophilus* C3480 | 0 | 0 | 40.80002 |
| 0.24012289 | −0.191448288 | [*Clostridium*] *spiroforme* C2146 | 0 | 0 | 40.50858134 |
| 0.238875443 | −0.189503492 | *Holdemanella biformis* C2160 | 0 | 0 | 40.21288772 |
| 0.350722809 | −0.18109626 | *Bifidobacterium longum* C0000 | 0 | 0 | 39.91278036 |
| 0.092953142 | −0.093698754 | *Roseburia* sp. OM04-15AA C2892 | 0.232754614 | 0 | 39.82976685 |
| 0.511730372 | −0.167126002 | Firmicutes bacterium AF36-3BH C2905 | 0 | 0 | 39.60809076 |
| 0.002091197 | −0.163492912 | *Clostridium* sp. AM18-55 C2845 | 0 | 0 | 38.98423732 |
| 0.044817697 | −0.161787704 | *Ruminococcus* sp. AF31-8BH C2903 | 0 | 0 | 38.66468002 |
| 0.163286482 | −0.158568078 | *Bacteroides stercoris* C0134 | 0 | 0 | 38.00921984 |
| 0.196410058 | −0.123209619 | *Coprococcus eutactus* C2642 | 0 | 0 | 36.98143604 |
| 0.645760506 | −0.111096287 | *Eisenbergiella tayi* C2259 | 0 | 0 | 35.51525914 |
| 0.247286492 | −0.107393237 | *Eubacterium saphenum* ATCC 49989 C2183 | 0 | 0 | 35.12919314 |
| 0.194954789 | −0.103823837 | *Eubacterium ramulus* C2442 | 0 | 0 | 33.91686307 |
| 0.072831555 | −0.103576385 | *Bacteroides uniformis* C0132 | 0 | 0 | 33.49285783 |
| 0.568492801 | −0.100055999 | [*Eubacterium*] *siraeum* C2135 | 0 | 0 | 33.05783641 |
| 0.505564788 | −0.096838499 | *Intestinibacter bartlettii* C2141 | 0 | 0 | 32.15168231 |
| 0.083226778 | −0.087543931 | *Blautia obeum* C2901 | 0 | 0 | 30.68817687 |
| 0.025598358 | −0.081852178 | *Ruminococcus* sp. AF24-32LB C2894 | 0 | 0 | 30.16793778 |
| 0.992080795 | −0.077567242 | *Megamonas funiformis* C2294 | 0 | 0 | 29.629109 |
| 0.933770138 | −0.076490222 | *Akkermansia* sp. KLE1605 C1918 | 0 | 0 | 29.06993521 |
| 0.386824312 | −0.074691634 | *Bacteroides nordii* C0263 | 0 | 0 | 28.48837982 |
| 0.085278665 | −0.074297589 | *Blautia wexlerae* C2171 | 0 | 0 | 27.88205907 |
| 0.330051192 | −0.073609518 | *Clostridium* sp. TM06-18 C2922 | 0 | 0 | 27.24815505 |
| 0.083262321 | −0.072959896 | *Candidatus Ishikavaella capsulata* Mpkobe C4922 | 0 | 0 | 26.58329888 |
| 0.683600356 | −0.066234762 | *Parabacteroides goldsteinii* C0282 | 0 | 0 | 25.88341081 |
| 0.643910037 | −0.061735341 | *Alistipes* sp. 5CBH24 C0283 | 0 | 0 | 25.14347607 |
| 0.242773051 | −0.052348168 | *Lachnospira pectinoschiza* C2649 | 0 | 0 | 24.35722212 |
| 0.283452611 | −0.048932599 | *Clostridium* sp. AF34-13 C2653 | 0 | 0 | 23.5166394 |
| 0.792065697 | −0.04739511 | *Catenibacterium mitsuokai* DSM 15897 C2204 | 0 | 0 | 22.61124205 |
| 0.75605445 | −0.045467144 | *Eubacterium* sp. TM06-47 C2917 | 0 | 0 | 21.626875 |
| 0.47084588 | −0.041470873 | *Coprococcus eutactus* C2140 | 0 | 0 | 20.54367678 |
| 0.903395164 | −0.032159744 | *Roseburia faecis* C2648 | 0 | 0 | 19.33234001 |
| 0.776663172 | −0.022510129 | *Bacteroides faecis* C0221 | 0 | 0 | 17.94655471 |
| 0.686897002 | −0.016216198 | *Bacteroides* sp. OF04-15BH C1226 | 0 | 0 | 16.30552706 |
| 0.77256713 | −0.008006904 | *Lawsonibacter asaccharolyticus* C2612 | 0 | 0.303877071 | 14.43735499 |
| 0.226827239 | −0.011837149 | *Bacteroides fragilis* C0096 | 0 | 0 | 14.24418991 |
| 0.804445324 | −0.006154069 | *Odoribacter splanchnicus* C0185 | 0 | 0 | 0 |

Table 13 (illustrated as FIG. 22). Microbe rankings were based on classified species results using the GTDB database with a mean abundance of at least 0.005% with significant differences between cancer and control cohorts for inclusion into the therapeutic (inverse p value, Mann Whitney U test). For each classified species hit, CD3+ and CD3+CD56+ correlations are included in the table as per the linear mixed model analysis or set to zero if the mixed model correlation is negative or if the Spearman correlation was not significant enough to necessitate mixed model analysis. The cancer and control fold change, CD3+ correlation, and CD3+CD56+ correlation for each OSU were converted to percentile scores, and a combined score for each species level hit was generated by computing the geometric mean of each of the three percentiles.

Table 14 (illustrated as FIG. 23). Microbe rankings were based on classified species results using the GTDB database with a mean abundance of at least 0.005% with significant differences between cancer and control cohorts for inclusion into the therapeutic (LDA score, LEfSe). For each classified species hit, CD3+ and CD3+CD56+ correlations are included in the table as per the linear mixed model analysis or set to zero if the mixed model correlation is negative or if the Spearman correlation was not significant enough to necessitate mixed model analysis. The cancer and control fold change, CD3+ correlation, and CD3+CD56+ correlation for each OSU were converted to percentile scores, and a combined score for each species level hit was generated by computing the geometric mean of each of the three percentiles.

Machine Learning for Live Biotherapeutic Design

The top 32 scoring organisms from Example 9 (Table 6) is selected for screening in simulated microbial mixes. Each combination of 4 organisms from the 32 (listed in Table 15, below) is evaluated in silico using the trained machine learning model. For the cancer samples in the model, relative species abundances for the four organisms in the putative mix are increased in silico by a certain amount (here 0.5%). This simulates in silico the physical action of adding microbes to the gut microbiome. Classification is then performed using the machine learning model to estimate the probability that each augmented sample is a cancer sample. The hypothesis is that combinations of microbes that make cancer samples appear more like control samples according to the model are better candidates for therapeutic mixes. Each putative mix is scored by its mean predicted cancer probability across all the augmented cancer samples, with lower mean predicted cancer probabilities corresponding to notionally better therapeutic candidates. The top 30 exemplary live biotherapeutic compositions (exemplary microbial combinations) are then validated experimentally as described in Examples 12, and 16 to 22 as described below.

A similar procedure was then followed by selecting each possible combination of 4 organisms from the top 6 listed in Table 13. These combinations are shown in Table 16.

TABLE 15

List of exemplary live biotherapeutic compositions,
i.e., list of exemplary microbial combinations.

| Mix | Organism Name (Operational Species Unit) |
|---|---|
| 1 | *Bifidobacterium bifidum* C0005 |
| | *Clostridium* sp. AF36-4 C2893 |
| | *Dorea* sp. AM58-8 C2913 |
| | Erysipelotrichaceae bacterium GAM147 C2844 |
| 2 | *Bifidobacterium bifidum* C0005 |
| | *Dorea* sp. AM58-8 C2913 |
| | Erysipelotrichaceae bacterium GAM147 |
| | *Ruminococcus lactaris* C2149 |
| 3 | *Bifidobacterium bifidum* C0005 |
| | *Dorea* sp. AM58-8 C2913 |
| | Erysipelotrichaceae bacterium GAM147 C2844 |
| | Firmicutes bacterium AF12-30 C2644 |
| 4 | *Bifidobacterium bifidum* C0005 |
| | *Dorea* sp. AM58-8 C2913 |
| | Erysipelotrichaceae bacterium GAM147 C2844 |
| | *Ruminococcus* sp. OF03-6AA C2904 |
| 5 | *Bifidobacterium bifidum* C0005 |
| | *Dorea longicatena* C2131 |
| | *Dorea* sp. AM58-8 C2913 |
| | Erysipelotrichaceae bacterium GAM147 C2844 |
| 6 | *Bifidobacterium bifidum* C0005 |
| | *Blautia obeum* C2129 |
| | *Dorea* sp. AM58-8 C2913 |
| | Erysipelotrichaceae bacterium GAM147 C2844 |
| 7 | *Bifidobacterium bifidum* C0005 |
| | *Coprococcus comes* C2152 |
| | *Dorea* sp. AM58-8 C2913 |
| | Erysipelotrichaceae bacterium GAM147 C2844 |
| 8 | *Clostridium* sp. AF36-4 C2893 |
| | *Dorea* sp. AM58-8 C2913 |
| | Erysipelotrichaceae bacterium GAM147 C2844 |
| | *Ruminococcus lactaris* C2149 |
| 9 | *Clostridium* sp. AF36-4 C2893 |
| | *Dorea* sp. AM58-8 C2913 |
| | Erysipelotrichaceae bacterium GAM147 C2844 |
| | Firmicutes bacterium AF12-30 C2644 |
| 10 | *Clostridium* sp. AF36-4 C2893 |
| | *Dorea* sp. AM58-8 C2913 |
| | Erysipelotrichaceae bacterium GAM147 C2844 |
| | *Ruminococcus* sp. OF03-6AA C2904 |
| 11 | *Clostridium* sp. AF36-4 C2893 |
| | *Dorea longicatena* C2131 |
| | *Dorea* sp. AM58-8 C2913 |
| | Erysipelotrichaceae bacterium GAM147 C2844 |
| 12 | *Blautia obeum* C2129 |
| | *Clostridium* sp. AF36-4 C2893 |
| | *Dorea* sp. AM58-8 C2913 |
| | Erysipelotrichaceae bacterium GAM147 C2844 |
| 13 | *Clostridium* sp. AF36-4 C2893 |
| | *Coprococcus comes* C2152 |
| | *Dorea* sp. AM58-8 C2913 |
| | Erysipelotrichaceae bacterium GAM147 C2844 |
| 14 | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| 15 | *Dorea* sp. AM58-8 C2913 |
| | Erysipelotrichaceae bacterium GAM147 C2844 |
| | *Ruminococcus lactaris* C2149 |
| | *Ruminococcus* sp. OF03-6AA C2904 |

TABLE 15-continued

List of exemplary live biotherapeutic compositions,
i.e., list of exemplary microbial combinations.

| Mix | Organism Name (Operational Species Unit) |
|---|---|
| 16 | *Dorea longicatena* C2131 |
| | *Dorea* sp. AM58-8 C2913 |
| | Erysipelotrichaceae bacterium GAM147 C2844 |
| | *Ruminococcus lactaris* C2149 |
| 17 | *Blautia obeum* C2129 |
| | *Dorea* sp. AM58-8 C2913 |
| | Erysipelotrichaceae bacterium GAM147 C2844 |
| | *Ruminococcus lactaris* C2149 |
| 18 | *Coprococcus comes* C2152 |
| | *Dorea* sp. AM58-8 C2913 |
| | Erysipelotrichaceae bacterium GAM147 C2844 |
| | *Ruminococcus lactaris* C2149 |
| 19 | *Dorea* sp. AM58-8 C2913 |
| | Erysipelotrichaceae bacterium GAM147 C2844 |
| | Firmicutes bacterium AF12-30 C2644 |
| | *Ruminococcus* sp. OF03-6AA C2904 |
| 20 | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| 21 | *Blautia obeum* C2129 |
| | *Dorea* sp. AM58-8 C2913 |
| | Erysipelotrichaceae bacterium GAM147 C2844 |
| | Firmicutes bacterium AF12-30 C2644 |
| 22 | *Coprococcus comes* C2152 |
| | *Dorea* sp. AM58-8 C2913 |
| | Erysipelotrichaceae bacterium GAM147 C2844 |
| | Firmicutes bacterium AF12-30 C2644 |
| 23 | *Dorea longicatena* C2131 |
| | *Dorea* sp. AM58-8 C2913 |
| | Erysipelotrichaceae bacterium GAM147 C2844 |
| | *Ruminococcus* sp. OF03-6AA C2904 |
| 24 | *Blautia obeum* C2129 |
| | *Dorea* sp. AM58-8 C2913 |
| | Erysipelotrichaceae bacterium GAM147 C2844 |
| | *Ruminococcus* sp. OF03-6AA C2904 |
| 25 | *Coprococcus comes* C2152 |
| | *Dorea* sp. AM58-8 C2913 |
| | Erysipelotrichaceae bacterium GAM147 C2844 |
| | *Ruminococcus* sp. OF03-6AA C2904 |
| 26 | *Blautia obeum* C2129 |
| | *Dorea longicatena* C2131 |
| | *Dorea* sp. AM58-8 C2913 |
| | Erysipelotrichaceae bacterium GAM147 C2844 |
| 27 | *Coprococcus comes* C2152 |
| | *Dorea longicatena* C2131 |
| | *Dorea* sp. AM58-8 C2913 |
| | Erysipelotrichaceae bacterium GAM147 C2844 |
| 28 | *Blautia obeum* C2129 |
| | *Coprococcus comes* C2152 |
| | *Dorea* sp. AM58-8 C2913 |
| | Erysipelotrichaceae bacterium GAM147 C2844 |
| 29 | *Bifidobacterium bifidum* C0005 |
| | *Clostridium* sp. AF36-4 C2893 |
| | Erysipelotrichaceae bacterium GAM147 C2844 |
| | *Ruminococcus lactaris* C2149 |
| 30 | *Bifidobacterium bifidum* C0005 |
| | *Clostridium* sp. AF36-4 C2893 |
| | Erysipelotrichaceae bacterium GAM147 C2844 |
| | Firmicutes bacterium AF12-30 C2644 |
| 31 | *Bifidobacterium bifidum* C0005 |
| | *Clostridium* sp. AF36-4 C2893 |
| | Erysipelotrichaceae bacterium GAM147 C2844 |
| | *Ruminococcus* sp. OF03-6AA C2904 |
| 32 | *Bifidobacterium bifidum* C0005 |
| | *Clostridium* sp. AF36-4 C2893 |
| | *Dorea longicatena* C2131 |
| | Erysipelotrichaceae bacterium GAM147 C2844 |
| 33 | *Bifidobacterium bifidum* C0005 |
| | *Blautia obeum* C2129 |
| | *Clostridium* sp. AF36-4 C2893 |
| | Erysipelotrichaceae bacterium GAM147 C2844 |

TABLE 15-continued

List of exemplary live biotherapeutic compositions,
i.e., list of exemplary microbial combinations.

| Mix | Organism Name (Operational Species Unit) |
|---|---|
| 34 | *Bifidobacterium bifidum* C0005<br>*Clostridium* sp. AF36-4 C2893<br>*Coprococcus comes* C2152<br>Erysipelotrichaceae bacterium GAM147 C2844 |
| 35 | *Bifidobacterium bifidum* C0005<br>Erysipelotrichaceae bacterium GAM147 C2844<br>Firmicutes bacterium AF12-30 C2644<br>*Ruminococcus lactaris* C2149 |
| 36 | *Bifidobacterium bifidum* C0005<br>Erysipelotrichaceae bacterium GAM147 C2844<br>*Ruminococcus lactaris* C2149<br>*Ruminococcus* sp. OF03-6AA C2904 |
| 37 | *Bifidobacterium bifidum* C0005<br>*Dorea longicatena* C2131<br>Erysipelotrichaceae bacterium GAM147 C2844<br>*Ruminococcus lactaris* C2149 |
| 38 | *Bifidobacterium bifidum* C0005<br>*Blautia obeum* C2129<br>Erysipelotrichaceae bacterium GAM147 C2844<br>*Ruminococcus lactaris* C2149 |
| 39 | *Bifidobacterium bifidum* C0005<br>*Coprococcus comes* C2152<br>Erysipelotrichaceae bacterium GAM147 C2844<br>*Ruminococcus lactaris* C2149 |
| 40 | *Bifidobacterium bifidum* C0005<br>Erysipelotrichaceae bacterium GAM147 C2844<br>Firmicutes bacterium AF12-30 C2644<br>*Ruminococcus* sp. OF03-6AA C2904 |
| 41 | *Bifidobacterium bifidum* C0005<br>*Dorea longicatena* C2131<br>Erysipelotrichaceae bacterium GAM147 C2844<br>Firmicutes bacterium AF12-30 C2644 |
| 42 | *Bifidobacterium bifidum* C0005<br>*Blautia obeum* C2129<br>Erysipelotrichaceae bacterium GAM147 C2844<br>Firmicutes bacterium AF12-30 C2644 |
| 43 | *Bifidobacterium bifidum* C0005<br>*Coprococcus comes* C2152<br>Erysipelotrichaceae bacterium GAM147 C2844<br>Firmicutes bacterium AF12-30 C2644 |
| 44 | *Bifidobacterium bifidum* C0005<br>*Dorea longicatena* C2131<br>Erysipelotrichaceae bacterium GAM147 C2844<br>*Ruminococcus* sp. OF03-6AA C2904 |
| 45 | *Bifidobacterium bifidum* C0005<br>*Blautia obeum* C2129<br>Erysipelotrichaceae bacterium GAM147 C2844<br>*Ruminococcus* sp. OF03-6AA C2904 |
| 46 | *Bifidobacterium bifidum* C0005<br>*Coprococcus comes* C2152<br>Erysipelotrichaceae bacterium GAM147 C2844<br>*Ruminococcus* sp. OF03-6AA C2904 |
| 47 | *Bifidobacterium bifidum* C0005<br>*Blautia obeum* C2129<br>*Dorea longicatena* C2131<br>Erysipelotrichaceae bacterium GAM147 C2844 |
| 48 | *Bifidobacterium bifidum* C0005<br>*Coprococcus comes* C2152<br>*Dorea longicatena* C2131<br>Erysipelotrichaceae bacterium GAM147 C2844 |
| 49 | *Bifidobacterium bifidum* C0005<br>*Blautia obeum* C2129<br>*Coprococcus comes* C2152<br>Erysipelotrichaceae bacterium GAM147 C2844 |
| 50 | *Clostridium* sp. AF36-4 C2893<br>Erysipelotrichaceae bacterium GAM147 C2844<br>Firmicutes bacterium AF12-30 C2644<br>*Ruminococcus lactaris* C2149 |
| 51 | *Clostridium* sp. AF36-4 C2893<br>Erysipelotrichaceae bacterium GAM147 C2844<br>*Ruminococcus lactaris* C2149<br>*Ruminococcus* sp. OF03-6AA C2904 |

TABLE 15-continued

List of exemplary live biotherapeutic compositions,
i.e., list of exemplary microbial combinations.

| Mix | Organism Name (Operational Species Unit) |
|---|---|
| 52 | *Clostridium* sp. AF36-4 C2893<br>*Dorea longicatena* C2131<br>Erysipelotrichaceae bacterium GAM147 C2844<br>*Ruminococcus lactaris* C2149 |
| 53 | *Blautia obeum* C2129<br>*Clostridium* sp. AF36-4 C2893<br>Erysipelotrichaceae bacterium GAM147 C2844<br>*Ruminococcus lactaris* C2149 |
| 54 | *Clostridium* sp. AF36-4 C2893<br>*Coprococcus comes* C2152<br>Erysipelotrichaceae bacterium GAM147 C2844<br>*Ruminococcus lactaris* C2149 |
| 55 | *Clostridium* sp. AF36-4 C2893<br>Erysipelotrichaceae bacterium GAM147 C2844<br>Firmicutes bacterium AF12-30 C2644<br>*Ruminococcus* sp. OF03-6AA C2904 |
| 56 | *Clostridium* sp. AF36-4 C2893<br>*Dorea longicatena* C2131<br>Erysipelotrichaceae bacterium GAM147 C2844<br>Firmicutes bacterium AF12-30 C2644 |
| 57 | *Blautia obeum* C2129<br>*Clostridium* sp. AF36-4 C2893<br>Erysipelotrichaceae bacterium GAM147 C2844<br>Firmicutes bacterium AF12-30 C2644 |
| 58 | *Clostridium* sp. AF36-4 C2893<br>*Coprococcus comes* C2152<br>Erysipelotrichaceae bacterium GAM147 C2844<br>Firmicutes bacterium AF12-30 C2644 |
| 59 | *Clostridium* sp. AF36-4 C2893<br>*Dorea longicatena* C2131<br>Erysipelotrichaceae bacterium GAM147 C2844<br>*Ruminococcus* sp. OF03-6AA C2904 |
| 60 | *Blautia obeum* C2129<br>*Clostridium* sp. AF36-4 C2893<br>Erysipelotrichaceae bacterium GAM147 C2844<br>*Ruminococcus* sp. OF03-6AA C2904 |
| 61 | *Clostridium* sp. AF36-4 C2893<br>*Coprococcus comes* C2152<br>Erysipelotrichaceae bacterium GAM147 C2844<br>*Ruminococcus* sp. OF03-6AA C2904 |
| 62 | *Blautia obeum* C2129<br>*Clostridium* sp. AF36-4 C2893<br>*Dorea longicatena* C2131<br>Erysipelotrichaceae bacterium GAM147 C2844 |
| 63 | *Clostridium* sp. AF36-4 C2893<br>*Coprococcus comes* C2152<br>*Dorea longicatena* C2131<br>Erysipelotrichaceae bacterium GAM147 C2844 |
| 64 | *Blautia obeum* C2129<br>*Clostridium* sp. AF36-4 C2893<br>*Coprococcus comes* C2152<br>Erysipelotrichaceae bacterium GAM147 C2844 |
| 65 | Erysipelotrichaceae bacterium GAM147 C2844<br>Firmicutes bacterium AF12-30 C2644<br>*Ruminococcus lactaris* C2149<br>*Ruminococcus* sp. OF03-6AA C2904 |
| 66 | *Dorea longicatena* C2131<br>Erysipelotrichaceae bacterium GAM147 C2844<br>Firmicutes bacterium AF12-30 C2644<br>*Ruminococcus lactaris* C2149 |
| 67 | *Blautia obeum* C2129<br>Erysipelotrichaceae bacterium GAM147 C2844<br>Firmicutes bacterium AF12-30 C2644<br>*Ruminococcus lactaris* C2149 |
| 68 | *Coprococcus comes* C2152<br>Erysipelotrichaceae bacterium GAM147 C2844<br>Firmicutes bacterium AF12-30 C2644<br>*Ruminococcus lactaris* C2149 |
| 69 | *Dorea longicatena* C2131<br>Erysipelotrichaceae bacterium GAM147 C2844<br>*Ruminococcus lactaris* C2149<br>*Ruminococcus* sp. OF03-6AA C2904 |

TABLE 15-continued

List of exemplary live biotherapeutic compositions,
i.e., list of exemplary microbial combinations.

| Mix | Organism Name (Operational Species Unit) |
|---|---|
| 70 | *Blautia obeum* C2129 |
| | Erysipelotrichaceae bacterium GAM147 C2844 |
| | *Ruminococcus lactaris* C2149 |
| | *Ruminococcus* sp. OF03-6AA C2904 |
| 71 | *Coprococcus comes* C2152 |
| | Erysipelotrichaceae bacterium GAM147 C2844 |
| | *Ruminococcus lactaris* C2149 |
| | *Ruminococcus* sp. OF03-6AA C2904 |
| 72 | *Blautia obeum* C2129 |
| | *Dorea longicatena* C2131 |
| | Erysipelotrichaceae bacterium GAM147 C2844 |
| | *Ruminococcus lactaris* C2149 |
| 73 | *Coprococcus comes* C2152 |
| | *Dorea longicatena* C2131 |
| | Erysipelotrichaceae bacterium GAM147 C2844 |
| | *Ruminococcus lactaris* C2149 |
| 74 | *Blautia obeum* C2129 |
| | *Coprococcus comes* C2152 |
| | Erysipelotrichaceae bacterium GAM147 C2844 |
| | *Ruminococcus lactaris* C2149 |
| 75 | *Dorea longicatena* C2131 |
| | Erysipelotrichaceae bacterium GAM147 C2844 |
| | Firmicutes bacterium AF12-30 C2644 |
| | *Ruminococcus* sp. OF03-6AA C2904 |
| 76 | *Blautia obeum* C2129 |
| | Erysipelotrichaceae bacterium GAM147 C2844 |
| | Firmicutes bacterium AF12-30 C2644 |
| | *Ruminococcus* sp. OF03-6AA C2904 |
| 77 | *Coprococcus comes* C2152 |
| | Erysipelotrichaceae bacterium GAM147 C2844 |
| | Firmicutes bacterium AF12-30 C2644 |
| | *Ruminococcus* sp. OF03-6AA C2904 |
| 78 | *Blautia obeum* C2129 |
| | *Dorea longicatena* C2131 |
| | Erysipelotrichaceae bacterium GAM147 C2844 |
| | Firmicutes bacterium AF12-30 C2644 |
| 79 | *Coprococcus comes* C2152 |
| | *Dorea longicatena* C2131 |
| | Erysipelotrichaceae bacterium GAM147 C2844 |
| | Firmicutes bacterium AF12-30 C2644 |
| 80 | *Blautia obeum* C2129 |
| | *Coprococcus comes* C2152 |
| | Erysipelotrichaceae bacterium GAM147 C2844 |
| | Firmicutes bacterium AF12-30 C2644 |
| 81 | *Blautia obeum* C2129 |
| | *Dorea longicatena* C2131 |
| | Erysipelotrichaceae bacterium GAM147 C2844 |
| | *Ruminococcus* sp. OF03-6AA C2904 |
| 82 | *Coprococcus comes* C2152 |
| | *Dorea longicatena* C2131 |
| | Erysipelotrichaceae bacterium GAM147 C2844 |
| | *Ruminococcus* sp. OF03-6AA C2904 |
| 83 | *Blautia obeum* C2129 |
| | *Coprococcus comes* C2152 |
| | Erysipelotrichaceae bacterium GAM147 C2844 |
| | *Ruminococcus* sp. OF03-6AA C2904 |
| 84 | *Blautia obeum* C2129 |
| | *Coprococcus comes* C2152 |
| | *Dorea longicatena* C2131 |
| | Erysipelotrichaceae bacterium GAM147 C2844 |
| 85 | *Bifidobacterium bifidum* C0005 |
| | *Clostridium* sp. AF36-4 C2893 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| 86 | *Bifidobacterium bifidum* C0005 |
| | *Clostridium* sp. AF36-4 C2893 |
| | *Dorea* sp. AM58-8 C2913 |
| | Erysipelotrichaceae bacterium GAM147 C2844 |
| | *Ruminococcus lactaris* C2149 |
| | *Ruminococcus* sp. OF03-6AA C2904 |

TABLE 15-continued

List of exemplary live biotherapeutic compositions,
i.e., list of exemplary microbial combinations.

| Mix | Organism Name (Operational Species Unit) |
|---|---|
| 87 | *Bifidobacterium bifidum* C0005 |
| | *Clostridium* sp. AF36-4 C2893 |
| | *Dorea longicatena* C2131 |
| | *Dorea* sp. AM58-8 C2913 |
| | Erysipelotrichaceae bacterium GAM147 C2844 |
| | *Ruminococcus lactaris* C2149 |
| 88 | *Bifidobacterium bifidum* C0005 |
| | *Blautia obeum* C2129 |
| | *Clostridium* sp. AF36-4 C2893 |
| | *Dorea* sp. AM58-8 C2913 |
| | Erysipelotrichaceae bacterium GAM147 C2844 |
| | *Ruminococcus lactaris* C2149 |
| 89 | *Bifidobacterium bifidum* C0005 |
| | *Clostridium* sp. AF36-4 C2893 |
| | *Coprococcus comes* C2152 |
| | *Dorea* sp. AM58-8 C2913 |
| | Erysipelotrichaceae bacterium GAM147 C2844 |
| | *Ruminococcus lactaris* C2149 |
| 90 | *Bifidobacterium bifidum* C0005 |
| | *Clostridium* sp. AF36-4 C2893 |
| | *Dorea* sp. AM58-8 C2913 |
| | Erysipelotrichaceae bacterium GAM147 C2844 |
| | Firmicutes bacterium AF12-30 C2644 |
| | *Ruminococcus* sp. OF03-6AA C2904 |
| 91 | *Bifidobacterium bifidum* C0005 |
| | *Clostridium* sp. AF36-4 C2893 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| 92 | *Bifidobacterium bifidum* C0005 |
| | *Blautia obeum* C2129 |
| | *Clostridium* sp. AF36-4 C2893 |
| | *Dorea* sp. AM58-8 C2913 |
| | Erysipelotrichaceae bacterium GAM147 C2844 |
| | Firmicutes bacterium AF12-30 C2644 |
| 93 | *Bifidobacterium bifidum* C0005 |
| | *Clostridium* sp. AF36-4 C2893 |
| | *Coprococcus comes* C2152 |
| | *Dorea* sp. AM58-8 C2913 |
| | Erysipelotrichaceae bacterium GAM147 C2844 |
| | Firmicutes bacterium AF12-30 C2644 |
| 94 | *Bifidobacterium bifidum* C0005 |
| | *Clostridium* sp. AF36-4 C2893 |
| | *Dorea longicatena* C2131 |
| | *Dorea* sp. AM58-8 C2913 |
| | Erysipelotrichaceae bacterium GAM147 C2844 |
| | *Ruminococcus* sp. OF03-6AA C2904 |
| 95 | *Bifidobacterium bifidum* C0005 |
| | *Blautia obeum* C2129 |
| | *Clostridium* sp. AF36-4 C2893 |
| | *Dorea* sp. AM58-8 C2913 |
| | Erysipelotrichaceae bacterium GAM147 C2844 |
| | *Ruminococcus* sp. OF03-6AA C2904 |
| 96 | *Bifidobacterium bifidum* C0005 |
| | *Clostridium* sp. AF36-4 C2893 |
| | *Coprococcus comes* C2152 |
| | *Dorea* sp. AM58-8 C2913 |
| | Erysipelotrichaceae bacterium GAM147 C2844 |
| | *Ruminococcus* sp. OF03-6AA C2904 |
| 97 | *Bifidobacterium bifidum* C0005 |
| | *Blautia obeum* C2129 |
| | *Clostridium* sp. AF36-4 C2893 |
| | *Dorea longicatena* C2131 |
| | *Dorea* sp. AM58-8 C2913 |
| | Erysipelotrichaceae bacterium GAM147 C2844 |
| 98 | *Bifidobacterium bifidum* C0005 |
| | *Clostridium* sp. AF36-4 C2893 |
| | *Coprococcus comes* C2152 |
| | *Dorea longicatena* C2131 |
| | *Dorea* sp. AM58-8 C2913 |
| | Erysipelotrichaceae bacterium GAM147 C2844 |

TABLE 15-continued

List of exemplary live biotherapeutic compositions,
i.e., list of exemplary microbial combinations.

| Mix | Organism Name (Operational Species Unit) |
|---|---|
| 99 | *Bifidobacterium bifidum* C0005 |
| | *Blautia obeum* C2129 |
| | *Clostridium* sp. AF36-4 C2893 |
| | *Coprococcus comes* C2152 |
| | *Dorea* sp. AM58-8 C2913 |
| | Erysipelotrichaceae bacterium GAM147 C2844 |
| 100 | *Bifidobacterium bifidum* C0005 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 101 | *Bifidobacterium bifidum* C0005 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| 102 | *Bifidobacterium bifidum* C0005 |
| | *Blautia obeum* C2129 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| 103 | *Bifidobacterium bifidum* C0005 |
| | *Coprococcus comes* C2152 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| 104 | *Bifidobacterium bifidum* C0005 |
| | *Dorea longicatena* C2131 |
| | *Dorea* sp. AM58-8 C2913 |
| | Erysipelotrichaceae bacterium GAM147 C2844 |
| | *Ruminococcus lactaris* C2149 |
| | *Ruminococcus* sp. OF03-6AA C2904 |
| 105 | *Bifidobacterium bifidum* C0005 |
| | *Blautia obeum* C2129 |
| | *Dorea* sp. AM58-8 C2913 |
| | Erysipelotrichaceae bacterium GAM147 C2844 |
| | *Ruminococcus lactaris* C2149 |
| | *Ruminococcus* sp. OF03-6AA C2904 |
| 106 | *Bifidobacterium bifidum* C0005 |
| | *Coprococcus comes* C2152 |
| | *Dorea* sp. AM58-8 C2913 |
| | Erysipelotrichaceae bacterium GAM147 C2844 |
| | *Ruminococcus lactaris* C2149 |
| | *Ruminococcus* sp. OF03-6AA C2904 |
| 107 | *Bifidobacterium bifidum* C0005 |
| | *Blautia obeum* C2129 |
| | *Dorea longicatena* C2131 |
| | *Dorea* sp. AM58-8 C2913 |
| | Erysipelotrichaceae bacterium GAM147 C2844 |
| | *Ruminococcus lactaris* C2149 |
| 108 | *Bifidobacterium bifidum* C0005 |
| | *Coprococcus comes* C2152 |
| | *Dorea longicatena* C2131 |
| | *Dorea* sp. AM58-8 C2913 |
| | Erysipelotrichaceae bacterium GAM147 C2844 |
| | *Ruminococcus lactaris* C2149 |
| 109 | *Bifidobacterium bifidum* C0005 |
| | *Blautia obeum* C2129 |
| | *Coprococcus comes* C2152 |
| | *Dorea* sp. AM58-8 C2913 |
| | Erysipelotrichaceae bacterium GAM147 C2844 |
| | *Ruminococcus lactaris* C2149 |
| 110 | *Bifidobacterium bifidum* C0005 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| | *Ruminococcus* sp. OF03-6AA C2904 |

TABLE 15-continued

List of exemplary live biotherapeutic compositions,
i.e., list of exemplary microbial combinations.

| Mix | Organism Name (Operational Species Unit) |
|---|---|
| 111 | *Bifidobacterium bifidum* C0005 |
| | *Blautia obeum* C2129 |
| | *Dorea* sp. AM58-8 C2913 |
| | Erysipelotrichaceae bacterium GAM147 C2844 |
| | Firmicutes bacterium AF12-30 C2644 |
| | *Ruminococcus* sp. OF03-6AA C2904 |
| 112 | *Bifidobacterium bifidum* C0005 |
| | *Coprococcus comes* C2152 |
| | *Dorea* sp. AM58-8 C2913 |
| | Erysipelotrichaceae bacterium GAM147 C2844 |
| | Firmicutes bacterium AF12-30 C2644 |
| | *Ruminococcus* sp. OF03-6AA C2904 |
| 113 | *Bifidobacterium bifidum* C0005 |
| | *Blautia obeum* C2129 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| 114 | *Bifidobacterium bifidum* C0005 |
| | *Coprococcus comes* C2152 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| 115 | *Bifidobacterium bifidum* C0005 |
| | *Blautia obeum* C2129 |
| | *Coprococcus comes* C2152 |
| | *Dorea* sp. AM58-8 C2913 |
| | Erysipelotrichaceae bacterium GAM147 C2844 |
| | Firmicutes bacterium AF12-30 C2644 |
| 116 | *Bifidobacterium bifidum* C0005 |
| | *Blautia obeum* C2129 |
| | *Dorea longicatena* C2131 |
| | *Dorea* sp. AM58-8 C2913 |
| | Erysipelotrichaceae bacterium GAM147 C2844 |
| | *Ruminococcus* sp. OF03-6AA C2904 |
| 117 | *Bifidobacterium bifidum* C0005 |
| | *Coprococcus comes* C2152 |
| | *Dorea longicatena* C2131 |
| | *Dorea* sp. AM58-8 C2913 |
| | Erysipelotrichaceae bacterium GAM147 C2844 |
| | *Ruminococcus* sp. OF03-6AA C2904 |
| 118 | *Bifidobacterium bifidum* C0005 |
| | *Blautia obeum* C2129 |
| | *Coprococcus comes* C2152 |
| | *Dorea* sp. AM58-8 C2913 |
| | Erysipelotrichaceae bacterium GAM147 C2844 |
| | *Ruminococcus* sp. OF03-6AA C2904 |
| 119 | *Bifidobacterium bifidum* C0005 |
| | *Blautia obeum* C2129 |
| | *Coprococcus comes* C2152 |
| | *Dorea longicatena* C2131 |
| | *Dorea* sp. AM58-8 C2913 |
| | Erysipelotrichaceae bacterium GAM147 C2844 |
| 120 | *Clostridium* sp. AF36-4 C2893 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 121 | *Clostridium* sp. AF36-4 C2893 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| 122 | *Blautia obeum* C2129 |
| | *Clostridium* sp. AF36-4 C2893 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |

TABLE 15-continued

List of exemplary live biotherapeutic compositions,
i.e., list of exemplary microbial combinations.

| Mix | Organism Name (Operational Species Unit) |
|---|---|
| 123 | *Clostridium* sp. AF36-4 C2893 |
| | *Coprococcus comes* C2152 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| 124 | *Clostridium* sp. AF36-4 C2893 |
| | *Dorea longicatena* C2131 |
| | *Dorea* sp. AM58-8 C2913 |
| | Erysipelotrichaceae bacterium GAM147 C2844 |
| | *Ruminococcus lactaris* C2149 |
| | *Ruminococcus* sp. OF03-6AA C2904 |
| 125 | *Blautia obeum* C2129 |
| | *Clostridium* sp. AF36-4 C2893 |
| | *Dorea* sp. AM58-8 C2913 |
| | Erysipelotrichaceae bacterium GAM147 C2844 |
| | *Ruminococcus lactaris* C2149 |
| | *Ruminococcus* sp. OF03-6AA C2904 |
| 126 | *Clostridium* sp. AF36-4 C2893 |
| | *Coprococcus comes* C2152 |
| | *Dorea* sp. AM58-8 C2913 |
| | Erysipelotrichaceae bacterium GAM147 C2844 |
| | *Ruminococcus lactaris* C2149 |
| | *Ruminococcus* sp. OF03-6AA C2904 |
| 127 | *Blautia obeum* C2129 |
| | *Clostridium* sp. AF36-4 C2893 |
| | *Dorea longicatena* C2131 |
| | *Dorea* sp. AM58-8 C2913 |
| | Erysipelotrichaceae bacterium GAM147 C2844 |
| | *Ruminococcus lactaris* C2149 |
| 128 | *Clostridium* sp. AF36-4 C2893 |
| | *Coprococcus comes* C2152 |
| | *Dorea longicatena* C2131 |
| | *Dorea* sp. AM58-8 C2913 |
| | Erysipelotrichaceae bacterium GAM147 C2844 |
| | *Ruminococcus lactaris* C2149 |
| 129 | *Blautia obeum* C2129 |
| | *Clostridium* sp. AF36-4 C2893 |
| | *Coprococcus comes* C2152 |
| | *Dorea* sp. AM58-8 C2913 |
| | Erysipelotrichaceae bacterium GAM147 C2844 |
| | *Ruminococcus lactaris* C2149 |
| 130 | *Clostridium* sp. AF36-4 C2893 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| | *Ruminococcus* sp. OF03-6AA C2904 |
| 131 | *Blautia obeum* C2129 |
| | *Clostridium* sp. AF36-4 C2893 |
| | *Dorea* sp. AM58-8 C2913 |
| | Erysipelotrichaceae bacterium GAM147 C2844 |
| | Firmicutes bacterium AF12-30 C2644 |
| | *Ruminococcus* sp. OF03-6AA C2904 |
| 132 | *Clostridium* sp. AF36-4 C2893 |
| | *Coprococcus comes* C2152 |
| | *Dorea* sp. AM58-8 C2913 |
| | Erysipelotrichaceae bacterium GAM147 C2844 |
| | Firmicutes bacterium AF12-30 C2644 |
| | *Ruminococcus* sp. OF03-6AA C2904 |
| 133 | *Blautia obeum* C2129 |
| | *Clostridium* sp. AF36-4 C2893 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| 134 | *Clostridium* sp. AF36-4 C2893 |
| | *Coprococcus comes* C2152 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |

TABLE 15-continued

List of exemplary live biotherapeutic compositions,
i.e., list of exemplary microbial combinations.

| Mix | Organism Name (Operational Species Unit) |
|---|---|
| 135 | *Blautia obeum* C2129 |
| | *Clostridium* sp. AF36-4 C2893 |
| | *Coprococcus comes* C2152 |
| | *Dorea* sp. AM58-8 C2913 |
| | Erysipelotrichaceae bacterium GAM147 C2844 |
| | Firmicutes bacterium AF12-30 C2644 |
| 136 | *Blautia obeum* C2129 |
| | *Clostridium* sp. AF36-4 C2893 |
| | *Dorea longicatena* C2131 |
| | *Dorea* sp. AM58-8 C2913 |
| | Erysipelotrichaceae bacterium GAM147 C2844 |
| | *Ruminococcus* sp. OF03-6AA C2904 |
| 137 | *Clostridium* sp. AF36-4 C2893 |
| | *Coprococcus comes* C2152 |
| | *Dorea longicatena* C2131 |
| | *Dorea* sp. AM58-8 C2913 |
| | Erysipelotrichaceae bacterium GAM147 C2844 |
| | *Ruminococcus* sp. OF03-6AA C2904 |
| 138 | *Blautia obeum* C2129 |
| | *Clostridium* sp. AF36-4 C2893 |
| | *Coprococcus comes* C2152 |
| | *Dorea* sp. AM58-8 C2913 |
| | Erysipelotrichaceae bacterium GAM147 C2844 |
| | *Ruminococcus* sp. OF03-6AA C2904 |
| 139 | *Blautia obeum* C2129 |
| | *Clostridium* sp. AF36-4 C2893 |
| | *Coprococcus comes* C2152 |
| | *Dorea longicatena* C2131 |
| | *Dorea* sp. AM58-8 C2913 |
| | Erysipelotrichaceae bacterium GAM147 C2844 |
| 140 | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 141 | *Blautia obeum* C2129 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 142 | *Coprococcus comes* C2152 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 143 | *Blautia obeum* C2129 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| 144 | *Coprococcus comes* C2152 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| 145 | *Blautia obeum* C2129 |
| | *Coprococcus comes* C2152 |
| | *Dorea* sp. AM58-8 C2913 |
| | Erysipelotrichaceae bacterium GAM147 C2844 |
| | Firmicutes bacterium AF12-30 C2644 |
| | *Ruminococcus lactaris* C2149 |
| 146 | *Blautia obeum* C2129 |
| | *Dorea longicatena* C2131 |
| | *Dorea* sp. AM58-8 C2913 |
| | Erysipelotrichaceae bacterium GAM147 C2844 |
| | *Ruminococcus lactaris* C2149 |
| | *Ruminococcus* sp. OF03-6AA C2904 |

TABLE 15-continued

List of exemplary live biotherapeutic compositions,
i.e., list of exemplary microbial combinations.

| Mix | Organism Name (Operational Species Unit) |
|---|---|
| 147 | *Coprococcus comes* C2152 |
| | *Dorea longicatena* C2131 |
| | *Dorea* sp. AM58-8 C2913 |
| | Erysipelotrichaceae bacterium GAM147 C2844 |
| | *Ruminococcus lactaris* C2149 |
| | *Ruminococcus* sp. OF03-6AA C2904 |
| 148 | *Blautia obeum* C2129 |
| | *Coprococcus comes* C2152 |
| | *Dorea* sp. AM58-8 C2913 |
| | Erysipelotrichaceae bacterium GAM147 C2844 |
| | *Ruminococcus lactaris* C2149 |
| | *Ruminococcus* sp. OF03-6AA C2904 |
| 149 | *Blautia obeum* C2129 |
| | *Coprococcus comes* C2152 |
| | *Dorea longicatena* C2131 |
| | *Dorea* sp. AM58-8 C2913 |
| | Erysipelotrichaceae bacterium GAM147 C2844 |
| | *Ruminococcus lactaris* C2149 |
| 150 | *Blautia obeum* C2129 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| | *Ruminococcus* sp. OF03-6AA C2904 |
| 151 | *Coprococcus comes* C2152 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| | *Ruminococcus* sp. OF03-6AA C2904 |
| 152 | *Blautia obeum* C2129 |
| | *Coprococcus comes* C2152 |
| | *Dorea* sp. AM58-8 C2913 |
| | Erysipelotrichaceae bacterium GAM147 C2844 |
| | Firmicutes bacterium AF12-30 C2644 |
| | *Ruminococcus* sp. OF03-6AA C2904 |
| 153 | *Blautia obeum* C2129 |
| | *Coprococcus comes* C2152 |
| | *Dorea longicatena* C2131 |
| | *Dorea* sp. AM58-8 C2913 |
| | Erysipelotrichaceae bacterium GAM147 C2844 |
| | Firmicutes bacterium AF12-30 C2644 |
| 154 | *Blautia obeum* C2129 |
| | *Coprococcus comes* C2152 |
| | *Dorea longicatena* C2131 |
| | *Dorea* sp. AM58-8 C2913 |
| | Erysipelotrichaceae bacterium GAM147 C2844 |
| | *Ruminococcus* sp. OF03-6AA C2904 |
| 155 | *Bifidobacterium bifidum* C0005 |
| | *Clostridium* sp. AF36-4 C2893 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 156 | *Bifidobacterium bifidum* C0005 |
| | *Clostridium* sp. AF36-4 C2893 |
| | *Dorea longicatena* C2131 |
| | Erysipelotrichaceae bacterium GAM147 C2844 |
| | Firmicutes bacterium AF12-30 C2644 |
| | *Ruminococcus lactaris* C2149 |
| 157 | *Bifidobacterium bifidum* C0005 |
| | *Blautia obeum* C2129 |
| | *Clostridium* sp. AF36-4 C2893 |
| | Erysipelotrichaceae bacterium GAM147 C2844 |
| | Firmicutes bacterium AF12-30 C2644 |
| | *Ruminococcus lactaris* C2149 |
| 158 | *Bifidobacterium bifidum* C0005 |
| | *Clostridium* sp. AF36-4 C2893 |
| | *Coprococcus comes* C2152 |
| | Erysipelotrichaceae bacterium GAM147 C2844 |
| | Firmicutes bacterium AF12-30 C2644 |
| | *Ruminococcus lactaris* C2149 |

TABLE 15-continued

List of exemplary live biotherapeutic compositions,
i.e., list of exemplary microbial combinations.

| Mix | Organism Name (Operational Species Unit) |
|---|---|
| 159 | *Bifidobacterium bifidum* C0005 |
| | *Clostridium* sp. AF36-4 C2893 |
| | *Dorea longicatena* C2131 |
| | Erysipelotrichaceae bacterium GAM147 C2844 |
| | *Ruminococcus lactaris* C2149 |
| | *Ruminococcus* sp. OF03-6AA C2904 |
| 160 | *Bifidobacterium bifidum* C0005 |
| | *Blautia obeum* C2129 |
| | *Clostridium* sp. AF36-4 C2893 |
| | Erysipelotrichaceae bacterium GAM147 C2844 |
| | *Ruminococcus lactaris* C2149 |
| | *Ruminococcus* sp. OF03-6AA C2904 |
| 161 | *Bifidobacterium bifidum* C0005 |
| | *Clostridium* sp. AF36-4 C2893 |
| | *Coprococcus comes* C2152 |
| | Erysipelotrichaceae bacterium GAM147 C2844 |
| | *Ruminococcus lactaris* C2149 |
| | *Ruminococcus* sp. OF03-6AA C2904 |
| 162 | *Bifidobacterium bifidum* C0005 |
| | *Blautia obeum* C2129 |
| | *Clostridium* sp. AF36-4 C2893 |
| | *Dorea longicatena* C2131 |
| | Erysipelotrichaceae bacterium GAM147 C2844 |
| | *Ruminococcus lactaris* C2149 |
| 163 | *Bifidobacterium bifidum* C0005 |
| | *Clostridium* sp. AF36-4 C2893 |
| | *Coprococcus comes* C2152 |
| | *Dorea longicatena* C2131 |
| | Erysipelotrichaceae bacterium GAM147 C2844 |
| | *Ruminococcus lactaris* C2149 |
| 164 | *Bifidobacterium bifidum* C0005 |
| | *Blautia obeum* C2129 |
| | *Clostridium* sp. AF36-4 C2893 |
| | *Coprococcus comes* C2152 |
| | Erysipelotrichaceae bacterium GAM147 C2844 |
| | *Ruminococcus lactaris* C2149 |
| 165 | *Bifidobacterium bifidum* C0005 |
| | *Clostridium* sp. AF36-4 C2893 |
| | *Dorea longicatena* C2131 |
| | Erysipelotrichaceae bacterium GAM147 C2844 |
| | Firmicutes bacterium AF12-30 C2644 |
| | *Ruminococcus* sp. OF03-6AA C2904 |
| 166 | *Bifidobacterium bifidum* C0005 |
| | *Blautia obeum* C2129 |
| | *Clostridium* sp. AF36-4 C2893 |
| | Erysipelotrichaceae bacterium GAM147 C2844 |
| | Firmicutes bacterium AF12-30 C2644 |
| | *Ruminococcus* sp. OF03-6AA C2904 |
| 167 | *Bifidobacterium bifidum* C0005 |
| | *Clostridium* sp. AF36-4 C2893 |
| | *Coprococcus comes* C2152 |
| | Erysipelotrichaceae bacterium GAM147 C2844 |
| | Firmicutes bacterium AF12-30 C2644 |
| | *Ruminococcus* sp. OF03-6AA C2904 |
| 168 | *Bifidobacterium bifidum* C0005 |
| | *Blautia obeum* C2129 |
| | *Clostridium* sp. AF36-4 C2893 |
| | *Dorea longicatena* C2131 |
| | Erysipelotrichaceae bacterium GAM147 C2844 |
| | Firmicutes bacterium AF12-30 C2644 |
| 169 | *Bifidobacterium bifidum* C0005 |
| | *Clostridium* sp. AF36-4 C2893 |
| | *Coprococcus comes* C2152 |
| | *Dorea longicatena* C2131 |
| | Erysipelotrichaceae bacterium GAM147 C2844 |
| | Firmicutes bacterium AF12-30 C2644 |
| 170 | *Bifidobacterium bifidum* C0005 |
| | *Blautia obeum* C2129 |
| | *Clostridium* sp. AF36-4 C2893 |
| | *Coprococcus comes* C2152 |
| | Erysipelotrichaceae bacterium GAM147 C2844 |
| | Firmicutes bacterium AF12-30 C2644 |

TABLE 15-continued

List of exemplary live biotherapeutic compositions,
i.e., list of exemplary microbial combinations.

| Mix | Organism Name (Operational Species Unit) |
|---|---|
| 171 | *Bifidobacterium bifidum* C0005 |
| | *Blautia obeum* C2129 |
| | *Clostridium* sp. AF36-4 C2893 |
| | *Dorea longicatena* C2131 |
| | Erysipelotrichaceae bacterium GAM147 C2844 |
| | *Ruminococcus* sp. OF03-6AA C2904 |
| 172 | *Bifidobacterium bifidum* C0005 |
| | *Clostridium* sp. AF36-4 C2893 |
| | *Coprococcus comes* C2152 |
| | *Dorea longicatena* C2131 |
| | Erysipelotrichaceae bacterium GAM147 C2844 |
| | *Ruminococcus* sp. OF03-6AA C2904 |
| 173 | *Bifidobacterium bifidum* C0005 |
| | *Blautia obeum* C2129 |
| | *Clostridium* sp. AF36-4 C2893 |
| | *Coprococcus comes* C2152 |
| | Erysipelotrichaceae bacterium GAM147 C2844 |
| | *Ruminococcus* sp. OF03-6AA C2904 |
| 174 | *Bifidobacterium bifidum* C0005 |
| | *Blautia obeum* C2129 |
| | *Clostridium* sp. AF36-4 C2893 |
| | *Coprococcus comes* C2152 |
| | *Dorea longicatena* C2131 |
| | Erysipelotrichaceae bacterium GAM147 C2844 |
| 175 | *Bifidobacterium bifidum* C0005 |
| | *Dorea longicatena* C2131 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 176 | *Bifidobacterium bifidum* C0005 |
| | *Blautia obeum* C2129 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 177 | *Bifidobacterium bifidum* C0005 |
| | *Coprococcus comes* C2152 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 178 | *Bifidobacterium bifidum* C0005 |
| | *Blautia obeum* C2129 |
| | *Dorea longicatena* C2131 |
| | Erysipelotrichaceae bacterium GAM147 C2844 |
| | Firmicutes bacterium AF12-30 C2644 |
| | *Ruminococcus lactaris* C2149 |
| 179 | *Bifidobacterium bifidum* C0005 |
| | *Coprococcus comes* C2152 |
| | *Dorea longicatena* C2131 |
| | Erysipelotrichaceae bacterium GAM147 C2844 |
| | Firmicutes bacterium AF12-30 C2644 |
| | *Ruminococcus lactaris* C2149 |
| 180 | *Bifidobacterium bifidum* C0005 |
| | *Blautia obeum* C2129 |
| | *Coprococcus comes* C2152 |
| | Erysipelotrichaceae bacterium GAM147 C2844 |
| | Firmicutes bacterium AF12-30 C2644 |
| | *Ruminococcus lactaris* C2149 |
| 181 | *Bifidobacterium bifidum* C0005 |
| | *Blautia obeum* C2129 |
| | *Dorea longicatena* C2131 |
| | Erysipelotrichaceae bacterium GAM147 C2844 |
| | *Ruminococcus lactaris* C2149 |
| | *Ruminococcus* sp. OF03-6AA C2904 |
| 182 | *Bifidobacterium bifidum* C0005 |
| | *Coprococcus comes* C2152 |
| | *Dorea longicatena* C2131 |
| | Erysipelotrichaceae bacterium GAM147 C2844 |
| | *Ruminococcus lactaris* C2149 |
| | *Ruminococcus* sp. OF03-6AA C2904 |

TABLE 15-continued

List of exemplary live biotherapeutic compositions,
i.e., list of exemplary microbial combinations.

| Mix | Organism Name (Operational Species Unit) |
|---|---|
| 183 | *Bifidobacterium bifidum* C0005 |
| | *Blautia obeum* C2129 |
| | *Coprococcus comes* C2152 |
| | Erysipelotrichaceae bacterium GAM147 C2844 |
| | *Ruminococcus lactaris* C2149 |
| | *Ruminococcus* sp. OF03-6AA C2904 |
| 184 | *Bifidobacterium bifidum* C0005 |
| | *Blautia obeum* C2129 |
| | *Coprococcus comes* C2152 |
| | *Dorea longicatena* C2131 |
| | Erysipelotrichaceae bacterium GAM147 C2844 |
| | *Ruminococcus lactaris* C2149 |
| 185 | *Bifidobacterium bifidum* C0005 |
| | *Blautia obeum* C2129 |
| | *Dorea longicatena* C2131 |
| | Erysipelotrichaceae bacterium GAM147 C2844 |
| | Firmicutes bacterium AF12-30 C2644 |
| | *Ruminococcus* sp. OF03-6AA C2904 |
| 186 | *Bifidobacterium bifidum* C0005 |
| | *Coprococcus comes* C2152 |
| | *Dorea longicatena* C2131 |
| | Erysipelotrichaceae bacterium GAM147 C2844 |
| | Firmicutes bacterium AF12-30 C2644 |
| | *Ruminococcus* sp. OF03-6AA C2904 |
| 187 | *Bifidobacterium bifidum* C0005 |
| | *Blautia obeum* C2129 |
| | *Coprococcus comes* C2152 |
| | Erysipelotrichaceae bacterium GAM147 C2844 |
| | Firmicutes bacterium AF12-30 C2644 |
| | *Ruminococcus* sp. OF03-6AA C2904 |
| 188 | *Bifidobacterium bifidum* C0005 |
| | *Blautia obeum* C2129 |
| | *Coprococcus comes* C2152 |
| | *Dorea longicatena* C2131 |
| | Erysipelotrichaceae bacterium GAM147 C2844 |
| | Firmicutes bacterium AF12-30 C2644 |
| 189 | *Bifidobacterium bifidum* C0005 |
| | *Blautia obeum* C2129 |
| | *Coprococcus comes* C2152 |
| | *Dorea longicatena* C2131 |
| | Erysipelotrichaceae bacterium GAM147 C2844 |
| | *Ruminococcus* sp. OF03-6AA C2904 |
| 190 | *Clostridium* sp. AF36-4 C2893 |
| | *Dorea longicatena* C2131 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 191 | *Blautia obeum* C2129 |
| | *Clostridium* sp. AF36-4 C2893 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 192 | *Clostridium* sp. AF36-4 C2893 |
| | *Coprococcus comes* C2152 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 193 | *Blautia obeum* C2129 |
| | *Clostridium* sp. AF36-4 C2893 |
| | *Dorea longicatena* C2131 |
| | Erysipelotrichaceae bacterium GAM147 C2844 |
| | Firmicutes bacterium AF12-30 C2644 |
| | *Ruminococcus lactaris* C2149 |
| 194 | *Clostridium* sp. AF36-4 C2893 |
| | *Coprococcus comes* C2152 |
| | *Dorea longicatena* C2131 |
| | Erysipelotrichaceae bacterium GAM147 C2844 |
| | Firmicutes bacterium AF12-30 C2644 |
| | *Ruminococcus lactaris* C2149 |

TABLE 15-continued

List of exemplary live biotherapeutic compositions,
i.e., list of exemplary microbial combinations.

| Mix | Organism Name (Operational Species Unit) |
|---|---|
| 195 | *Blautia obeum* C2129 |
| | *Clostridium* sp. AF36-4 C2893 |
| | *Coprococcus comes* C2152 |
| | Erysipelotrichaceae bacterium GAM147 C2844 |
| | Firmicutes bacterium AF12-30 C2644 |
| | *Ruminococcus lactaris* C2149 |
| 196 | *Blautia obeum* C2129 |
| | *Clostridium* sp. AF36-4 C2893 |
| | *Dorea longicatena* C2131 |
| | Erysipelotrichaceae bacterium GAM147 C2844 |
| | *Ruminococcus lactaris* C2149 |
| | *Ruminococcus* sp. OF03-6AA C2904 |
| 197 | *Clostridium* sp. AF36-4 C2893 |
| | *Coprococcus comes* C2152 |
| | *Dorea longicatena* C2131 |
| | Erysipelotrichaceae bacterium GAM147 C2844 |
| | *Ruminococcus lactaris* C2149 |
| | *Ruminococcus* sp. OF03-6AA C2904 |
| 198 | *Blautia obeum* C2129 |
| | *Clostridium* sp. AF36-4 C2893 |
| | *Coprococcus comes* C2152 |
| | Erysipelotrichaceae bacterium GAM147 C2844 |
| | *Ruminococcus lactaris* C2149 |
| | *Ruminococcus* sp. OF03-6AA C2904 |
| 199 | *Blautia obeum* C2129 |
| | *Clostridium* sp. AF36-4 C2893 |
| | *Coprococcus comes* C2152 |
| | *Dorea longicatena* C2131 |
| | Erysipelotrichaceae bacterium GAM147 C2844 |
| | *Ruminococcus lactaris* C2149 |
| 200 | *Blautia obeum* C2129 |
| | *Clostridium* sp. AF36-4 C2893 |
| | *Dorea longicatena* C2131 |
| | Erysipelotrichaceae bacterium GAM147 C2844 |
| | Firmicutes bacterium AF12-30 C2644 |
| | *Ruminococcus* sp. OF03-6AA C2904 |
| 201 | *Clostridium* sp. AF36-4 C2893 |
| | *Coprococcus comes* C2152 |
| | *Dorea longicatena* C2131 |
| | Erysipelotrichaceae bacterium GAM147 C2844 |
| | Firmicutes bacterium AF12-30 C2644 |
| | *Ruminococcus* sp. OF03-6AA C2904 |
| 202 | *Blautia obeum* C2129 |
| | *Clostridium* sp. AF36-4 C2893 |
| | *Coprococcus comes* C2152 |
| | Erysipelotrichaceae bacterium GAM147 C2844 |
| | Firmicutes bacterium AF12-30 C2644 |
| | *Ruminococcus* sp. OF03-6AA C2904 |
| 203 | *Blautia obeum* C2129 |
| | *Clostridium* sp. AF36-4 C2893 |
| | *Coprococcus comes* C2152 |
| | *Dorea longicatena* C2131 |
| | Erysipelotrichaceae bacterium GAM147 C2844 |
| | Firmicutes bacterium AF12-30 C2644 |
| 204 | *Blautia obeum* C2129 |
| | *Clostridium* sp. AF36-4 C2893 |
| | *Coprococcus comes* C2152 |
| | *Dorea longicatena* C2131 |
| | Erysipelotrichaceae bacterium GAM147 C2844 |
| | *Ruminococcus* sp. OF03-6AA C2904 |
| 205 | *Blautia obeum* C2129 |
| | *Dorea longicatena* C2131 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 206 | *Coprococcus comes* C2152 |
| | *Dorea longicatena* C2131 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |

TABLE 15-continued

List of exemplary live biotherapeutic compositions,
i.e., list of exemplary microbial combinations.

| Mix | Organism Name (Operational Species Unit) |
|---|---|
| 207 | *Blautia obeum* C2129 |
| | *Coprococcus comes* C2152 |
| | Erysipelotrichaceae bacterium GAM147 C2844 |
| | Firmicutes bacterium AF12-30 C2644 |
| | *Ruminococcus lactaris* C2149 |
| | *Ruminococcus* sp. OF03-6AA C2904 |
| 208 | *Blautia obeum* C2129 |
| | *Coprococcus comes* C2152 |
| | *Dorea longicatena* C2131 |
| | Erysipelotrichaceae bacterium GAM147 C2844 |
| | Firmicutes bacterium AF12-30 C2644 |
| | *Ruminococcus lactaris* C2149 |
| 209 | *Blautia obeum* C2129 |
| | *Coprococcus comes* C2152 |
| | *Dorea longicatena* C2131 |
| | Erysipelotrichaceae bacterium GAM147 C2844 |
| | *Ruminococcus lactaris* C2149 |
| | *Ruminococcus* sp. OF03-6AA C2904 |
| 210 | *Blautia obeum* C2129 |
| | *Coprococcus comes* C2152 |
| | *Dorea longicatena* C2131 |
| | Erysipelotrichaceae bacterium GAM147 C2844 |
| | Firmicutes bacterium AF12-30 C2644 |
| | *Ruminococcus* sp. OF03-6AA C2904 |
| 211 | Erysipelotrichaceae bacterium GAM147 C2844 |
| | *Dorea* sp. AM58-8 C2913 |
| | *Bifidobacterium bifidum* C0005 |
| | *Clostridium* sp. AF36-4 C2893 |
| | *Ruminococcus lactaris* C2149 |
| | Firmicutes bacterium AF12-30 C2644 |
| | *Ruminococcus* sp. OF03-6AA C2904 |
| | *Dorea longicatena* C2131 |
| | *Blautia obeum* C2129 |
| | *Coprococcus comes* C2152 |
| | *Bifidobacterium catenulatum* C0014 |
| | *Blautia* sp. AF19-10LB C2906 |
| 212 | *Ruminococcus* sp. OF03-6AA C2904 |
| | *Dorea longicatena* C2131 |
| | *Blautia obeum* C2129 |
| | *Coprococcus comes* C2152 |
| | *Bifidobacterium catenulatum* C0014 |
| | *Blautia* sp. AF19-10LB C2906 |
| 213 | *Ruminococcus* sp. OF03-6AA C2904 |
| | *Dorea longicatena* C2131 |
| | *Blautia obeum* C2129 |
| | *Coprococcus comes* C2152 |
| | *Bifidobacterium catenulatum* C0014 |
| | *Blautia* sp. AF19-10LB C2906 |
| | Erysipelotrichaceae bacterium GAM147 C2844 |
| 214 | *Dorea* sp. OM07-5 C2890 |
| | *Faecalibacterium prausnitzii* C2184 |
| | *Dorea longicatena* C2413 |
| | *Anaerobutyricum hallii* C2206 |
| | *Faecalibacterium prausnitzii* C2650 |
| | *Faecalibacterium prausnitzii* C2651 |
| | *Anaerostipes hadrus* C2144 |
| | *Dorea formicigenerans* C2197 |
| | [*Ruminococcus*] *torques* C2636 |
| | *Coprococcus catus* C2881 |
| | *Faecalibacterium* sp. AF28-13AC C2810 |
| | [*Clostridium*] *amygdalinum* C2887 |
| | *Roseburia inulinivorans* C2207 |
| | *Asaccharobacter celatus* C1952 |

TABLE 15-continued

List of exemplary live biotherapeutic compositions,
i.e., list of exemplary microbial combinations.

| Mix | Organism Name (Operational Species Unit) |
| --- | --- |
| 215 | Erysipelotrichaceae bacterium GAM147 C2844 |
| | *Dorea* sp. AM58-8 C2913 |
| | *Bifidobacterium bifidum* C0005 |
| | *Clostridium* sp. AF36-4 C2893 |
| | *Dorea longicatena* C2131 |
| | Firmicutes bacterium AF12-30 C2644 |
| | *Ruminococcus* sp. OF03-6AA C2904 |
| | *Coprococcus comes* C2152 |
| | *Bifidobacterium catenulatum* C0014 |
| | *Blautia* sp. AF19-10LB C2906 |
| | *Dorea formicigenerans* C2197 |
| | *[Ruminococcus] torques* C2636 |
| | *Coprococcus catus* C2881 |
| 216 | Erysipelotrichaceae bacterium GAM147 C2844 |
| | *Dorea* sp. AM58-8 C2913 |
| | *Dorea longicatena* C2131 |
| | *Bifidobacterium catenulatum* C0014 |
| | *Dorea formicigenerans* C2197 |
| | *Coprococcus comes* C2152 |
| | *Coprococcus catus* C2881 |
| 217 | Erysipelotrichaceae bacterium GAM147 C2844 |
| | *Dorea* sp. AM58-8 C2913 |
| | Firmicutes bacterium AF12-30 C2644 |
| | *Ruminococcus* sp. OF03-6AA C2904 |
| | *Dorea longicatena* C2131 |
| | *Blautia obeum* C2129 |
| | *Dorea* sp. OM07-5 C2890 |
| | *Coprococcus comes* C2152 |
| | *Dorea longicatena* C2413 |
| | *Faecalibacterium prausnitzii* C2650 |
| | *Blautia* sp. AF19-10LB C2906 |
| | *[Ruminococcus] torques* C2636 |
| 218 | Erysipelotrichaceae bacterium GAM147 C2844 |
| | *Dorea* sp. AM58-8 C2913 |
| | *Bifidobacterium bifidum* C0005 |
| | *Clostridium* sp. AF36-4 C2893 |
| | *Ruminococcus lactaris* C2149 |
| 219 | Erysipelotrichaceae bacterium GAM147 C2844 |
| | *Dorea* sp. AM58-8 C2913 |
| | *Ruminococcus lactaris* C2149 |
| | *Dorea formicigenerans* C2197 |
| | *[Clostridium] amygdalinum* C2887 |
| | *Roseburia inulinivorans* C2207 |
| | *Asaccharobacter celatus* C1952 |
| 220 | Erysipelotrichaceae bacterium GAM147 C2844 |
| | *Dorea* sp. AM58-8 C2913 |
| | *Bifidobacterium bifidum* C0005 |
| | *Clostridium* sp. AF36-4 C2893 |
| | *Ruminococcus lactaris* C2149 |
| | *Dorea formicigenerans* C2197 |
| | *[Clostridium] amygdalinum* C2887 |
| | *Roseburia inulinivorans* C2207 |
| | *Asaccharobacter celatus* C1952 |
| 221 | Erysipelotrichaceae bacterium GAM147 C2844 |
| | *Dorea* sp. AM58-8 C2913 |
| | *Ruminococcus lactaris* C2149 |
| 222 | *Bifidobacterium bifidum* C0005 |
| | *Bifidobacterium catenulatum* C0014 |
| | *Bifidobacterium pseudocatenulatum* C0013 |
| 223 | *Blautia luti* C2436 |
| | *Blautia obeum* C2129 |
| | *Blautia obeum* C2901 |
| | *Blautia* sp. AF19-10LB C2906 |
| 224 | *Blautia luti* C2436 |
| | *Blautia obeum* C2129 |
| | *Blautia obeum* C2901 |
| | *Blautia* sp. AF19-10LB C2906 |
| | *Blautia* sp. KGMB01111 C3003 |
| | *Blautia* sp. TF11-31AT C2841 |
| | *Blautia wexlerae* C2171 |

TABLE 15-continued

List of exemplary live biotherapeutic compositions,
i.e., list of exemplary microbial combinations.

| Mix | Organism Name (Operational Species Unit) |
| --- | --- |
| 225 | *Clostridium* sp. AF20-17LB C2921 |
| | *Clostridium* sp. AF23-8 C2908 |
| | *Clostridium* sp. AF34-13 C2653 |
| | *Clostridium* sp. AF36-4 C2893 |
| | *Clostridium* sp. AM18-55 C2845 |
| | *Clostridium* sp. AM49-4BH C2934 |
| | *Clostridium* sp. OF10-22XD C2132 |
| 226 | *Collinsella aerofaciens* C1933 |
| | *Collinsella bouchesdurhonensis* C1956 |
| | *Collinsella* sp. TM05-38 C1984 |
| 227 | *Coprococcus catus* C2881 |
| | *Coprococcus comes* C2152 |
| | *Coprococcus eutactus* C2642 |
| 228 | *Dorea formicigenerans* C2197 |
| | *Dorea longicatena* C2131 |
| | *Dorea longicatena* C2413 |
| | *Dorea* sp. AM58-8 C2913 |
| | *Dorea* sp. OM07-5 C2890 |
| 229 | *Eubacterium ramulus* C2442 |
| | *Eubacterium ramulus* C2852 |
| | *Eubacterium saphenum* ATCC 49989 C2183 |
| | *Eubacterium ventriosum* C2128 |
| 230 | *Faecalibacterium prausnitzii* C2138 |
| | *Faecalibacterium prausnitzii* C2184 |
| | *Faecalibacterium prausnitzii* C2650 |
| | *Faecalibacterium prausnitzii* C2651 |
| | *Faecalibacterium prausnitzii* C2863 |
| | *Faecalibacterium prausnitzii* C2864 |
| | *Faecalibacterium* sp. AF28-13AC C2810 |
| 231 | Firmicutes bacterium AF12-30 C2644 |
| | Firmicutes bacterium AF22-6AC C2933 |
| | Firmicutes bacterium AF25-13AC C2695 |
| | Firmicutes bacterium AM41-11 C2946 |
| | Firmicutes bacterium TM09-10 C2909 |
| 232 | *Roseburia inulinivorans* C2207 |
| | *Roseburia* sp. AM59-24XD C2936 |
| | *Roseburia* sp. OM04-15AA C2892 |
| 233 | *Ruminococcus callidus* C2440 |
| | *Ruminococcus lactaris* C2149 |
| | *Ruminococcus* sp. AF31-8BH C2903 |
| | *Ruminococcus* sp. AM42-11 C2945 |
| | *Ruminococcus* sp. KGMB03662 C2557 |
| | *Ruminococcus* sp. OF03-6AA C2904 |
| 234 | *Flavonifractor plautii* C2284 |
| | *[Clostridium] scindens* C2143 |
| | *[Clostridium] bolteae* C2137 |
| 234 | *Flavonifractor plautii* C2284 |
| | *[Clostridium] scindens* C2143 |
| | *[Clostridium] bolteae* C2137 |
| | *Blautia hansenii* C3044 |
| | *[Clostridium] clostridioforme* C2275 |
| 235 | Erysipelotrichaceae bacterium GAM147 C2844 |
| | *Ruminococcus* sp. OF03-6AA C2904 |
| | *Blautia* sp. AF19-10LB C2906 |
| 236 | Erysipelotrichaceae bacterium GAM147 C2844 |
| | *Ruminococcus* sp. OF03-6AA C2904 |
| | *Blautia* sp. AF19-10LB C2906 |
| | Firmicutes bacterium AF12-30 C2644 |
| 237 | *Dorea longicatena* C2131 |
| | *Coprococcus comes* C2152 |
| | *Blautia obeum* C2129 |
| | *Faecalibacterium prausnitzii* C2184 |
| | *Dorea longicatena* C2413 |
| 238 | *Dorea longicatena* C2131 |
| | *Coprococcus comes* C2152 |
| | *Blautia obeum* C2129 |
| | *Faecalibacterium prausnitzii* C2184 |
| | *Dorea longicatena* C2413 |
| | *[Ruminococcus] torques* C2636 |
| 239 | Erysipelotrichaceae bacterium GAM147 C2844 |
| | *Dorea longicatena* C2131 |
| | *Coprococcus comes* C2152 |
| | *Blautia obeum* C2129 |
| | *Faecalibacterium prausnitzii* C2184 |
| | *Dorea longicatena* C2413 |

TABLE 15-continued

List of exemplary live biotherapeutic compositions,
i.e., list of exemplary microbial combinations.

| Mix | Organism Name (Operational Species Unit) |
|---|---|
| 240 | Erysipelotrichaceae bacterium GAM147 C2844 |
| | Ruminococcus sp. OF03-6AA C2904 |
| | Blautia sp. AF19-10LB C2906 |
| | Firmicutes bacterium AF12-30 C2644 |
| | Dorea longicatena C2131 |
| | Coprococcus comes C2152 |
| | Blautia obeum C2129 |
| | Faecalibacterium prausnitzii C2184 |
| | Dorea longicatena C2413 |
| | [Ruminococcus] torques C2636 |
| 241 | Erysipelotrichaceae bacterium GAM147 C2844 |
| | Dorea longicatena C2131 |
| | Coprococcus comes C2152 |
| | Blautia obeum C2129 |
| | Faecalibacterium prausnitzii C2184 |
| | Dorea longicatena C2413 |
| | [Ruminococcus] torques C2636 |

TABLE 16

The top 6 scoring organisms using LEfSe from Table 13 have been
selected for screening in simulated microbial mixes. All possible
combinations of 4 organisms from the top 6 are shown.

| | Organism Name |
|---|---|
| Mix 1 | Erysipelatoclostridium sp000752095 |
| | Blautia_A obeum |
| | Mediterraneibacter faecis |
| | Faecalibacterium prausnitzii_C |
| Mix 2 | Blautia_A obeum |
| | Dorea longicatena_B |
| | Mediterraneibacter faecis |
| | Faecalibacterium prausnitzii_C |
| Mix 3 | Blautia_A obeum |
| | Dorea longicatena_B |
| | Mediterraneibacter faecis |
| | CAG-269 sp000431335 |
| Mix 4 | Erysipelatoclostridium sp000752095 |
| | Blautia_A obeum |
| | Dorea longicatena_B |
| | Faecalibacterium prausnitzii_C |
| Mix 5 | Erysipelatoclostridium sp000752095 |
| | Dorea longicatena_B |
| | Faecalibacterium prausnitzii_C |
| | CAG-269 sp000431335 |
| Mix 6 | Erysipelatoclostridium sp000752095 |
| | Blautia_A obeum |
| | Dorea longicatena_B |
| | CAG-269 sp000431335 |
| Mix 7 | Erysipelatoclostridium sp000752095 |
| | Blautia_A obeum |
| | Faecalibacterium prausnitzii_C |
| | CAG-269 sp000431335 |
| Mix 8 | Erysipelatoclostridium sp000752095 |
| | Dorea longicatena_B |
| | Mediterraneibacter faecis |
| | Faecalibacterium prausnitzii_C |
| Mix 9 | Dorea longicatena_B |
| | Mediterraneibacter faecis |
| | Faecalibacterium prausnitzii_C |
| | CAG-269 sp000431335 |
| Mix 10 | Erysipelatoclostridium sp000752095 |
| | Mediterraneibacter faecis |
| | Faecalibacterium prausnitzii_C |
| | CAG-269 sp000431335 |
| Mix 11 | Blautia_A obeum |
| | Dorea longicatena_B |
| | Faecalibacterium prausnitzii_C |
| | CAG-269 sp000431335 |

TABLE 16-continued

The top 6 scoring organisms using LEfSe from Table 13 have been
selected for screening in simulated microbial mixes. All possible
combinations of 4 organisms from the top 6 are shown.

| | Organism Name |
|---|---|
| Mix 12 | Blautia_A obeum |
| | Mediterraneibacter faecis |
| | Faecalibacterium prausnitzii_C |
| | CAG-269 sp000431335 |
| Mix 13 | Erysipelatoclostridium sp000752095 |
| | Dorea longicatena_B |
| | Mediterraneibacter faecis |
| | CAG-269 sp000431335 |
| Mix 14 | Erysipelatoclostridium sp000752095 |
| | Blautia_A obeum |
| | Mediterraneibacter faecis |
| | CAG-269 sp000431335 |
| Mix 15 | Erysipelatoclostridium sp000752095 |
| | Blautia_A obeum |
| | Dorea longicatena_B |
| | Mediterraneibacter faecis |

Example 12: Cytokine and Immune Cell Characterization in Patient Blood Samples Cytokine Analysis of Blood Plasma Plasma was obtained from 1 mL blood by centrifugation at 2000×g for 10 minutes. The plasma fraction was removed from the top and transferred to a clean tube. To remove any residual cells that may have carried over, the plasma was centrifuged again at 2000×g for 10 minutes, and the top layer was transferred to another tube, taking care to not take any red blood that may have settled to the bottom of the tube. Cytokine analysis was performed on 25 selected plasma samples by Eve Technologies (website link) using the 48-plex Luminex assay.

Mann-Whitney test was applied to each cytokine to identify those with significant differential abundance between samples corresponding to checkpoint inhibitor complete responders (CR, N=6) and non-responders (NR, N=8). The remaining 11 samples were from patients identified as partial responders (PR) or stable disease (SD); due to the unclear phenotype, these were not included in the statistical analysis. Compounds with significant concentration differences between CR and NR samples ($p<0.05$) are listed in Table 17.

TABLE 17

Average fluorescence values for CR and NR samples
exhibiting significant differential abundance.

| Compound | CR Average | NR Average | CR/NR ratio | P-value |
|---|---|---|---|---|
| Eotaxin | 20.91 | 36.11 | 0.58 | 0.0046 |
| IFNgamma | 0.51 | 4.41 | 0.12 | 0.0132 |
| IL.2 | 0.55 | 1.77 | 0.31 | 0.0141 |
| IL.27 | 1065.91 | 2326.60 | 0.46 | 0.0337 |
| MIP.1a | 30.02 | 44.87 | 0.67 | 0.0132 |

CyTOF Analysis of PBMCs Isolated from Whole Blood

Peripheral blood mononuclear cells (PBMCs) were isolated from approximately 8 mL blood using SepMate™ tubes following the manufacturer's instructions. Following isolation, cells were resuspended in 1 mL PBS+2% FBS. 10 uL of the cell suspension was mixed with 10 uL if Trypan Blue Stain 0.4% and applied to a cell counter plate to determine viable cell concentration. The cell suspension was then diluted in 90% PBS+10% DMSO to achieve a cell density of 1×10^7 cells/mL. Cells were then frozen at a controlled rate of 1° C./min to a final temperature of −150° C. in liquid nitrogen.

Mass cytometry (CyTOF) was performed on 25 selected PBMC samples by the University of Texas Health Center at San Antonio (UTHCSA). A 30 marker antibody panel focused on human immune-oncology relevant markers (Fluidigm) was used to quantify different cell populations. The markers and associated metal labels are given in Table 18. Markers were gated using the strategy shown in FIG. 21 to determine the immune cell types and subtypes. Cell populations were reported either as a percentage of all viable cells and/or of the parent cell type.

TABLE 18

List of antibodies and metal labels used for CyTOF analysis.

| Immune Marker | Metal |
| --- | --- |
| CCR4 | 158Gd |
| CCR5 | 144Nd |
| CCR7 | 159Tb |
| CD11a | 142Nd |
| CD127 | 176Yb |
| CD134 [0X40] | 150Nd |
| CD137 [4-1BB] | 173Yb |
| CD152 [CTLA-4] | 161Dy |
| CD16 | 148Nd |
| CD161 | 164Dy |
| CD2 | 151Eu |
| CD223 [LAG3] | 175Lu |
| CD25 | 149Sm |
| CD27 | 167Er |
| CD278 [ICOS] | 168Er |
| CD279 [PD-1] | 155Gd |
| CD28 | 160Gd |
| CD3 | 170Er |
| CD366 [Tim-3] | 153Eu |
| CD4 | 145Nd |
| CD44 | 166Er |
| CD45 | 154Sm |
| CD45RA | 169Tm |
| CD45RO | 165Ho |
| CD49d | 141Pr |
| CD5 | 143Nd |
| CD57 | 172Yb |
| CD69 | 162Dy |
| CD7 | 147Sm |
| CD8a | 146Nd |
| CD9 | 171Yb |
| CD95 [Fas] | 152Sm |
| CXCR3 | 156Gd |
| HLA-DR | 174Yb |

Figure 21:
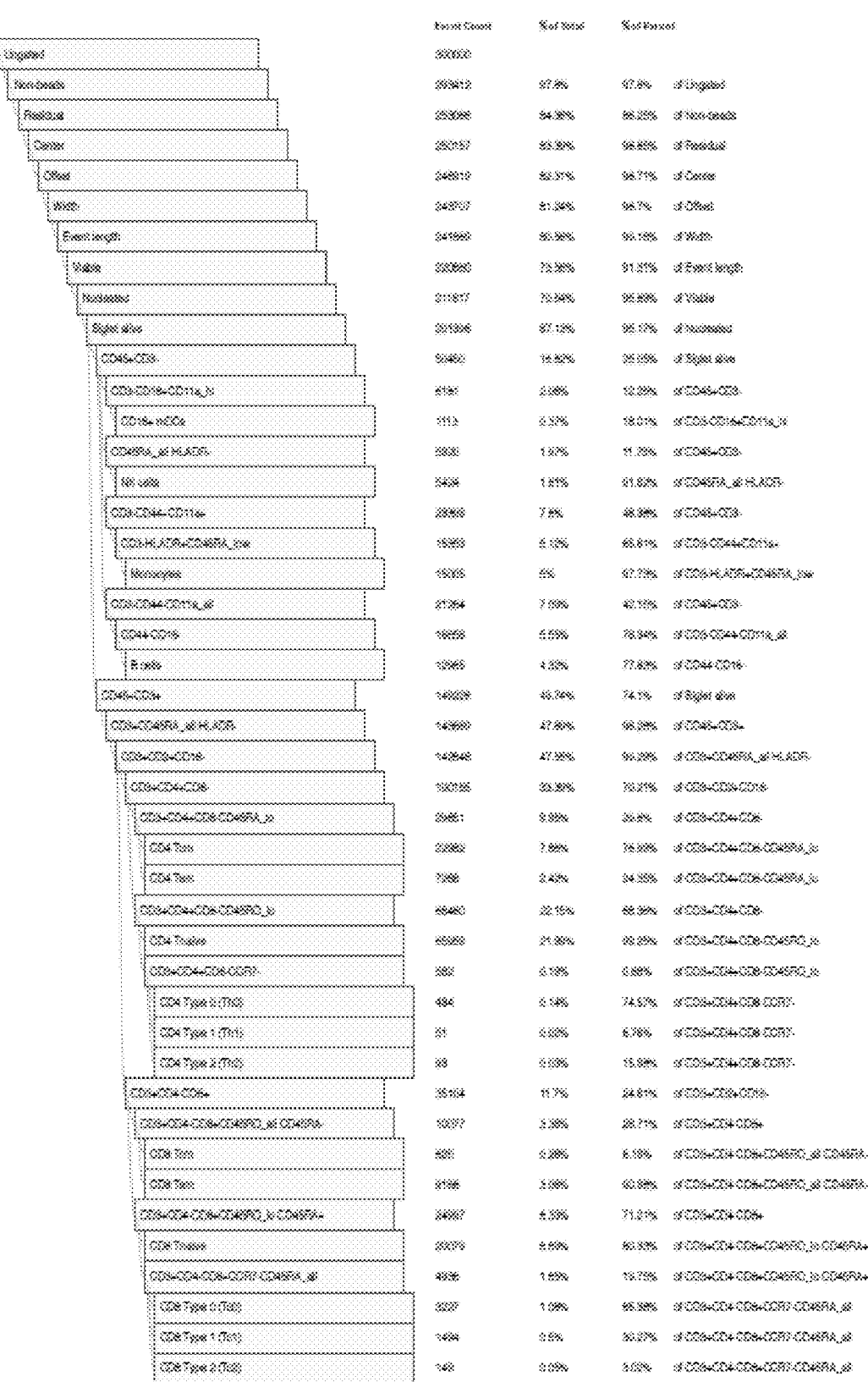
FIG. 21 illustrates the gating strategy used to classify immune cell populations based on metal-labeled peptide markers, and cell counts for a representative sample, as discussed in Example 11, below.

FIG. 21. Gating strategy used to classify immune cell populations based on metal-labeled peptide markers, and cell counts for a representative sample.

Mann-Whitney test was applied to each population type or subtype to identify those with significant differential abundance between samples corresponding to checkpoint inhibitor complete responders (CR, N=6) and non-responders (NR, N=8). The remaining 11 samples were from patients identified as partial responders (PR) or stable disease (SD); due to the unclear phenotype, these were not included in the statistical analysis. Cell populations with significant abundance differences between CR and NR samples (p<0.05) are listed in Table 19.

TABLE 19

Cell population abundance values, as a percentage either of total live cells or of the parent cell type, as indicated, for CR and NR samples exhibiting significant differential abundance.

| Cell Population | CR Average | NR Average | CR/ NR | P- value |
| --- | --- | --- | --- | --- |
| % of CD3−CD44+CD11a+ in Siglet alive | 13.09 | 31.67 | 0.41 | 0.0132 |
| % of B cells in Siglet alive | 9.92 | 4.92 | 2.02 | 0.0046 |
| % of CD3−HLADR+CD45RA__low in Siglet alive | 10.44 | 23.57 | 0.44 | 0.0095 |
| % of Monocytes in Siglet alive | 10.12 | 22.29 | 0.45 | 0.0183 |
| % of CD3+CD4−CD8+CD45RO__lo CD45RA+ in alive | 13.40 | 8.28 | 1.62 | 0.0337 |
| % in B cells in CD45+CD3− | 43.37 | 26.18 | 1.66 | 0.0132 |

Example 12: Gene Expression Analysis of Microbial Treatment in Co-Culture

Live biotherapeutic compositions as provided herein, including the exemplary combinations of microbes 1 to 241, as described in Table 15, Example 10, are evaluated in co-culture for immunomodulatory effects. Live biotherapeutics are co-cultured with human colonic cells (CaCo2) to investigate the effects of the bacteria on the host. Live biotherapeutic compositions are also co-cultured on CaCo2 cells that were stimulated with Interleukin 1 (IL1) to mimic the effect of the bacteria in an inflammatory environment. The effects in both scenarios are evaluated through gene expression analysis either by PCR or by next generation sequencing approaches.

Cytokine Production in THP-1 Cells Induced by Live Biotherapeutics

Live biotherapeutic compositions as provided herein, including for example the exemplary combinations of microbes 1 to 241, Table 15, Example 10, and single bacterial strains are evaluated alone and in combination with lipopolysaccharide (LPS) on cytokine production in THP-1 cells, a model cell line for monocytes and macrophages.

THF-1 cells are differentiated into M0 medium for 48 h with 5 ng/mL phorbol-12-myristate-13-acetate (PMA). These cells are subsequently incubated with the live biotherapeutic composition at a final concentration of 10^8/ml, with or without the addition of LPS at a final concentration of 100 ng/ml. Alternatively, the bacterial cells are centrifuged, and the resulting supernatant is added to the THF-1 cell preparation. The bacteria are then washed off and the cells allowed to incubate under normal growing conditions for 24 h. The cells are then spun down and the resulting supernatant is analyzed for cytokine content using a Luminex 200 analyzer or equivalent method.

Cytokine Production in Immature Dendritic Cells Induced by Live Biotherapeutic Compositions Live biotherapeutic compositions as provided herein, including the exemplary combinations of microbes 1 to 241, as described in Table 15, Example 10, and single bacterial strains are evaluated alone and in combination with LPS on cytokine production in immature dendritic cells. A monocyte population is isolated from peripheral blood mononuclear cells (PBMCs). The monocyte cells are subsequently differentiated into immature dendritic cells. The immature dendritic cells are plated out at 200,000 cells/well and incubated with the live biotherapeutic composition at a final concentration of 10^7/ml in RPMI media, with the optional addition of LPS at a final concentration of 100 ng/ml. Alternatively, the bacterial cells are centrifuged, and the resulting supernatant is added to the dendritic cell preparation. The negative control involves incubating the cells with RPMI media alone and positive controls incubating the cells with LPS at a final concentration of 100 ng/ml. The cytokine content of the cells is then analyzed.

Cytokine Production and Analysis in PBMCs

Peripheral blood mononuclear cells (PBMC's) are isolated from subject blood using a standard kit and stored in liquid nitrogen at $1×10^6$ cells per mL until use. Prior to storage, PBMC's may be processed using flow sorting or an antibody spin separation kit to select for a certain purified lymphocyte subpopulation, such as T cells.

PBMCs are thawed at 37° C. and then transferred to a growth medium consisting of RPMI-1640 (Lonza, Switzerland), with 10% heat inactivated FCS added, as well as 0.1% penicillin-streptavidin, 1% L-glutamine, and DNase at 10 mg/mL to inhibit aggregation. Cells are centrifuged at 200×g for 15 minutes and then counted using trypan blue and spread into 24 well plates at $1×10^6$ cells per well (1 mL per well) (Kechaou et al. (2013) Applied and Environmental Microbiology 79:1491-1499; Martin et al. (2017) Frontiers in Microbiology 8:1226).

An overnight bacterial culture is inoculated using a prestocked isolated bacterial strain. This strain is grown at 37° C. for 10 to 20 hours in a YBHI medium with added cellobiose (1 mg/mL), maltose (1 mg/mL) and cysteine (0.5 mg/mL) in an anaerobic chamber filled with 85% nitrogen, 10% carbon dioxide, and 5% hydrogen (Martin et al., 2017). The growth medium may also be Reinforced Clostridial Medium (RCM) (Thermo Fisher, USA), which may also be supplemented with cysteine (0.5 mg/mL) or arginine (1 mg/mL).

At the end of the anaerobic culture, the culture supernatant and bacterial cells alone are saved for co-culture with PBMC's. Microbial culture supernatant is saved directly after centrifugation at −80° C. Cells are saved by washing with phosphate buffered saline (PBS) and then storing in PBS with 15% glycerol. Bacteria are quantified using phase contrast microscopy and stored at a final concentration of $10^5$ or $10^6$ cells per mL (Haller et al. (2000) Infection and Immunity 68; Rossi et al. (2015) Scientific Reports 6:18507) at −80° C. Bacteria may also be pasteurized prior to storage by treatment at 70° C. for 30 minutes (Plovier et al. (2017) Nature Medicine 23:107-113).

Prior to co-culture, supernatant is thawed on ice and 200 μL of supernatant is diluted in 1 mL of total volume of PBMC growth medium. Microbial growth medium is used as a negative control. This 1 mL is added to the 1 mL of PBMC in each well, resulting in a 10% final level of microbial culture supernatant in a 2 mL culture containing $1×10^6$ PBMCs. Each combination of PBMCs and supernatant is performed in duplicate or triplicate.

Prior to co-culture, bacteria are thawed on ice and then washed at 4° C. with PBMC growth medium. 1 mL of the bacterial suspension is added to the 1 mL of PBMC culture in each well of the plate, resulting in a final 2 mL culture containing $1×10^6$ PBMC's and $1×10^5$ or $1×10^6$ (potentially pasteurized) bacteria.

The co-culture of PBMC's and supernatant or purified bacteria is incubated for 2, 6, 16, 24, or 48 hours at 37° C. in 10% carbon dioxide.

After co-culture, the supernatant is harvested and treated with a protease inhibitor (Complete EDTA-Free protease inhibitor, Roche Applied Bioscience) to protect cytokines and stored directly at −80° C. for cytokine profiling. The pelleted cells are treated with RNAlater (Thermo Fisher, USA) and saved for RNA sequencing.

Cytokine analysis is performed on saved co-culture supernatant using ELISA or a Luminex system. Cytokines measured may include but are not limited to, IL-10, IL-2, and IFN-gamma.

RNA sequencing is performed on PBMC's saved in RNAlater post co-culture. Standard pseudo-alignment is performed using Kallisto (Bray et al. (2016) Nature Biotechnology 34:525-527) and differential expression is analyzed using DESeq2 (Love et al. (2014) Genome Biology 15:550) to identify differential expression between different microbes and different PBMC donors.

Statistical analyses are performed to identify microbes that exhibit desired immunomodulatory effects in vitro, which include but are not limited to inducing production of IFN-gamma and lowering expression of genes associated with T cell exhaustion (PD1, CTLA4, VISTA, TIM3, TIGIT, LAG3).

Example 13: Genetic Modification of Therapeutic Microbes

Microbes of interest, including microbes as provided herein, e.g., as listed in Table 1, 5, 10, 11 or 12, including bacteria from all the genuses listed herein, and including the combinations of microbes as provided herein, e.g., the exemplary combinations 1 to 241 as described in Table 15, Example 10, or as identified from the in vivo and ex vivo analyses described in Example 10 and Example 11, are interrogated or investigated to identify mechanisms of action, and the discovered mechanisms are leveraged using a genetic modification or modifications to amplify the microbe's therapeutic effect.

In alternative embodiments, this is accomplished in two stages. First, complementary bioinformatic and experimental approaches are used to identify the genes within a microbe of interest responsible for its therapeutic effect. Second, synthetic biology techniques are used to engineer over-expression of the identified genes within the original organism of discovery or inserted for overexpression in the genome of a chassis organism. Chassis organisms include any microbe as described herein, including genuses of bacteria as provided herein, and also include bacteria as listed in Tables 1, 3, 4, 5, 6, 7 and/or 8, including *Bacillus subtilis, Escherichia coli Nissle, or any microbes listed in the combinations as provided herein in Table* 15 or Table 16, or the original organism of interest itself.

In alternative embodiments, microbes as provided herein are genetically modified to increase expression of existing therapeutically effective genes, or to install extra copies of these genes, or to install into a microbe lacking these functions any one of these genes. Methods for genetic engineering/augmenting a microbe of interest, e.g., a gut microbe, to alter expression of existing therapeutically effective genes or to install extra copies of said genes or to install said genes in a microbe lacking these functions are numerous in the art. Techniques applied to gut microbes and related organisms for experimental gene disruption, gene replacement or gene expression modulation include CRISPR-Cas9 genome editing (Bruder et al (2016) Applied and Environmental Microbiology 82:6109-6119), bacterial conjugation (Cuiv et al (2015) Nature Scientific Reports 5:13282; Ronda et al. (2019) Nature Methods 16:167-170), gene replacement mutagenesis by homologous recombination (Cartman et al (2012) Applied Environmental Microbiology 78:4683-4690; Heap et al (2007) Journal of Microbiological Methods 70:452-464), random transposon mutagenesis (Cartman and Minton (2010) Applied Environmental Microbiology 76:1103-1109), and antisense-based gene expression attenuation (Forsyth et al (2002) Molecular Microbiology 43:1387-1400; Kedar et al (2007) Antimicrobial Agents and Chemotherapy 51:1708-1718.

Genes of interest inserted into microbes as provided herein, or whose expression is increased in microbes as provided herein, can be engineered to immediately follow and be under inducible control by various promotor elements that are functional in gut microbes. Highly inducible and controllable promoter elements are available for bacteria in the gram-negative genus *Bacteroides* (Lim et al (2017) Cell 169:547-558; Bencivenga-Barry et al (2019) Journal of Bacteriology doi: 10.1128/JB.00544-19). Some of these are responsive to various diet-derived polysaccharides, while those often most useful for use for inducible function determination in animal models such as mouse rely on induction by tetracycline derivatives like anhydrotetracycline at sub-bactericidal levels. Anhydrotetracycline can be employed as an inducer for engineered promoters in gut Clostridia (Dembek et al (2017) Frontiers of Microbiology 8:1793). Promoters that respond to bile acids are identified in gram-positive gut *Clostridium* species (Wells and Hyemon (2000) Applied Environmental Microbiology 66:1107-1113) and in *Eubacterium* species (Mallonee et al. (1990) Journal of Bacteriology 172:7011-7019. Also, inducible promoters that respond to sugars such as lactose (Banerjee et al (2014) Applied Environmental Microbiology 80-2410-2416) and arabinose (Zhang et al (2015) Biotechnology for Biofuels 8:36) are identified and useful in related Clostridial species. Genes inserted in exemplary recombinant bacterium can be induced under low-oxygen conditions from promoters driven by transcriptions factors such as FNR (fumarate and nitrate reductase) (Oxer et al (1991) Nucleic Acids Research, 19, 11: 2889-2892). Genes of interest inserted in microbes as provided herein can also be engineered to immediately follow and be under constitutive control by various promotor elements that are functional in gut microbes. Constitutive promoter libraries and promoter-RBS (ribosome binding site) pairs have been created for bacteria in the gram-negative genus *Bacteroides* (Mimee et al (2015) Cell Syst. 1, 62-71) and computational models have been developed from *Bacillus subtilis* promoter sequences data sets for promoter prediction in Gram-positive bacteria (Coelho et al (2018) Data Br. 19, 264-270).

Engineering of Metabolic Pathways in Therapeutic Microbes

In one embodiment, an organism used to practice embodiments as provided herein is genetically modified to overexpress a pathway for production of any short chain fatty acid (SCFA), including butyrate or butyric acid, propionate and acetate. Butyric acid is naturally produced in many gut microorganisms and is derived from two molecules of acetyl-CoA, a central metabolic intermediate that is ubiquitous in microorganisms. In one embodiment, the native pathway is overexpressed, e.g., as discussed herein. In another embodiment, a heterologous pathway is constructed by introducing one or more genes from a different organism, including all genes derived from different organisms. Condensation of two acetyl-CoA molecules is catalyzed by a ketothiolase (EC:2.3.1.9), such as the atoB gene from *Escherichia coli*, to produce one molecule of acetoacetyl-CoA (Sato et al. (2007) J. Biosci. Bioengineer. 103:38-44). Alternative candidates are obtained by Basic Local Alignment Search Tool (BLAST) search of this sequence (Altschul et al. (1997) Nuc. Acids. Res. 25:3389-3402), obtaining homologous genes either known or predicted to encode similar enzyme function. Exemplary gene candidates are obtained using the following GenBank accession numbers.

| atoB | *Escherichia coli* | NP_416728.1 |
| yqeF | *Escherichia coli* | NP_417321.2 |
| phaA | *Cupriavidus necator* | YP_725941 |
| bktB | *Cupriavidus necator* | AAC38322.1 |
| thiA | *Clostridium acetobutylicum* | NP_349476.1 |
| thiB | *Clostridium acetobutylicum* | NP_149242.1 |

The second step in the pathway involves reduction of acetoacetyl-CoA to 3-hydroxybutyryl-CoA by a hydroxyacyl-CoA dehydrogenase (EC:1.1.1.35), such as that encoded by hbd in *Clostridium acetobutylicum* (Atsumi et al. (2008) Metab. Eng. 10(6):305-311). Similarly, to above, alternate candidates are identified in the literature or by BLAST. Exemplary candidates are as follows.

| paaH | *Escherichia coli* | NP_415913.1 |
| hbd | *Clostridium acetobutylicum* | NP_349314.1 |
| hbd | *Pseudomonas putida* | KT2440 NC_002947.4 |
| RSP_3970 | *Rhodobacter sphaeroides* 2.4.1 | YP_345236.1 |

The next step is the dehydration of 3-hydroxybutyryl-CoA to crotonyl-CoA by an enoyl-CoA hydratase, also known as crotonase (EC:42.1.55), such as that encoded by the crt gene of *Clostridium acetobutylicum* (Kim et al. (2014) Biochem. Biophys. Res. Commun. 451:431-435) or the homologs listed below.

| crt | *Clostridium acetobutylicum* | NC_003030.1 |
| echA18 | *Mycobacterium bovis* AF2122/97 | NC_002945.4 |
| maoC | *Escherichia coli* | NP 415905.1 |
| crt | *Bacillus thuringiensis* | NC_005957.1 |

Next, crotonyl-CoA is reduced to butyryl-CoA through the action of an enoyl-CoA reductase (EC:1.3.1.38 or EC:1.3.1.44), such as that encoded by the bcd gene of *Clostridium acetobutylicum* (Boynton et al. (1996) J. Bacteriol. 178:3015-3024). Activity of this enzyme can be enhanced by expressing bcd in conjunction with expression of the *C. acetobutylicum* etfAB genes, which encode an electron transfer flavoprotein. Several eukaryotic enzymes with this activity have also been identified, such as TER from *Euglena gracilis*, that upon removal of the mitochondrial targeting leader sequence have demonstrated superior activity in *E. coli* (Hoffmeister et al. (2005) J. Biol. Chem. 280:4329-4338). Protein sequences for these and other exemplary sequences can be obtained using the following GenBank accession numbers.

| bcd | *Clostridium acetobutylicum* | NP 34.9317.1 |
| etfA | *Clostridium acetobutylicum* | NP 349315.1 |
| etfB | *Clostridium acetobutylicum* | NP 349316.1 |
| TER | *Euglena gracilis* | Q5EU90.1 |
| TDE0597 | *Treponema denticola* | NP 97.1211.1 |

The final step of this pathway is CoA removal from butyryl-CoA to generate butyric acid. Although numerous CoA hydrolases occur in most bacteria, e.g., tesB from *E. coli* ((Naggert et al. (1991) J. Biol. Chem. 266:11044-11050), it is desirable to recover energy from hydrolysis of the thioester bond in the form of ATP. The sucCD complex of *E. coli* (EC:6.2.1.5) is one example of this, known to catalyze the conversion of succinyl-CoA and ADP to succinate and ATP (Buck et al. (1985) Biochem. 24:6245-6252). Another example is sucD, succinic semialdehyde dehydrogenase, from *Porphyromonas gingivalis* (Yim et al. (2011) Nat. Chem. Biol. 7:445-452). Another option, using phosphotransbutylase/butyrate kinase (EC:2.3.1.19, EC:2.7.2.7), is catalyzed by the gene products of buk1, buk2, and ptb from *C. acetobutylicum* (Walter et al. (1993) Gene 134:107-111) or homologs thereof. Finally, an acetyltransferase capable of transferring the CoA group from butyryl-CoA to acetate can be applied (EC:2.8.3.9), such as Cat3 from *C. kluyveri* (Sohling and Gottschalk (1996) J. Bacteriol. 178:871-880). Protein sequences for these and other exemplary sequences can be obtained using the following GenBank accession numbers.

| ptb | *Clostridium acetobutylicum* | NP 349676 |
|---|---|---|
| buk1 | *Clostridium acetobutylicum* | NP 349675 |
| buk2 | *Clostridium acetobutylicum* | Q97II1 |
| sucC | *Escherichia coli* | NP_415256.1 |
| sucD | *Escherichia coli* | AAC73823.1 |
| cat3 | *Clostridium kluyveri* | EDK35586.1 |
| tesB | *Escherichia coli* | NP_414986 |

In another embodiment, a microbe used to practice embodiments as provided herein is genetically modified to metabolize bile acids, also referred to as bile salts to indicate the predominant form at neutral pH, that are produced in the liver and present in the gut at about 1 mM concentration. Two such types of bile acid conversion processes are catalyzed by bacteria. The first is deconjugation, which removes either taurine or glycine that is frequently found conjugated to bile acids (Ridlon et al. (2016) Gut Microbes 7:22-39; Masuda et al. (1981) Microbiol. Immunol. 25:1-11). This is catalyzed by bile salt hydrolase (BSH) enzymes (EC: 3.5.1.24), which are widespread in many gut bacteria. Some BSHs have broad substrate specificity, while others are very specific for a particular bile salt. The substrate range of a BSH of interest is determined by assay of purified BSH or crude lysates from the native host, on a panel of glycine and taurine conjugated bile salts (Jones et al. (2008) Proc. Nat. Acad. Sci. USA 105:13580-13585). To enhance the activity and substrate range of bile salt deconjugation in the engineered microbe, native BSHs of interest and/or heterologous genes from other microbes are introduced. Exemplary genes are listed below. Still others are found by GenBank search or BLAST of these sequences to identify homologs.

| bsh | *Bifidobacterium longum* | AF148138.1 |
|---|---|---|
| bsh | *Bifidobacterium animalis* | AY530821.1 |
| bsh | *Enterococcus faecalis* | GG688660.1 |
| bsh3 | *Lactobacillus plantarum* | ACL98170.1 |
| cbh2 | *Bacteroides vulgatis* | RIB33278.1 |
| cbah | *Clostridium butyricum* | EEP54620.1 |

The other type of bile acid metabolism introduced into a microbe used to practice embodiments as provided herein is capable of converting primary to secondary bile acids, which entails removal of the 7-alpha-hydroxy or 7-beta hydroxy group from the primary bile acid; for example, the conversion of cholic acid to deoxycholic acid or chenodeoxycholic acid to lithocholic acid. The archetype pathway for this process is encoded by the bai gene cluster in *Clostridium scindens* (Coleman et al. (1987) J. Bacteriol. 169:1516-1521; Ridlon et al. (2006) J. Lipid. Res. 47:241-259) and has been well characterized. In addition, a functional *C. scindens* dihydroxylation was established in

*Clostridium sporogenes* (Funabashi et al. (2019) BioRxiv). The first step is a bile acid-CoA ligase (baiB, EC:6.2.1.7) to activate the molecule for the subsequent reaction steps. Next, an alcohol dehydrogenase (baiA, EC:1.1.1.395) oxidizes the 3-hydroxyl to a keto group. An NADH:flavin oxidoreductase then introduces a double bond into the ring by either baiCD (EC:1.3.1.115) or baiH (EC:1.3.1.116), depending on the substrate. The coA is then removed or transferred to another primary bile acid by a CoA transferase (baiF, EC:2.8.3.25). The 7-alpha or 7-beta-hydroxy group is then removed by a dehydratase (baiE or baiI, respectively, EC:4.2.1.106) to form a second double bond in a conjugated position to the other one. Enzymes encoded by baiH and baiCD then serve to reduce the double bonds consecutively, and finally the alcohol dehydrogenase reduces the 3-keto back to a hydroxyl. High bile acid dihydroxylation activity has also been observed in *Eubacterium* sp. strain VPI 12708, *Eubacterium* sp. strain Y-1113, *Eubacterium* sp. strain I-10, *Eubacterium* sp. strain M-18, *Eubacterium* sp. strain TH-82, *Clostridium* sp. strain TO-931, and *Clostridium* sp. strain HD-17. Homologs for some of the bai genes have been identified in these organisms (Doemer et al. (1997) Appl. Environ. Microbiol. 63:1185-1188), and thus represent alternate gene candidates. Homologs of all essential genes for pathway function were also identified in *Clostridium hylemonae* DSM 15053, *Dorea* sp. D7, and a novel Firmicutes bacterium (Das et al. (2019) BMC Genomics 20:517).

To introduce the conversion pathway into the genetically modified host, the following *C. scindens* genes or suitable homologs are expressed: baiA, baiB, baiCD, baiE, baiF, and baiH. In some embodiments, the baiG gene, encoding a transporter, is also expressed. In other embodiments, the baiI gene predicted to encode a delta-5-ketoisomerase, is introduced in order to enable dihydroxylation of secondary bile acids requiring this step.

Tryptophan derivatives are produced by many microbes, including gut bacteria, and have been implicated in strengthening the epithelial cell barrier and modulating the expression of pro-inflammatory genes by T cells in the GI tract (Bercik et al. (2011) Gastroenterology 141:599-609). A gut microbe is engineered to overexpress one or more tryptophan derivatives by either overexpressing native genes or introducing heterologous genes described below.

In one embodiment, a microbe used to practice embodiments as provided herein is engineered to convert tryptophan to indole by introduction of a tryptophanase, such as that encoded by the tnaA gene of *E. coli* (Li and Young (2013) Microbiology 159:402-410). Other candidates are found by literature search or BLAST of the sequence to find homologs, as exemplified by the following:

| tnaA | *Escherichia coli* | NP_415256.1 |
|---|---|---|
| tnaA | *Bacteroides thetaiotamicron* | NP_810405.1 |
| tnaA | *Vibrio tasmaniensis* | LGP32 VS_RS05915 |
| tnaA | *Treponema denticola* | TDE0251 |

In another embodiment, a microbe used to practice embodiments as provided herein is engineered to convert tryptophan to indoleacetate. This pathway begins with a tryptophan aminotransferase (EC:2.6.1.27) such as that encoded by the Tam1 gene of *Ustilago maydis* (Zuther et al. (2008) Mol. Microbiol. 68:152-172), which uses a-ketoglutarate as the amino acceptor and produces indole pyruvate. Although a microbial sequence for this enzyme is not currently in GenBank, activity has been reported in *Clostridium sporogenes* (O'Neil et al. (1968) Arch.

Biochem. Biophys. 127:361-369). Alternatively, a deaminating tryptophan oxidase (EC:1.3.3.10) such as that encoded by the vioA gene of *Chromobacterium violaceum* (August et al. (2000) J. Mol. Microbiol. Biotechnol. 2:513-519) uses molecular oxygen to oxidize and deaminate tryptophan to produce indole pyruvate. Alternative candidates include those indicated as follows:

| vioA | *Chromobacterium violaceum* | CV_RS16140 |
|---|---|---|
| WP_133678757 | *Paludibacterium purpuratum* | WP_133678757.1 |
| WP_034786442 | *Janthinobacterium lividum* | WP_034786442.1 |

The next gene to be introduced encodes an indole pyruvate decarboxylase (EC:4.1.1.74), which produces indole-3-acetaldehyde from indole pyruvate. An example is the ipdC gene from *Enterobacter cloacae* (Koga et al. (1991) Mol. Gen. Genet. 226:10-16). Other exemplary genes can be accessed by the GenBank accession numbers listed below:

| ipdC | *Enterobacter cloacae* | WP_013098183.1 |
|---|---|---|
| CFNIH1_RS23020 | *Citrobacter freundii* | CFNIH1_RS23020 |
| ipdC | *Rhodopseudomonas palustris* CGA009 | TX73_RS15890 |
| ipdC | *Azospirillum brasilense* | AMK58_RS11560 |

Indole-3-acetaldehyde is then oxidized to indoleacetate by an aldehyde dehydrogenase (EC:1.2.1.3), such as that encoded by the aldA gene of *Pseudomonas syringae* (McClerklin et al. (2018) PLoS Pathog. 14:e1006811). Numerous aldehyde dehydrogenases exist, though the best candidates are those homologous to this aldA or others with known activity on indole-3-aldehyde or similar molecules. Exemplary gene candidates can be accessed by the GenBank accession numbers listed below:

| aldA | *Pseudomonas syringae* | PSPT0 0092 |
|---|---|---|
| CFNIH1_RS23020 | *Citrobacter freundii* | CFNIH1_RS23020 |
| WP_005887684.1 | *Pseudomonas coronafaciens* | WP_005887684.1 |
| SPOG_02634 | *Schizosaccharomyces cryophilus* OY26 | SPOG_02634 |

In another embodiment, a tryptophan decarboxylase (EC: 4.1.1.28) is introduced into a microbe used to practice embodiments as provided herein to produce tryptamine. This activity is rare among bacteria, but two such enzymes have recently been identified: CLOSPO_02083 from *Clostridium sporogenes* and RUMGNA_01526 from *Ruminococcus gnavus* (Williams et al. (2014) Cell Host Microbe 16:495-503).

In another embodiment, the pathway to produce indole-propionate (IPA) is introduced into the genetically modified microbe. IPA has been implicated in intestinal barrier fortification by engaging the pregnane X receptor (Venkatesh et al. (2014) Immunity 41:296-310) and is known to be synthesized by a small number of gut bacteria (Elsden et al. (1976) Arch. Microbiol. 107:283-288). However, the pathway for its synthesis is uncharacterized. The genes encoding this pathway have recently been discovered in *Clostridium sporogenes*, enabling a pathway to be proposed. Indole pyruvate, synthesized as described above, is reduced to indolelactate which is then dehydrated to produce indoleacrylate. Finally, indoleacrylate is reduced to IPA by an acyl-CoA dehydrogenase. These are encoded by the fldH, fldBC, and acdA genes in *C. sporogenes*, respectively (Dodd et al. (2017) Nature 551:648-652). Homologs of these genes in other microbes are also candidates for expression, found by BLAST of the *C. sporogenes* genes.

In another embodiment, a microbe used to practice embodiments as provided herein is engineered to consume a sugar or polysaccharide, e.g., a cellobiose, which is a reducing sugar consisting of two β-glucose molecules linked by a 13 (1-4) bond that is recalcitrant to catabolism by most gut microbes. Consumption of cellobiose first requires a specific enzyme II complex (EC:2.7.1.205) of the phosphotransferase system (PTS), such as the celABC operon in *E. coli* (Keyhani et al. (2000) J. Biol. Chem. 275:33091-33101). When expressed in a heterologous host, this component functions together with the native PTS machinery to import and phosphorylate cellobiose to generate cellobiose-6-phosphate. Alternate candidates for this step are listed below:

| celA | *Enterococcus gilvus* | WP_10781765.1 |
|---|---|---|
| celB | *Enterococcus gilvus* | WP_010780456.1 |
| celC | *Enterococcus gilvus* | WP_010780458.1 |
| celA | *Lactococcus lactis* subsp. *lactis* | NP_266573.1 |
| celB | *Lactococcus lactis* subsp. *lactis* | NP_266330.1 |
| ptcA | *Lactococcus lactis* subsp. *lactis* | NP_266570.1 |
| celB | *Bacillus coagulans* | BF29_RS14550 |

A 6-phospho-beta-glucosidase (EC:3.2.1.86) is then required to convert the cellobiose-6P into one molecule of glucose and one molecule of glucose-6-P, both of which are readily used by the host. An example is the 6-phospho-beta-glucosidase from *Bacillus coagulans*, which has successfully been expressed in *E. coli* (Zheng et al. (2018) Biotechnology for Biofuels 18:320). Alternate candidates are listed below:

| celA | *Enterococcus gilvus* | WP_10781765.1 |
|---|---|---|
| celB | *Enterococcus gilvus* | WP_010780456.1 |
| celC | *Enterococcus gilvus* | WP_010780458.1 |
| celA | *Lactococcus lactis* subsp. *lactis* | NP_266573.1 |
| celB | *Lactococcus lactis* subsp. *lactis* | NP_266330.1 |
| ptcA | *Lactococcus lactis* subsp. *lactis* | NP_266570.1 |
| celB | *Bacillus coagulans* | BF29_RS14550 |

In another embodiment, a microbe used to practice embodiments as provided herein is genetically modified by deleting or reducing expression of genes to eliminate or reduce production of metabolites, such as the polyamines putrescine, spermidine, and cadaverine. These molecules are essential for gastrointestinal mucosal cell growth and function, but excess of these compounds has been linked to gut dysbiosis and poor nutrient absorption (Forget et al. (1997) J. Pediatr. Gastroenterol. Nutr. 24:285-288). The primary routes for polyamine synthesis in bacteria are decarboxylation of the amino acid's arginine or ornithine. Ornithine decarboxylase (ODC, EC:4.1.1.17) converts ornithine to putrescine, while arginine decarboxylase (ADC, EC:4.1.1.19) converts arginine to agmatine, which is subsequently converted to putrescine by agmatinase (EC: 3.5.3.11). Putrescine can then be converted to other derivatives such as spermidine. Therefore, a reduction in ODC and/or ADC expression will reduce polyamine production in the host microbe. *E. coli* contains two ODC isomers, encoded by the speC and speF genes, as well as two isomers of ADC encoded by speA and adiA. BLAST searches using these sequences, or other known bacterial ODC and ADC genes, applied to the genome of the organism of interest is used to identify genes encoding these functions in the organism to be genetically modified. One or both of these genes, or homologs thereof, are then deleted from the host genome using tools such as lambda-red mediated recombination (Datsenko and Wanner (2000) Proc. Nat. Acad. Sci. USA 97:6640-6645), CRISPR-Cas9 genome editing (Bruder et al (2016) Appl. Environ. Microbiol. 82:6109-6119), or any other method resulting in the removal of genes or portions of genes from the chromosome. In another embodiment, these methods are used to replace the native promoters of these genes with alternate promoters of different strengths, or to modify the ribosome binding site, resulting in reduced production of the ODC and ADC enzymes. In yet another embodiment, expression is reduced through a gene silencing mechanism such as antisense RNA-based attenuation (Nakashima et al. (2012) Methods Mol. Biol. 815:307-319) or CRISPR interference (Choudhary et al. (2015) Nat. Comm. 6:6267).

Bioinformatic Discovery of Putative Immunomodulatory Proteins and Genetic Modification of Exemplary Therapeutic Microbes In alternative embodiments, genetically modified microorganisms as provided herein, including microorganisms as listed in Tables 1, 5, 10, 11 or 12, and a bacterium from a combination of microbes as provided herein, e.g., as in Table 15 or Table 16, are engineered to express immunomodulatory, e.g., immunostimulatory, proteins, or to overexpress endogenous immunomodulatory proteins. In alternative embodiments, the immunomodulatory are secreted or are cell surface-expressed or membrane-expressed proteins.

Organisms of interest are bioinformatically interrogated for expression of putative immunomodulatory proteins. Based on immune correlation analysis and the differential relative abundance of organisms between cancer and control samples, certain organisms are identified as being missing from the cancer microbiome and potentially immunostimulatory and having anti-cancer properties. These identified organisms can be incorporated into formulations as provided herein, or into combinations of microbes as provided herein; or, the immunomodulatory proteins they express are identified and genetically engineered into organisms as provided herein, e.g., as listed in Tables 1, 5, 10, 11 or 12. In alternative embodiments, an organism as provided herein (as used in a method as provided herein) is genetically modified to overexpress the discovered immunomodulatory protein or proteins. Organisms potentially immunostimulatory and having anti-cancer properties are highlighted in Example 10.

For example, Dorea formicigenerans is one such organism, with strong positive correlations in both cancer and control cohorts to CD3+ and CD3+CD56+ immune cells in peripheral blood. First, a database of proteins is downloaded and clustered by similarity. Predicted proteins are downloaded from the NCBI RefSeq genomic database for a representative set of microbial genome assemblies. All complete genome assemblies for bacteria and archaea are included. For the taxa of special interest, which include Verrucomicrobia, Clostridia, and Coriobacteria, all assemblies of any status are included. Predicted proteins are downloaded from RefSeq and clustered using mmseqs2 (Steinegger and Soding. (2017) Nature Biotechnology 35:1026-1028). The resulting clusters contain proteins with identical or highly similar sequences. For a specific organism of interest, the protein clustering analysis is used to identify genes that are mostly unique to the organism yet ubiquitous across the organism's pangenome. These genes are likely candidates to mediate the immunomodulatory functions that are specific to the organism of interest. A standard bioinformatic analysis is performed on genes unique to the organism of interest to identify protein domains within each gene as being signal, cytoplasmic, non-cytoplasmic, or transmembrane domains. Because immunomodulatory genes need to interact with immune cells, they are generally secreted proteins (Quévrain et al. (2016) Gut 65:415-425) or membrane proteins (Plovier et al. (2017) Nature Medicine 23:107-113). Secreted proteins are identified from the analysis using the signal domains, while membrane proteins are identified by the presence of transmembrane domains. Because proteins with several transmembrane domains tend to be transporters, the focus is on proteins with one or two transmembrane domains. Membrane proteins or secreted proteins from the analysis of genes unique to the organism are prioritized for overexpression in genetically modified microorganisms as provided herein.

In alternative embodiments, genetically modified microorganisms as provided herein are engineered to express exogenous membrane proteins or secreted proteins. Genes unique to the organism of interest that are also membrane proteins or secreted proteins are investigated in a bespoke manner using the publicly available BLAST or Pfam search engines. In one embodiment, the organism is genetically modified to express these or homologues of identified membrane proteins. From this analysis, one protein from Dorea formicigenerans, NCBI Reference Sequence WP_118145075.1 is a particularly attractive candidate. The protein family for WP_118145075.1 contains 28 protein sequences, of which 26 are from Dorea formicigenerans genomes. There are 27 total Dorea formicigenerans assemblies in the database, so 26 out of 27 assemblies contains a version of protein WP_118145075.1. When analyzed on BLAST and Pfam, WP_118145075.1 is identified as a pilus-like protein. Pili and related proteins have a known role in interaction with human cells (Lizano et al. (2007) Journal of Bacteriology 189:1426-1434; Plovier et al. (2017) Nature Medicine 23:107-113; Ottman, N., et al. (2017) PLOS ONE 12(3):e0173004). Genes may also be identified as containing pilus-like structures or other known immunomodulatory structures using public available techniques such as PilFind (Imam et al. (2011) PLOS ONE 6(12): e28919). In alternative embodiments, these pilus-like structures or other known immunomodulatory structures are engineered into genetically modified microorganisms as provided herein.

Other pili-like proteins of interest and corresponding homologs used in genetically engineered organism as provided herein include the highly abundant outer membrane protein of Akkermansia muciniphila Amuc_1100 and members of the Amuc_1098-Amuc_1102 gene cluster, have been shown to induce the production of specific cytokines (IL-8, IL-1β, IL-6, IL-10 and TNF-α) through activation of Toll-like receptors (TLR) 2 and TLR4 (Ottman et al (2017) PLoS One 12, e0173004). Similar outer membrane proteins are believed to be responsible for the induction of cytokine IL-10 by commensal gut microbes such as Faecalibacterium prausnitzii A2-165 and Lactobacillus plantarum WCFS1.

In another embodiment, a genetically engineered organism as provided herein is genetically modified to express homologues of bacterial flagellin to induce TLR5 signaling. TLR5 response to flagellin promotes both innate and adaptive immune functions for gut homeostasis (Leifer et al (2014) Immunol. Lett. 162, 3-9). Recently, flagellin been examined for anti-tumor and radioprotective properties and has shown potential in reducing tumor growth and radiation-associated tissue damage (Hajam et al (2017) Exp. Mol. Med. 49, e373-e373). Some flagellin-based anti-tumor vaccines have also successfully entered into human clinical trials. Flagellins (fliC) and homologues of interest include but are not limited to those from *Salmonella Typhimurium* (FliCi), *Escherichia coli, Pseudomonas aeruginosa, Listeria monocytogenes*, and *Serratia marcescens*.

Identification of Immunomodulatory Proteins Via Pooled Screening

In alternative embodiments, microbes used in compositions as provided herein, or as used in methods as provided herein, have enhanced immunomodulatory effects, e.g., immune-stimulatory effects, and these microbes can be generated or derived either by selection using assays, as described below, or by inserting or enhancing the microbe's immunomodulatory effects by genetic engineering, e.g., by inserting a heterologous nucleic acid into the microbe. In alternative embodiments, microbes that can express or over-express immunomodulatory proteins or peptides are used with (in addition to, are administered with) microbes used in compositions as provided herein, or microbes used to practice methods as provided herein.

Microbial populations are assayed directly for immunomodulatory effects on dendritic cells. Starting with a fecal sample of interest containing an endogenous microbial population or starting with a synthetic microbial population consisting of pooled microbial isolates of interest, the population can be tested against dendritic cells ex vivo.

Purified dendritic cells are generated as described in previous work (Svensson and Wick. (1999) European Journal of Immunology 29(1):180-188; Svensson et al. (1997) Journal of Immunology 158(9):4229-4236; Yrlid et al. (2001) Infection and Immunity 69(9):5726-5735). Heat-inactivated, incubated for 30 minutes at 70° C., or live bacteria are added at a 50:1 ratio and incubated for 4 hours at 37° C. in IMDM containing 5% FBS. Following incubation, cells are washed 3× in HBSS to remove excess antigen. A portion of the dendritic cells are saved in RNAlater for future RNA sequencing. When activated, dendritic cells express several co-stimulatory molecules that aid in activating T cells. These molecules (CD40, CD80, and CD86) are upregulated alongside the chemokine receptor CCR7 which homes the activated DC to the spleen or local lymph node (Wilson and O'Neill. (2003) Blood 102(5):1661-1669; Ohl et al. (2004) Immunity 21(2):279-288). This set of genes can therefore be used to sort mature, activated DCs from immature DCs that do not stimulate T cells effectively. Cells are stained for expression of one or more of CD86, CD40 and CD80, and sorted via Fluorescence Activated Cell Sorting (FACS).

Purified cells are processed as described previously (Abelin et al. (2017) Immunity 46(2):315-326) for HLA-peptide identification. Briefly, purified cells are dissociated in protein lysis buffer containing protease inhibitors and DNAse, and then sonicated. Following sonication, soluble lysates are incubated with SEPHAROSE™ beads linked to W6/32 antibody which are washed with lysis buffer lacking protease inhibitor, and finally washed with DI water. Peptides are then eluted from the HLA complex on EMPORE C18 STAGETIPS™. Purified protein preparations are then subjected to nanoLC-ESI-MS/MS.

Following LC-MS/MS, individual peptides are identified and matched to the reference genomes of the mix of microbes used in the in vitro activation experiment. A list of candidate peptides is generated by combining peptide abundance data with bioinformatics analysis of protein conservation, localization data, and their likelihood to express and localize to the membrane (Marshall et al. (2016) Cell Reports 16(8):2169-2177; Saladi et al. (2018) Journal of Biological Chemistry 293(13):4913-4927).

Identification and Validation of Microbes that Activate Immune Cell Receptors

In alternative embodiments, microbes used in compositions as provided herein, or as used in methods as provided herein, can activate immune cell receptors (e.g., such as T cell receptors), and these microbes can be generated or derived either by selection using assays, as described below, or by inserting or enhancing the microbe's immunomodulatory effects by genetic engineering, e.g., by inserting a heterologous nucleic acid into the microbe. In alternative embodiments, microbes that can express or overexpress proteins or peptides that can activate immune cell receptors are used with (in addition to, are administered with) microbes used in compositions as provided herein, or microbes used to practice methods as provided herein.

In alternative embodiments, ex vivo analyses are used to identify microbes that activate immune cell receptors including but not limited to dendritic cell Toll-like receptors (TLR's). \Briefly, microbes of interest are co-incubated with human dendritic cells as described in the previous section, except that the co-incubation occurs with a pasteurized and washed microbial isolate rather than a microbial population. Dendritic cells are washed post-incubation. As described in Example 11, dendritic cells are saved and analyzed using RNA sequencing to identify gene expression changes relative to control conditions. The control conditions include both no stimulation i.e. microbial media alone, as well as known agonists for different TLR's. A computational analysis is performed to ascribe the gene expression of dendritic cells in response to each microbe to some amount of activation of each TLR, thus predicting microbe-TLR interactions.

For each predicted microbe-TLR interaction, the pasteurized and washed microbe is co-incubated with TLR reporter cells (HEK-Blue, InvivoGen), and a plate-based colorimetric assay used to measure TLR activation over time. Validated microbes can be further screened as described previously for specific genes that mediate their mechanistic effects.

Amplification of Therapeutic Effect by Overexpression of Immunomodulatory Genes

In alternative embodiments, microbes used in compositions as provided herein, or as used in methods as provided herein, overexpress immunomodulatory genes (e.g., immunostimulatory genes), and these microbes can be generated or derived either by selection using assays, as described below, or by inserting or enhancing the microbe's immunomodulatory effects by genetic engineering, e.g., by inserting a heterologous nucleic acid into the microbe.

In alternative embodiments, microbes used in compositions as provided herein, or used to practice methods as provided herein, are selected to express, or overexpress, immunostimulatory proteins or peptides, which can be non-specific immunostimulatory proteins such as a cytokine, e.g., a cytokine such as an interferon (e.g., IFN-α2a, IFN-α2b) IL-2, IL-4, IL-7, IL-12, IFNs, TNF-α, granulocyte colony-stimulating factor (G-CSF, also known as filgrastim, lenograstim or Neupogen®) and granulocyte monocyte colony-stimulating factor (GM-CSF, also known as molgramostim, sargramostim, Leukomax®, Mielogen® or Leukine®), or a specific immunostimulatory protein or peptide, e.g., such as an immunogen that can generate a specific humeral or cellular immune response, e.g., an immune response to a cancer antigen. In alternative embodiments, microbes that can express or overexpress immunostimulatory proteins or peptides are used with (in addition to, are administered with) microbes used in compositions as provided herein, or used to practice methods as provided herein.

Genes identified from a bioinformatic or pooled experimental approach as having an immunomodulatory effect are validated using recombinant expression in an engineered chassis organism. In alternative embodiments, the engineered chassis organism is used as a strong modulator (e.g., stimulator) of immune activity as a component of a live biotherapeutic as provided herein (e.g., as a component of a combination of microbes as provided herein, e.g., as a component of an exemplary combination as listed in Table 15 or Table 16), or the engineered chassis organism can be used in addition to a live biotherapeutic as provided herein.

Nucleic acids encoding protein sequences capable of enhancing a microbe's immunomodulatory effects are synthesized and cloned or inserted into a microbe, e.g., bacterium, used in a combination of microbes as provided herein (as in e.g., Table 15 or Table 16), including for example any bacterium as listed in Table 1, 5, 10, 11, or 12, e.g., such as a *B. subtilis*. *B. subtilis* is a generally recognized as safe (GRAS) organism that has extensive tools available for the cloning and expression of synthetically encoded proteins (see e.g., Popp et al. (2017) Scientific Reports 7(1):15058). Following cloning, colonies containing each different synthetic protein are grown until logarithmic phase. Each culture is pasteurized and washed as described previously. The cultures are validated for immunomodulatory activity relative to a negative control consisting of the unmodified chassis organism and positive control consisting of the unmodified original microbe of interest.

Each overexpressed gene can be validated for immunomodulatory activity using a TLR reporter assay as described previously, or a co-incubation with dendritic cells followed by mass spectrometry or RNA sequencing as described previously. Validated immunomodulatory engineered microbes can be incorporated into the candidate live biotherapeutic and advanced to in vivo screening in animal models.

Example 14: Whole Cell Mutagenesis and Selection Procedures for Therapeutic Microbes In alternative embodiments, microbes as provided herein (including bacteria from all the genuses listed herein), and including the combinations of microbes as provided herein, e.g., the exemplary combinations 1 to 241 as described in Table 15, Example 10, are genetically modified to enhance a cancer treatment, e.g., to enhance or prolong the efficacy of a chemotherapy, a radiation therapy, an immune checkpoint inhibitor, a Chimeric Antigen Receptor (CAR) T-cell therapy (CAR-T) or other immunotherapy or cancer treatment.

Candidate live biotherapeutic strains are randomly mutagenized to generate a microbe with increased level of production of either a protein or metabolite of interest that may impact cancer treatment. When cells are mutagenized, changes occur in the DNA sequence that could result in changes of expression levels of certain genes. Often these mutations are lethal, but some strains survive and have altered phenotype, including some with increased expression of genes encoding proteins or metabolic pathways identified from patient data (Examples 9 and 10) or in vitro assays (Example 11). Mutagenesis is carried out by an established treatment such as ultraviolet light, N-ethyl-N-nitrosourea, or ethyl methanesulfonate, followed by culturing on non-selective media to obtain viable cells. Mutagen exposure is first tuned by varying the time or intensity of treatment to a small culture, then selecting the conditions which yield approximately 10-20% of the number of viable colonies compared to a non-treated control. These treatment conditions are then applied to a larger culture of cells, and mutagenized colonies obtained are screened for the phenotype of interest, such as increased production of a protein or metabolite of interest. Clones obtained from this screen are then further characterized by whole genome sequencing.

Example 15: Production of Live Biotherapeutics

In alternative embodiments, microbes as provided herein (including bacteria from all the genuses listed herein), and including the combinations of microbes as provided herein, e.g., the exemplary combinations 1 to 241 as described in Table 15, Example 10, comprise anaerobic bacteria, including anaerobic bacteria isolated from a fecal sample, cultured anaerobic bacteria, or a combination thereof.

Individual Culture of Anaerobic Microbes for Mouse Studies

Anaerobic microbes of interest are cultured in multiples of 1-liter volumes in anaerobic media bottles as follows. Microbes in cryostorage are plated and struck on appropriate anaerobic solid medium and then cultured at 37° C. to obtain isolated colonies. For each microbe, a single colony is inoculated into a Hungate tube containing 10 ml appropriate anaerobic growth medium and allowed to grow at 37° C. until turbid to create a starter culture. For each microbe of interest, multiple 0.9-liter volumes of appropriate liquid anaerobic medium in 1 L anaerobic bottles (as described in Example 1) are inoculated with 2 ml starter culture each using a needle and syringe. The number of 1-liter cultures for each microbe is dependent on the necessary final amount of live cell mass for formulation into live biotherapeutics for mouse studies. Inoculated bottles are placed upright on a platform shaker at 115 rpm at 37° C. for 48 hours or until growth turbidity is evident. Growth density is monitored by taking 1 ml samples during the course of the cultures for optical density measurements at 600 nm. Optical densities of 1.0 to 4.0 can be obtained after 48 hours depending on the microbe cultured. Prior to large scale culture, cell densities are determined empirically for each microbe by dilution plating and colony counting to determine the colony forming units (CFU) per ml at an optical density of 1.0.

Large scale cultures are grown to attain a final live density of 1.0E8 to 1.0E9 CFU/ml, and then the culture bottles are brought into the anaerobic chamber for harvesting of live cell mass. Once in the chamber, the aluminum collars and butyl rubber bungs are removed, and the 1-liter contents of each culture bottle are poured into two 500 ml centrifuge bottles with rubber gasketed screw caps. After decanting growth medium, the caps of the centrifuge bottles are tightened for an airtight seal, brought out of the anaerobic chamber, then centrifuged for 20 minutes at 6000 g at 4° C. Centrifuged bottles are then brought into the anaerobic chamber, uncapped, and then the supernatants are poured off and discarded. The remaining cell pellets are then combined with 250 ml ice cold Vehicle Buffer (Phosphate Buffered Saline plus 1 g/L L-cysteine plus 15% glycerol, filter sterilized and made anoxic by bubbling with filtered nitrogen). The cell pellets are carefully resuspended in the Vehicle Buffer on ice; the resuspended volumes of two pellets are combined into one 500 ml bottle, recapped for an air-tight seal, removed from the anaerobic chamber, then centrifuged for 20 minutes at 6000 g at 4° C. After decanting supernatants in the anaerobic chamber, resulting cell pellets are then carefully resuspended once more with 250 ml ice cold Vehicle Buffer in the anaerobic chamber, removed from the anaerobic chamber, then centrifuged for 20 minutes at 6000 g at 4° C. After removal of supernatant in the anaerobic chamber, each pellet is resuspended in 100 ml ice cold Vehicle Buffer to establish a ten-fold concentration of the original culture cell density.

Within the anaerobic chamber, final resuspended cell pellet volumes for an anaerobic microbe of interest are combined and thoroughly mixed in a sterile bottle by gentle stirring on a stir plate on ice. The volume is then dispensed into 25 ml aliquots in 50 ml conical tubes using a serological pipette, then a stream of sterile filtered gaseous argon is introduced to each tube to displace the headspace and to serve as an oxygen barrier. Each tube is then tightly capped, and the seal is wrapped with several layers of parafilm. The tubes are then racked upright, removed from the anaerobic chamber, and then allowed to slowly freeze at −80° C. A smaller 5 ml aliquot is also made for each preparation and stored as described above. After 18 hours, the 5 ml aliquots for each microbial strain of interest are removed and allowed to thaw standing in ice water within the anaerobic chamber. The thawed volumes are gently mixed by inversion several times, then subjected to dilution plating on appropriate solid anaerobic medium to determine the live cell density in CFU/ml after freezer storage.

Live Biotherapeutic Assembly for Mouse Studies

Live biotherapeutic compositions of anaerobic microbes of interest, including the combinations of microbes as provided herein, e.g., the exemplary combinations 1 to 241 as described in Table 15, Example 10, are assembled in volumes that are pertinent for projected mouse studies. Enough aliquots for each microbe of interest are removed from storage at −80° C. and gently thawed in ice water in the anaerobic chamber. The thawed multiple aliquots are combined in a sterile bottle, gently remixed and then placed on ice. The amount of volume of each microbe to add to a mix is adjusted so that the determined live cell densities for each microbe are equivalent, and final total cell densities can be adjusted by further addition of ice-cold vehicle buffer. Once all requisite volumes for each microbe are added together in a larger sterile bottle, the volume is gently mixed by stirring on a stir plate on ice.

Live biotherapeutic volumes are then re-aliquoted in individual volumes that each comprise a projected daily dose of live microbes in anticipated mouse studies. Determined volumes are each dispensed in 15 ml conical tubes up to 10 ml per aliquot. The volume in each tube is overlaid with a stream of sterile filtered argon to displace oxygen, followed by capping. Live biotherapeutic aliquot tubes are racked upright and allowed to slowly freeze at −80° C. After 48 hours, one aliquot for each microbe mix preparation is thawed and dilution plated to validate the final total CFU/ml, optimally at greater than $1.0 \times 10^9$ CFU/ml.

Example 16—Efficacy of Live Biotherapeutics as an Anticancer Monotherapy

Microorganisms in Mouse Study

The sets of microbes to be administered are chosen from either Table 15 (1-241) or Table 16 (1-15), described in Example 10 or from engineered microbes described in Examples 13 and 14. Each microbe is isolated from healthy donors, as described in Example 3, or the genetically modified derivatives described in Examples 13 and 14. The live biotherapeutic is cultured and assembled as described in Example 15.

After assembly, PBS-C-G is added to each live biotherapeutic to reduce the total cell density of each live biotherapeutic to the desired dosage level, which can be between $1 \times 10^8/0.2$ ml and $1 \times 10^{12}/0.2$ ml. Live biotherapeutics are aliquoted into eight 5.0 ml volumes into 15 ml conical tubes and stored at −20° C. until required.

Animals and Tumor Model

BALB/c mice are obtained from Shanghai Lingchang Biotechnology Co., Ltd (Shanghai, China) or Jackson Laboratory. 6-8-week-old female mice are used. For tumor growth experiments, mice are injected subcutaneously with $2.5 \times 10^5$ CT-26 colon cancer tumor cells (Griswold and Corbett (1975) Cancer 36:2441-2444), MC38 col on tumor cells (Juneja et al. (2017) J. Exp. Med. 214(4):895), LL/2 lung carcinoma cells (Bertram and Janik (1980) Cancer Lett. 11:63-73), or EMT6 breast cancer cells (Rockwell et al. (1972) J. Nat. Cancer Inst. 49:735-749). Tumor size is measured twice a week until endpoint, and tumor volume determined as length×width×0.5.

Tumor Cell Preparation

Cryo vials containing CT-26, MC38, LL/2, or EMT6 tumor cells are thawed and cultured according to manufacturer's protocol (ATCC CRL-2638). On the day of injection cells are washed in serum free media, counted, and resuspended in cold serum free media at a concentration of 250,000 viable cells/100 µl.

Antibiotic Pre-Treatment

In some studies, mice are treated daily with 200 µL of antibiotic solution via oral gavage for a duration of 1-2 weeks. The antibiotic solution consists of ampicillin (1 mg/mL)(Alfa Aesar J6380706), gentamicin (1 mg/mL)(Acros Organics AC455310050), metronidazole (1 mg/mL) (Acros Organics AC210440050), neomycin (1 mg/mL)(Alfa Aesar AAJ6149922), and vancomycin (0.5 mg/mL) (Alfa Aesar J6279006) via oral gavage. Animals are given at least 48 hours rest period between antibiotic pre-treatment and the treatment phase to allow for antibiotics to go through the system.

Fecal Microbiota Transplantation (FMT)

Fecal Microbiota Transplantation (FMT) of a human gut microbiome into antibiotic treated mice is a method for standardizing microbiome composition. FMT is performed in some experiments with fecal material derived from responders to checkpoint inhibitor therapy (R) or non-responders to checkpoint inhibitor therapy (NR). Not only does this standardize the mice microbiomes, but also conditions them to favor response or non-response, respectively. Following antibiotic pre-treatment, colonization is performed by oral gavage with 200 µl of suspension obtained by homogenizing the fecal samples in PBS. Mouse fecal samples are collected 1-2 times during this period, so that the efficacy of the FMT can be evaluated. Following FMT, a rest period of 5-7 days is allowed to pass prior to treatment initiation.

Tumor Challenge and Treatment

After pre-treatment is complete, tumor inoculation is performed. 100 µl of the cell suspension is subcutaneously injected into the rear flank of the mouse. During implantation, a new syringe and needle will be used for every mouse inoculated to minimize tumor ulceration. The cells are drawn up into a 1 mL syringe (no needle attached) to 150 µL with the 50 µL nearest to the plunger being air and 100 µL of cell suspension. Once the cells are drawn up the needle is attached (without priming the needle). For implant, skin is lifted using forceps to ensure a subcutaneous injection, and cells are injected. Mice are marked by ear tagging. Animals are randomized the day following tumor inoculation (Study Day 0). Treatment begins the following day (Study Day 1) and continues for 3 weeks or longer and consists of 200 uL microbe mix or vehicle control (PBS-C-G). Total microbial load is between $10^9$ and $10^{12}$ colony forming units (cfu) per dose. Doses are administered at a frequency of at least twice per week, and up to twice per day. Tumor size is routinely monitored by means of a caliper. Stool is collected on day 0, and twice per week until the end of the study, normally 8 hours following a treatment dose.

Peripheral Blood Extraction and Processing

Whole blood is taken via cardiac puncture at the end of the experiment, or via tail bleed during the experiment, and collected into an EDTA tube. Plasma is isolated from an aliquot of the whole blood by centrifugation at 1500×g for 10 minutes, taking the supernatant. A second centrifugation is performed to remove any residual blood cells.

Peripheral blood mononuclear cells (PBMCs) are isolated from blood using a standard kit and stored in liquid nitrogen at $1\times10^6$ cells/mL until use. Prior to storage, PBMC's may be processed using flow sorting or antibody spin separation kit to select for a certain purified lymphocyte subpopulation, such as T cells.

GI Tract Removal and Analysis

After mice are euthanized at the termination of the study, the intact digestive tract of each mouse from stomach to rectum are removed and kept in a 5 ml Eppendorf tube on ice prior to dissection. Forceps are sterilized by soaking in 100% ethanol and then used to remove the intestine length and stretch it on a work surface covered with cellophane. With the use of ethanol-sterilized dissection scissors, 3 cm lengths of the jejunum nearest to the stomach and the ilium nearest to the cecum/large intestine are excised and then each placed with forceps in a 1.5 ml Eppendorf tube and placed on ice. A 2 cm segment of the cecum/ascending colon is then excised, as are 2 cm segments of the transcending colon and the descending colon, and all are placed in 1.5 ml Eppendorf tubes on ice. Dissection instruments are sterilized by dipping in 100% ethanol between each intestine fragment removal. To each tube containing dissected intestinal segments is added 0.5 ml ice cold PBS buffer. A plastic pestle is used to press and massage the intestinal segment in each tube to expel ruminal matter, which is then removed by pipette and placed in a fresh Eppendorf tube. Tubes containing expelled ruminal matter from each intestinal segment are immediately placed on dry ice and then stored for later analyses at −80° C. Remaining intestinal tissues are then rinsed twice by adding and then removing 0.5 ml ice cold PBS. Rinsed intestinal fragment tissues are then frozen on dry ice and then stored at −80° C. for later analysis.

Analyses of Dendritic Cell Subsets in Treated Mice

Cell suspensions from mouse spleen and lymph nodes are prepared by digestion with collagenase and DNase for 60 min and subsequently strained through a 70 mm mesh. Colonic and small intestinal lymphocytes are isolated as previously described (Viaud, S. et al. Science 80(342): 971-976 (2013). In brief, cecum, colon and small intestine are digested in PBS containing 5 mM EDTA and 2 mM DTT shaking at 37° C. A plastic pestle is used to press and massage the intestinal segment in each tube to expel ruminal matter, which is then removed by pipette and placed in a fresh Eppendorf tube. Tubes containing expelled ruminal matter from each intestinal segment are immediately placed on dry ice and then stored for later analyses at −80° C. Remaining intestinal tissues are then rinsed twice by adding and then removing 0.5 ml ice cold PBS. Rinsed intestinal fragment tissues are then frozen on dry ice in RNALater (Thermo Fisher Scientific) and then stored at −80° C. for later analysis.

After initial digestion colonic and small intestinal tissue pieces are digested in collagenase/Dnase containing RPMI medium for 30 min. Tissue pieces are further strained through a 70 mm mesh. For flow cytometry analyses, cell suspensions are stained with antibodies against the following surface markers: CD11c (N418), CD11b (M1/70), Lytic (HK1.4), MHC class II (M5/114.15.2), CD24 (M1/69), CD64 (X54-5/7.1), CD317 (ebio927), CD45 (30-F11), F4/80 (C1:A3-1), CD8α (53-6.7). DAPI is used for dead cell exclusion. Antibodies are purchased from eBiosciences, BD Biosciences or BioLegend respectively. Cell populations are gated as follows: small intestine (migratory fraction): CD103+DC (CD45+CD11c+MHC-II+CD103+CD24+), CD11b+CD103+ (CD45+CD11c+MHC-II+CD103+ CD11b+CD24+), CD11b+ (CD45+CD11c+MHC-II+ CD11b+CD24+), inflammatory DC (CD45+CD11c+MHC-II+CD11b+CD64+Ly6c+), large intestine: CD103+DC (CD45+CD11c+MHC-II+CD103+CD24+), CD11b+ (CD45+CD11c+MHC-II+CD11b+CD24+), inflammatory DC (CD45+CD11c+MHC-II+CD11b+CD64+Ly6c+).

Whole Genome Sequencing

Fecal gDNA is extracted for whole genome sequencing (WGS). Experimental methods for DNA extraction and library preparation are performed using protocols modeled after the Human Microbiome Project (Lloyd-Price et al. (2017) Nature 550(7674):61-66) and validated with samples from healthy volunteers. Sequencing is performed by an outside service provider, using a HISEQ-X® (Illumina) with 2×150 bp paired-end reads, providing approximately 4 million reads per sample. Analysis software such as Centrifuge (Kim, D., et al., Centrifuge: rapid and sensitive classification of metagenomic sequences. Genome Res, 2016. 26 (12): p. 1721-1729) are used to align sequence reads to reference genomes and obtain species and strain-level identification.

Metabolomics

Metabolites are extracted from fecal material or blood plasma, using methanol under vigorous shaking for 2 min (Glen Mills GenoGrinder 2000) to precipitate protein and dissociate small molecules bound to protein or trapped in the precipitated protein matrix, followed by centrifugation to recover chemically diverse metabolites. The resulting extract was divided into five fractions: two for analysis by two separate reverse phase (RP)/UPLC-MS/MS methods using positive ion mode electrospray ionization (ESI), one for analysis by RP/UPLC-MS/MS using negative ion mode ESI, one for analysis by HILIC/UPLC-MS/MS using negative ion mode ESI, and one reserved for backup. Samples are placed briefly on a TurboVap® (Zymark) to remove the organic solvent, followed by injection on one of the instruments mentioned above. Compounds are identified by comparison to library entries of purified standards, that contains the retention time/index (RI), mass to charge ratio (m/z), and chromatographic data (including MS/MS spectral data) on all molecules present in the library. Furthermore, biochemical identifications are based on three criteria: retention index within a narrow RI window of the proposed identification, accurate mass match to the library +/−10 ppm, and the MS/MS forward and reverse scores. MS/MS scores are based on a comparison of the ions present in the experimental spectrum to ions present in the library entry spectrum. While there may be similarities between these molecules based on one of these factors, the use of all three data points can be utilized to distinguish and differentiate bio-chemicals. Peaks are quantified as area-under-the-curve detector ion counts.

Immunophenotyping Assays

Immune profiling of whole blood is utilized to assess T cell activation in response to microbial treatment. In some experiments, immune phenotyping is also performed on tissue obtained from the GI tract.

For flow cytometry analysis, 1 mL of RBC Lysis Buffer is added to 0.1 mL of whole blood or homogenized tissue and allowed to incubate at room temperature for 10 minutes. Lysis is quenched by adding 10 mL of cold DPBS. Samples are centrifuged at 1500 rpm for 5 minutes at 4° C. The pellet is aspirated and resuspend in another 10 mL of cold DPBS. Samples are recentrifuged at 1500 rpm for 5 minutes at 4° C. Samples are resuspended in 500 μL of FACS buffer and transferred to a 96-well plate. Samples are stained with Fixable Viability ef780™ (eBioscience), CD45-PEcy7 (BioLegend), CD3-BV605™ (BioLegend), CD8-AF700™ (BioLegend), and CD4-AF488™ (BioLegend). Stained samples are run on a BD LSRFortessa™ flow cytometer and analyses are performed with FlowJo™ (Tree Star).

Alternatively, CyTOF® is applied to characterize the immune profile of the PBMCs. This work is conducted by the Bioanalytical and Single-Cell Facility at the University of Texas, San Antonio, and entails a comprehensive panel of 29 different immune markers, allowing for deep interrogation of cellular phenotype and function (https://www.fluidigm.com/products/helios). To complement these results, RNA sequencing is applied to the entire population of the PBMCs, sorted populations, and also to single cells. Single cell RNAseq is applied using the method developed by 10× Genomics (https://www.10xgenomics.com/solutions/single-cell/). Finally, cytokine levels are determined using the Human Cytokine 30-Plex Luminex assay (https://www.thermofisher.com/order/catalog/product/LHC6003M).

Example 17—Therapeutic Effect of Microbes on Efficacy of Cancer Immunotherapy

In this study, live biotherapeutics as provided herein, including combinations of microbes as provided herein, are administered in combination with checkpoint inhibitors (anti-CTLA-4, anti-PD-1, or anti-PD-L1), to demonstrate the ability of these microbes to enhance the tumor reduction that can be achieved with the checkpoint inhibitor.

Microorganisms in Mouse Study

The sets (or combinations) of microbes to be administered are chosen from the list of exemplary bacterial combinations as set forth in Table 15, listing combinations 1 to 241, or Table 16, as described in Example 10, or from the exemplary engineered microbes described in Examples 12 and 13. Each microbe is isolated from healthy donors, as described in Example 3, or the genetically modified derivatives described in Examples 12 and 13. The live biotherapeutic is cultured and assembled as described in Example 14.

After assembly, PBS-C-G is added to each microbe mix to reduce the total cell density of each microbe mix to the desired dosage level, which can be between $1 \times 10^8/0.2$ ml and $1 \times 10^{12}/0.2$ ml. Live biotherapeutics are aliquoted into eight 5.0 ml volumes into 15 ml conical tubes and stored at −20° C. until required.

Animals and Tumor Model

BALB/c mice are obtained from Shanghai Lingchang Biotechnology Co., Ltd (Shanghai, China). 6-8-week-old female mice are used. For tumor growth experiments, mice are injected subcutaneously with $2.5 \times 10^5$ CT-26 colon cancer tumor cells (Griswold and Corbett (1975) Cancer 36:2441-2444), MC38 colon tumor cells (Juneja et al. (2017) J. Exp. Med. 214(4):895), LL/2 lung carcinoma cells (Bertram and Janik (1980) Cancer Lett. 11:63-73), or EMT6 breast cancer cells (Rockwell et al. (1972) J. Nat. Cancer Inst. 49:735-749). Tumor size is measured twice a week until endpoint, and tumor volume determined as length× width×0.5.

Tumor Cell Preparation

Cryo vials containing CT-26, MC38, LL/2, or EMT6 tumor cells are thawed and cultured according to manufacturer's protocol (ATCC CRL-2638). On the day of injection cells are washed in serum free media, counted, and resuspended in cold serum free media at a concentration of 250,000 viable cells/100 μl.

Antibiotic Pre-Treatment

In some studies, mice are treated daily with 200 μL of antibiotic solution via oral gavage for a duration of 1-2 weeks. The antibiotic solution consists of ampicillin (1 mg/mL)(Alfa Aesar J6380706), gentamicin (1 mg/mL)(Acros Organics AC455310050), metronidazole (1 mg/mL) (Acros Organics AC210440050), neomycin (1 mg/mL)(Alfa Aesar AAJ6149922), and vancomycin (0.5 mg/mL) (Alfa Aesar J6279006) via oral gavage. Animals are given at least 48 hrs rest period between antibiotic pre-treatment and the treatment phase to allow for antibiotics to go through system.

Fecal Microbiota Transplantation (FMT)

In alternative embodiments, methods as provided herein comprise use of Fecal Microbiota Transplantation (FMT), or elements used to practice FMT, as described e.g., in U.S. Pat. Nos. 10,493,111; 10,463,702; 10,383,519; 10,369,175; 10,328,107.

FMT of a human gut microbiome into antibiotic treated mice is a method for standardizing microbiome composition. FMT is performed in some experiments with fecal material derived from responders to checkpoint inhibitor therapy (R) or non-responders to checkpoint inhibitor therapy (NR). Not only does this standardize the mice microbiomes, but also conditions them to favor response or non-response, respectively. Following antibiotic pre-treatment, colonization is performed by oral gavage with 200 μl of suspension obtained by homogenizing the fecal samples in PBS. Mouse fecal samples are collected 1-2 times during this period, so that the efficacy of the FMT can be evaluated. Following FMT, a rest period of 5-7 days can pass prior to treatment initiation.

Tumor Challenge and Treatment

Tumor inoculation is performed immediately following either the FMT or antibiotic dosing. 100 μl of the cell suspension is subcutaneously injected into the rear flank of the mouse. During implantation, a new syringe and needle will be used for every mouse inoculated to minimize tumor ulceration. The cells are drawn up into a 1 mL syringe (no needle attached) to 150 μL with the 50 μL nearest to the plunger being air and 100 μL of cell suspension. Once the cells are drawn up the needle is attached (without priming the needle). For implant, skin is lifted using forceps to ensure a subcutaneous injection, and cells are injected. Mice are marked by ear tagging. Animals are randomized once the tumor volume reaches 40 to 60 mm³ (Study Day 0), or alternatively 80 to 100 mm³, or 100 to 120 mm³.

Treatment consists of checkpoint inhibitor, alone or in conjunction with the live biotherapeutics described above. Checkpoint inhibitor is injected intraperitoneally the day following randomization (Day 1) with 100 μg anti-PD1 mAb (BioXCell), or with 100 μg anti-PD-L1 mAb, or with 100 μg anti-CTLA-4 mAb (BioXCell) in 100 µl PBS. Dosing of the checkpoint inhibitor is continued twice per week for three weeks starting from day 1. Microbe dosing consists of 200 uL microbe mix or vehicle control (PBS-C-G). Total microbial load is between $10^9$ and $10^{12}$ colony forming units (cfu) per dose. Doses are administered at a frequency of at least twice per week, and up to twice per day. Tumor size is routinely monitored by means of a caliper. Stool is collected on day 0, and twice per week until the end of the study, normally 8 hours following a treatment dose.

Peripheral Blood Extraction and Processing

Whole blood is taken via cardiac puncture at the end of the experiment, or via tail bleed during the experiment, and collected into an EDTA tube. Plasma is isolated from an aliquot of the whole blood by centrifugation at 1500×g for 10 minutes, taking the supernatant. A second centrifugation is performed to remove any residual blood cells.

Peripheral blood mononuclear cells (PBMCs) are isolated from blood using a standard kit and stored in liquid nitrogen at 1×10⁶ cells/mL until use. Prior to storage, PBMC's may be processed using flow sorting or antibody spin separation kit to select for a certain purified lymphocyte subpopulation, such as T cells.

GI Tract Removal and Analysis

After mice are euthanized at the termination of the study, the intact digestive tract of each mouse from stomach to rectum are removed and kept in a 5 ml Eppendorf tube on ice prior to dissection. Forceps are sterilized by soaking in 100% ethanol and then used to remove the intestine length and stretch it on a work surface covered with cellophane. With the use of ethanol-sterilized dissection scissors, 3 cm lengths of the jejunum nearest to the stomach and the ilium nearest to the cecum/large intestine are excised and then each placed with forceps in a 1.5 ml Eppendorf tube and placed on ice. A 2 cm segment of the cecum/ascending colon is then excised, as are 2 cm segments of the transcending colon and the descending colon, and all are placed in 1.5 ml Eppendorf tubes on ice. Dissection instruments are sterilized by dipping in 100% ethanol between each intestine fragment removal. To each tube containing dissected intestinal segments is added 0.5 ml ice cold PBS buffer. A plastic pestle is used to press and massage the intestinal segment in each tube to expel ruminal matter, which is then removed by pipette and placed in a fresh Eppendorf tube. Tubes containing expelled ruminal matter from each intestinal segment are immediately placed on dry ice and then stored for later analyses at −80° C. Remaining intestinal tissues are then rinsed twice by adding and then removing 0.5 ml ice cold PBS. Rinsed intestinal fragment tissues are then frozen on dry ice and then stored at −80° C. for later analysis.

Analyses of Dendritic Cell Subsets in Treated Mice

Cell suspensions from mouse spleen and lymph nodes are prepared by digestion with collagenase and DNase for 60 min and subsequently strained through a 70 mm mesh. Colonic and small intestinal lymphocytes are isolated as previously described (Viaud, S. et al. Science (80-). 342, 971-976 (2013). In brief, cecum, colon and small intestine are digested in PBS containing 5 mM EDTA and 2 mM DTT shaking at 37° C. A plastic pestle is used to press and massage the intestinal segment in each tube to expel ruminal matter, which is then removed by pipette and placed in a fresh Eppendorf tube. Tubes containing expelled ruminal matter from each intestinal segment are immediately placed on dry ice and then stored for later analyses at −80° C. Remaining intestinal tissues are then rinsed twice by adding and then removing 0.5 ml ice cold PBS. Rinsed intestinal fragment tissues are then frozen on dry ice in RNALater (Thermo Fisher Scientific) and then stored at −80° C. for later analysis.

After initial digestion colonic and small intestinal tissue pieces are digested in collagenase/Dnase containing RPMI medium for 30 min. Tissue pieces are further strained through a 70 mm mesh. For flow cytometry analyses, cell suspensions are stained with antibodies against the following surface markers: CD11c (N418), CD11b (M1/70), Lytic (HK1.4), MHC class II (M5/114.15.2), CD24 (M1/69), CD64 (X54-5/7.1), CD317 (ebio927), CD45 (30-F11), F4/80 (C1:A3-1), CD8a (53-6.7). DAPI is used for dead cell exclusion. Antibodies are purchased from eBiosciences, BD Biosciences or BioLegend respectively. Cell populations are gated as follows: small intestine (migratory fraction): CD103+DC (CD45+CD11c+MHC-II+CD103+CD24+), CD11b+CD103+ (CD45+CD11c+MHC-II+CD103+CD11b+CD24+), CD11b+ (CD45+CD11c+MHC-II+CD11b+CD24+), inflammatory DC (CD45+CD11c+MHC-II+CD11b+CD64+Ly6c+), large intestine: CD103+DC (CD45+CD11c+MHC-II+CD103+CD24+), CD11b+ (CD45+CD11c+MHC-II+CD11b+CD24+), inflammatory DC (CD45+CD11c+MHC-II+CD11b+CD64+Ly6c+).

Analysis of Fecal and Blood Samples

Whole genome sequencing, metabolomics, and immunophenotyping are performed on samples collected, as described in Example 15.

Example 18: Fecal Composition Analysis of Tumor Bearing Mice Treated with Fecal Microbiota Transplant Animals and Tumor Model BALB/c mice were obtained from the Jackson Laboratory and 6-8-week-old female mice were used. For tumor growth experiments, mice were injected subcutaneously with 2.5× 10⁵ CT-26 colon cancer tumor cells (Griswold and Corbett (1975) Cancer 36:2441-2444). Tumor size was measured twice a week until endpoint, and tumor volume determined as length×width×0.5.

Tumor Cell Preparation

Cryo vials containing CT-26 tumor cells were thawed and cultured according to manufacturer's protocol (ATCC CRL-2638). On the day of injection cells were washed in serum free media, counted, and resuspended in cold serum free media at a concentration of 250,000 viable cells/100 µl. Cells were prepared for injections by withdrawing 100 µL of the cell suspension into a 1 ml syringe. The cell suspension and filled syringes were kept on ice.

Tumor Implantation

Animals were prepared for injection using standard approved anesthesia and shaved prior to injection. 100 µl of the cell suspension was subcutaneously injected into the rear flank of the mouse. Mice were marked by ear tagging.

Antibiotics Protocols

Mice were treated daily with 200 µL of antibiotics via oral gavage 1 week before fecal microbiota transplantation (FMT). Mouse fecal samples were collected twice a week. Animals were given a mix of ampicillin (1 mg/mL)(Alfa Aesar J6380706), gentamicin (1 mg/mL)(Acros Organics AC455310050), metronidazole (1 mg/mL)(Acros Organics AC210440050), neomycin (1 mg/mL)(Alfa Aesar AAJ6149922), and vancomycin (0.5 mg/mL)(Alfa Aesar J6279006) via oral gavage.

Fecal Microbiota Transplantation (FMT)

Fecal Microbiota Transplantation (FMT) of a favorable gut microbiome into antibiotic treated mice is a method for standardizing microbiome composition. FMT was performed with fecal material derived from healthy and cancer patients. Colonization was performed by oral gavage with 200 μl of suspension obtained by homogenizing the fecal samples in PBS. Efficient colonization was first checked before tumor inoculation. Mouse fecal samples were collected 1-2 times during this period so that the efficacy of the FMT can be evaluated. Following FMT, a rest period of 5-7 days was allowed prior to checkpoint inhibitor and/or microbe dosing. Blood and fecal pellets were collected at different time points during the experiment.

Mice were pre-treated with antibiotics, FMT was performed, and tumors were inoculated. Randomization began at a tumor volume of 50 mm³. Tumor size was measured in all animals receiving antibiotic pre-treatment, followed by FMT transfer from cancer patients. Four FMTs (NR(1)-FMT, NR(2)-FMT, R(1)-FMT, R(2)-FMT) were selected for administration to the mice based on donor cancer patient response to therapy. FMTs NR(1)-FMT and NR(2)-FMT are derived from non-responding cancer patients and FMTs R(1)-FMT and R(2)-FMT are from cancer patients that respond to immunotherapy.

Figure 11:
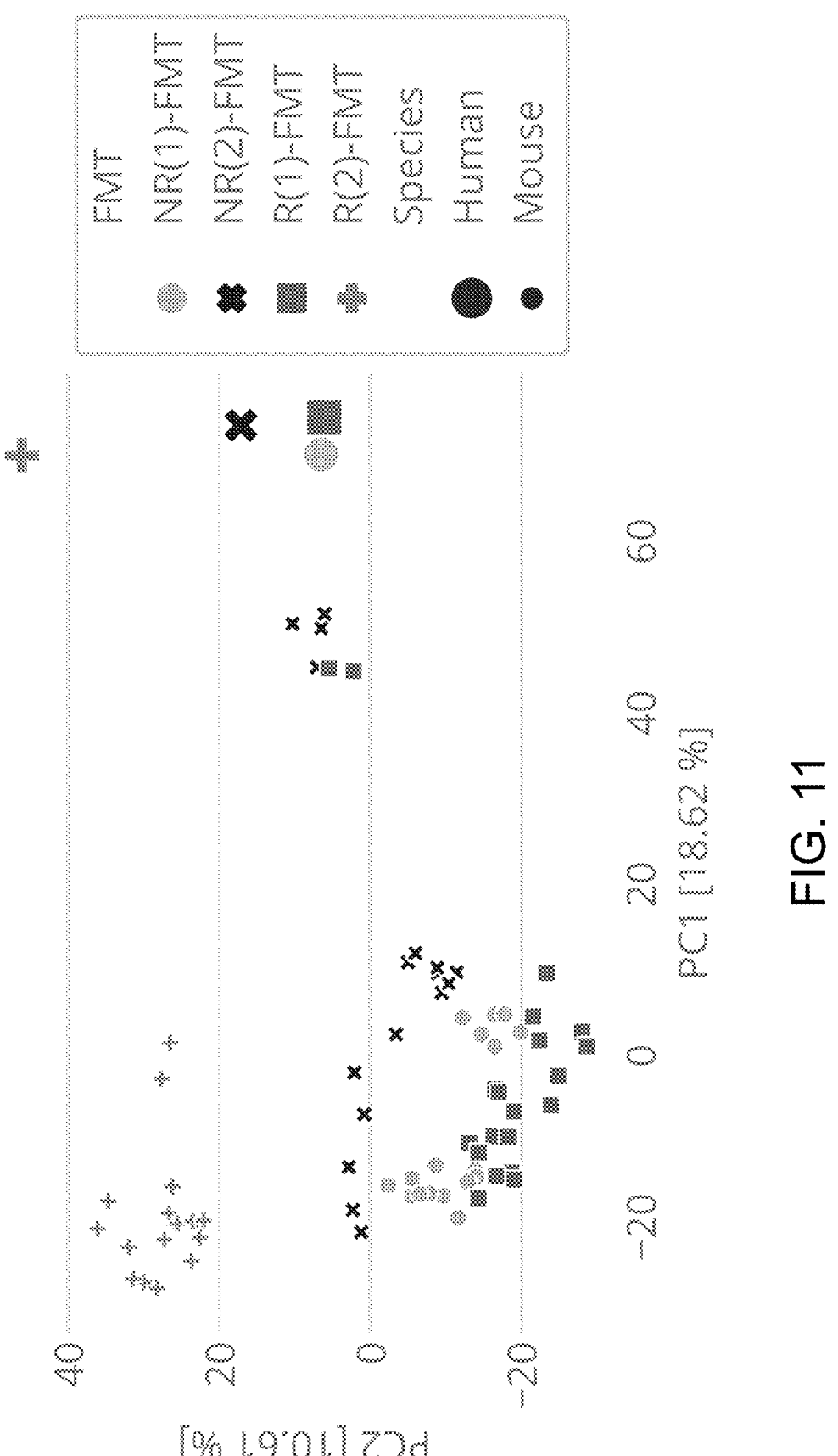
FIG. 11 graphically illustrates the first two principal components of a PCA of centered-log-ratio transformed microbial species abundance values obtained from fecal samples of FMT-treated mice 7 days post-treatment. Circles and Xs represent samples from mice treated with fecal material from two different non-responder patients. Squares and plusses represent samples from mice treated with fecal material from two different responder patients. The large symbols of each type indicate species composition of the human fecal material used for each transplant.
Figure 12:
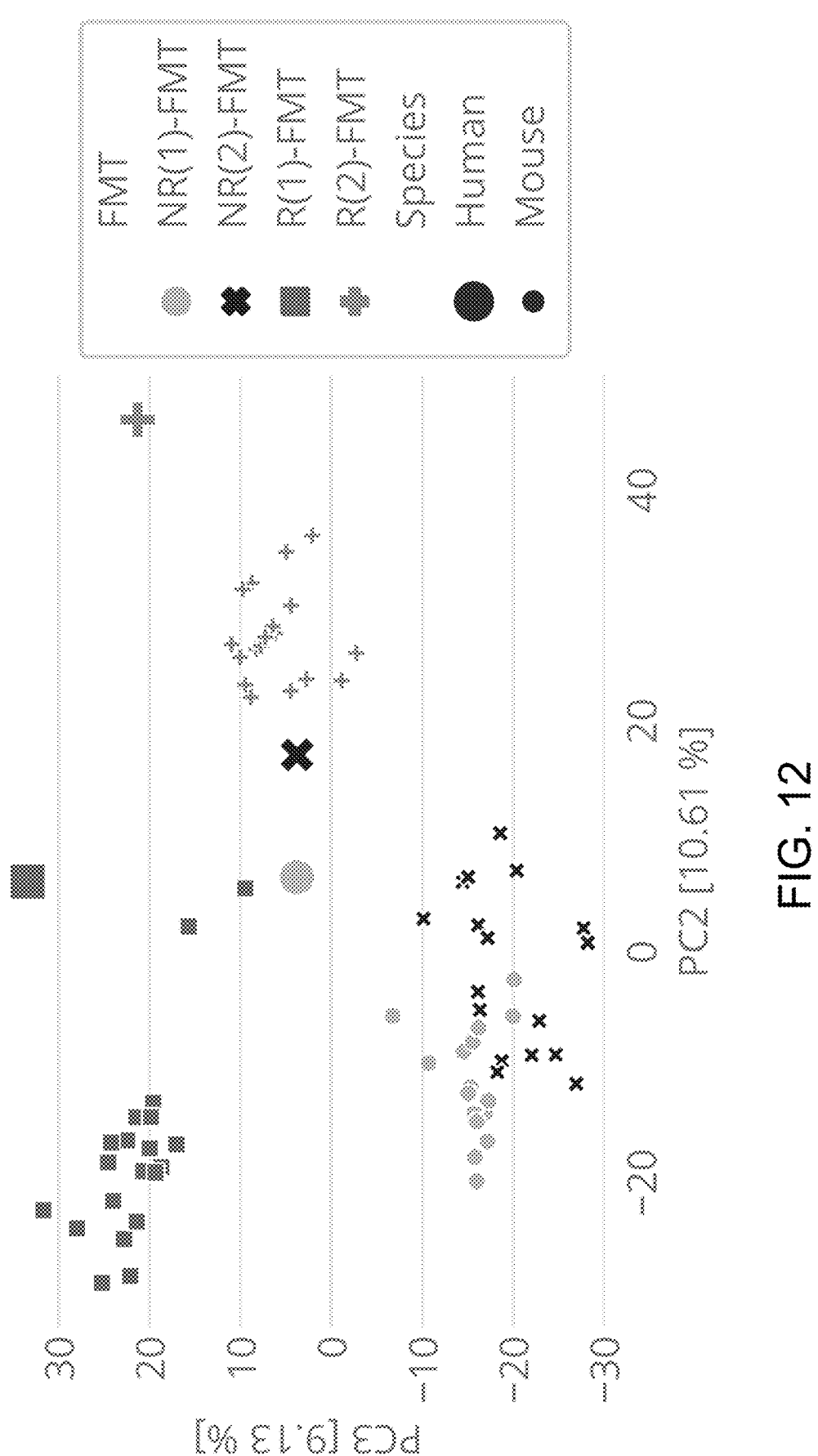
FIG. 12 graphically illustrates principal components 2 and 3 of a PCA of centered-log-ratio transformed microbial species abundance values obtained from fecal samples of FMT-treated mice 7 days post-treatment. Symbols are as described for FIG. 11.
Figure 13:
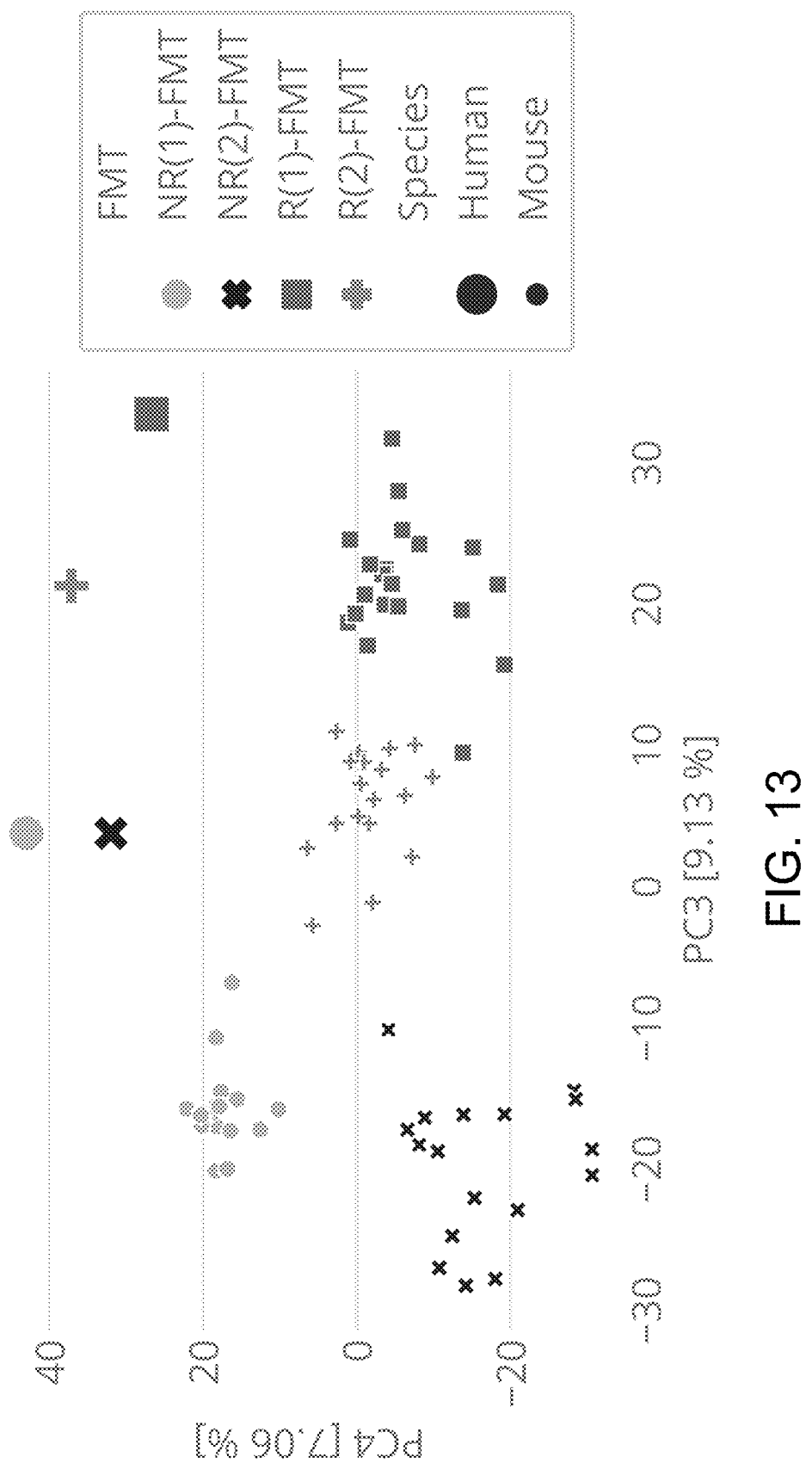
FIG. 13 graphically illustrates principal components 3 and 4 of a PCA of centered-log-ratio transformed microbial species abundance values obtained from fecal samples of FMT-treated mice 7 days post-treatment. Symbols are as described for FIG. 11.
Figure 14:
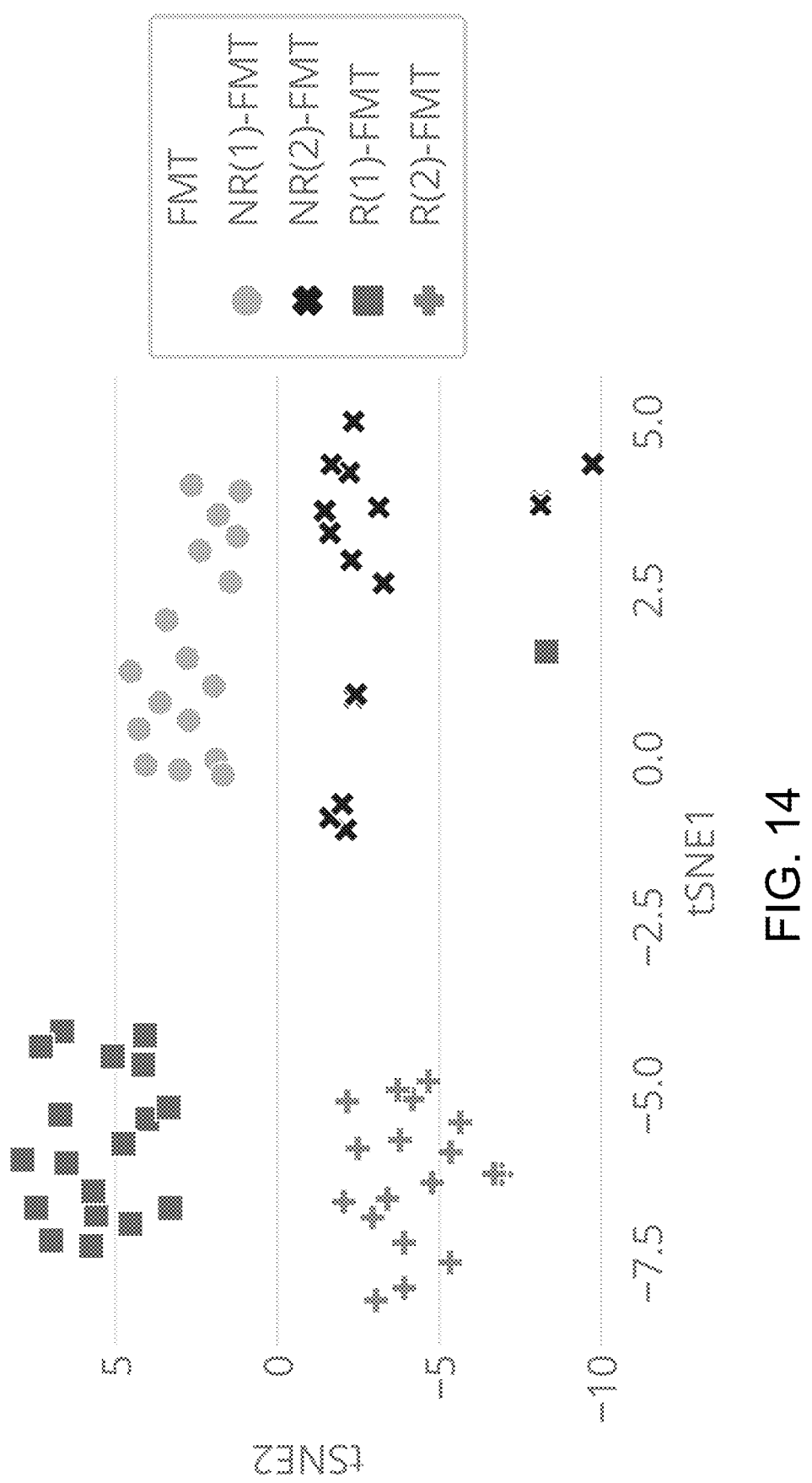
FIG. 14 graphically illustrates the first two components of a t-Distributed Stochastic Neighbor Embedding (tSNE) of centered-log-ratio transformed microbial species abundance values obtained from fecal samples of FMT-treated mice 7 days post-treatment. Circles and Xs represent samples from mice treated with fecal material from two different non-responder patients. Squares and plusses represent samples from mice treated with fecal material from two different responder patients.
Figure 15:
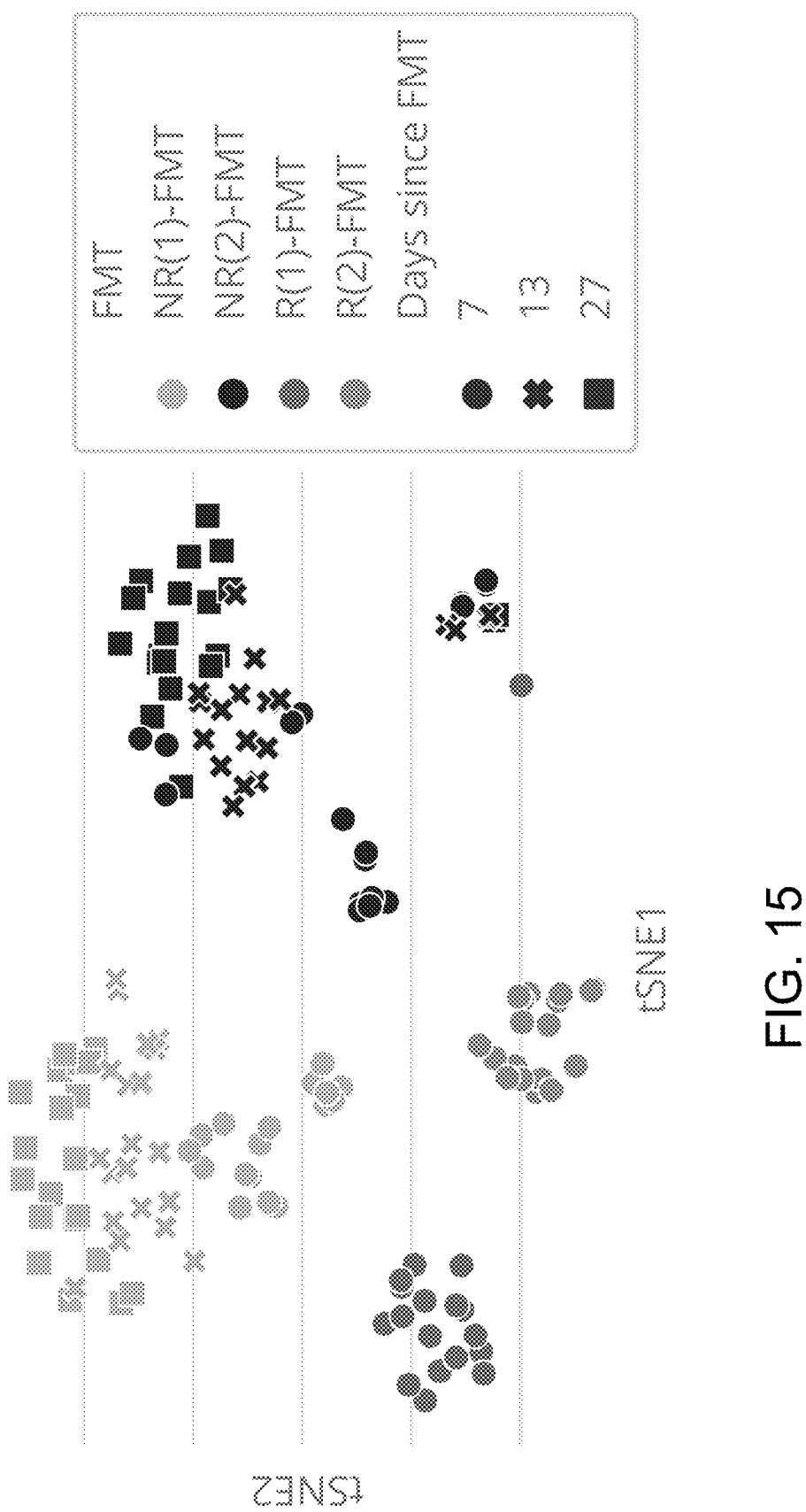
FIG. 15 graphically illustrates the first two components of a tSNE of centered-log-ratio transformed microbial species abundance values obtained from fecal samples of FMT-treated mice 7, 13, and 27 days post-treatment. Shading intensity of the points indicates different donors. Circles, 7 days post-treatment; Xs, 13 days post-treatment; squares, 27 days post-treatment.

Fecal samples were collected from FMT treated mice 7 days post-dosing and whole genome sequencing was performed. Whole genome sequencing was also performed on the human fecal samples from which the FMT material was generated. The sequencing reads were processed and the species abundances for both mouse and human fecal samples were estimated. The abundances were centered-log-ratio transformed and principal component analysis was performed. As illustrated in FIG. 11, the first principal component clearly separates mouse and human samples, showing a strong difference between species. In contrast, in the second, third, and fourth principal components, mice that received their FMT from the same human donor are nearer to each other as illustrated in FIGS. 12 and 13).

t-Distributed Stochastic Neighbor Embedding (tSNE), a machine learning algorithm for visualization was performed (as, see, e.g., (van der Maaten, L. J. P.; Hinton, G. E. (2008) Journal of Machine Learning Research. 9: 2579-2605) on the centered-log-ratio transformed species abundances from the whole genome sequencing with a Euclidean distance metric in order to embed the data in two dimensions. The tSNE was repeated 50 times to explore hyperparameter space for the best objective value for Kullback-Leibler divergence (also called relative entropy). When performed at only the initial timepoint (7 days post-FMT dosing), tSNE shows that mice receiving their FMT from the same human cluster together in the embedded space as illustrated in FIG. 14. When performed on data from multiple time points (7, 13, 27 days post-FMT dosing), tSNE shows that there is some time variation in the microbiomes of mice that have received an FMT, but that this variation is much less than the variation imparted by different FMT donors as illustrated in FIG. 15.

Example 19: Method of Treating a Subject with a Live Exemplary Biotherapeutic This example describes administration of a live exemplary biotherapeutic as provided herein, including a combination of bacteria as provided herein, e.g., as set forth in Table 15 or 16, Example 10, to an individual in need thereof A patient is suffering from cancer. The patient is administered live biotherapeutic compositions, i.e., a formulation or a pharmaceutical composition comprising a combination of microbes (e.g., bacteria) as provided herein, (Table 15 or Table 16, and as described in Example 10) either in monotherapy or in combination with chemotherapy, radiation therapy, a checkpoint inhibitor, a Chimeric Antigen Receptor (CAR) T-cell therapy (CAR-T) or other immunotherapy or cancer treatment, and the patient can be administered the live biotherapeutic for the duration of treatment or for only one or several segments of treatment.

In alternative embodiments, each or one of the microbes used in the bacterial combination is (at least initially) isolated from a healthy donor or donors, as described in Example 3, or is a genetically modified derivative as described in Examples 12 and 13, or is a cultured derivative either.

In alternative embodiments, the patient is administered a live biotherapeutic at a dose of between about $10^5$ to $10^{15}$ bacteria, or at a dose of about $10^{10}$, $10^{11}$ or $10^{12}$ bacteria total or per dose, which can be in a lyophilized form, e.g., or formulated in an enteric coated capsule. In alternative embodiments, the patient takes 1, 2, 3, 4, 5, 6, 7, 8, 9, 10 or 11 or more live biotherapeutic capsules (e.g., by mouth or suppository) once, twice or three times or more per day, and the patient can resume a normal diet after about 1, 2, 4, 8, 12, or 24 or more hours.

In another embodiment, the patient may take the live biotherapeutic capsule(s) by mouth before, during, and/or immediately after a meal.

In another embodiment, the patient is given a course of antibiotics before treatment, e.g., between one to seven days, or between about one to two weeks prior to the first dose of the live biotherapeutic (e.g., as capsule(s)), or three weeks prior, or four weeks prior, or up to 6 months prior to the first dose of live biotherapeutic.

In another embodiment, dosing of the live biotherapeutic, e.g., as capsule(s), is started one to seven days, or one to two weeks, prior to administration of a first dose of a chemotherapy, a first checkpoint inhibitor dose, start of a CAR-T therapy or any immunotherapy or cancer therapy.

In another embodiment, dosing of the live biotherapeutic capsule(s) is continued 1 month, 6 months, 1 year, or more, or between about one week and 2 years, following termination of the treatment, e.g., checkpoint inhibitor administration, chemotherapy or any immunotherapy.

In alternative embodiments, patient response to the combination therapy is a measure of success and for solid tumors is based on radiographic assessment using the Response Evaluation Criteria in Solid Tumors (RECIST 1.1) criteria (Schwartz, et al. (2016) Eur. J. Cancer. 62:132-137) at 6 months after treatment initiation, and again after 12 months and 24 months. Patients are classified as complete responders if all target lesions are gone, partial responders if there is at least 30% reduction in the sum of diameters of all target lesions, progressive disease if there is at least 20% increase in the sum of diameters of all target lesions, and stable disease otherwise. For blood cancers, the Response Evaluation Criteria in Lymphoma (RECIL) criteria is used, based on [18F]2-fluoro-2-deoxy-D-glucose positron-emission tomography (FDG-PET) (Younes, A. et al (2017) Ann. Oncol. 28:1436-1447).

Example 20: Method of Treating a Subject with an Exemplary Live Biotherapeutic Based on Stool Biomarkers This example describes administration of a live exemplary biotherapeutic as provided herein, including a combination of bacteria as provided herein, e.g., as set forth in Table 15 to Table 16, Example 10, to an individual in need thereof.

A patient is suffering from cancer. The patient's stool is collected and analyzed using the methods described in Example 9. In one embodiment, whole genome sequencing is performed and the presence of microbes that are characteristic of healthy individuals or checkpoint inhibitor responders is evaluated. The complete organism abundance profile is also plotted on the PCA axes shown in FIG. 3. Based on the abundance profiles of healthy individuals, responders and non-responders collected to date, a classifier is developed to predict if any given microbiome composition represents a responder or non-responder. This may be based on the amount of one or more particular organisms present, position in the PCA plot, or other criteria that combines aspects of the whole genome sequence data. This classifier is applied to the patient's microbiome composition, to predict whether the patient will likely respond to a checkpoint inhibitor treatment applied in a monotherapy.

In another embodiment, metabolomics is performed on the stool or plasma; a classifier is developed based concentrations of one or more metabolites in all patient data collected to date, and the patient is predicted to be a responder or non-responder based on this classification.

If the patient is classified as a non-responder, a live biotherapeutic will be administered to change the microbiome to be more like that of a responder. The patient is administered one of the present live biotherapeutics (Table 15 or Table 16, and as described in Example 10) in combination with a checkpoint inhibitor, radiation therapy, CAR-T or other immunotherapy for the duration of treatment. Each microbe is isolated from healthy donors, as described in Example 3, or the genetically modified derivatives described in Examples 12 and 13.

In alternative embodiments, the patient is administered a live biotherapeutic at a dose of between about $10^5$ to $10^{15}$ bacteria, or at a dose of about $10^{10}$, $10^{11}$ or $10^{12}$, bacteria total or per dose, which can be in a lyophilized form, e.g., formulated in an enteric coated capsule. The patient takes 1, 2, 3, 4, 5, 6, 7, 8, 9, 10 or 11 or more live biotherapeutic capsules by mouth once, twice or three times per day, and resumes a normal diet after 2, 4, 8, 12, or 24 hours.

In another embodiment, the patient takes the capsule by mouth before, during, or immediately after a meal.

In another embodiment, the patient is given a course of antibiotics before treatment, e.g., between one to seven days, or between about one to two weeks prior to the first dose of microbial cocktail, or three weeks prior, or four weeks prior, or up to 6 months prior to the first dose of live biotherapeutic.

In another embodiment, dosing of the live biotherapeutic is started one to two weeks prior to administration of the first checkpoint inhibitor dose or start of CAR-T therapy. In another embodiment, dosing of the live biotherapeutic is continued 1 month, 6 months, 1 year, or more following termination of checkpoint inhibitor administration.

Patient response to the combination therapy is a measure of success and in solid tumors is based on radiographic assessment using the Response Evaluation Criteria in Solid Tumors (RECIST 1.1) criteria (Schwartz, et al. (2016) Eur. J. Cancer. 62:132-137) at 6 months after treatment initiation, and again after 12 months and 24 months. Patients are classified as complete responders if all target lesions are gone, partial responders if there is at least 30% reduction in the sum of diameters of all target lesions, progressive disease if there is at least 20% increase in the sum of diameters of all target lesions, and stable disease otherwise. For blood cancers, the Response Evaluation Criteria in Lymphoma (RECIL) criteria is used, based on [18F]2-fluoro-2-deoxy-D-glucose positron-emission tomography (FDG-PET) (Younes, A. et al (2017) Ann. Oncol. 28:1436-1447).

Example 21: Diagnosis of Disease and Method of Treating a Subject with an Exemplary Microbial Therapeutic This example describes administration of a live exemplary biotherapeutic as provided herein, including a combination of bacteria as provided herein, e.g., as set forth in Table 15 to Table 16, Example 10, to an individual in need thereof.

Stool biomarkers based on microbes present in patients that respond to immuno-oncology (TO) therapy that are also lacking in patients that fail to respond to TO biotherapy can be used to predict the composition of live biotherapeutics for use as co-therapies to augment and improve outcomes of TO treatments for cancer. Conversely, the absence of these microbes in stool samples, as well as the presence of others found to associate with non-responding cancer patients, as detected in NGS analysis of stool samples taken from individuals during routine biomedical tests and procedures, can form a diagnostic pattern of biomarkers that can predict the likelihood that said individuals have or will develop cancer. This diagnostic may be based on the amount of one or more organisms present, position in the PCA plot, or other criteria that combines aspects of the whole genome sequence data. Reliability of such diagnostic is determined by the area under the ROC curve, as exemplified in FIG. 8. Such a diagnostic method can be used by itself or in combination with other established tests to detect the presence of cancer. The diagnostic method can also detect gut microbial population patterns that can predict likelihood of a patient to develop cancer in the future, thereby redirecting a patient to further diagnoses, appropriate life-style changes, or prophylactic treatments such as the administration of a live biotherapeutic or live biotherapeutics to restore healthy gut microbe populations.

Example 22: Prophylactic Application of a Live Exemplary Biotherapeutic to Prevent Cancer Occurrence in Healthy Individuals or Cancer Recurrence in Patients in Remission This example describes administration of a live exemplary biotherapeutic as provided herein, including a combination of bacteria as provided herein, e.g., as set forth in Table 15 or Table 16, Example 10, to an individual in need thereof to prevent cancer recurrence, or as a prophylactic in healthy individuals or individuals determined to be at risk of acquiring cancer, e.g., because of (wherein the greater than normal risk is determined by) genetic analysis, family history or predisposing factors.

An individual with no history of cancer, or alternatively a cancer patient currently in remission, is administered one of the present live biotherapeutics (Table 15 or 16, and as described in Example 10, or genetically modified variants described in Examples 12 and 13), thereby conditioning the microbiome to best enable the individual's immune system to eliminate tumors before they substantially form. Specifically, the individual is administered a live biotherapeutic at a dose of between about $10^5$ to $10^{15}$ bacteria, or at a dose of about $10^{10}$, $10^{11}$ or $10^{12}$ bacteria total or per dose, which can be in a lyophilized form, e.g., formulated in an enteric coated capsule. The individual takes 1, 2, 3, 4, 5, 6, 7, 8, 9, 10 or 11 or more live biotherapeutic capsules by mouth once, twice or three times per day, and resumes a normal diet after 2, 4, 8, 12, or 24 hours. In another embodiment, the individual may take the capsule by mouth before, during, or immediately after a meal.

A number of embodiments of the invention have been described. Nevertheless, it can be understood that various modifications may be made without departing from the spirit and scope of the invention. Accordingly, other embodiments are within the scope of the following claims.

What is claimed is:

1. A formulation or a pharmaceutical composition comprising:

(a) a combination of microbes comprising:

(i) *Thomasclavelia ramosa* (deposited as ATCC 25582);

(ii) *Blautia obeum* (deposited as DSMZ 25238);

(iii) *Dorea longicatena* (deposited as DSMZ 13814); and (iv) *Faecalibacterium prausnitzii* (deposited as ATCC 27768), or (b) the combination of microbes of (a)

(b) the combination of (a), wherein the *Thomasclavelia ramosa* bacteria are in spore form, or the combination comprises *Thomasclavelia ramose* bacteria and *Thomasclavelia ramosa* spores.

2. The formulation or a pharmaceutical composition of claim 1, wherein the formulation comprises a combination of microbes consisting of:

(a)

(i) *Thomasclavelia ramosa* (deposited as ATCC 25582);

(ii) *Blautia obeum* (deposited as DSMZ 25238);

(iii) *Dorea longicatena* (deposited as DSMZ 13814); and (iv) *Faecalibacterium prausnitzii* (deposited as ATCC 27768), or (b) the combination of (a), wherein the *Thomasclavelia ramosa* bacteria are in spore form, or the combination comprises *Thomasclavelia ramose* bacteria and *Thomasclavelia ramosa* spores.

3. The formulation or pharmaceutical composition of claim 1, wherein the formulation comprises an inner core surrounded by an outer layer of polymeric material enveloping the inner core.

4. The formulation or pharmaceutical composition of claim 1, wherein the plurality of non-pathogenic colony forming live bacteria are substantially dormant colony forming live bacteria, or the plurality of non-pathogenic colony forming live bacteria or the plurality of non-pathogenic germinable bacterial spores are lyophilized.

5. The formulation or pharmaceutical composition of claim 1, wherein the formulation comprises at least $1\times10^4$ colony forming units (CFUs), or between about $1\times10^2$ and $1\times10^8$ CFUs, $1\times10^3$ and $1\times10^7$ CFUs, or $1\times10^4$ and $1\times10^6$ CFUs, of live non-pathogenic bacteria and/or non-pathogenic germinable bacterial spores.

6. The formulation or pharmaceutical composition of claim 1, wherein the formulation or pharmaceutical composition comprises water, saline, a pharmaceutically acceptable preservative, a carrier, a buffer, a diluent, an adjuvant or a combination thereof.

7. A kit or product of manufacture comprising or having contained therein a formulation or pharmaceutical composition of claim 1.

8. The formulation or pharmaceutical composition of claim 3, wherein the non-pathogenic bacteria or the non-pathogenic germinable bacterial spores are substantially in the inner core.

9. The formulation or pharmaceutical composition of claim 3, wherein the polymeric material comprises a natural polymeric material.

10. The formulation or pharmaceutical composition of claim 4, wherein the non-pathogenic dormant colony forming live bacteria comprise live vegetative bacterial cells that have been rendered dormant by lyophilization or freeze drying.

11. The formulation or pharmaceutical composition of claim 1, wherein the formulation or pharmaceutical composition is formulated for administration orally or rectally, or is formulated as a liquid, a food, a gel, a geltab, a candy, a lozenge, a tablet, pill or capsule, or a suppository.

12. The formulation or pharmaceutical composition of claim 1, further comprising a biofilm disrupting or dissolving agent, an antibiotic, an inhibitor of an inhibitory immune checkpoint molecule and/or a stimulatory immune checkpoint molecule or any composition for use in checkpoint blockade immunotherapy.

13. The formulation or pharmaceutical composition of claim 12, wherein the inhibitor of an inhibitory immune checkpoint molecule comprises a protein or polypeptide that binds to an inhibitory immune checkpoint protein.

14. The formulation or pharmaceutical composition of claim 12, wherein the inhibitor of the inhibitory immune checkpoint molecule is an antibody or an antigen binding fragment thereof that binds to an inhibitory immune checkpoint protein.

15. The formulation or pharmaceutical composition of claim 12, wherein the inhibitor of an inhibitory immune checkpoint molecule targets a compound or protein comprising: cytotoxic T-lymphocyte-associated protein 4; Programmed cell Death protein 1; Programmed Death-Ligand 1 (PD-L1); adenosine $A_{2A}$ receptor; B7-H3; B7-H4; B- and T-lymphocyte attenuator protein; Killer-cell Immunoglobulin-like Receptor; Indoleamine-pyrrole 2,3-dioxygenase; Lymphocyte-Activation Gene 3 protein; TIM-3; V-domain Ig suppressor of T cell activation protein, or any combination thereof.

16. The formulation or pharmaceutical composition of claim 12, wherein the inhibitor of an inhibitory immune checkpoint molecule comprises: ipilimumab; pembrolizumab; nivolumab; atezolizumab; avelumab; durvalumab; AMP-224, AMP-514 anti-programmed cell death 1 (PD-1) monoclonal antibody (mAb), PDR001 humanized mAb that targets PD-1, STI-A1110 or STI-A1010, BMS-936559, BMS-986016, TSR-042, JNJ-61610588, MSB-0020718C, AUR-012, enoblituzumab, MBG453, LAG525, BMS-986015, cemiplimab, or any combination thereof.

17. The formulation or pharmaceutical composition of claim 12, wherein the stimulatory immune checkpoint molecule comprises a member of the tumor necrosis factor (TNF) receptor superfamily.

18. The formulation or pharmaceutical composition of claim 14, wherein the inhibitor of the inhibitory immune checkpoint molecule comprises CD27, CD40, OX40, GITR glucocorticoid-Induced TNFR family Related gene protein or, CD137, or a CD28 or Inducible T-cell co-stimulator (ICOS).

19. The kit or product of manufacture of claim 7, wherein the product of manufacture is an implant.

20. The formulation or the pharmaceutical composition of claim 1, wherein the combination of microbes comprises:

(a)

(i) *Thomasclavelia ramosa* VPI 0427 (deposited as ATCC 25582);

(ii) *Blautia obeum* VPI B3-21 (deposited as DSMZ 25238);

(iii) *Dorea longicatena* 111-35 (deposited as DSMZ 13814); and (iv) *Faecalibacterium prausnitzii* VPI C13-51 (deposited as ATCC 27768), or (b) the combination of (a), wherein the *Thomasclavelia ramosa* bacteria are in spore form, or the combination comprises *Thomasclavelia ramose* bacteria and *Thomasclavelia ramosa* spores.

* * * * *